US011518742B2

(12) United States Patent
Feilding-Mellen et al.

(10) Patent No.: US 11,518,742 B2
(45) Date of Patent: Dec. 6, 2022

(54) COMPOSITION COMPRISING A BENZOATE SALT OF 5-METHOXY-N,N-DIMETHYLTRYPTAMINE

(71) Applicant: Beckley Psytech Limited, Oxford (GB)

(72) Inventors: Cosmo Feilding-Mellen, Oxford (GB); Timothy Mason, Oxford (GB)

(73) Assignee: Beckley Psytech Limited, Oxford (GB)

( * ) Notice: Subject to any disclaimer, the term of this patent is extended or adjusted under 35 U.S.C. 154(b) by 0 days.

(21) Appl. No.: 17/660,873

(22) Filed: Apr. 27, 2022

(65) Prior Publication Data
US 2022/0259147 A1 Aug. 18, 2022

Related U.S. Application Data

(63) Continuation of application No. PCT/GB2021/051475, filed on Jun. 14, 2021.

(30) Foreign Application Priority Data

| Jun. 12, 2020 | (GB) | 2008961 |
| Jun. 12, 2020 | (GB) | 2008964 |
| Jun. 12, 2020 | (GB) | 2008968 |
| Dec. 7, 2020 | (GB) | 2019241 |
| Feb. 5, 2021 | (GB) | 2101634 |
| Feb. 5, 2021 | (GB) | 2101640 |
| Feb. 15, 2021 | (GB) | 2102095 |
| Feb. 15, 2021 | (GB) | 2102100 |
| Apr. 8, 2021 | (GB) | 2105047 |
| Apr. 8, 2021 | (GB) | 2105049 |
| Apr. 16, 2021 | (GB) | 2105462 |

(51) Int. Cl.
*C07D 209/16* (2006.01)
*A61P 25/24* (2006.01)

(52) U.S. Cl.
CPC ............ *C07D 209/16* (2013.01); *A61P 25/24* (2018.01); *C07B 2200/13* (2013.01)

(58) Field of Classification Search
CPC .... C07D 209/16; A61P 25/24; C07B 2200/13
See application file for complete search history.

(56) References Cited

U.S. PATENT DOCUMENTS

| 2,774,763 | A | 12/1956 | Garbrecht |
| 2,997,470 | A | 8/1961 | Pioch |
| 3,078,214 | A | 2/1963 | Hofmann et al. |
| 3,224,945 | A | 12/1965 | Tyler, Jr. |
| 2012/0108510 | A1 | 5/2012 | Young et al. |
| 2017/0348303 | A1 | 12/2017 | Bosse et al. |
| 2018/0021326 | A1 | 1/2018 | Stamets |
| 2018/0147142 | A1 | 5/2018 | Knight |
| 2020/0179349 | A1 | 6/2020 | Yun et al. |
| 2020/0187777 | A1 | 6/2020 | Luderer et al. |
| 2021/0058956 | A1 | 2/2021 | Chatterjee et al. |
| 2021/0069170 | A1 | 3/2021 | Stamets |
| 2021/0085671 | A1 | 3/2021 | Chadeayne |
| 2021/0322743 | A1 | 10/2021 | Rinti et al. |

FOREIGN PATENT DOCUMENTS

| CH | 578565 | A5 | 8/1976 |
| CN | 103816150 | A | 5/2014 |
| CN | 113288883 | A | 8/2021 |
| DE | 2617738 | A1 | 11/1976 |
| EP | 0026899 | A1 | 4/1981 |
| EP | 3868364 | A1 | 8/2021 |
| GB | 981192 | A | 1/1965 |
| GB | 1410349 | A | 10/1975 |
| GB | 1584464 | A | 2/1981 |
| GB | 2596884 | A | 1/2022 |
| WO | 0115677 | A2 | 3/2001 |
| WO | 0115677 | A3 | 3/2001 |
| WO | 0238142 | A2 | 5/2002 |
| WO | 2004000849 | A2 | 12/2003 |
| WO | 2008003028 | A2 | 1/2008 |
| WO | 2010054202 | A2 | 5/2010 |
| WO | 2013063492 | A1 | 5/2013 |
| WO | 2018195455 | A1 | 10/2018 |
| WO | 2019073379 | A1 | 4/2019 |
| WO | 2019081764 | A1 | 5/2019 |
| WO | 2019173797 | A1 | 9/2019 |
| WO | 2019246532 | A1 | 12/2019 |
| WO | 2020169850 | A1 | 8/2020 |
| WO | 2020169851 | A1 | 8/2020 |
| WO | 2020176597 | A1 | 9/2020 |
| WO | 2020181194 | A1 | 9/2020 |
| WO | 2020212951 | A1 | 10/2020 |
| WO | 2021003467 | A1 | 1/2021 |
| WO | 2021041407 | A1 | 3/2021 |
| WO | 2021089872 | A1 | 5/2021 |
| WO | 2021209815 | A1 | 10/2021 |

(Continued)

OTHER PUBLICATIONS

Sherwood, A. M., "Synthesis and Characterization of 5-MeO-DMT succinate for clinical use." ACS omega 5.49 (2020): 32067-32075.*
International Search Report in International Application No. PCT/GB2021/051475, dated Sep. 16, 2021 (3 pages).
International Search Report in International Application No. PCT/GB2021/051476, dated Sep. 15, 2021 (5 pages).
Uthaug, M.V. et al., "Prospective examination of synthetic 5-methoxy-N,N-dimethyltryptamine inhalation: effects on IL-6, cortisol levels, affect, and non-judgment," Psychopharmacology, vol. 237, pp. 773-785 (2020).
Database Registry Chemical Abstracts Service: Columbus, OH. Chemical Name: 1H-Indole-3-ethanamine, 5-methoxy-N,N dimethyl-, benzoate (1:1); RN 282103-25-7; ED Aug. 1, 2000 (1 page).
Benington, F. et al., "Synthesis of O- and N-Methylated Derivatives of 5-Hydroxytryptamine," The Journal of Organic Chemistry, vol. 23, pp. 1977-1979 (1958).

(Continued)

*Primary Examiner* — John M Mauro
(74) *Attorney, Agent, or Firm* — Bookoff McAndrews, PLLC

(57) ABSTRACT

A composition comprising a pharmaceutically effective amount of a pharmaceutically acceptable benzoate salt of 5-methoxy-N,N-dimethyltryptamine (5MeODMT).

14 Claims, 87 Drawing Sheets

(56) References Cited

FOREIGN PATENT DOCUMENTS

| WO | 2021222885 A1 | 11/2021 |
| WO | 2021225796 A1 | 11/2021 |
| WO | 2021250435 A1 | 12/2021 |

OTHER PUBLICATIONS

Falkenberg, G. et al., "The Crystal and Molecular Structure of 5-Methoxy-(N,N)-dimethyltryptamine Hydrochloride," Acta Crystallographica Section B, vol. 27, pp. 411-418 (1971).

Roseman, L. et al., "Increased amygdala responses to emotional faces after psilocybin treatment-resistant depression," Neuropharmacology, vol. 142, pp. 263-269 (2018).

Griffiths, R.R. et al., "Psilocybin produces substantial and sustained decreases in depression and anxiety in patients with life-threatening cancer: A randomized double-blind trial," Journal of Psychopharmacology, vol. 30, pp. 1181-1197 (2016).

Carhart-Harris, R.L. et al., "Psilocybin with psychological support for treatment-resistant depression: six-month follow-up," Psychopharmacology, vol. 235, pp. 399-408 (2018).

Monte, A.P. et al., "Stereoselective LSD-like Activity in a Series of d-Lysergic Acid Amides of (R) and (S)-2-Aminoalkanes," Journal of Medicinal Chemistry, vol. 38, pp. 958-966 (1995).

Ishii, H. et al., "Studies on Lysergic Acid Diethylamide and Related Compounds. Part 8. Structural Identification of New Metabolites of Lysergic Acid Diethylamide obtained by Microbial Transformation using Streptomyces roseochromogenes," Journal of the Chemical Society, Perkin Transactions 1: Organic & Bio-organic Chemistry, vol. 4, pp. 902-905 (1980).

Nakahara, Y. et al., "Studies on Lysergic Acid Diethylamide and Related Compounds. III. Improvement of Amidation of Lysergic Acid," Yakugaku Zasshi, vol. 94, pp. 407-412 (1974).

Huang, X. et al., "Drug Discrimination and Receptor Binding Studies of N-Isopropyl Lysergamide Derivatives," Pharmacology Biochemistry and Behavior, vol. 47, pp. 667-673 (1994).

Ishii, H. et al., "Studies on Lysergic Acid Diethylamide and Related Compounds. IX. Microbial Transformation of Amides Related to Lysergic Acid Diethylamide by Streptomyces roseochromogenes," Chemical & Pharmaceutical Bulletin, vol. 27, pp. 3029-3038 (1979).

Johnson, F.N. et al., "Emetic Activity of Reduced Lysergamides," Journal of Medicinal Chemistry, vol. 16, pp. 532-537 (1973).

Vangveravong, S. et al., "Synthesis and Serotonin Receptor Affinities of a Series of trans-2-(Indol-3-yl) cyclopropylamine Derivatives," Journal of Medicinal Chemistry, vol. 41, pp. 4995-5001 (1998).

Schneller, S.W. et al., "Synthesis of 4-Amino-1H-pyrrolo[2,3-b]pyridine (1,7-Dideazaadenine) and 1H-Pyrrolo[2,3-b]pyridin-4-ol (1,7-Dideazahypoxanthine)," The Journal of Organic Chemistry A, vol. 45, pp. 4045-4048 (1980).

Singh, S.K. et al., "An ab Initio Study of the Effect of Substituents on the n → π Interactions between 7-Azaindole and 2,6 Difluorosubstituted Pyridines," The Journal of Physical Chemistry A, vol. 120, pp. 6258-6269 (2016).

Monson, C.M. et al., "MDMA-facilitated cognitive-behavioural conjoint therapy for posttraumatic stress disorder: an uncontrolled trial," European Journal of Psychotraumatology, vol. 11, pp. 1-7 (2020).

Wolfson, P.E. et al., "MDMA-assisted psychotherapy for treatment of anxiety and other psychological distress related to life-threatening illnesses: a randomized pilot study," Scientific Reports, vol. 10, pp. 1-15 (2020).

Yazar-Klosinski, B.B. et al., "Potential Psychiatric Uses for MDMA," Developments, vol. 101, pp. 194-196 (2017).

PharmaTher Holdings Ltd. Dec. 14, 2021. PharmaTher Announces Positive Research Results for LSD Microneedle Patch. Press Release. <URL: https://psychedelicinvest.com/pharmather-announces-positive-research-results-for-lsd-microneedle-patch/>.

Szabo, A. et al., "Psychedelic N,N-Dimethyltryptamine and 5-Methoxy-N,N-Dimethyltryptamine Modulate Innate and Adaptive Inflammatory Responses through the Sigma-1 Receptor of Human Monocyte-Derived Dendritic Cells," PLoS One, vol. 9, pp. 1-12 (2014).

Sherwood, A.M. et al., "Synthesis and Characterization of 5-MeO-DMT Succinate for Clinical Use," ACS Omega, vol. 5, pp. 32067-32075 (2020).

Galeffi, C. et al., "N,N-Dimethyl-5-Methoxytryptamine, a Component of a Dart Poison of the Yanoáma Indians," Journal of Natural Products, vol. 46, pp. 586-587 (1983).

Shulgin, A. et al. TiHKAL: The Continuation. #38. 5-Meo-Dmt. Tryptamine, 5-Methoxy-N,N-Dimethyl; Indole, 5-Methoxy-3-[2-(Dimethylamino)Ethyl]; 5-Methoxy-N,N-Dimethyltryptamine; 5-Methoxy-3-[2-(Dimethylamino)Ethyl]Indole; N,N,O-Trimethylserotonin; N,N,O-Tms; Bufotenine Methyl Ether; O-Methylbufotenine; Omb. <URL: https://erowid.org/library/books_online/tihkal/tihkal38.shtml.>.

Chemcats. Chemical Abstracts Service: Columbus, OH. Chemical Name: 4H-Pyrrolo[2,3-b]pyridine-4-one, 1,7-dihydro-. Chemcats Accession No. 1756550559. Catalog Name: Sagechem Limited Product List. Order No. Catalog: S243355. CAS Registry No. 1076197-59-5 (1 page).

Chemcats. Chemical Abstracts Service: Columbus, OH. Chemical Name: 1-methyl-1H-pyrrolo[2,3-b]pyridin-4-ol. Chemcats Accession No. 1545199867. Catalog Name: Azepine Product List. Order No. Catalog: AZ04819515. CAS Registry No. 1781876-60-5 (1 page).

Chemcats. Chemical Abstracts Service: Columbus, OH. Chemical Name: 1-methylpyrrolo[2,3-b]pyridin-4-ol. Chemcats Accession No. 1442516433. Catalog Name: Aurora Building Blocks 2. Order No. Catalog: 115.267.167. CAS Registry No. 1781876-60-5 (1 page).

Chemcats. Chemical Abstracts Service: Columbus, OH. Chemical Name: 1-methyl-1H-pyrrolo[2,3-b]pyridin-4-ol. Chemcats Accession No. 0002254898. Catalog Name: FCH Group Reagents for Synthesis. Order No. Catalog FCH1635008. CAS Registry No. 1781876-60-5 (1 page).

Chemcats. Chemical Abstracts Service: Columbus, OH. Chemical Name: 1H-Pyrrolo[2,3-B]Pyridin-4(7H)-One. Chemcats Accession No. 2022337458. Catalog Name: Chemieliva Pharmaceutical Product List. Order No. Catalog: CE0957308. CAS Registry No. 1076197-59-5 (1 page).

Chemcats. Chemical Abstracts Service: Columbus, OH. Chemical Name: 1H-Pyrrolo[2,3-b]pyridin-4(7H)-one. Chemcats Accession No. 1621739382. Catalog Name: Ambeed, Inc. Product List. Order No. Catalog: A763560. CAS Registry No. 1076197-59-5 (1 page).

Chemcats. Chemical Abstracts Service: Columbus, OH. Chemical Name: 1H-Pyrrolo[2,3-b]pyridin-4-ol hydrate. Chemcats Accession No. 1773869211. Catalog Name: Aurora Building Blocks 3. Order No. Catalog: 129.194.895. CAS Registry No. 2031269-35-7 (1 page).

Chemcats. Chemical Abstracts Service: Columbus, OH. Chemical Name: 1H-pyrrolo[2,3-b]pyridin-4-ol hydrate. Chemcats Accession No. 0968477988. Catalog Name: ASW MedChem Product List. Order No. Catalog: TH-45275. CAS Registry No. 2031269-35-7 (1 page).

CAplus. Chemical Abstracts Service: Columbus. CAplus Accession No. 2017:1595854. Title: Preparation of tetrahydropyridoindolylcycloalkylacrylic acid derivatives and analogs for us as estrogen receptor modulators. Inventor: Huang, P.Q. et al. (4 pages).

Sohlberg, E. et al., "The impact of the site of blood sampling on pharmacokinetic parameters following sublingual dosing to dogs," Journal of Pharmacological and Toxicological Methods, vol. 67, pp. 1-4 (2013).

Illum, L. et al., "The Effect of Blood Sampling Site and Physicochemical Characteristics of Drugs on Bioavailability after Nasal Administration in the Sheep Model," Pharmaceutical Research, vol. 20, pp. 1474-1484 (2003).

Gupta, S.P., "QSAR Studies on Drugs Acting at the Central Nervous System," Chemical Reviews, vol. 89, pp. 1765-1800 (1989).

Stoll, A. et al., "49. Amide der stereoisomeren Lysergsäuren und Dihydro-lysergsäuren," Helvetica Chimica Acta, vol. 38, pp. 421-433 (1955).

(56) References Cited

OTHER PUBLICATIONS

Halberstadt, A.L. et al., "Pharmacological characterization of the LSD analog N-ethyl-N-cyclopropyl lysergamide (ECPLA)," Psychopharmacology, vol. 236, pp. 799-808 (2019).

McKenna, D.J. et al., "Differential interactions of indolealkylamines with 5-hydroxytryptamine receptor subtypes," Neuropharmacology, vol. 29, pp. 193-198 (1990).

Glennon, R.A. et al., "Serotonin Receptor Binding Affinities of Tryptamine Analogues," Journal of Medicinal Chemistry, vol. 22, pp. 428-432 (1979).

Klein, A.K. et al., "Investigation of the Structure—Activity Relationships of Psilocybin Analogues," ACS Pharmacology & Translational Science, vol. 4, pp. 533-542 (2021).

Sard, H. et al., "SAR of psilocybin analogs: Discovery of a selective 5-HT2C agonist," Bioorganic & Medicinal Chemistry Letters, vol. 15, pp. 4555-4559 (2005).

Lyon, R.A. et al., "Indolealkylamine analogs share 5-HT2 binding characteristics with phenylalkylamine hallucinogens," European Journal of Pharmacology, vol. 145, pp. 291-297 (1988).

Glässer, A., "Some Pharmacological Actions of D-Lysergic Acid Methyl Carbinolamide," Nature, vol. 189, pp. 313-314 (1961).

\* cited by examiner (A)
(B)
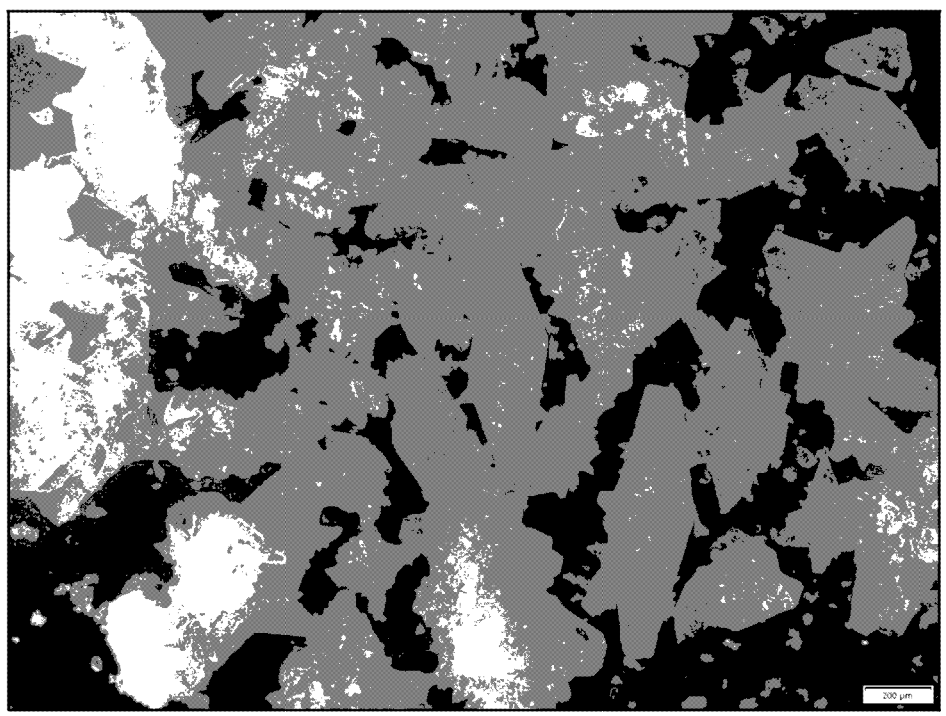
Fig. 13

(A)
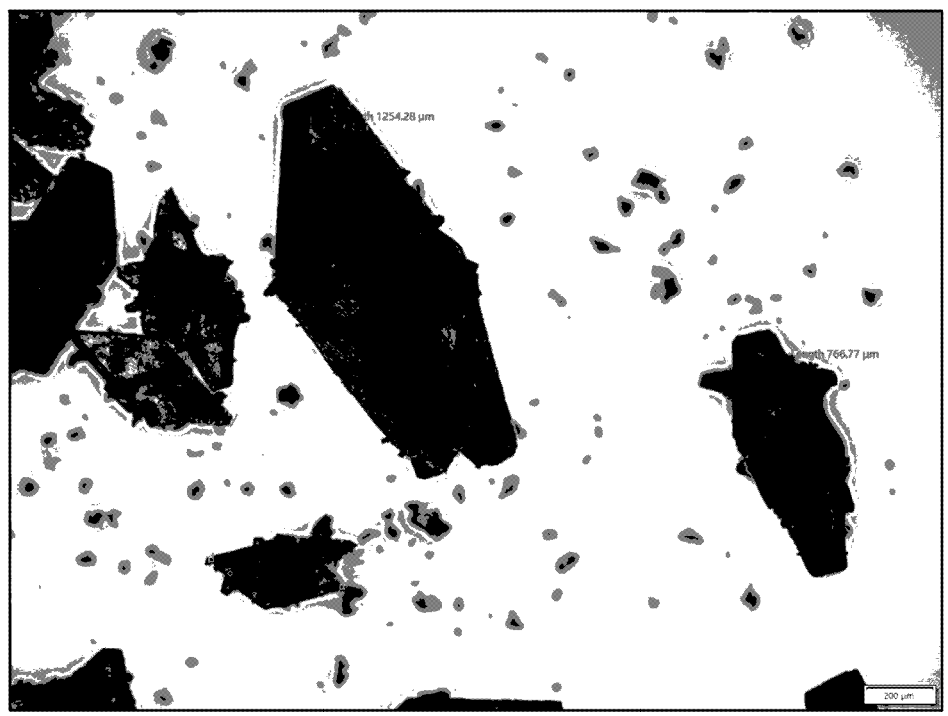
(B)
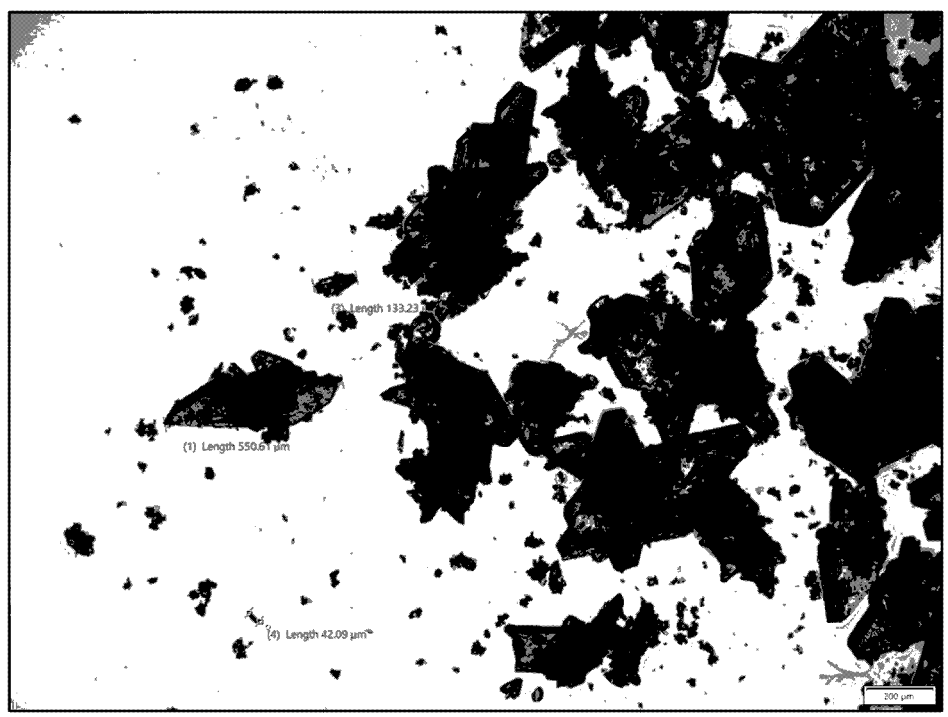
Fig. 14

(A)
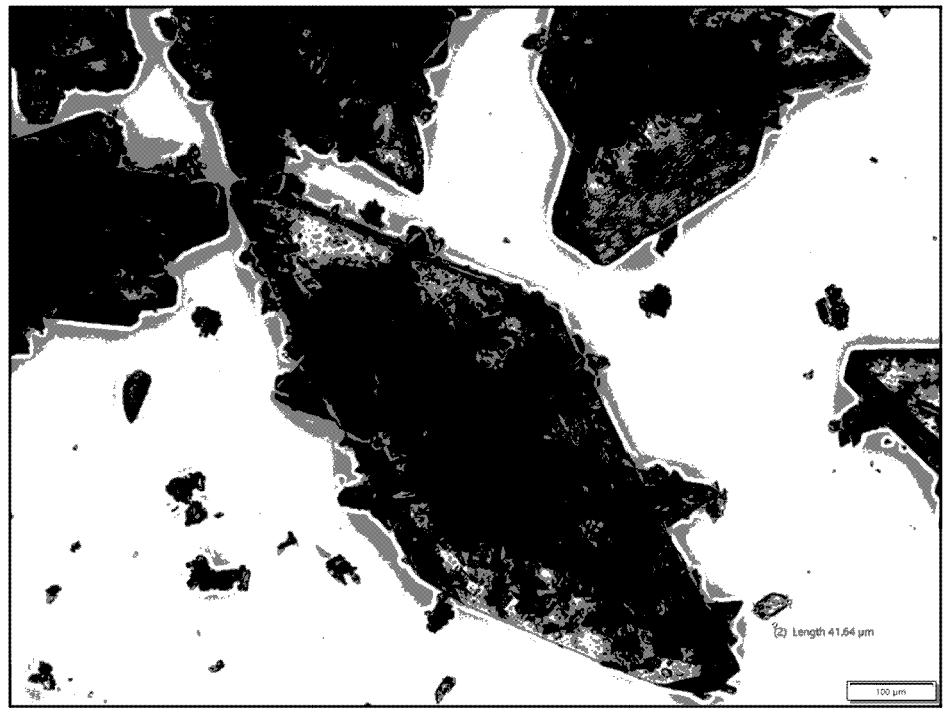
(B)
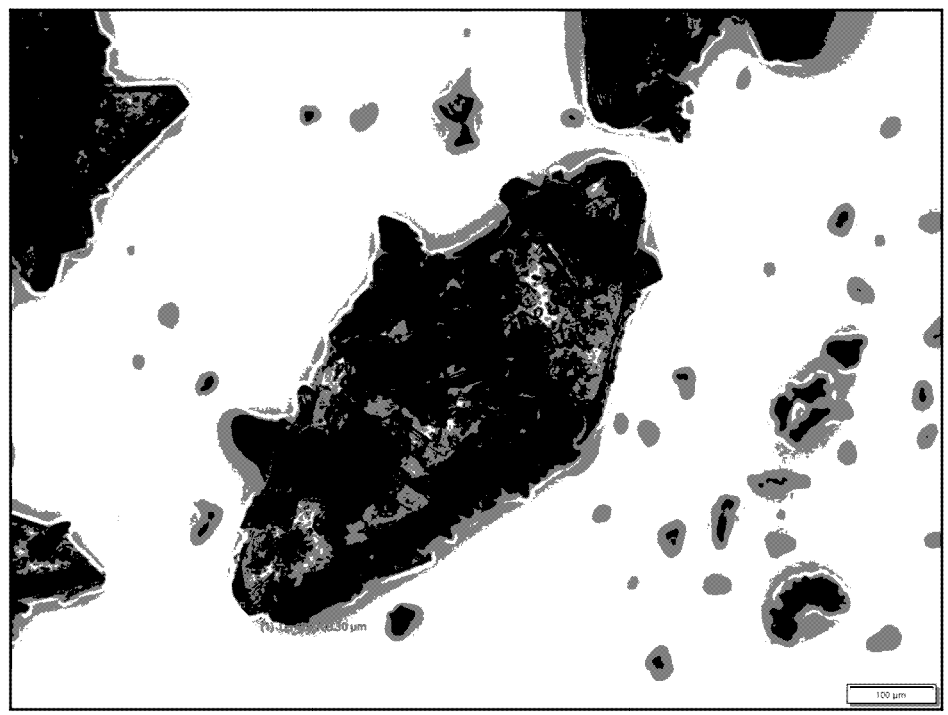
Fig. 15

(A)
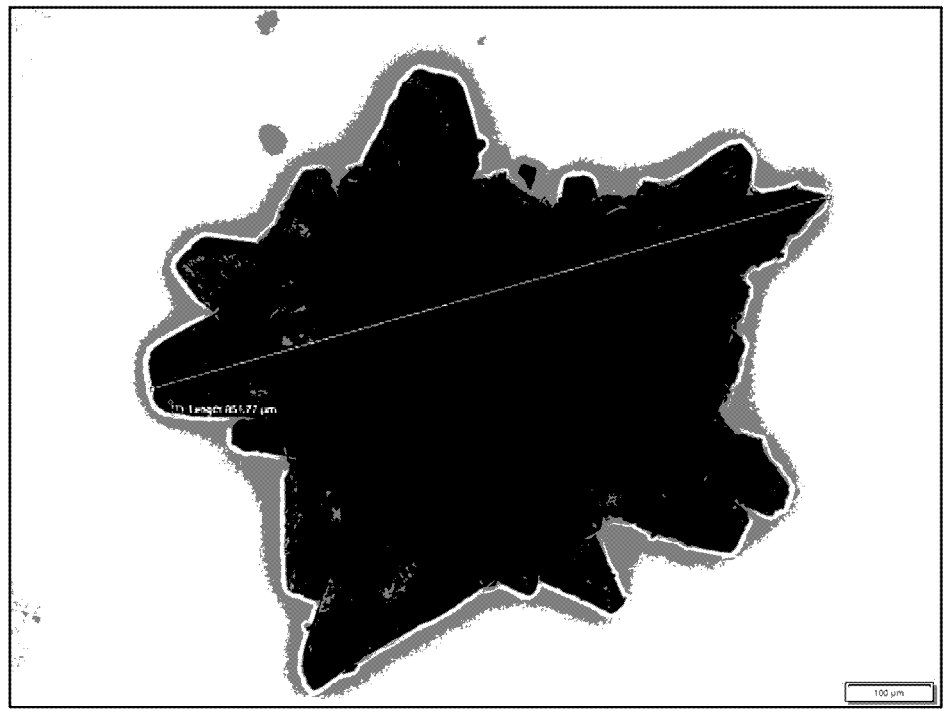
(B)
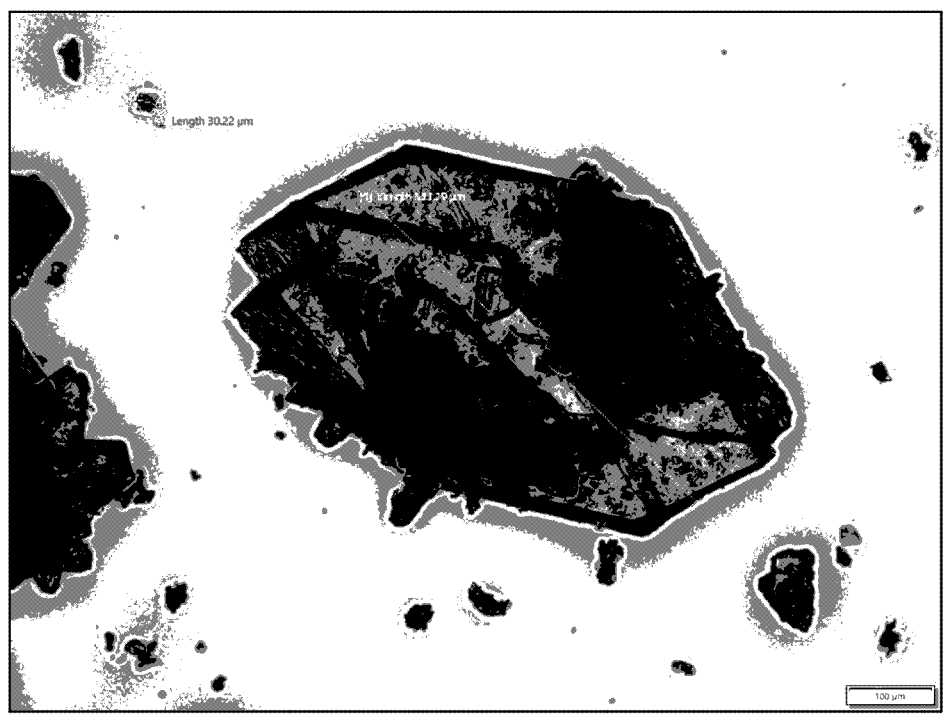
Fig. 16

COMPOSITION COMPRISING A BENZOATE SALT OF 5-METHOXY-N,N-DIMETHYLTRYPTAMINE

CROSS-REFERENCE TO RELATED APPLICATIONS

This application is a continuation of International Application No. PCT/GB2021/051475, filed on Jun. 14, 2021, incorporated by reference herein, which claims the benefit of priority to GB Application No. 2008964.5, filed on Jun. 12, 2020, GB Application No. 2008961.1, filed on Jun. 12, 2020, GB Application No. 2008968.6, filed on Jun. 12, 2020, GB Application No. 2019241.5, filed on Dec. 7, 2020, GB Application No. 2101640.7, filed on Feb. 5, 2021, GB Application No. 2101634.0, filed on Feb. 5, 2021, GB Application No. 2102100.1, filed on Feb. 15, 2021, GB Application No. 2102095.3, filed on Feb. 15, 2021, GB Application No. 2105049.7, filed on Apr. 8, 2021, GB Application No. 2105047.1, filed on Apr. 8, 2021, and GB Application No. 2105462.2, filed on Apr. 16, 2021.

FIELD OF THE INVENTION

This invention relates to pharmaceutically acceptable salts of 5-methoxy-N,N-dimethyltryptamine. In particular, though not exclusively, the invention relates to formulations and uses of the same as a medicament.

BACKGROUND OF THE INVENTION 5-methoxy-N,N-dimethyltryptamine (5MeODMT) is a pharmacologically active compound of the tryptamine class and has the chemical formula:

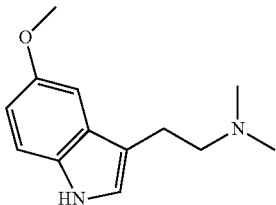 [SMILES: COc1ccc2[nH]cc(CCN(C)C)c2c1]

5MeODMT is a psychoactive/psychedelic substance found in nature and is believed to act mainly through serotonin receptors. It is also believed to have a high affinity for the $5\text{-}HT_2$ and $5\text{-}HT_{1A}$ subtypes, and/or inhibits monoamine reuptake.

However, 5MeODMT is not well understood and uses of this compound have not been well explored. Further, 5MeODMT is not easy to handle, and there are challenges in formulating it for effective delivery in pharmaceutically useful compositions.

There remains a need in the art for improved formulations and uses of 5MeODMT.

SUMMARY OF THE INVENTION

Herein disclosed, there is provided a composition comprising a pharmaceutically effective amount of a pharmaceutically acceptable salt of 5-methoxy-N,N-dimethyltryptamine (5MeODMT).

In an embodiment, the salt anion is an aryl carboxylate. In an embodiment, the aryl carboxylate is substituted with one to three R groups.

In an embodiment the one or more R groups are independently selected from: alkynyl, carbonyl, aldehyde, haloformyl, alkyl, halide, hydroxy, alkoxy, carbonate ester, carboxylate, carboxyl, carboalkoxy, methoxy, hydroperoxy, peroxy, ether, hemiacetal, hemiketal, acetal, ketal, orthoester, methylenedioxy, orthocarbonate ester, carboxylic anhydride, carboxamide, secondary, tertiary or quaternary amine, primary or secondary ketimine, primary or secondary aldimine, imide, azide, azo, cyanate, isocyanate, nitrate, nitrile, isonitrile, nitrosooxy, nitro, nitroso, oxime, pyridyl, carbamate, sulfhydryl, sulfide, disulfide, sulfinyl, sulfonyl, sulfino, sulfo, thiocyanate, isothiocyanate, carbonothioyl, carbothioic S-acid, carbothioic O-acid, thiolester, thionoester, carbodithioic acid, carbodithio, phosphino, phosphono, phosphate, borono, boronate, borino or borinate.

In an embodiment the one or more R groups are independently selected from: $C_1$-$C_6$ alkyl, $C_1$-$C_6$ alkoxy, $C_1$-$C_6$ alkenyl or $C_1$-$C_6$ alkynyl, and where each of these may be optionally substituted with one to three R groups as previously described.

In a first aspect of the invention, there is provided a composition comprising a pharmaceutically effective amount of a pharmaceutically acceptable benzoate salt of 5-methoxy-N,N-dimethyltryptamine (5MeODMT).

The invention provides for improved formulations and uses of 5MeODMT salts.

In an embodiment the composition comprises a dosage amount of 5MeODMT in the range of 0.05 mg to 100 mg.

In an embodiment the composition comprises a dosage amount of 5MeODMT in the range of 0.1 mg to 50 mg.

In an embodiment the composition comprises a dosage amount of 5MeODMT in the range of 0.5 mg to 25 mg.

In an embodiment the composition comprises a dosage amount of 5MeODMT in the range of 0.5 mg to 10 mg.

In an embodiment the composition comprises a dosage amount of 5MeODMT in the range of 1 mg to 10 mg.

In an embodiment the composition comprises a dosage amount of 5MeODMT in the range of 1 mg to 8 mg.

In an embodiment the composition comprises a dosage amount of 5MeODMT in the range of 3 mg to 15 mg.

In an embodiment the composition comprises a dosage amount of 5MeODMT in the range of 0.005 mg to 100 mg.

In an embodiment the composition comprises a dosage amount of 5MeODMT in the range of 0.001 mg to 100 mg.

In an embodiment the composition comprises a dosage amount of 5MeODMT in the range of 0.0005 mg to 100 mg.

The level of the active agent can be adjusted as required by need for example to suit a certain patient group (e.g. the elderly) or the conditions being treated.

In an embodiment the composition is formulated in a dosage form selected from: oral, transdermal, inhalable, intravenous, or rectal dosage form.

It is advantageous to be able to deliver the active agent in different forms, for example to suit a certain patient group (e.g. the elderly) or the conditions being treated.

In an embodiment the composition is formulated in a dosage form selected from: tablet, capsule, granules, powder, free-flowing powder, inhalable powder, aerosol, nebulised, vaping, buccal, sublingual, sublabial, injectable, or suppository dosage form.

In an embodiment the powder is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

In an embodiment the powder comprises particles, the particles having a median diameter of less than 2000 μm, 1000 μm, 500 μm, 250 μm, 100 μm, 50 μm, or 1 μm.

In an embodiment the powder comprises particles, the particles having a median diameter of greater than 500 μm, 250 μm, 100 μm, 50 μm, 1 μm or 0.5 μm.

In an embodiment the powder comprises particles, and wherein the powder has a particle size distribution of d10=20-60 μm, and/or d50=80-120 μm, and/or d90=130-300 μm.

The nature of the powder can be adjusted to suit need. For example, if being made for nasal inhalation, then the particles may be adjusted to be much finer than if the powder is going to be formulated into a gelatine capsule, or differently again if it is going to be compacted into a tablet.

In an embodiment the 5MeODMT salt is amorphous or crystalline.

In an embodiment the 5MeODMT salt is in a polymorphic crystalline form, optionally 5MeODMT salt is Polymorph A.

In an embodiment the 5MeODMT salt is a benzoate, fumarate, citrate, acetate, succinate, halide, fluoride, chloride, bromide, iodide, oxalate, or triflate salt, optionally the salt is the chloride, benzoate or fumarate salt.

In an embodiment the 5MeODMT salt is formulated into a composition for mucosal delivery. In an embodiment, the 5MeODMT salt is a benzoate salt.

In an embodiment, the 5MeODMT benzoate conforms to Pattern A as characterised by an XRPD diffractogram.

In an embodiment, the 5MeODMT benzoate is characterised by peaks in an XRPD diffractogram at 17.5, 17.7 and 21.0° 2θ±0.1° 2θ as measured by x-ray powder diffraction using an x-ray wavelength of 1.5406 Å.

In an embodiment, 5MeODMT benzoate is characterised by peaks in an XRPD diffractogram as substantially illustrated in FIG. 6 or FIG. 7.

In an embodiment, the 5MeODMT benzoate is characterised by bands at ca. 3130, 1540, 1460, 1160 and 690 cm-1 in a fourier-transform infrared spectroscopy (FTIR) spectra.

In an embodiment, the 5MeODMT benzoate is characterised by a FTIR spectra for lot FP2 as substantially illustrated in FIG. 93.

In an embodiment, the 5MeODMT benzoate conforms to Pattern B by XRPD.

In an embodiment, the 5MeODMT benzoate conforms to Pattern B as characterised by peaks in an XRPD diffractogram between 18.5 and 20° 2θ±0.1° 2θ.

In an embodiment, the 5MeODMT benzoate conforms to Pattern B as substantially illustrated by the XRPD diffractogram for lots P1, R1 and Q1 as substantially illustrated in FIG. 24.

In an embodiment, the 5MeODMT benzoate conforms to Pattern B as substantially illustrated by the XRPD diffractogram for lot R2 as substantially illustrated in FIG. 28.

In an embodiment, the 5MeODMT benzoate conforms to Pattern B as substantially illustrated by the XRPD diffractogram for lots A1 and B1 as substantially illustrated in FIG. 38 or 39.

In an embodiment, the 5MeODMT benzoate corresponds to the Pattern B form as characterised by FTIR spectra for lot C2 as substantially illustrated in FIG. 93.

In an embodiment, the 5MeODMT benzoate corresponds to the Pattern C form as characterised by a minor broad endotherm with a peak temperature of 108° C. in a DSC thermograph.

In an embodiment, the 5MeODMT benzoate corresponds to Pattern C as characterised by a DSC thermograph as substantially illustrated in FIG. 65.

In an embodiment, the 5MeODMT benzoate corresponds to the Pattern C form as characterised by a DSC thermograph as substantially illustrated in FIG. 66.

In an embodiment, the 5MeODMT benzoate conforms to Pattern C by XRPD.

In an embodiment, the 5MeODMT benzoate conforms to Pattern C as characterised by a peak in an XRPD diffractogram at 10.3° 2θ±0.1° 2θ.

In an embodiment, the 5MeODMT benzoate conforms to Pattern C as substantially illustrated by the XRPD diffractogram for lot A1 as substantially illustrated in FIG. 68.

In an embodiment, the 5MeODMT benzoate corresponds to the Pattern C form as characterised by FTIR spectra for lot C1 as substantially illustrated in FIG. 93.

In an embodiment, the 5MeODMT benzoate conforms to Pattern D by XRPD.

In an embodiment, the 5MeODMT benzoate conforms to Pattern D as substantially illustrated by the XRPD diffractogram in FIG. 73 or FIG. 74.

In an embodiment, the 5MeODMT benzoate corresponds to Pattern D as characterised by an endothermic event in a DSC thermograph at 118° C.

In an embodiment, the 5MeODMT benzoate corresponds to the Pattern D form as characterised by an endothermic event in a DSC thermograph at 118.58° C.

In an embodiment, the 5MeODMT benzoate conforms to Pattern E by XRPD.

In an embodiment, the 5MeODMT benzoate corresponds to Pattern E as substantially illustrated by the XRPD diffractogram for lot D in FIG. 77 or FIG. 78.

In an embodiment, the 5MeODMT corresponds to the Pattern E form as characterised by a major bimodal endothermic event with peak temperatures of 110.31° C. and 113.13° C. in a DSC thermograph.

In an embodiment, the 5MeODMT corresponds to Pattern E as characterised by a minor endothermic event with a peak temperature of 119.09° C. in a DSC thermograph.

In an embodiment, the 5MeODMT corresponds to the Pattern E form as characterised by a DSC thermograph as substantially illustrated in FIG. 79.

In an embodiment, the 5MeODMT benzoate corresponds to Pattern E as substantially illustrated by the XRPD diffractogram in FIG. 80.

In an embodiment, the 5MeODMT benzoate corresponds to Pattern F by XRPD.

In an embodiment, the 5MeODMT benzoate conforms to Pattern F as characterised by an XRPD diffractogram for lot F (rerun) as substantially illustrated in FIG. 84.

In an embodiment, the 5MeODMT benzoate conforms to Pattern F as characterised by an XRPD diffractogram for lot F (rerun) as substantially illustrated in FIG. 85.

In an embodiment, the 5MeODMT benzoate conforms to Pattern F as characterised by an XRPD diffractogram for lot F (rerun) as substantially illustrated in FIG. 89.

In an embodiment, the 5MeODMT benzoate corresponds to the Pattern F form as characterised by endothermic events at 90° C., 106° C. and 180° C. in a DSC thermograph.

In an embodiment, the 5MeODMT benzoate corresponds to the Pattern F form as characterised by endothermic events at 90.50° C., 106.65° C. and 180.35° C. in a DSC thermograph.

In an embodiment, the 5MeODMT benzoate conforms to Pattern G by XRPD.

In an embodiment, the 5MeODMT benzoate conforms to Pattern G, as characterised by an XRPD diffractogram for lot K as substantially illustrated in FIG. 87.

In an embodiment, the 5MeODMT benzoate corresponds to the Pattern G form, as characterised by an endothermic event in a DSC thermograph of 119.61° C.

In an embodiment, the composition comprises 5MeODMT benzoate which conforms to a mixture of two or more of Patterns A to G by XRPD.

For the salt, the dosage amount is the equivalent amount of the free base delivered when the salt is taken. So 100 mg dosage amount of 5MeODMT corresponds to 117 mg of the hydrochloride salt (i.e. both providing the same molar amount of the active substance). The greater mass of the salt needed is due to the larger formula weight of the hydrogen chloride salt (i.e. 218.3 g/mol for the free base as compared to 254.8 g/mol for the salt). Similarly, for the deuterated or triturated version of 5MeODMT (also considered within the scope of the invention), a slight increase in mass can be expected due to the increased formula weight of these isotopic compounds.

Amorphous and crystalline substances often show different chemical/physical properties, e.g. improved rate of dissolution in a solvent, or improved thermal stability. Similarly, different polymorphs may also show different and useful chemical/physical properties.

In an embodiment the composition comprises one or more pharmaceutically acceptable carriers or excipients.

In an embodiment the composition comprises one or more of: mucoadhesive enhancer, penetrating enhancer, cationic polymers, cyclodextrins, Tight Junction Modulators, enzyme inhibitors, surfactants, chelators, and polysaccharides.

In an embodiment the composition comprises one or more of: chitosan, chitosan derivatives (such as N,N,N-trimethyl chitosan (TMC), n-propyl-(QuatPropyl), n-butyl-(Quat-Butyl) and n-hexyl (QuatHexyl)-N,N-dimethyl chitosan, chitosan chloride), β-cyclodextrin, *Clostridium perfringens* enterotoxin, zonula occludens toxin (ZOT), human neutrophil elastase Inhibitor (ER143), sodium taurocholate, sodium deoxycholate sodium, sodium lauryl sulphate, glycodeoxycholat, palmitic acid, palmitoleic acid, stearic acid, oleyl acid, oleyl alcohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid.

In an embodiment the composition disclosed herein is for use as a medicament. In an embodiment the composition disclosed herein is for use in a method of treatment of a human or animal subject by therapy.

In an embodiment the method of treatment is a method of treatment of:
  conditions caused by dysfunctions of the central nervous system,
  conditions caused by dysfunctions of the peripheral nervous system,
  conditions benefiting from sleep regulation (such as insomnia),
  conditions benefiting from analgesics (such as chronic pain),
  migraines,
  trigeminal autonomic cephalgias (such as short-lasting unilateral neuralgiform headache with conjunctival injection and tearing (SUNCT), and short-lasting neuralgiform headaches with cranial autonomic symptoms (SUNA)),
  conditions benefiting from neurogenesis (such as stroke, traumatic brain injury, Parkinson's dementia),
  conditions benefiting from anti-inflammatory treatment,
  depression,
  treatment resistant depression
  anxiety,
  substance use disorder,
  addictive disorder,
  gambling disorder,
  eating disorders,
  obsessive-compulsive disorders, or
  body dysmorphic disorders,
  optionally the condition is SUNCT and/or SUNA.

Treatment of the above conditions may be beneficially improved by taking the invention.

In an embodiment, the method of treatment is a method of treatment of alcohol-related diseases and disorders, eating disorders, impulse control disorders, nicotine-related disorders, tobacco-related disorders, methamphetamine-related disorders, amphetamine-related disorders, cannabis-related disorders, cocaine-related disorders, hallucinogen use disorders, inhalant-related disorders, benzodiazepine abuse or dependence related disorders, and/or opioid-related disorders.

In an embodiment, the method of treatment is a method of treatment of tobacco addiction. In an embodiment, the method is a method of reducing tobacco use. In an embodiment, the method of treatment is a method of treatment of nicotine addiction. In an embodiment, the method is a method of reducing nicotine use.

In an embodiment, the method of treatment is a method of treating alcohol abuse and/or addiction. In an embodiment, the method of treatment is a method of reducing alcohol use.

In an embodiment, the method of treatment is a method of treating or preventing heavy drug use.

In an embodiment, the method of treatment is a method of treating or preventing heavy drug use, including, but not limited to, alcohol, tobacco, nicotine, cocaine, methamphetamine, other stimulants, phencyclidine, other hallucinogens, marijuana, sedatives, tranquilizers, hypnotics, and opiates. It will be appreciated by one of ordinary skill in the art that heavy use or abuse of a substance does not necessarily mean the subject is dependent on the substance.

In an embodiment the method of treatment is a method of treatment of more than one of the above conditions, for example, the method of treatment may be a method of treatment of depression and anxiety.

In an embodiment the composition is administered one or more times a year.

In an embodiment the composition is administered one or more times a month.

In an embodiment the composition is administered one or more times a week.

In an embodiment the composition is administered one or more times a day.

In an embodiment the composition is administered at such a frequency as to avoid tachyphylaxis.

In an embodiment the composition is administered together with a complementary treatment and/or with a further active agent.

In an embodiment the further active agent is a psychedelic compound, optionally a tryptamine.

In an embodiment the further active agent is lysergic acid diethylamide (LSD), psilocybin, psilocin or a prodrug thereof.

In an embodiment the further active agent is an antidepressant compound.

In an embodiment the further active agent is selected from an SSRI, SNRI, TCA or other antidepressant compounds.

In an embodiment the further active agent is selected from Citalopram (Celexa, Cipramil), Escitalopram (Lexapro, Cipralex), Fluoxetine (Prozac, Sarafem), Fluvoxamine (Luvox, Faverin), Paroxetine (Paxil, Seroxat), Sertraline (Zoloft, Lustral), Desvenlafaxine (Pristiq), Duloxetine (Cymbalta), Levomilnacipran (Fetzima), Milnacipran (Ixel, Savella), Venlafaxine (Effexor), Vilazodone (Viibryd), Vortioxetine (Trintellix), Nefazodone (Dutonin, Nefadar, Serzone), Trazodone (Desyrel), Reboxetine (Edronax), Teniloxazine (Lucelan, Metatone), Viloxazine (Vivalan), Bupropion (Wellbutrin), Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Opipramol (Insidon), Pipofezine (Azafen/Azaphen), Protriptyline (Vivactil), Trimipramine (Surmontil), Amoxapine (Asendin), Maprotiline (Ludiomil), Mianserin (Tolvon), Mirtazapine (Remeron), Setiptiline (Tecipul), Isocarboxazid (Marplan), Phenelzine (Nardil), Tranylcypromine (Parnate), Selegiline (Eldepryl, Zelapar, Emsam), Caroxazone (Surodil, Timostenil), Metralindole (Inkazan), Moclobemide (Aurorix, Manerix), Pirlindole (Pirazidol), Toloxatone (Humoryl), Agomelatine (Valdoxan), Esketamine (Spravato), Ketamine (Ketalar), Tandospirone (Sediel), Tianeptine (Stablon, Coaxil), Amisulpride (Solian), Aripiprazole (Abilify), Brexpiprazole (Rexulti), Lurasidone (Latuda), Olanzapine (Zyprexa), Quetiapine (Seroquel), Risperidone (Risperdal), Trifluoperazine (Stelazine), Buspirone (Buspar), Lithium (Eskalith, Lithobid), Modafinil (Provigil), Thyroxine (T4), Triiodothyronine (T3).

In an embodiment the further active agent is selected from Celexa (citalopram), Cymbalta (duloxetine), Effexor (venlafaxine), Lexapro (escitalopram), Luvox (fluvoxamine), Paxil (paroxetine), Prozac (fluoxetine), Remeron (mirtazapine), Savella (milnacipran), Trintellix (vortioxetine), Vestra (reboxetine), Viibryd (vilazodone), Wellbutrin (bupropion), Zoloft (sertraline).

In an embodiment the complementary treatment is psychotherapy.

In an embodiment, there is provided a composition comprising a pharmaceutically effective amount of a pharmaceutically acceptable benzoate salt of 5MeODMT for use in a method of treatment of treatment resistant depression.

In an embodiment, there is provided a composition comprising a pharmaceutically effective amount of a pharmaceutically acceptable benzoate salt of 5MeODMT for use in a method of treatment of depression.

In an embodiment, there is provided a composition comprising a pharmaceutically effective amount of a pharmaceutically acceptable benzoate salt of 5MeODMT for use in a method of treatment of PTSD.

In an embodiment, there is provided a composition comprising a pharmaceutically effective amount of a pharmaceutically acceptable benzoate salt of 5MeODMT for use in a method of treatment of addiction/substance misuse disorders.

In an embodiment, there is provided a nasal inhalation composition comprising a pharmaceutically effective amount of a pharmaceutically acceptable benzoate salt of 5MeODMT for use in a method of treatment of treatment resistant depression.

Treatment of the above conditions may be beneficially improved by taking the invention together with some complementary treatments; also these treatments may occur much less regularly than some other treatments that require daily treatments or even multiple treatments a day.

For the sake of brevity only, various forms of the 5MeODMT benzoate salt may be referred to herein below as 'Pattern #', wherein the # refers to the corresponding XRPD pattern obtained for that form. For example 'Pattern A' may be used as an abbreviation to refer to the form of 5MeODMT benzoate salt giving rise to the Pattern A by XRPD. Likewise, 'Pattern B' may be used as an abbreviation to refer to the form of 5MeODMT benzoate salt giving rise to the Pattern B by XRPD, and so on.

The present invention will now be further described with reference to the following, and the accompanying drawings, of which:

BRIEF DESCRIPTION OF THE DRAWINGS

FIG. 12 shows a Dynamic Vapour Sorption (DVS) isotherm for 5MeODMT benzoate.

FIG. 13 shows an optical micrograph of 5MeODMT benzoate salt (A) and dark field (B) at ×4 magnification.

FIG. 14 shows two further optical micrographs of 5MeODMT benzoate salt (A) and (B) at ×4 magnification.

FIG. 15 shows optical micrographs of 5MeODMT benzoate salt (A) and (B) at ×10 magnification.

FIG. 16 shows further optical micrographs of 5MeODMT benzoate salt (A) and (B) at 10× magnification.

DETAILED DESCRIPTION OF THE INVENTION

Figure 1:
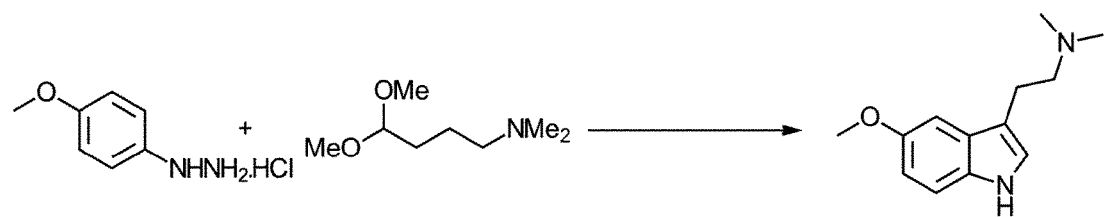
FIG. 1 is a schematic route for the synthesis of 5MeODMT.

FIG. 1 shows a one-step synthesis of 5MeODMT from the reaction of 4-methoxyphenylhydrazine hydrochloride with (N,N)-dimethylamino)butanal dimethyl acetal.

Figure 2:
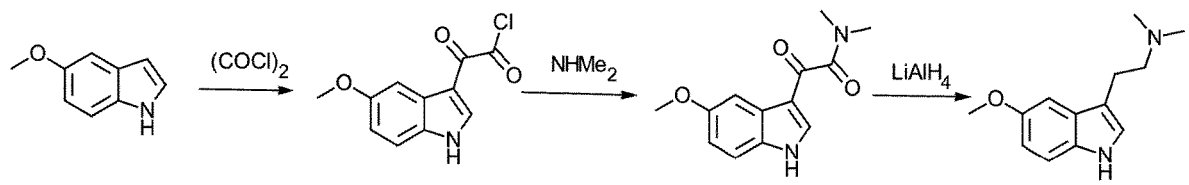
FIG. 2 is a further schematic route for the synthesis of 5MeODMT.

FIG. 2 shows a three step synthesis of 5MeODMT. The first step involves the reaction of 5-methoxyindole with oxalyl chloride. The resultant product is aminated with dimethylamine and then is reduced with lithium aluminium hydride.

Figure 3:
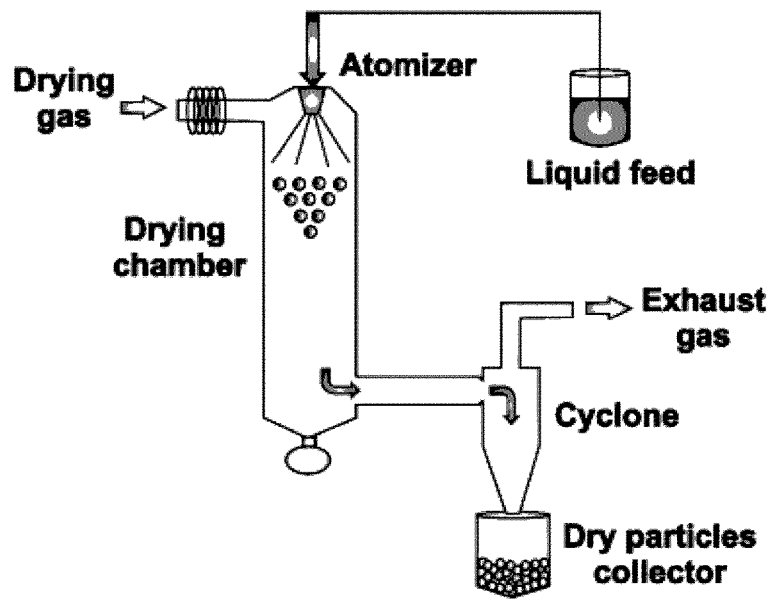
FIG. 3 is a schematic route for the preparation of a powder form of 5MeODMT.

FIG. 3 shows the schematic route for the formation of a powder form of 5MeODMT using a spray drying process.

EXAMPLES

Example 1: Synthesis of 5MeODMT (the Free Base) in on Step (the Free Base)

A schematic representation of this reaction is shown in FIG. 1.

Hydrazine (1.0 eq), diethyl acetal (1.2 eq), and aqueous sulfuric acid (0.1 eq) where heated together at 65-75° C. for 18 hours. MTBE (10 vol) was added, followed by adjustment to about pH10 using 12% caustic (about 1.1 eq.). The layers were separated and the aqueous fraction back extracted with MTBE (10 vol). The combined organic fractions were washed with water (10 vol) twice, then evaporated to dryness under vacuum. Yield 100%.

Example 2: Synthesis of 5MeODMT (the Free Base) in Three Steps

A schematic representation of this reaction is shown in FIG. 2.

Step 1—Add methyl tert-butyl ether (MTBE) (15 vol) into the reaction vessel and cool to −20 to −30° C., before adding oxalyl chloride (1.5 eq), maintaining the temperature at no more than −20° C. Add a solution of 5-methoxyindole (1.0 eq) in THF (1 vol) to the reaction vessel, maintaining the temperature at no more than −20° C. Allow the reaction to warm to 0-5° C. and stir for at least 1 hour, ensuring that no more than 2% of the starting material indole remains.

Cool the reaction to between −20 to −30° C. and add a solution of methanol (1 vol) and MTBE (1 vol), maintaining the temperature at no more than −20° C. Allow the reaction to warm to 0-5° C. over no less than 30 minutes and stir for at least 1 hour.

Filter and wash the solids with MTBE cooled to 0-5° C. Add the washed filtered solids and methanol (20 vol) to a reaction vessel. Heat to 60-65° C. and stir for no more than 30 minutes. Cool to 0-5° C. over no less than 2 hours and stir for no less than 2 hours. Filter and wash the solids with MTBE cooled to 0-5° C. Dry the solids obtained at no more than 40° C. for no less than 12 hours. Yield 95%.

Step 2—Add the compound obtained in step 1 (1.0 eq) to a reaction vessel together with dimethylamine hydrochloride (3.0 eq) and methanol (2 vol). Add 25% NaOMe in methanol (3.5 eq), to the reaction maintaining the temperature at no more than 30° C. Warm to and stir for no less than 5 hours, ensuring that no more than 0.5% of the starting material from step 1 remains. Adjust the temperature to 0-5° C. over no less than 2 hours, then add water (5 vol) over no less than 1 hour with stirring at 0-5° C. for no less than 1 hour.

Filter and wash the solids with water cooled to 0-5° C., and dry the solids obtained at no more than 40° C. for no less than 12 hours. Yield 85%.

Step 3—Add the compound obtained in step 2 (1.0 eq) to a reaction vessel. Add 1M LiAlH4 in THF (1.5 eq) in THF (8 vol) to the reaction maintaining no more than 40° C. Heat at reflux for no less than 4 hours ensuring that no more than 2% of the starting material from step 2 remains.

Adjust to 0-5° C. and add water (0.25 vol) in THF (0.75 vol) over no less than 30 minutes, maintaining no more than 10° C. Then add 15% caustic (0.25 vol) maintaining the temperature at no more than 10° C. Add water (0.65 vol) maintaining the temperature at no more than 10° C. Add THF (0.25 vol) as a vessel rinse and stir the contents at 0-5° C. for no less than 30 minutes. Add sodium sulfate (100 wt %) and stir contents at 0-5° C. for no less than 30 minutes.

Filter and wash the solids with toluene (2×10 vol) and keep liquors separate. Recharge THF liquors to a clean vessel and distil under vacuum to minimum stir. Charge toluene liquors and distil under vacuum to about 10 vol. Then add water (5 vol) and stir for no less than 15 minutes. Stop, settle and remove aqueous layer to waste. Charge with 4% HCl to a pH of between 1-2 (about 4 vol) and stir for no less than 15 minutes. Stop, settle and remove organic layer to waste. Charge MTBE (15 vol). Charge with 15% caustic to a pH between 11-13 (about 0.9 vol). Stir for no less than 15 minutes. Stop, settle and remove aqueous layer to waste. Charge with water (5 vol). Stir for no less than 15 minutes. Stop, settle and remove the aqueous layer to waste.

Example 3: Synthesis of 5MeODMT Hydrochloride Salt

5MeODMT (the free base) is dissolved in toluene (1.0 to 2.5 vol). Isopropyl alcohol (IPA) was then added (2.5 vol) followed by 1.25M HCl in IPA (1.0 eq) and the temperature adjusted to 0-5° C. over 1 hour.

If no precipitation/crystallization occurs, toluene (6.25 vol) is added over 30 minutes. The mixture was then stirred at 0-5° C. for 2 hours. The resultant solid is filtered, washed with toluene (3.8 vol). The solid was dried under vacuum at ambient temperature. Yield 58%.

Example 4: Synthesis of 5MeODMT Benzoate Salt

5MeODMT (the free base) is dissolved in toluene (1 eq) and benzoic acid (1 eq) in toluene (10 vol) is added over a period of 20 minutes and stirred at room temperature for 2 hours. The resultant precipitation/crystallization was filtered and washed with toluene (2.5 vol) and dried under vacuum at room temperature.

Isopropyl acetate (IPAc) (15.8 vol) was added to the solids obtained above and the temperature was raised to about 73° C. until the solid dissolved. The solution was allowed to cool to 0-5° C. over 2 hours and this temperature was maintained for 1 hour with stirring. The resultant benzoate salt was filtered and vacuum dried at room temperature. Yield 68%.

Example 5: Synthesis of 5MeODMT Fumarate Salt

5MeODMT (the free base) is added to a solution of fumaric acid (0.5 eq) in IPA over 15 minutes at 40-45° C. The resultant solution was cooled at room temperature and stirred for 16 hours. The solution was then cooled to 0-5° C. with stirring for 2 hours. The resulting precipitation/crystallization was filtered and was rinsed with toluene (2.5 vol). Yield 68%.

Example 6: 5MeODMT Powder

A schematic route for the preparation of a powder form of 5MeODMT (or the salt thereof) is shown in FIG. 3. The three main steps in the process are:

1. Spray drying a solution containing the substance(s) of interest (e.g. 5MeODMT, or the salt, thereof inclusive of any excipients). This can be done via an atomizing nozzle such as with rotary atomizers, pressure atomizers, twin fluid nozzles, ultrasonic atomizers, four-fluid nozzles. This is done so as to form droplets capable of generating co-formed particles in the desired particle size range.
2. Drying of the atomized droplets (e.g. with nitrogen gas, optionally at an elevated temperature).
3. Separating and collecting the dried particles from the gas stream (e.g. using a cyclone separator to capture the required size fraction).

Example 7: Slug Mucosal Irritation Assay

The Slug Mucosal Irritation (SMI) assay was initially developed at the Laboratory of Pharmaceutical Technology (UGent) to predict the mucosal irritation potency of pharmaceutical formulations and ingredients. The test utilizes the terrestrial slug *Arion lusitanicus*. The body wall of the slugs is a mucosal surface composed of different layers.

The outer single-layered columnar epithelium that contains cells with cilia, cells with micro-villi and mucus secreting cells covers the subepithelial connective tissue. Slugs that are placed on an irritating substance will produce mucus. Additionally tissue damage can be induced which results in the release of proteins and enzymes from the mucosal surface. Several studies have shown that the SMI assay is a useful tool for evaluating the local tolerance of pharmaceutical formulations and ingredients. A classification prediction model that distinguishes between irritation (mucus production) and tissue damage (release of proteins and enzymes) has been developed. Furthermore, several studies with ophthalmic preparations have shown that an increased mucus production is related to increased incidence of stinging, itching and burning sensations. In 2010 a clinical trial was set up to evaluate the stinging and burning sensations of several diluted shampoos. A 5% shampoo dilution or artificial tears were instilled in the eye and the discomfort was scored by the participants on a 5 point scale during several time points up to 30 min after instillation. The same shampoos were tested in the SMI assay using the Stinging, Itching and Burning (SIB) protocol. This study showed that an increased mucus production was related with an increased incidence of stinging and burning sensations in the human eye irritation test. The relevance of the assay to reliably predict nasal irritation and stinging and burning sensations was demonstrated using several OTC nasal formulations, isotonic, and hypertonic saline.

Furthermore, the test was validated using reference chemicals for eye irritation (ECETOC eye reference data bank). These studies have shown that the SMI assay can be used as an alternative to the in vivo eye irritation tests. Moreover, a multi-center prevalidation study with four participating laboratories showed that the SMI assay is a relevant, easily transferable and reproducible alternative to predict the eye irritation potency of chemicals.

The purpose of this assay was to assess the stinging, itching or burning potential of the test item(s) defined below. Using the objective values obtained for the mucus production the stinging, itching or burning potential of the test item(s) can be estimated by means of the prediction model that is composed of four categories (no, mild, moderate and severe).

Control items:
  Negative control—Name: Phosphate buffered saline (PBS)
  Positive control—Name: 1% (w/v) Benzalkonium chloride in PBS
Test Items:
Compound 1
  Name: 10% (w/v) Disodium fumarate in PBS
  CASRN: 17013-01-3
  Batch: KBSJ-P0
  Description: colourless solution
  Storage condition: room temperature (compounded on the day of the experiment)
Compound 2
  Name: 10% (w/v) Sodium phosphate monobasic in PBS
  CASRN: 7558-80-7
  Batch: 2A/220991
  Description: colourless solution
  Storage condition: room temperature (compounded on the day of the experiment)
Compound 3
  Name: 10% (w/v) Sodium acetate in PBS
  CASRN: 127-09-3
  Batch: 5A/233258
  Description: colourless solution
  Storage condition: room temperature (compounded on the day of the experiment)
Compound 4
  Name: 10% (w/v) Sodium citrate in PBS
  CASRN: 68-04-2
  Batch of vial: 5A/241516
  Description: colourless solution
  Storage condition: room temperature (compounded on the day of the experiment)

Test System: Slugs (*Arion lusitanicus*); 3 slugs per treatment group. The parental slugs of *Arion lusitanicus* collected in local gardens along Gent and Aalter (Belgium) are bred in the laboratory in an acclimatized room (18-20° C.). The slugs are housed in plastic containers and fed with lettuce, cucumber, carrots and commercial dog food.

Test Design: A single study was performed. Treatment time was 15 minutes three times on the same day.

Preparation of Slugs:
  Slugs weighing between 3 and 6 g were isolated from the cultures two days before the start of an experiment. The body wall was inspected carefully for evidence of macroscopic injuries. Only slugs with clear tubercles and with a foot surface that shows no evidence of injuries were used for testing purposes. The slugs were placed in a plastic box lined with paper towel moistened with PBS and were kept at 18-20° C. Daily the body wall of the slugs was wetted with 300 µl PBS using a micropipette.

Figure 4:
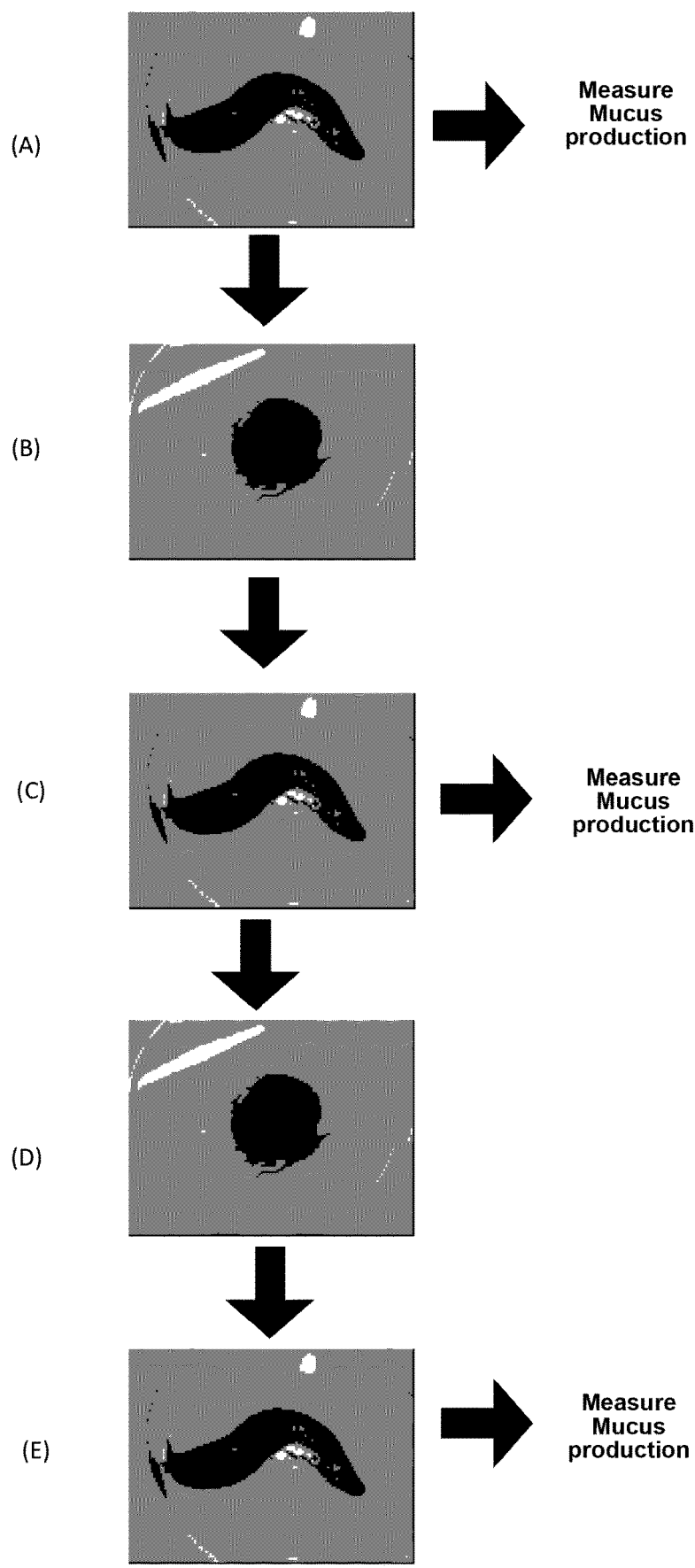
FIG. 4 is an overview of the slug mucosal irritation (SMI) test. (A) First 15 minute contact period between slug and test item. (B) Slug is transferred onto a wet paper towel in a new Petri dish for 1 hour. (C) Second 15 minute contact period between slug and test item. (D) Slug is transferred onto a wet paper towel in a new Petri dish for 1 hour. (E) Third 15 minute contact period between slug and test item.

Test Procedure:
  The stinging, itching or burning potency of the test item(s), was evaluated by placing 3 slugs per treatment group 3 times a day on 100 µL of test item in a Petri dish for 15±1 min. After each 15-min contact period the slugs were transferred for 60 min into a fresh Petri dish on paper towel moistened with 1 mL PBS to prevent desiccation. An overview of this can be seen in FIG. 4.

Mucus Production:
  The amount of mucus produced during each contact period was measured by weighing the Petri dishes with the test item before and after each 15-min contact period. The mucus production was expressed as % of the body weight. The slugs were weighed before and after each 15-min contact.

Classification Prediction Model
  Based on the endpoint of the SMI assay the stinging, itching or burning potency of the test item(s) was estimated using a classification prediction model.

The evaluation of the test results was based upon the total amount of mucus production during 3 repeated contact periods with the test item.

For each slug, the mucus production was expressed in % of the body weight by dividing the weight of the mucus produced during each contact period by the body weight of the slug before the start of that contact period. The total mucus was calculated for each slug and then the mean per treatment group was calculated. The classification prediction model shown in Table 1 was used to classify the compounds.

TABLE 1

| Cut-off values for classification - potency for nasal mucosal discomfort | |
|---|---|
| Total Mucus production in % (mean of n = 3) | Stinging, Itching and Burning (SIB) |
| <5.5% | No |
| ≥5.5 and <10% | Mild |
| ≥10 and <17.5% | Moderate |
| ≥17.5% | Severe |

Acceptance Criteria
  Before a test was considered valid, the following criteria must be met:
    the negative control should be classified as causing no stinging, itching and burning (Total mucus production <5.5%)
    the positive control item should be classified as causing severe stinging, itching and burning (Total mucus production ≥17.5%)

Irritation Potential

TABLE 2

Amount of mucus produced (MP) during each 15-min contact period (CP) and total amount of mucus produced

| Formulation | MP CP1[1] (%) | MP CP2[1] (%) | MP CP3[1] (%) | Total MP[1] (%) | SIB Category[2] |
|---|---|---|---|---|---|
| NC - PBS | −0.2 ± 0.3 | −0.6 ± 0.1 | 0.3 ± 0.6 | −0.5 ± 0.7 | No |
| PC - 1% BAC | 9.2 ± 1.5 | 8.4 ± 1.2 | 5.9 ± 3.1 | 23.4 ± 3.6 | Severe |
| Disodium fumarate, 10% | 5.0 ± 2.5 | 4.7 ± 1.7 | 3.6 ± 0.8 | 13.3 ± 1.8 | Moderate |
| Sodium phosphate, 10% monobasic | 3.3 ± 0.9 | 5.6 ± 0.3 | 6.2 ± 1.3 | 15.2 ± 1.8 | Moderate |
| Sodium acetate 10% | 3.3 ± 0.2 | 3.9 ± 0.4 | 3.9 ± 0.2 | 11.0 ± 0.8 | Moderate |
| Sodium citrate, 10% | 4.2 ± 0.5 | 4.2 ± 0.3 | 4.1 ± 1.1 | 12.5 ± 1.4 | Moderate |

NC: negative control; PC: positive control; BAC: benzalkonium chloride

[1] Mean ± SD, n = 3

[2] No: total MP < 5.5%; Mild: 5.5% ≤ total MP < 10%; Moderate: 10% ≤ total MP < 17.5%; Severe: total MP ≥ 17.5%

The average amount of mucus produced during each 15-min contact period and total mucus production (total MP) is presented in Table 2. According to the classification prediction model of the SMI test, the negative control (untreated slugs) did not induce reactions in the slugs (mean total MP<5.5%). The positive control on the other hand (DDWM/SLS 80/20) induced a high mucus production during each contact period (mean total MP≥17.5%) resulting in a classification as severe stinging, itching, and burning (SIB) reactions. The acceptance criteria were met and the experiment was considered valid.

In total, 4 different solutions were tested. The amount of mucus produced during each 15-min contact period was between 10% and 17.5%, indicating moderate SIB reactions. The test items can be ranked according to increasing total mucus production: sodium acetate (10% w/v)<sodium citrate (10% w/v)<disodium fumarate (10% w/v)<sodium phosphate (10% w/v).

| | Numerical Data | | | | |
|---|---|---|---|---|---|
| Treatment | Replicate | MP CP1 | MP CP2 | MP CP3 | Total MP |
| NC | 1 | −0.32 | −0.59 | 0.97 | 0.06 |
| | 2 | −0.44 | −0.57 | −0.32 | −1.33 |
| | 3 | 0.14 | −0.70 | 0.35 | −0.21 |

-continued

| | Numerical Data | | | | |
|---|---|---|---|---|---|
| Treatment | Replicate | MP CP1 | MP CP2 | MP CP3 | Total MP |
| PC | 1 | 8.08 | 7.91 | 9.29 | 25.28 |
| | 2 | 10.82 | 9.71 | 5.23 | 25.77 |
| | 3 | 8.59 | 7.49 | 3.17 | 19.25 |
| Disodium fumarate, 10% | 1 | 7.83 | 3.56 | 3.14 | 14.53 |
| | 2 | 4.39 | 6.64 | 3.11 | 14.14 |
| | 3 | 2.87 | 3.84 | 4.47 | 11.17 |
| Sodium phosphate, 10% monobasic | 1 | 4.33 | 5.34 | 7.41 | 17.07 |
| | 2 | 2.93 | 5.69 | 6.40 | 15.02 |
| | 3 | 2.74 | 5.83 | 4.89 | 13.46 |
| Sodium acetate, 10% | 1 | 3.47 | 4.24 | 4.10 | 11.80 |
| | 2 | 3.44 | 3.93 | 3.81 | 11.18 |
| | 3 | 3.06 | 3.43 | 3.69 | 10.17 |
| Sodium citrate, 10% | 1 | 4.16 | 4.01 | 3.78 | 11.95 |
| | 2 | 4.75 | 4.03 | 5.33 | 14.12 |
| | 3 | 3.68 | 4.55 | 3.25 | 11.48 |

TABLE 3

Amount of mucus produced (MP) during each 15-min contact period (CP) and total amount of mucus produced

| Formulation | MP CP1[1] (%) | MP CP2[1] (%) | MP CP3[1] (%) | Total MP[1] (%) | SIB Category[2] |
|---|---|---|---|---|---|
| NC - PBS | −0.2 ± 0.3 | −0.6 ± 0.1 | 0.3 ± 0.6 | −0.5 ± 0.7 | No |
| PC - 1% BAC | 9.2 ± 1.5 | 8.4 ± 1.2 | 5.9 ± 3.1 | 23.4 ± 3.6 | Severe |
| Disodium fumarate, 10% | 5.0 ± 2.5 | 4.7 ± 1.7 | 3.6 ± 0.8 | 13.3 ± 1.8 | Moderate |
| Sodium phosphate, 10% monobasic | 3.3 ± 0.9 | 5.6 ± 0.3 | 6.2 ± 1.3 | 15.2 ± 1.8 | Moderate |
| Sodium acetate, 10% | 3.3 ± 0.2 | 3.9 ± 0.4 | 3.9 ± 0.2 | 11.0 ± 0.8 | Moderate |
| Sodium citrate, 10% | 4.2 ± 0.5 | 4.2 ± 0.3 | 4.1 ± 1.1 | 12.5 ± 1.4 | Moderate |

NC: negative control; PC: positive control; BAC: benzalkonium chloride

[1] Mean ± SD, n = 3

[2] No: total MP < 5.5%; Mild: 5.5% ≤ total MP < 10%; Moderate: 10% ≤ total MP < 17.5%; Severe: total MP ≥ 17.5%

TABLE 4

Amount of mucus produced (MP) during each 30-min contact period (CP) and total amount of mucus produced (Code 00E04)

| Treatment | CP1 30-min | CP2 30-min | Total MP |
|---|---|---|---|
| PBS | −1.0 ± 0.6 | −1.1 ± 0.8 | −2.2 ± 0.6 |
| BAC (1%) | 13.2 ± 4.2 | 18.6 ± 9.8 | 31.8 ± 12.6 |
| Sodium oxalate (1%) | 4.5 ± 1.3 | 6.6 ± 1.0 | 11.1 ± 2.0 |

TABLE 5

Amount of mucus produced (MP) during each 60-min contact period (CP) and total amount of mucus produced

| Treatment | Day 1 CP1 60-min | Day 2 CP2 60-min | Total MP |
|---|---|---|---|
| PBS | −0.2 ± 0.7 | −0.7 ± 0.5 | −0.9 ± 0.5 |
| BAC (1% CP1 & 3.5% CP2) | 21.9 ± 4.8 | 9.7 ± 3.2 | 31.6 ± 2.5 |
| Sodium oxalate (1% CP1 & 3.5% CP2) | 11.2 ± 3.9 | 16.0 ± 4.0 | 27.1 ± 2.3 |

TABLE 6

Amount of mucus produced (MP) during a 60-min contact period (CP)

| Treatment | CP1 60-min |
|---|---|
| PBS | −0.2 ± 1.0 |
| BAC (1%) | 15.0 ± 1.9 |
| Sodium benzoate (1%) | 2.6 ± 0.3 |
| Sodium benzoate (10%) | 6.9 ± 1.2 |

Results

The total MP for a 60-min treatment (historical data) was compared with the total MP of the SIB protocol (3×15-min treatment; current data). In the table below a ranking is proposed from least SIB reactions to highest SIB reactions:

| Compound | Concentration | Treatment time | Total MP (% body weight) |
|---|---|---|---|
| Sodium benzoate | 1% | 60-min | 2.6 |
| Sodium benzoate | 10% | 60-min | 6.9 |
| Sodium acetate | 10% | 45-min (3× 15-min) | 11.0 |
| Sodium citrate | 10% | 45-min (3× 15-min) | 12.5 |
| Disodium fumarate | 10% | 45-min (3× 15-min) | 13.3 |
| Sodium phosphate | 10% | 45-min (3× 15-min) | 15.2 |
| Sodium oxalate | 1% | 60-min | 11.2 |

Sodium oxalate appears to be the most irritating salt since a 1% concentration results in 11.2% total MP after 1 hour of contact. Sodium benzoate is the least irritating salt.

Example 8: Further Slug Mucosal Irritation (SMI) Testing

5MeODMT as a freebase compound is known to be highly irritating to the mucosal lining; therefore, it is commonly prepared as a salt for insufflation. The hydrochloride (HCl) salt of 5MeODMT is most commonly used due to ease of crystallisation. However, it is known that the HCl salt of 5MeODMT is still quite irritating to the mucosal lining.

Following the results above indicating that sodium benzoate is the least irritating salt of those studied; further SMI testing was performed on 5MeODMT benzoate and the common 5MeODMT HCl salt according to the previously described methods (of Example 7). The results of this are shown below:

| Compound | Concentration (w/v) | Total MP (% body weight) |
|---|---|---|
| 5MeODMT benzoate | 10% | 7.38 |
| 5MeODMT HCl | 10% | 10.27 |
| Benzylkonium (positive control) | 10% | 17.56 |
| PBS (negative control) | 10% | −0.77 |

The 5MeODMT benzoate produced 'mild' irritation compared to the 5MeODMT HCl which scored as 'moderate' on testing.

Example 9: Permeation Data

The use of ovine nasal epithelium to study nasal drug absorption is a technique which is well known to the person skilled in the art.

The permeation of 5MeODMT benzoate and 5MeODMT HCl has been studied by the current applicants. Dosing solutions corresponding to 1.25% concentration were prepared in water and applied to ovine nasal epithelium. The average cumulative ($\mu g/cm^2$) of permeation of the benzoate and hydrochloride salt are shown in the table below (mean±SD, n=5):

| | Time (min) | 0.0 | 10.0 | 20.0 | 30.0 | 40.0 | 50.0 | 60.0 | 75.0 | 90.0 |
|---|---|---|---|---|---|---|---|---|---|---|
| Cumulative amount ($\mu g/cm^2$ (SD)) | 5-MeO-DMT Benzoate | 0.00 (0.00) | 0.20 (0.35) | 3.46 (3.07) | 9.30 (6.46) | 15.46 (10.00) | 21.51 (11.42) | 27.30 (13.73) | 33.34 (14.80) | 39.77 (14.81) |
| | 5-MeO-DMT Hydrochloride | 0.00 (0.00) | 0.33 (0.52) | 3.30 (3.51) | 8.26 (6.70) | 13.33 (8.58) | 18.77 (10.75) | 23.43 (11.38) | 29.52 (12.77) | 35.36 (13.29) |

Figure 5:
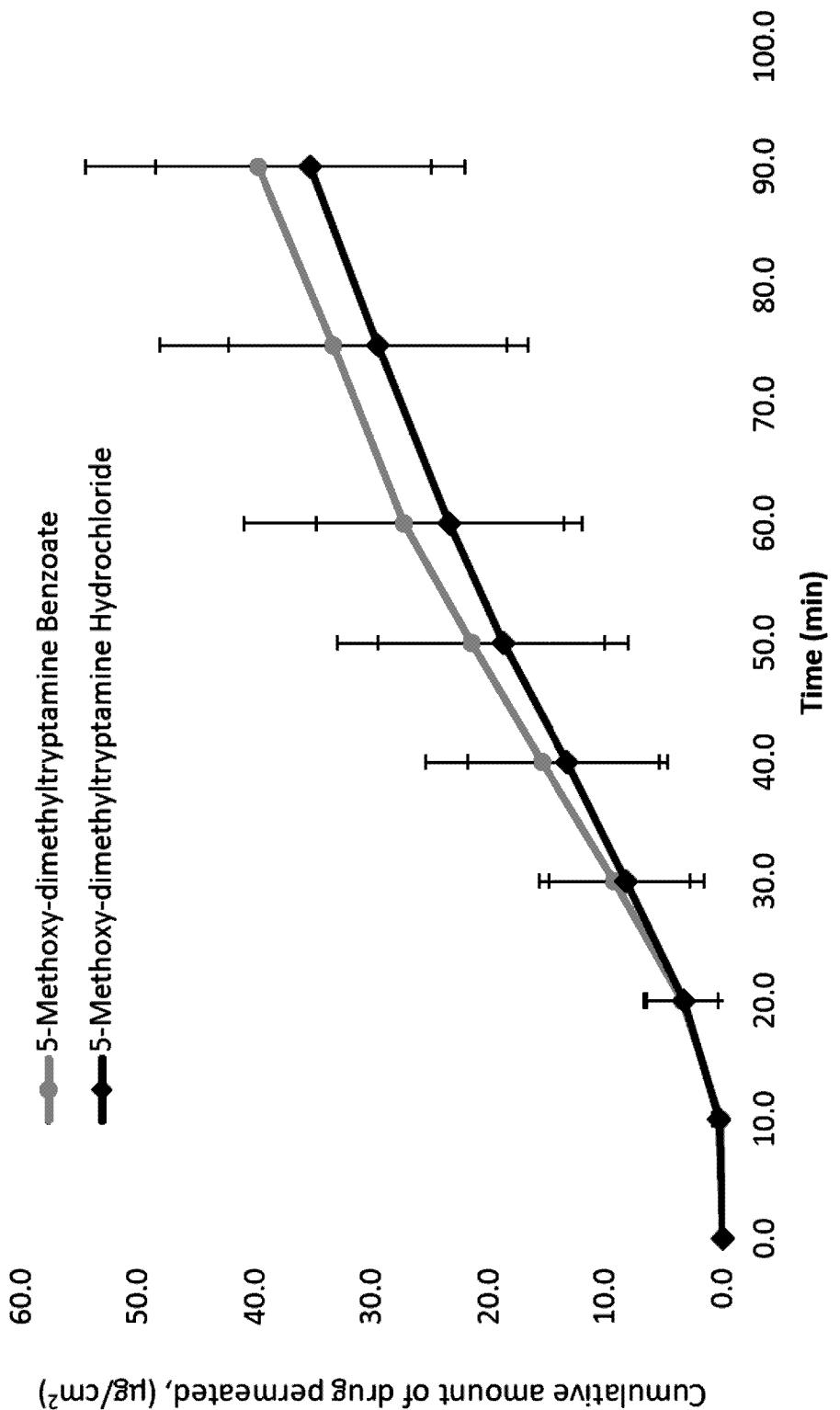
FIG. 5 is a graph showing that the benzoate salt of 5MeODMT has higher permeation compared with the hydrochloride salt, as per the experiment detailed in Example 9.

The cumulative amount of 5MeODMT benzoate and 5MeODMT hydrochloride which permeated through ovine nasal epithelium per unit area following application of 1.25% dosing solutions prepared in water (mean±SD, n=5) can be seen in FIG. 5.

As can clearly be seen, the benzoate salt has higher permeation across the epithelium.

The above data obtained in the above test show that the 5MeODMT benzoate salt gives higher permeation with less mucosal irritation than the commonly used HCl salt; and so this combination of properties makes the benzoate salt an ideal candidate for mucosal delivery. For example, less 5MeODMT benzoate salt may be needed by inhalation to provide the same benefit as the HCl salt and the benzoate salt is less irritating, and so provides a synergistic benefit. Smaller amounts of compound also make inhalation easier to accomplish.

Example 10: Effects on the Central Nervous System Function

In the following examples, BPL-5MEO refers to 5-methoxy-N,N-dimethyltryptamine (5MeODMT).

In the following examples, the hydrochloride salt of 5MeODMT was used.

The following Examples (10-14) summarizes applicant-sponsored safety pharmacology studies to assess the effects of BPL-5MEO on CNS, cardiovascular system, and respiratory system function. The study designs are based on in the International Council for Harmonisation (ICH) S7A/B Guidance and were conducted in compliance with GLP regulations.

The pharmacological effects of BPL-5MEO on CNS function was assessed using a Functional Observational Battery (FOB) in male Sprague-Dawley rats following a single intranasal administration (ITR study 15951).

The test and control/vehicle items were administered by single dose intranasal administration to both nostrils, as shown in Table 7.

TABLE 7

Experimental Design of Study 15951

| Group No. | Group Designation[a] | Dose Level (mg/kg) | Dose Concentration (mg/mL) | Dose Volume[c] (L/kg) | No. of Male Animals |
|---|---|---|---|---|---|
| 4 | Control[b] | 0 | 0 | 75 Right Nostril + | 6 |
| 3 | Low Dose | 1.5 | 10 | 75 Left Nostril | 6 |
| 2 | Mid Dose | 3 | 20 | | 6 |
| 1 | High Dose | 10 | 66.67 | | 6 |

[a]The observers performing the FOB were not aware of the specific treatment administered to the animals.
[b]Control animals were administered 0.1% hydroxypropyl methyl cellulose (HPMC) in water.
[c]Dose volume did not exceed 25 uL/nostril for all animals regardless of their bodyweight.

Parameters monitored included mortality and clinical signs. General behavioral changes were assessed using FOB at 6 timepoints: before dosing, and at 15 minutes, 1, 2, 4, and 24 hours postdosing. On each occasion, the FOB was performed at 4 stages: when the animals were in their home cage, while handling the animals, when the animals were freely moving in an open-field, and when they received diverse stimuli for reactivity evaluation. The body temperature and neuromuscular strength were also measured on each of the occasions detailed above.

The FOB examinations were grouped according to functional domains of the nervous system as shown in Table 8.

TABLE 8

Functional Domains of the Nervous System and Associated Observations

| Domain | Behavioral Observations Performed |
|---|---|
| Behavioral | Posture and activity in home cage/bin |
| | Ease of removal from the cage/bin |
| | Handling reactivity |
| | Arousal |
| | Rearing |
| | Exploratory activity |
| | Touch response |
| | Abnormal or stereotyped behavior |
| Neurological (sensorimotor)/ Neuromuscular | Vision test |
| | Touch response |
| | Auditory test |
| | Tail pinch response |
| | Eye blink response |

TABLE 8-continued

Functional Domains of the Nervous System and Associated Observations

| Domain | Behavioral Observations Performed |
|---|---|
| | Flexor reflex |
| | Extensor thrust reflex |
| | Pinna reflex |
| | Proprioceptive positioning |
| | Righting reaction |
| | Hindlimb foot splay |
| | Involuntary motor movements (such as convulsion and tremors) |
| | Gait |
| | Forelimb and hindlimb grip strength |
| Autonomic | Lacrimation |
| | Salivation |
| | Pupil response to light |
| | Palpebral closure |
| | Defecation |
| | Urination |
| | Piloerection |
| | Exophthalmos |
| | Body temperature |

There was no treatment-related mortality/morbidity. Transient BPL-5MEO-related clinical signs were noted immediately following dosing and consisted mainly of decreased activity, lying on the cage floor, shallow/increased respiration and dilated pupils at all dose groups. Tremors, salivation, and gasping were observed in some animals at the 3 and 10 mg/kg doses, and twitching was noted in one animal at 10 mg/kg.

In the behavioral domain of the FOB, a single intranasal administration of BPL-5MEO at doses of 1.5, 3, and 10 mg/kg resulted in transient decreased activity, lying on the cage floor, and decreased rearing at 15 minutes postdose. All behavioral parameters were comparable to control animals at 1-hour postdose.

In the neurological (sensorimotor)/neuromuscular domain of the FOB, a single intranasal administration of BPL-5MEO at 1, 5, and 10 mg/kg resulted in transient changes in gait (difficulty in movement) at all dose levels. All neurological (sensorimotor)/neuromuscular parameters were comparable to control animals at 1-hour postdose.

In the autonomic domain, a single intranasal administration of BPL-5MEO of 1, 5, and 10 mg/kg was associated with salivation, piloerection, increased respiration, dilated pupils and changes in body temperature was noted across all dose levels. All autonomic parameters were comparable with control animals at 2 hours postdose.

In conclusion, the single intranasal administration of BPL-5MEO at doses of 1.5, 3, and 10 mg/kg resulted in transient clinical signs, consistent with observable changes in behavior, neurological (sensorimotor)/neuromuscular and autonomic parameters which were fully resolved within 1 or 2 hours following dosing.

Example 11: Effects on Cardiovascular Function

In Vitro Study

The in vitro effect of 5MeODMT on the hERG potassium channel current ($I_{Kr}$), the rapidly activating, delayed rectifier cardiac potassium current, was assessed using the patch clamp technique in stably transfected human embryonic kidney (HEK-293) cells that expressed the hERG gene (CRL study 1020-5458). This assay is employed as a screen to assess potential risks for QT interval prolongation.

The study was conducted in 2 phases: Phase 1 assessed the onset and steady-state inhibition of hERG at a selected concentration of 30 μm 5MeODMT; Phase 2 assessed the concentration response if the results from Phase 1 showed inhibition of 20% or more. The initial concentration of 30 μm was selected based on the results of an exploratory dose-range finding study in dogs, where intranasal administration of 2.5 mg/kg BPL-5MEO resulted in a mean $C_{max}$ of 803 ng/mL (3.67 μM) 5MeODMT. A solution of 30 μM used in Phase 1 provided an 8-fold margin over this concentration.

In Phase 1, the 30 μM concentration of 5MeODMT in protein free perfusate inhibited hERG potassium ion current by 77.8±7.4% (n=3). Therefore, Phase 2 was undertaken using concentrations of 1, 3, 10, and 35 μm 5MeODMT in protein free perfusate (corresponding to 0.2, 0.6, 2.0, and 7.2 μg/mL of unbound drug substance).

In Phase 2, 5MeODMT inhibited hERG potassium ion channel current in a concentration-dependent manner as presented in Table 9.

TABLE 9

Mean Percent Inhibition of hERG Potassium ion Channel Current by 5MeODMT (in protein free perfusate)

| | Concentration of 5MeODMT (μM) | | | |
|---|---|---|---|---|
| | 1 | 3 | 10 | 35 |
| Mean ± SD % inhibition (n = 3 cells) | 5.03 ± 1.95% | 23.77 ± 6.10% | 52.72 ± 2.61% | 82.22 ± 1.91% |

The calculated $IC_{50}$ of 5MeODMT for hERG potassium channel current was 8.69 μm (95% confidence limits 5.78-13.06 μm) compared to 12.8 nM (95% confidence limits 6.8-24.3 nM) for the positive control, terfenadine.

In Vivo Study

The pharmacological effects of BPL-5MEO on cardiovascular function (arterial blood pressure and ECG) was monitored by telemetry, in conscious male beagle dogs, following a single intranasal administration.

The highest dose level was selected based on the results from an intranasal maximum tolerated dose (MTD) toxicity study in dogs (Study 62958) where repeated daily dosing 2.5 mg/kg/day of BPL-MEO once daily for 5 consecutive days was marginally tolerable and associated with transient clinical observations of moderate to severe incoordination, vocalization, salivation, shaking, circling, sneezing, decreased activity, and labored respiration that resolved within 60 minutes post dosing. Therefore, the highest dose selected for this study was 1.2 mg/kg/day. The lowest dose of 0.4 mg/kg/day was based on consideration of a maximum clinical dose of 14 mg/day, with the mid-dose of 0.8 mg/kg/day selected to provide a dose-response assessment.

BPL-5MEO and control/vehicle were administered by intranasal instillation to both nostrils per session to a total of 4 dogs. Each dog received 4 administrations (control/vehicle and 3 dose levels of BPL-5MEO) according to a Latin-square design, such that each dog received the various administrations in a unique sequence, as in Table 10. A washout period of at least 2 days was allowed between each successive dose.

TABLE 10

Latin-square design for Dog Cardiovascular Study

| Test Session | Treatment | | | | |
|---|---|---|---|---|---|
| | 1001A | 1002A | 1003A | 1004A[a] | 1104A |
| 1 | Control/Vehicle | Low Dose | Mid Dose | High Dose | — |
| 2 | High Dose | Control/Vehicle | Low Dose | Mid Dose | — |
| 3 | Mid Dose | High Dose | Control/Vehicle | — | Low Dose |
| 4 | Low Dose | Mid Dose | High Dose | — | Control/Vehicle |

[a]Animal 1004A was replaced prior to dosing for Test Session 3 with animal 1104A due to low implant battery.

Low Dose, Mid Dose, High Dose were 0.4, 0.8, and 1.2 mg/kg/day, respectively. The nominal dose levels refer to the freebase of 5MeODMT salt form.

The dose volume administered to each animal was 7 μL/kg/nostril. No animal exceeded a dose volume of 100 μL/nostril.

The Control/Vehicle was 0.1% hydroxypropyl methyl cellulose (HPMC) in water.

The telemetry signals for arterial blood pressure and pulse rate, ECGs (heart rate [HR], RR, PR, QT, and QTcV intervals and QRS complex duration), body temperature, and locomotor activity, were recorded continuously over the telemetry recording period of at least 1.5 hours before the start of dosing and for at least 24 hours postdosing. Systolic, diastolic and mean arterial blood pressures and pulse rate were obtained from transmitter catheter inserted into the femoral artery. ECGs were obtained from the biopotential leads, from the telemetry transmitter, in a Lead II configuration.

During the study, all animals were also monitored for mortality and clinical signs. Body weights were recorded for general health status check and for dose calculation purposes only.

There were no deaths and no BPL-5MEO-related clinical signs during the study.

The morphology of the P-QRS-T waveforms remained normal and no rhythm or conduction abnormalities were observed in the ECGs between control and treated groups. There were minor differences in the % change of mean HR averaged between approximately 0 and 150 minutes post-dose between all dose levels and the control vehicle. While mean % increases in mean HR increased by 3.7% in the control vehicle during this period, compared to baseline, the observed increases with the low, mid and high dose levels of BPL-5MEO were respectively 7.6%, 10.3%, and 17.2%. However, arterial blood pressure did not seem to show any appreciable differences that were sufficient to have any effect on HR. No other findings were observed. The observed increases in mean HR with all dose levels were non-adverse, reversible and did not show a typical dose relationship.

In conclusion, the single intranasal instillation of BPL-5MEO to both nostrils at doses of 0.4, 0.8, and 1.2 mg/kg/day was well tolerated and did not result in any effects on the cardiovascular system of conscious male Beagle dogs.

Example 12: Absorption and Pharmacokinetics

In a 14-day intranasal toxicology in male and female rats (ITR report 700041), plasma concentrations of 5MeODMT increased as a function of the dose administered. Peak ($C_{max}$) concentrations were reached within 2 to 5 minutes post dosing ($T_{max}$) with apparent $t_{1/2}$ ranging from 6.8 to 9.4 minutes. Values trended lower on Day 14 compared to Day 1. There was no apparent sex difference and no evidence of accumulation with repeated dosing.

In a 14-day intranasal toxicology study in male and female dogs (ITR report 62959), plasma concentration of 5MeODMT increased as a function of the dose administered. Peak concentrations were reached within 3 to 14 minutes ($T_{max}$), post dosing with apparent elimination half-lives ranging from 19 to 95 minutes. The values were not markedly different on Day 1 and Day 14. There was no apparent sex difference and no evidence of accumulation with repeated dosing.

The data shows that across the dose ranges studied in rats (5, 20, 75 mg/kg), and dogs (0.4, 0.8, 1.5, and 2.5 mg/kg), exposure was generally increased dose-dependently, but not consistently in a dose-proportional manner as some increases were more or less than dose-proportional between different doses. The results do not indicate a saturation of MAOA-mediated metabolism at the doses studied in these species as seen previously in mice.

Example 13: Toxicology

The toxicology program completed with BPL-5MEO consisted of non-pivotal single/repeat dose intranasal studies to determine the MTD in order to help select the highest doses for the pivotal 14-day GLP intranasal toxicology studies in male and female Sprague Dawley rats and Beagle dogs. The intranasal route of administration was used as this is the clinical route of administration. The species selected were based upon information from the published literature, preliminary PK information, availability of historical control information from the testing laboratory, and their standard use and acceptance as appropriate surrogates for intranasal administration. The experimental design of the pivotal 14-day studies included an assessment of systemic exposures (toxicokinetics) and a 14-day recovery period to assess reversibility of any adverse or delayed responses. The once daily dosing for 14 consecutive days in the pivotal studies was intended to provide sufficient systemic exposure to characterize the toxicity potential for a drug substance with a very short half-life.

1. Non-pivotal Single/Repeat Dose and Tolerance Studies
   a. Maximum Tolerated Dose Followed by 7-Day Repeat-Dose Toxicology in Rats (Study 700040)

The objectives of this non-GLP study were to determine the maximum tolerated dose and the toxicity profile of BPL-5MEO following intranasal instillation in the rat. The study consisted of 2 parts. The objective of the first part (Dose Escalation Phase), was to determine the MTD of BPL-5MEO following a single intranasal administration to Sprague-Dawley rats. The doses used in part 1 were 15, 30, 50, 65, and 75 mg/kg. Each subsequent dose was administered following at least 24 hours from the commencement of the previous dose. There were 2 males and 2 females in each dose group. The objective of the second part (Main Study Phase), was to determine the toxicity of BPL-5MEO at the MTD of 75 mg/kg following once daily intranasal administration for 7 consecutive days to Sprague-Dawley rats.

All the dose formulation samples collected and analyzed were between 89.2% and 101.3% of nominal concentration, and as such met the acceptance criteria for accuracy (100±15% of their nominal concentration). Analysis was performed using a non-GLP HPLC-UV assay.

All female groups received their targeted doses in both parts. However, as the maximum feasible loading dose was not to exceed 25 μL/naris, regardless of body weight, mean achieved doses for the males at the 30 were still 99.3%, 90.0%, 88.2%, and 89.6%, respectively and were considered to be acceptable.

During Phase I, assessments of mortality, clinical signs and body weights were performed. All animals were observed for 14 days after dosing, following which they were euthanized on Day 15 and subjected to a gross necropsy examination. The necropsy consisted of an external examination, including reference to all clinically-recorded lesions, as well as a detailed internal examination.

Single intranasal administration of 5MeODMT at the dose levels up to 75 mg/kg was tolerated. There was no mortality and gross pathology findings at any dose. Body weight gain was slightly suppressed females at 75 mg/kg. A range of clinical signs were observed and included incoordination, shallow or increased respiration, sneezing, salivation, decreased activity, piloerection, white pasty material around penis (for males), ptosis, laying on the cage floor, and sensitive to touch and shaking. The incidence and severity of these findings evolved as a function of the administered dose and were transient, with most being resolved within 1-hour post dose. Based on the clinical signs and maximal feasible volume/dose, 75 mg/kg was judged to be the MTD, and this dose was selected for Phase 2.

During Phase 2, assessments of mortality, clinical signs and body weights were performed. Following dosing, all animals were euthanized and subjected to a necropsy examination on Day 8. The necropsy consisted of an external examination, including reference to all clinically-recorded lesions, as well as a detailed internal examination. Study plan specific tissues/organs were collected and retained, then trimmed and preserved promptly once the animal was euthanized but these were not further examined microscopically.

Intranasal administration of 5MeODMT at 75 mg/kg for 7 consecutive days was tolerated. There were no mortalities. Body weight gain was slightly suppressed for both sexes. Transient clinical signs similar to those of the Phase I included incoordination, mydriasis, increased or shallow respiration, gasping, sneezing, salivation, pale in colour, decreased activity, lying on the cage floor, piloerection, white pasty material around penis (for males), erect penis (for males), cold to touch, partially or completely closed eyes, sensitive to touch and shaking. These signs were generally less pronounced in terms of severity and incidence during the last few dosing days of this phase, and were resolved daily following dosing within 1-hour post administration. Macroscopic observations of note were limited to dark/pale area of the lungs in 2/10 animals; however, in the absence of histopathological examination, a possible test item-relationship of these findings could not be excluded.

b. Maximum Tolerated Dose Followed by 7-Day Repeat-Dose Toxicology in Dogs (Study 62958)

The objectives of this study were to determine the maximum tolerated dose and the toxicity of the test item, 5MeODMT (as the hydrochloride salt), following intranasal instillation in the dogs. In support of these objectives, the study consisted of 2 individual phases.

The test item was administered once by intranasal instillation to one male and female dog for up to 5 dose levels until the highest tolerable dose (MTD) was determined as described in Table 11.

and 9 (Dose 2) and for the female on Days 4 (Dose 1) and 9 (Dose 2). A range of clinical signs were observed and included gnawing cage wire, dilated pupils, changes in respiration, incoordination, decreased activity, vocalization, salivation, erect penis (for males) and shaking. After the last escalating dose at 3.5 mg/kg/day, the male animal presented a convulsion shortly after dosing which lasted for 8 minutes. All clinical signs disappeared within an hour after the dosing except for decreased activity, dilated pupils and lying on the cage floor which were present on few occasions at 1-hour post dose or a few minutes after. The MTD for the test item was considered to be 2.5 mg/kg.

In the phase 2 (dose confirmation), BPL-5MEO was administered at the MTD to one male and female dog once daily by intranasal instillation for 5 consecutive days and then twice daily on Days 6 and 7 (minimum 4 hours apart). During Phase 2, assessments of mortality, clinical signs, body weights and food consumption were performed. A series of blood samples were collected on Days 1 and 7 for determination of plasma concentrations of 5MeODMT using an LC/MS/MS method. Following the last dosing, all animals were euthanized and subjected to a necropsy examination on Day 8. The necropsy consisted of an external examination; including reference to all clinically-recorded lesions, as well as a detailed internal examination. Study plan specific tissues/organs were collected and preserved following necropsy but were not further examined microscopically.

There were no test item-related effects on mortality or bodyweights. Slight decreases in food intake were observed for the male animal on Day 7 and for the female animal on Days 5 and 7. A range of clinical signs were observed and included muscle stiffness, gnawing cage wire, dilated pupils, changes in respiration, decreased activity, incoordination, vocalization, salivation, erect penis (for the male) and shaking. All clinical signs disappeared within an hour after the dosing except for decreased activity, dilated pupils, and lying on the cage floor which were present on few occasions at 1-hour post dose or a few minutes after. All observations were considered transient.

Toxicokinetic assessments were performed on Days 1 and 7; the maximum BPL-5MEO plasma concentration ($C_{max}$) ranged from 541 to 803 ng/mL and was reached ($T_{max}$) within 2 to 15 minutes post dose in both sexes. Dose normalized AUCs ranged from 2980 to 7320 min*kg*ng/mL/mg in both sexes. After $T_{max}$, BPL-5MEO plasma

TABLE 11

Doses Administered in the Dose Escalation Phase in Study 62958

| Dosing Day[a] | Group Designation | Total Dose Level[b] (mg/kg) | Dose Concentration (mg/mL) | Dose Volume (μL/kg) | Number of Animals | |
|---|---|---|---|---|---|---|
| | | | | | Males | Females |
| Day 1 | Dose 1 | 2 | 100 | 10 Right Nostril + | 1 | 1 |
| Day 7 | Dose 2 | 4 | 200 | 10 Left Nostril | | |
| Day 10 | Dose 3 | 5[d] | 250 | | | |
| Day 14 | Dose 4 | 3 | 150 | | | |
| Day 17 | Dose 5 | 3.5 | 175 | | | |

[a]Each subsequent dose was administered following a washout period of minimum 3 days between doses.
[b]Dose levels refer to the freebase of BPL-5MEO salt form.
[c]Targeted dose concentrations were calculated based on an estimated body weight of 10 kg.
[d]These animals were dosed at higher dose level of 5 mg/kg.

There were no BPL-5MEO-related effects on mortality or bodyweights. Slight decreases in food intake were observed following administration for the male on Days 1 (Dose 1)

concentrations declined at an estimated $t_{1/2}$ from 19.1 to 34 minutes in both sexes. There were no sex differences in any of the measured toxicokinetic parameters on either occasion.

Over the 7-day treatment period, BPL-5MEO did not accumulate when administered daily by intranasal instillation.

2. Pivotal Studies a. A 14-Day Repeat-Dose Intranasal Toxicity Study Followed by a 14-Day Recovery Period in Rats (Study 700041)

The objective of this GLP study was to determine the toxicity and toxicokinetic (TK) profile of BPL-5MEO following intranasal instillation in Sprague Dawley rats for 14 consecutive days and to assess the persistence, delayed onset, or reversibility of any changes following a 14-day recovery period.

BPL-5MEO and control/vehicle were administered to groups of rats once daily by intranasal instillation for 14 consecutive days as described in Table 12.

TABLE 12

Doses Administered in 14-Day Repeat Dose Study in Rats

| Group No. | Group Designation | Total Dose Level[b] (mg/kg/day) | Dose Conc. (mg/mL) | Dose Volume[d] (μL/kg) | Main Male | Main Female | Recovery Male | Recovery Female | Toxicokinetic Male | Toxicokinetic Female |
|---|---|---|---|---|---|---|---|---|---|---|
| 1 | Vehicle Control[a] | 0 | 0 | 75 Right Nostril + | 10 | 10 | 5 | 5 | 3 | 3 |
| 2 | Low Dose | 5 | 33.3 | 75 | 10 | 10 | — | — | 6 | 6 |
| 3 | Mid Dose | 20 | 133.3 | Left | 10 | 10 | — | — | 6 | 6 |
| 4 | High Dose | 75 | 500 | Nostril | 10 | 10 | 5 | 5 | 6 | 6 |

[a]Vehicle control animals were administered 0.1% Hydroxypropyl methyl cellulose (HPMC) in water.
[b]Nominal dose levels refer to the freebase of 5MeODMT salt form.
[c]The dose volume administered to each animal was 75 uL/kg/nostril.
[d]Dose volume was not to exceed 25 μL/nostril for all animals regardless of their bodyweight.

The animals were monitored for mortality, clinical signs, respiratory measurements, body weights, food consumption, and body temperature. Ophthalmoscopic examinations and respiratory function tests were performed on all animals at scheduled timepoints. Clinical pathology assessments (hematology, coagulation, clinical chemistry, and urinalysis) were evaluated at termination. Blood samples were collected from the jugular vein from the TK animals on Days 1 and 14, for up to 8 hours after treatment for bioanalysis of 5MeODMT concentrations in plasma and the subsequent calculation of toxicokinetic parameters. Following dosing, the Main animals were euthanized and subjected to a complete necropsy examination on Day 15. The Recovery animals were observed for an additional 14 days and then euthanized and subjected to a complete necropsy examination on Day 28. TK animals were euthanized after the last blood collection and discarded without further examination. At terminal euthanasia, selected tissues/organs were weighed, and microscopic evaluations of a standard set of tissues including the nasal turbinates (4 sections) and brain (7 sections) were performed for all Main and Recovery study animals.

Following dosing, animals in the Main group were euthanized and subjected to a necropsy examination on Day 15. The animals in the Recovery group were observed for 14 days and then euthanized and subjected to a necropsy examination on Day 28. For toxicokinetics, a series of 8 blood samples (approximately 0.5 mL each) were collected from all rats in the Toxicokinetic group (3 rats/sex/timepoint) on Days 1 and 14 of the treatment period at 2, 5, 10, 15 and 30 minutes, and 1.0, 3.0 and 8 hours after treatment. For control rats (3 rats/sex) in the Toxicokinetic group only 1 sample was collected at the 15 minutes post dosing timepoint on Days 1 and 14.

Toxicity was based on the following parameters monitored: mortality/morbidity, clinical observations, body weights/gains, food consumption, ophthalmoscopy, clinical pathology (hematology, coagulation, chemistry, and urinalysis), necropsy observations, selected organ weights, and microscopic examination of a complete set of standard tissues including 4 cross levels of the nasal cavity and 7 sections of the brain.

Results

All the samples met the acceptance criteria for accuracy (100±10% of their nominal concentration).

All animals were dosed without any major incidents and no sneezing was noted. All groups received their targeted doses on Days 1 to 10. As the maximum feasible loading dose was not to exceed 25 μL/naris (due to limited nasal surface area), once the bodyweights exceeded 333 g, male animals in all groups received slightly lower dose levels on Days 11 to 14. This was considered to have no impact on the study data as the differences were negligible.

No mortality occurred over the course of this study.

The observed clinical signs were as follows:

Group 2 (Low Dose)

Both male and female animals exhibited incoordination, shaking, salivation, decreased activity, lying on cage floor and sensitive to touch. For one female animal on Day 3, increased respiration was also observed.

Group 3 (Mid Dose)

Both male and female animals exhibited incoordination, shaking (or tremor), increased or shallow respiration, mydriasis, salivation, decreased activity, partially closed eyes, lying on cage floor and sensitive to touch. Male animals also exhibited erect penis.

Group 4 (High Dose)

Both male and female animals exhibited incoordination, shaking (or tremor), increased or shallow respiration, mydriasis, salivation, decreased activity, partially closed eyes, lying on cage floor and sensitive to touch. Male animals also exhibited erect penis.

Increased respiration was recorded for the mid and high dose group, however, measured respiratory values using plethysmographs proved that there were actually decreases in respiratory rates.

All the above clinical signs were considered to be transient for all groups.

Slight, generally dose-dependent body weight gain suppression was observed for both sexes between Days 1 to 14. There were no changes in food consumption that could be attributed to treatment with at dose levels ≤75 mg/kg/day for 14 days.

On Day 14, slight body temperature increases were observed at 15 minutes and 30 minutes postdose for all treated male animals, for females on Day 14, the body temperature increases were observed in one or all treated groups for all the timepoints (until 2 hours postdose). These increases in body temperature were more pronounced in the mid (20 mg/kg/day) and high (75 mg/kg/day) dose groups.

When compared to pretreatment or control group, decreases in respiratory rates were observed at 20 minutes postdose timepoint which resulted in decreases in respiratory minute volumes. Tidal volume values were either comparable to pre-dose or to control values. The 20-minute postdose respiratory measurements on Day 1 was not performed for Group 2 female animals inadvertently. This considered to have no impact on the study data as the data could be extrapolated form the male animals in the same group. There were no significant between the sexes.

There was no adverse ocular effect, caused by the administration of BPL-5MEO at dose levels 75 mg/kg/day for 14 days.

All other clinical observations, bodyweight changes, food consumption changes, and body temperature changes were considered to be not BPL-5MEO-related as they were sporadic, comparable to pretreatment signs or control animals, and not dose-related.

When compared to control Group, platelet, neutrophil, monocyte and basophil counts were slightly increased in mid and high dose groups in both sexes, however, these values were still within the historical ranges. On Day 28, all these values were compared to those in control group.

All changes in the hematology parameters, including those that reached statistical significance, were not attributed to the administration of BPL-5MEO as they were minor (within the normal physiological range), comparable to control values, and/or not dose-related.

When compared to control Group, activated partial thromboplastin times (APTT) were increased for both sexes in the mid (20 mg/kg/day) and high (75 mg/kg/day) dose groups. All the coagulation values on Day 28 were comparable to control group. All other changes in the coagulation parameters were not attributed to the administration of BPL-5MEO as they were minor (within the normal physiological range), comparable to control values, and/or not dose-related.

There were no changes in clinical chemistry and urinalysis parameters that could be attributed to the administration of BPL-5MEO at dose levels ≤75 mg/kg/day for 14 days. All changes in the parameters, including those clinical chemistry parameters that reached statistical significance, were not attributed to the administration of BPL-5MEO as they were minor (within the normal physiological range), comparable to control values, and/or not dose-related.

Compared to control values, there were decreases in thymus weights (absolute and relative to terminal body weight) observed in male animals as shown in Table 13.

TABLE 13

Thymus Weights for Male Animals Compared to Control Group

| Group (Males only) | Thymus Mean Absolute Weight[a] | Mean Relative to the Body Weight[a] |
|---|---|---|
| Control (Group 1) | 0.6028 | 0.1756 |
| Group 2 | −4 | −6 |
| Group 3 | 18 | −16 |
| Group 4 | −31 | −28 |

[a]For Control group, the organ weight in grams is reported, for other groups, the percentage compared to the control value is shown.

All changes in the organ weight parameters, including those that reached statistical significance, were not attributed to the administration of BPL-5MeO as they were minor, comparable to control values, and/or not dose related.

There were no macroscopic findings related to treatment with BPL-5MEO in rats in either the Main Recovery groups.

For animals in the Main group, microscopic findings related to treatment with BPL-5MEO, were noted in the nasal cavity sections 1, 2, 3 and 4 of Main rats.

A range of minimal to mild changes were noted in the respiratory, transitional, and/or olfactory epithelium of the nasal cavities, 1, 2, 3, and 4. The incidence and severity of changes were greater in males compared to females and were proportional to the dose of BPL-5MEO.

Microscopic changes observed in rats dosed with 75 mg/kg/day of BPL-5MEO (Group 4) included: respiratory epithelium, minimal to mild degeneration, hyperplasia, and squamous metaplasia, minimal mononuclear infiltrate and/or lumen exudate in nasal cavities 1, 2, 3, and/or 4; transitional epithelium, minimal hyperplasia in nasal cavity 1, and; olfactory epithelium, minimal to mild degeneration and/or minimal mononuclear infiltrate and erosion in nasal cavities 2, 3, and/or 4. Minimal degeneration of the olfactory epithelium of the nasal cavities 2 and 3 was noted in male and/or female rats dosed with 5 and/or 20 mg/kg/day of BPL-5MEO (Group 2 and 3). Minimal degeneration of the respiratory epithelium of the nasal cavities 1 and 2 was noted in male and/or female rats dosed with 20 mg/kg/day of BPL-5MEO (Group 3).

For animals in the Recovery group, microscopic findings related to treatment with BPL-5MEO, were noted in the nasal cavity sections 1, 2, 3, and 4 of Recovery rats. Minimal to mild changes were noted in the respiratory and olfactory epithelium of the nasal cavities, 1, 2, 3, and/or 4. The incidence and severity of changes were greater in males compared to females. Microscopic changes included minimal to mild degeneration of respiratory epithelium in nasal cavities 1 and 2 and minimal degeneration olfactory epithelium in nasal cavities 2, 3, and 4 indicating incomplete but progressive ongoing reversal of epithelial degeneration following a 14-day recovery period. There was complete reversal of all other microscopic changes noted previously in the nasal cavities of Main rats following a 14-day recovery period including reversal of epithelial hyperplasia, squamous metaplasia, mononuclear infiltrate, erosion, and lumen exudate.

Other microscopic findings in both the Main and Recovery groups were considered to be procedure-related or incidental as they were not dose-related, of low incidence or severity, and/or as they were also seen in the control animals.

Toxicokinetics

Over the dose range, exposure to 5MeODMT (based on the area under the plasma drug concentration-time curve from the time of dosing to the last quantifiable concentration [$AUC_{0-Tlast}$] values) on Days 1 and 14 generally increased dose-dependently (except for Group 4 as stated below), but not consistently in a dose-proportional manner as some increases were more or less than dose-proportional between different doses. Furthermore, on Day 14, the exposure in Female group 4 (75 mg/kg/day) decreased compared to Female Group 3 (20 mg/kg/day).

The sex ratios ranged between 0.4 and 6.2, but as the sex ratio randomly varied between dose groups and occasions, it was considered there was no sex-related difference.

Accumulation ratios (based on $AUC_{0-Tlast}$) ranged sporadically from 0.3 to 2.9 (Day 14/Day 1) suggesting that 5MeODMT does not accumulate when administered once daily for 14 consecutive days (2 weeks) by intranasal instillation in the Sprague Dawley rats at doses up to 75 mg/kg/days.

The mean toxicokinetic parameters for Groups 2, 3, and 4 are presented in Table 14.

tially closed eyes, lying on cage floor and sensitive to touch. Male animals also exhibited erect penis. Slight dose dependent body temperature increases were observed for both sexes.

Decreases in respiratory rates were observed at 20 minutes post dose timepoint which resulted in decreases in respiratory minute volumes. Platelet, neutrophil, monocyte and basophil counts were slightly increased in mid and high dose groups in both sexes. APTT were increased for both sexes for main animals in the mid (20 mg/kg/day) and high (75 mg/kg/day) dose groups. There were decreases in thymus weights (absolute and relative to terminal bodyweight) observed in male animals. Microscopic changes were noted in nasal cavities 1, 2, 3, and/or 4 involving the respiratory, olfactory, and transitional epithelium. The incidence and severity of findings were greater in males compared to females and were proportional to the dose of BPL-5MEO with incomplete but progressive on-going reversal following a 14-day recovery period.

The NOAEL was reported as the lowest dose of 5 mg/kg.

b. A 14-Day Repeat-Dose Intranasal Toxicity Study Followed by a 14-Day Recovery Period in Dogs (Study 62959)

The objective of this GLP study (Study 62959) was to determine the toxicity and TK profile of BPL-5MEO fol-

TABLE 14

Mean Toxicokinetic Parameters From Study 700041

| Group | Dose (mg/kg/day) | Parameter | Day 1 Male | Day 1 Female | Day 14 Male | Day 14 Female |
|---|---|---|---|---|---|---|
| 2 | 5 | $T_{max}$ (h) | 0.0833 | 0.166 | 0.0833 | 0.0333 |
|   |   | $AUC_{0-Tlast}$ [SE] | 39.9 [7.35] | 53.2 [15.9] | 114 [13.8] | 63.8 [4.55] |
|   |   | ($AUC_{INF\_obs}$) (h * ng/mL) | (40.1) | (53.7) | (115) | (64.0) |
|   |   | $C_{max}$ [SE] (ng/mL) | 191 [45.6] | 186 [98.7] | 627 [102] | 645 [106] |
|   |   | $t_{1/2}$ (h) | 0.137 | 0.150 | 0.142 | 0.113 |
| 3 | 20 | $T_{max}$ (h) | 0.0333 | 0.0833 | 0.0333 | 0.0833 |
|   |   | $AUC_{0-Tlast}$ [SE] | 420 [62.1] | 198 [15.2] | 133 [57.2] | 169 [21.2] |
|   |   | ($AUC_{INF\_obs}$) (h * ng/mL) | (421) | (198) | (133) | (169) |
|   |   | $C_{max}$ [SE] (ng/mL) | 4190 [1040] | 679 [162] | 1200 [857] | 795 [115] |
|   |   | $t_{1/2}$ (h) | 0.125 | 0.140 | 0.143 | 0.147 |
| 4 | 75 | $T_{max}$ (h) | 0.0333 | 0.0333 | 0.0333 | 0.0333 |
|   |   | $AUC_{0-Tlast}$ [SE] | 1030 [114] | 228 [49.7] | 391 [228] | 155 [53.8] |
|   |   | ($AUC_{INF\_obs}$) (h * ng/mL) | (1040) | (228) | (392) | (156) |
|   |   | $C_{max}$ [SE] (ng/mL) | 7010 [1010] | 1310 [802] | 3290 [2510] | 870 [361] |
|   |   | $t_{1/2}$ (h) | 0.133 | 0.156 | 0.116 | 0.130 |

Abbreviations:

$AUC_{0-Tlast}$ = Area under the plasma drug concentration-time curve from the time of dosing to the last quantifiable concentration;

$AUC_{INF\_obs}$ = Area under the plasma drug concentration-time curve from the time of dosing extrapolated to infinity;

$C_{max}$ = The maximum plasma concentration;

h = hours;

SE = standard error of mean;

$t_{1/2}$ = Terminal elimination half-life;

$T_{max}$ = Time to maximum plasma concentration.

Conclusion

Intranasal administration of BPL-5MEO at dose levels ≤75 mg/kg/day for 14 consecutive days was tolerated with no BPL-5MEO-related effects on mortality, ophthalmology, clinical chemistry, macroscopic findings and urinalysis. Slight dose-dependent body weight gain suppression was observed for both sexes. Transient clinical signs included incoordination, shaking (or tremor), increased or shallow respiration, mydriasis, salivation, decreased activity, parlowing intranasal instillation in Beagle dogs for 14 consecutive days and to assess the persistence, delayed onset, or reversibility of any changes following a 14-day recovery period.

BPL-5MEO and control/vehicle were administered to groups of dogs once daily by intranasal instillation for 14 consecutive days as described in Table 15.

TABLE 15

Doses Administered in 14-Day Repeat Dose Study in Dogs

| Group Number | Group Designation | Total Dose Level[b] (mg/kg/day) | Dose Conc. (mg/mL) | Dose Volume[d,e] (μL/kg) | Number of Animals | | | |
|---|---|---|---|---|---|---|---|---|
| | | | | | Main | | Recovery | |
| | | | | | Male | Female | Male | Female |
| 1 | Vehicle Control[a] | 0 | 0 | 10 Right Nostril + 10 Left Nostril | 3 | 3 | 2 | 2 |
| 2 | Low Dose | 0.4 | 20 | | 3 | 3 | — | — |
| 3 | Mid Dose | 0.8 | 40 | | 3 | 3 | — | — |
| 4 | High Dose | 2.5 & 1.5[c] | 125 & 75[c] | | 3 | 3 | 2 | 2 |

[a] Vehicle control animals were administered 0.1% Hydroxypropyl methyl cellulose (HPMC) in water.
[b] Dose levels refer to the freebase of 5MeODMT salt form.
[c] Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.
[d] The dose volume administered to each animal was 10 μL/kg/nostril.
[e] Dose volume was not to exceed 100 μL/nostril for all animals regardless of their bodyweight.

Assessments of mortality, clinical signs, olfactory reflex, body weights, food consumption, ophthalmology, and electrocardiograms were performed. In addition, clinical pathology assessments (hematology, coagulation, clinical chemistry and urinalysis) were evaluated once pretreatment and at termination. Blood samples were collected from the jugular vein of all animals on Days 1 and 14, at up to 8 time points relative to treatment, for analysis of test item concentration in plasma and the subsequent calculation of toxicokinetic parameters. Following dosing, the Main animals were euthanized and subjected to a complete necropsy examination on Day 15. The Recovery animals were observed for an additional 14 days test article free and then euthanized and subjected to a complete necropsy examination on Day 28. All Main and Recovery study animals underwent complete necropsy examinations, selected tissues/organs were retained, and microscopic evaluations of a standard set of tissues were performed.

For toxicokinetics, a series of 8 blood samples were collected from the jugular vein from all treated animals on each of Days 1 and 14 of the treatment period at 2, 5, 10, 15, 30, and 60 minutes as well as 3 and 8 hours after treatment. For Group 1, only one sample was taken at 15 minutes post dosing on Days 1 and 14 in order to confirm the absence of BPL-5MEO in animals in the vehicle control group. Blood samples were analysed for the BPL-5MEO concentration in plasma and the subsequent calculation of TK parameters.

Results

All the dose formulation samples collected and analyzed met the acceptance criteria for accuracy (100±10% of their nominal concentration).

Daily intranasal administration of BPL-5MEO to both nostrils of Beagle dogs once daily for 14 consecutive days at dose levels up to 1.5 mg/kg/day did not cause any mortality. High dose animals initially given to a subset of dogs at 2.5 mg/kg and showed severe clinical signs of muscle stiffness (rigidity), tachycardia, tachypnea, hyperthermia and aggressiveness after dosing on Day 1 and this dose exceeded the MTD. The high dose was subsequently lowered on Day 2 to 1.5 mg/kg/day and this dose was tolerated. Animals in all treated Groups exhibited transient clinical observation of incoordination, vocalization, mydriasis, decreased or increased activity, increased respiration, gnawing cage wire, excessive licking of nose or lips and circling. In addition, eye discharge and shaking were observed in the Mid and High dose groups. Erect penis was also recorded for the high dose male animals. All these clinical signs were considered to be exacerbated pharmacology manifestations, occurred within 10 to 30 minutes of dosing, and were resolved within 90 minutes.

When compared to control Group, the triglyceride level of ⅓ Group 3 female, ⅕ Group 4 male and ⅘ Group 4 females were increased, these data are presented in Table 16. There were no other treatment-related clinical pathology findings.

TABLE 16

Mean ± SD Day 14 Triglyceride Values Compared to Control Group

| Group | Dose (mg/kg/day) | Triglyceride (mmol/L) | |
|---|---|---|---|
| | | Males[a] | Females[a] |
| Group 1 | Control | 0.38 ± 0.13 | 0.34 ± 0.12 |
| Group 2 | 0.4 | 0.40 ± 0.11 | 0.46 ± 0.61 |
| Group 3 | 0.8 | 0.44 ± 0.07 | 0.47 ± 0.22 |
| Group 4 | 2.5 & 1.5[b] | 0.42 ± 0.16 | 0.69 ± 0.24 |

Abbreviations:
SD = standard deviation
[a] for Control group, the control value is mentioned, for other groups, the percentage compared to the control value is shown.
[b] Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.

All other changes in the clinical chemistry parameters, including those that reached statistical significance, were not attributed to the administration of BPL-5MEO as they were minor (within the normal physiological range), comparable to control values, and/or not dose related.

There were no changes in olfactory reflex, food consumption, body weight, ocular effect, or ECG that could be clearly attributed to treatment with BPL-5MEO at a dose level ≤1.5 mg/kg/day for 14 days. All body weight changes were not attributed to the administration of the test item as they were minor, and not toxicologically relevant. All food consumption changes, including those that were statistically significant, were not attributed to the administration of the test item as they were minor, and not toxicologically relevant.

Animals showed hyperthermia at the dose level of 2.5 mg/kg/day on Day 1. Transient body temperature increases were observed on Day 14 for high dose group in both sexes at 15 and 30 minutes postdose. All other body temperature changes were not attributed to the administration of the test item as they were minor, and not toxicologically relevant.

Histopathological examination results for Main animals included minimal to moderate decreased cellularity of the thymic lymphocytes at dose levels of 0.8 (1 male) and 1.5 mg/kg/day (3 males), which was determined as stress related. Minimal epithelial metaplasia of respiratory epithelium in the nasal cavities found at dose levels of 0.8 (1 female) and 1.5 mg/kg/day (2 males) and minimal to mild mononuclear cell infiltrate of the olfactory epithelium in the nasal cavities seen at a dose level of 1.5 mg/kg/day (1 male/1 female) were considered to be signs of irritation caused by BPL-5MEO but not adverse.

In animals euthanized after a 14-day recovery period, only minimal mononuclear cell infiltrate of the olfactory epithelium in the nasal cavities was still present at a dose level of 1.5 mg/kg/day (1 female) but at a lower severity when compared with animals euthanized terminally, indicative of recovery. Decreased cellularity of thymic lymphocytes was no longer observed.

Toxicokinetics

BPL-5MEO was not detected in any of the samples collected from the Control (Group 1) animals on Days 1 and 14.

The mean toxicokinetic parameters for Groups 2, 3, and 4 are presented in the table below.

with the exception of Group 4 $T_{max}$, ranged sporadically from 0.5 to 1.7 on Days 1 and 14.

Accumulation ratios (based on $AUC_{0\text{-}Tlast}$) ranged sporadically from 0.6 to 2.0 (Day 14/Day 1) suggesting that BPL-5MEO does not accumulate when administered once daily for 14 consecutive days (2 weeks) by intranasal instillation in beagle dogs at doses up to 1.5 mg/kg/day.

Conclusion

Based on the parameters examined where all the changes noted were considered either non-adverse or related to exaggerated pharmacological effects, the reported NOAEL for BPL-5MEO, when dosed for 14 consecutive days by intranasal administration, followed by a 14-day recovery period was considered to be 1.5 mg/kg/day, corresponding to a $C_{max}$ of 421 ng/mL, and $AUC_{0\text{-}Tlast}$ ($AUC_{INT\_obs}$) of 213 (220) h*ng/mL (combined for both sexes).

Toxicokinetic Considerations

Based on preliminary data from another ongoing study in dogs, it has been observed that the site of blood sampling in dogs may impact the measured plasma exposure. Samples from the jugular vein may result in higher apparent exposure levels than samples from the cephalic vein, which might be

| | | | Mean Toxicokinetic Parameters From Study 62959 | | | |
|---|---|---|---|---|---|---|
| | Dose | | Day 1 | | Day 14 | |
| Group | (mg/kg/day) | Parameter | Male | Female | Male | Female |
| 2 | 0.4 | $T_{max}$ (h) | 0.0942 | 0.194 | 0.111 | 0.0942 |
| | | $AUC_{0\text{-}Tlast}$ ($AUC_{INF\_obs}$) (h * ng/mL) | 77.9 (80.9) | 104 (106) | 70.6 (77.7) | 86.4 (95.9) |
| | | $C_{max}$ (ng/mL) | 343 | 242 | 285 | 196 |
| | | $t_{1/2}$ (h) | 0.571 | 0.312 | 0.429 | 0.706 |
| 3 | 0.8 | $T_{max}$ (h) | 0.111 | 0.139 | 0.111 | 0.0833 |
| | | $AUC_{0\text{-}Tlast}$ ($AUC_{INF\_obs}$) (h * ng/mL) | 152 (160) | 261 (265) | 298 (322) | 248 (279) |
| | | $C_{max}$ (ng/mL) | 300 | 328 | 411 | 244 |
| | | $t_{1/2}$ (h) | 0.595 | 0.730 | 1.32 | 1.59 |
| 4 | 2.5 & 1.5[a] | $T_{max}$ (h) | 0.146 | 0.111 | 0.223 | 0.0898 |
| | | $AUC_{0\text{-}Tlast}$ ($AUC_{INF\_obs}$) (h * ng/mL) | 277 (280) | 263 (271) | 260 (287) | 165 (167) |
| | | $C_{max}$ (ng/mL) | 561 | 348 | 464 | 379 |
| | | $t_{1/2}$ (h) | 0.718 | 0.848 | 0.816 | 0.725 |

Abbreviations:
$AUC_{0\text{-}Tlast}$ = Area under the plasma drug concentration-time curve from the time of dosing to the last quantifiable concentration;
$AUC_{INF\_obs}$ = Area under the plasma drug concentration-time curve from the time of dosing extrapolated to infinity;
$C_{max}$ = The maximum plasma concentration;
h = hours;
$t_{1/2}$ = Terminal elimination half-life;
$T_{max}$ = Time to maximum plasma concentration.
[a]Replicate A high dose animals showed severe clinical signs of muscle stiffness (rigidity), tachycardia, tachypnea, hyperthermia and aggressiveness after dosing on Day 1 at the dose level of 2.5 mg/kg. The dose level was subsequently decreased on Day 1 for the Replicates B and C to 1.5 mg/kg. Replicate A received 1.5 mg/kg on Days 2 to 14.

Over the dose range, exposure to BPL-5MEO (based on $AUC_{0\text{-}Tlast}$ values) on Days 1 and 14 generally increased dose-dependently (except for Group 4 as stated below), but not consistently in a dose-proportional manner as some increases were more or less than dose-proportional between different doses. Furthermore, on Day 14, the exposure in Group 4 (1.5 mg/kg/day) decreased compared to Group 3 (0.8 mg/kg/day).

There were no marked sex-related differences in any of the measured toxicokinetic parameters, except on Day 14 where $T_{max}$ occurred slightly later in Group 4 males as compared to Group 4 females. The sex ratios (male/female), due to the local transmucosal route of administration (also reported in the scientific literature (Illum, 2003; Sohlberg, 2013)). Therefore, dose escalation criteria for the Phase 1 Single Ascending Dose study are based on assessment of clinical criteria, safety factors and exposure. A maximum dose of 14 mg has been designated. The Table below summarizes the clinical observations in the rat and dog toxicity studies performed with BPL-5MEO. These clinical signs are considered to be related to the pharmacological activity of BPL-5MEO and demonstrate a dose-related increase in severity of findings on both species, generally ranging from mild to moderate at 0.4 to 1.5 mg/kg in dogs and 1.5 to 5 mg/kg in rats.

| Summary of Clinical Observations in Applicant-Sponsored Animal Studies | | | | |
|---|---|---|---|---|
| Dog (HED) | | | | |
| 0.4 mg/kg (14 mg) | 0.8 mg/kg (26 mg) | 1.5 mg/kg[a] (50 mg) | 2.5 mg/kg (83 mg) | 3.0-5.0 mg/kg (100-166 mg) |
| Salivation Mydriasis Incoordination Vocalization Decreased activity Increased activity Increased respiration Gnawing cage wire Excessive licking Circling | Mydriasis Salivation Excessive licking Incoordination Vocalization Decreased activity Increased activity Increased respiration Gnawing cage wire Circling Eye discharge Shaking Head shaking Slighttremor (1.0 mg/kg)[b] | Mydriasis Salivation, Excessive licking Dilated pupil Vocalizing Tachypnea Increased respiration Tachycardia Muscle rigidity Erect penis Twitches Tense abdomen Splay posture Lying on cage floor Uncoordinated Circling Head shaking Tremor Myoclonic jerk[b] | Salivation Pupil dilated Circling Muscle stiffness Activity decreased Increased respiration Diarrhea Hunched Erect penis Excessive grooming Excessive fear Hypersensitive to stimuli Aggressiveness Tachycardia Loss of righting reflex Hyperthermia (single dose) Shaking Tremors | Mydriasis Salivation Excessive licking Dilated pupil Vocalizing Labored respiration Gnawing cage Tongue outside Hunched Erect penis Tremor Shaking Lying Decreased activity Uncoordinated Aggressiveness Circling Not responsive to stimuli Hyperthermia Convulsion |
| Rat (HED) | | | | |
| 1.5 mg/kg (14 mg) | 3.0 mg/kg (29 mg) | 5.0 mg/kg[a] (48 mg) | 10 mg/kg (96 mg) | 20-75 mg/kg (194-726 mg) |
| Salivation Piloerection Increased respiration Dilated pupils Decreased activity Decreased rearing Lying Hypothermia (single dose) | Salivation Piloerection Increased respiration Gasping Dilated pupils Decreased activity Decreased rearing Lying Hypothermia (single dose) | Salivation Piloerection Increased respiration Dilated pupils Slight hyperthermia (repeated dose) Uncoordinated Shaking Decreased activity Lying Uncoordinated Tremor Sensitive to touch | Salivation Piloerection Decreased activity Increased or shallow respiration Gasping Lying Decreased rearing Hypothermia (single dose) Twitching Tremor | Increased respiration Shallow respiration Mydriasis Salivation Decreased activity Partially closed eyes Lying on cage floor Sensitive to touch Erect penis Hyperthermia Uncoordinated Shaking (or tremor) |

Abbreviations:
HED = Human Equivalent Dose (for a 60 kg human)
[a]= NOAEL determined in the 14-day toxicology studies for both species.
[b]= Preliminary data, ongoing study (Slight tremor was observed at 1.0 mg/kg = 33 mg HED)
Note:
these signs were of short duration, and generally resolved within one to two hours in both species.

Example 14: Genotoxicity

The genotoxicity potential of 5MeODMT was evaluated in silico (computational analysis) for structural alerts and in vitro in GLP assays to assess mutagenic and clastogenic potential following the ICH 52 (R1) Guidance.

In Silico

5MeODMT, its primary active metabolite, bufotenine, and an identified drug substance impurity, MW234, were evaluated for quantitative structural activity relationships for potential mutagenicity and/or carcinogenicity using two computation analytical methods, Derek Nexus and the Leadscope Genetox Statistical Models. The evaluation from both analyses did not identify any structural alerts associated with 5MeODMT or bufotenine, and a possible nor an identified drug substance impurity MW234.

In Vitro Mutagenicity

The mutagenic potential of 5MeODMT was evaluated in a GLP Bacterial Reverse Mutation Test (Ames test) for the ability to induce reverse mutations at selected loci of *Salmonella typhimurium* tester strains TA98, TA100, TA1S35, and TA1537 and the *Escherichia coli* tester strain WP2uvrA. These strains were treated with 5MeODMT at concentrations of 1.6, 5, 16, 50, 160, 500, 1600 and 5000 µg per plate along with the vehicle/negative and appropriate positive controls. The assay was performed in triplicate using the pre-incubation method in the absence and presence of an exogenous metabolic activation system, phenobarbital/5,6-benzoflavone-induced rat liver S9 microsomal enzyme mix (S9 mix)

A slight cytotoxicity was seen at the concentration of 1600 µg/plate in all *S. typhimurium* strains. Although higher levels of cytotoxicity were observed at 5000 µg/plate in the absence of S9 mix, it remained slight in the presence of S9 mix in these strains. No cytotoxicity was noted in the *E. coli* strain in either the absence or presence of S9 mix.

Overall, no increases (≥2× of the vehicle/negative values) in the number of revertant colonies per plate was observed with 5MeODMT in *S. typhimurium* tester strains TA1535, TA100, *E. coli* WP2uvrA in either the absence and presence of S9 or with TA1537 and TA98 in the presence of S9 mix. Three exceptions were a 2.1-fold increase at 1600 μg/plate without S9 seen in *E. coli* WP2uvrA, a 2.0-fold increase in *S. typhimurium* TA1537 at 50 μg/plate with S9, and 2.1-fold increase in *S. typhimurium* TA1535 at 1600 μg/plate with S9. However, these values were not considered biologically relevant as the values were within laboratory's historical vehicle/negative control range and were not dose-related.

Two of the 5MeODMT-treated *S. typhimurium* strains, TA1537 and TA98, in the absence of S9 mix, showed a number of revertant colony counts slightly higher than twice of the vehicle/negative values at 160 μg/plate and 500 μg/plate with fold-increases at 2.3- and 2.7-fold in TA1537 and 2.2- and 2.4-fold in TA98. The increased colony counts observed in these strains were still within the laboratory's historical vehicle/negative control range and were not overall dose-related; therefore, they did not meet the criteria of positive results. However, as the increases were seen in TA98 and TA1537 in 2 adjacent dose levels and that 2 strains showed a similar trend of increases in revertant colony counts at the same concentration levels, the results were judged equivocal. Therefore, the bacterial reverse mutation test was repeated in the absence of S9 mix for these 2 strains in order to investigate these equivocal results. The repeat test used a narrower concentration range of 15, 30, 60, 120, 250, 500, 1000, and 2000 μg per plate. The results from repeated test showed no increases in the revertant colonies number per plate for both 5MeODMT-treated strains in all concentration levels tested up to the maximal dose of 2000 μg/plate. Therefore, it was concluded that the small increases observed in the first test for *S. typhimurium* tester stains TA 1537 and TA98 were not biologically relevant.

In conclusion, the results of the bacterial reverse mutation assays indicated that 5MeODMT did not induce any increase in revertant colony numbers with any of the bacteria strains tested either in the absence or presence of the rat liver S9 microsomal metabolic activation system. 5MeODMT has no mutagenic potential in the bacterial reverse mutation test. The expected response of the positive and negative controls affirmed the sensitivity and validity of assay.

In Vitro Clastogenicity

The clastogenic potential of 5MeODMT was evaluated in a GLP in vitro micronucleus test using Chinese hamster ovary (CHO)-K1 cells using flow cytometry. Exponentially growing cells were treated in duplicate with the 5MeODMT at 9 concentrations up to the recommended upper limit of 1 mM (corresponding to approximately 300 μg/mL): 1.25, 2.5, 5.0, 10, 20, 40, 80, 150 and 300 μg/mL. The treatment with the vehicle/negative and positive controls was concurrently performed. There were 3 treatment regimens: a 4-hour-short exposure in either absence or presence of an exogenous metabolic activation system, phenobarbital/5,6 benzoflavone rat liver S9 microsomal enzyme mix (S9 mix), and a 26 hour-extended exposure, considered a confirmatory phase, in the absence of S9 mix.

No cytotoxicity or precipitation was observed in 5MeODMT-treated cells up to the maximal dose level of 300 μg/mL throughout the treatment periods. In all treatment regimens, the results of the in vitro micronucleus test indicate that 5MeODMT did not induce any increases in micronuclei or hypodiploid cells either in the absence or presence of the rat liver S9 microsomal metabolic activation system. In conclusion, 5MeODMT showed no chromosome-damaging potential in the in vitro micronucleus test with CHO-K1 cells. The expected response of the positive and negative controls affirmed the sensitivity and validity of assay.

Reproductive and Development Toxicity

Reproductive and developmental toxicity studies have not been conducted. In the 14-day pivotal GLP intranasal toxicity studies in rats and dogs, there was no evidence of an adverse effect on reproductive tissues with systemic exposure to BPL-5MEO.

Example 15: Formulation

BPL-5MEO has been synthesised to Good Manufacturing Practice (GMP) standards and prefilled into the Aptar Unidose Intranasal Liquid Delivery System device. The device allows a single fixed dose of BPL-5MEO to be administered intranasally. The liquid is prefilled into and administered using a standard single unit dose nasal pump device. Excipients used in the formulation are water, 0.1% hydroxypropyl methylcellulose (HPMC) and sodium hydroxide (NaOH). Two concentrations of the formulation will be used, 70 mg/mL (for dose levels below 7 mg), and 140 mg/mL (for dose levels above 7 mg).

In an embodiment, there is provided a composition comprising 5MeODMT hydrochloride, wherein the composition comprises:
water;
0.1% hydroxypropyl methylcellulose (HPMC);
0.1% sodium hydroxide (NaOH); and
70 mg/ml 5MeODMT.

In an embodiment, there is provided a composition comprising 5MeODMT benzoate, wherein the composition comprises:
water;
0.1% hydroxypropyl methylcellulose (HPMC);
0.1% sodium hydroxide (NaOH); and
70 mg/ml 5MeODMT.

In an embodiment, there is provided a composition comprising 5MeODMT hydrochloride, wherein the composition comprises:
water;
0.1% hydroxypropyl methylcellulose (HPMC);
0.1% sodium hydroxide (NaOH); and
140 mg/ml 5MeODMT.

In an embodiment, there is provided a composition comprising 5MeODMT benzoate, wherein the composition comprises:
water;
0.1% hydroxypropyl methylcellulose (HPMC);
0.1% sodium hydroxide (NaOH); and
140 mg/ml 5MeODMT.

In an embodiment, there is provided an intranasal composition comprising 5MeODMT hydrochloride, wherein the composition comprises:
water;
0.1% hydroxypropyl methylcellulose (HPMC);
0.1% sodium hydroxide (NaOH); and
70 mg/ml 5MeODMT.

In an embodiment, there is provided an intranasal composition comprising 5MeODMT benzoate, wherein the composition comprises:
water;
0.1% hydroxypropyl methylcellulose (HPMC);
0.1% sodium hydroxide (NaOH); and
70 mg/ml 5MeODMT.

In an embodiment, there is provided an intranasal composition comprising 5MeODMT hydrochloride, wherein the composition comprises:
water;
0.1% hydroxypropyl methylcellulose (HPMC);
0.1% sodium hydroxide (NaOH); and
140 mg/ml 5MeODMT.

In an embodiment, there is provided an intranasal composition comprising 5MeODMT benzoate, wherein the water;
0.1% hydroxypropyl methylcellulose (HPMC);
0.1% sodium hydroxide (NaOH); and
140 mg/ml 5MeODMT.
composition comprises:

In an embodiment, the composition comprises 25-400 mg/mL; 25-300 mg/mL; 25-200 mg/mL; 25-100 mg/mL; 25-50 mg/mL; 50-400 mg/mL; 50-300 mg/mL; 60-400 mg/mL; 60-300 mg/mL; 150-400 mg/mL; 150-300 mg/mL; 200-300 mg/mL; 200-400 mg/mL; 30-100 mg/mL; 300-400 mg/mL; 300-500 mg/mL; 45-75 mg/mL; 50-70 mg/mL; 55-65 mg/mL; or 50-60 mg/mL 5MeODMT.

In an embodiment, there is provided an intranasal liquid delivery system comprising a composition of 5MeODMT.

In an embodiment, there is provided a single unit dose capsule of a composition of 5MeODMT.

In an embodiment, there is provided an intranasal composition comprising a dosage amount 50-150 mg/ml 5MeODMT in a liquid medium, wherein the 5MeODMT is formulated as the benzoate salt of 5MeODMT (5MeODMT benzoate).

In an embodiment, 5MeODMT benzoate is present as a suspension or emulsion in the liquid medium.

In an embodiment, there is provided an intranasal liquid delivery system comprising:
70 to 140 mg/ml of 5MeODMT benzoate as a suspension or emulsion in a liquid medium.

Example 16: Administration

BPL-5MEO is administered to subjects by a trained member of the research team using a single unit dose pump spray. The unit contains only 1 spray, so should not be tested before use. While sitting down the subject is asked to blow their nose to clear the nasal passages. Once the tip of the device is placed into the nostril the clinic staff will press the plunger to release the dose.

In an embodiment, there is provided a method for the administration of 5MeODMT comprising administering the 5MeODMT as an instranasal spray to a human subject wherein the human subject has followed patient preparation parameters that include blowing their nose to clear their nasal passages immediately prior to administration.

In an embodiment, the human subject is seated.

In an embodiment, there is provided a method for the delivery of 5MeODMT to the brain of a human subject comprising administering the 5MeODMT as an instranasal spray to a human subject wherein the human subject has followed patient preparation parameters that include blowing their nose to clear their nasal passages immediately prior to administration.

Example 17: X-Ray Powder Diffraction (XRPD) of 5MeODMT Benzoate

The XRPD pattern of 5MeODMT benzoate salt, was acquired before and following particle size reduction with a mortar and pestle. This reduced the intensity of dominant diffractions and revealed that the XRPD pattern of the benzoate salt was prone to preferred orientation prior to particle size reduction, which is a function of the habit and particle size of the material. XRPD patterns of the benzoate salt prior to and following particle size reduction can be seen in FIGS. 6 and 7 respectively. The XRPD patterns of the benzoate salt prior to and following particle size reduction overlaid on one another can be seen in FIG. 8.

In an embodiment, there is provided crystalline 5MeODMT benzoate, characterised by peaks in an XRPD diffractogram at 17.5, 17.7 and 21.0° 2θ±0.1° 2θ.

In an embodiment, there is provided crystalline 5MeODMT benzoate, characterised by peaks in an XRPD diffractogram at 17.5, 17.7 and 21.0° 2θ±0.2° 2θ.

In an embodiment, there is provided crystalline 5MeODMT benzoate, characterised by peaks in an XRPD diffractogram at 17.5, 17.7 and 21.0° 2θ±0.3° 2θ.

In an embodiment, there is provided crystalline 5MeODMT benzoate, characterised by peaks in an XRPD diffractogram at 17.5, 17.7 and 21.0° 2θ±0.1° 2θ as measured by x-ray powder diffraction using an x-ray wavelength of 1.5406 A.

In an embodiment, there is provided crystalline 5MeODMT benzoate, characterised by peaks in an XRPD diffractogram at 17.5, 17.7 and 21.0° 2θ±0.2° 2θ as measured by x-ray powder diffraction using an x-ray wavelength of 1.5406 A.

In an embodiment, there is provided crystalline 5MeODMT benzoate, characterised by peaks in an XRPD diffractogram at 17.5, 17.7 and 21.0° 2θ±0.3° 2θ as measured by x-ray powder diffraction using an x-ray wavelength of 1.5406 A.

In an embodiment, there is provided crystalline 5MeODMT benzoate, characterised by peaks in an XRPD diffractogram at 17.5, 17.7, 21.0 and 25.3° 2θ±0.1° 2θ.

In an embodiment, there is provided crystalline 5MeODMT benzoate, characterised by peaks in an XRPD diffractogram at 17.5, 17.7, 21.0 and 25.3° 2θ±0.2° 2θ.

In an embodiment, there is provided crystalline 5MeODMT benzoate, characterised by peaks in an XRPD diffractogram at 17.5, 17.7, 21.0 and 25.3° 2θ±0.3° 2θ.

In an embodiment, there is provided crystalline 5MeODMT benzoate, characterised by peaks in an XRPD diffractogram at 17.5, 17.7, 21.0 and 25.3° 2θ±0.1° 2θ as measured by x-ray powder diffraction using an x-ray wavelength of 1.5406 A.

In an embodiment, there is provided crystalline 5MeODMT benzoate, characterised by peaks in an XRPD diffractogram at 17.5, 17.7, 21.0 and 25.3° 2θ±0.2° 2θ as measured by x-ray powder diffraction using an x-ray wavelength of 1.5406 A.

In an embodiment, there is provided crystalline 5MeODMT benzoate, characterised by peaks in an XRPD diffractogram at 17.5, 17.7, 21.0 and 25.3° 2θ±0.3° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.1° 2θ.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.2° 2θ.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.3° 2θ.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.1° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.2° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.5, 17.5, 17.7, 18.5, 21.0, 22.7, 24.7 and 25.3° 2θ±0.3° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.1° 2θ.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.2° 2θ.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.3° 2θ.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.1° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.2° 2θ as measured by x-ray powder diffraction using an x-ray wavelength of 1.5406 A.

In an embodiment, there is provided crystalline 5MeODMT benzoate, characterised by peaks in an XRPD diffractogram at 9.0, 11.5, 14.5, 16.3, 16.5, 17.5, 17.7, 18.5, 21.0, 22.7, 24.7, 25.3 and 30.5° 2θ±0.3° 2θ as measured by x-ray powder diffraction using an x-ray wavelength of 1.5406 A.

Figure 6:
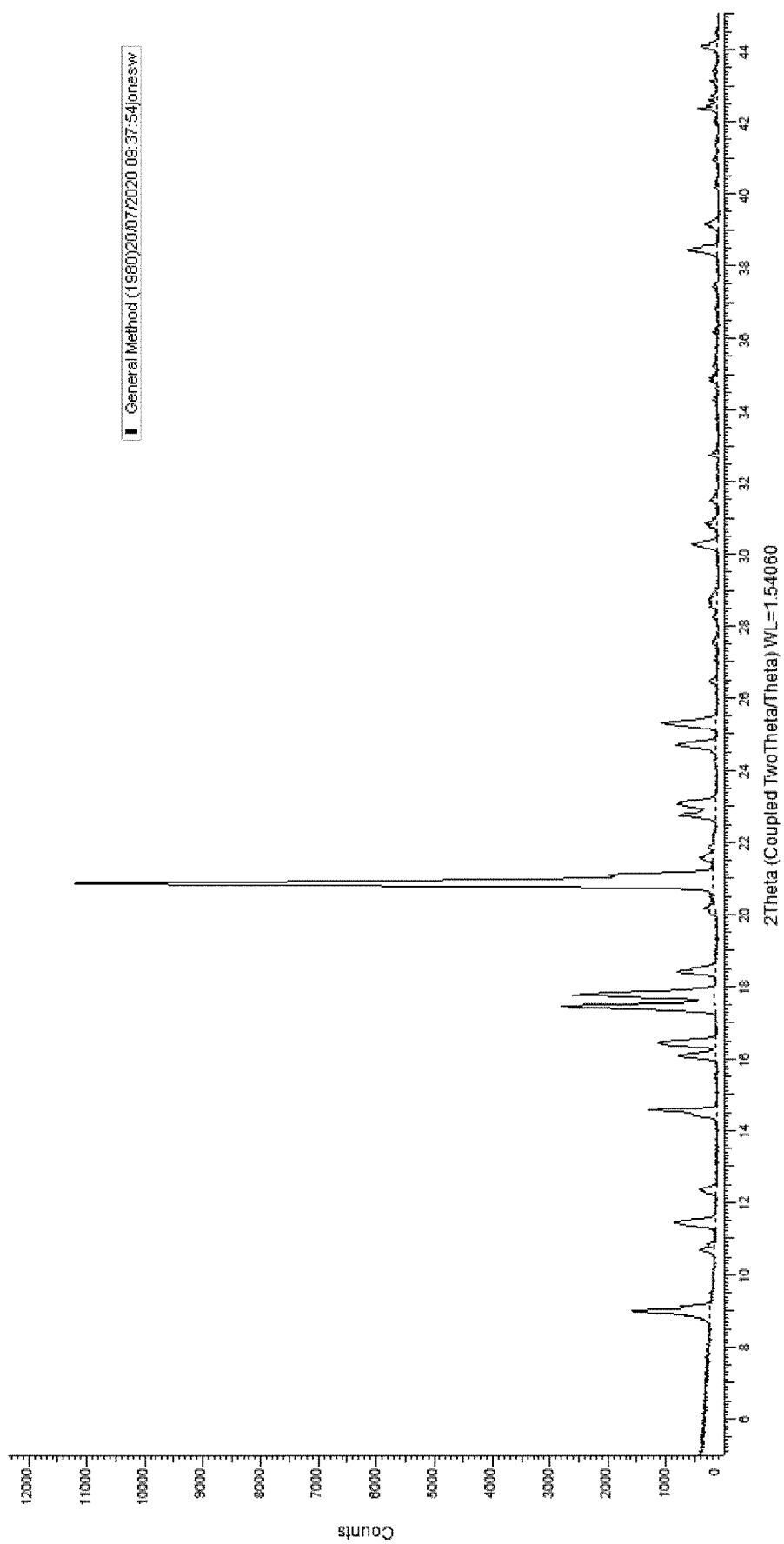
FIG. 6 shows an XRPD diffractogram of 5MeODMT benzoate prior to particle size reduction.
Figure 7:
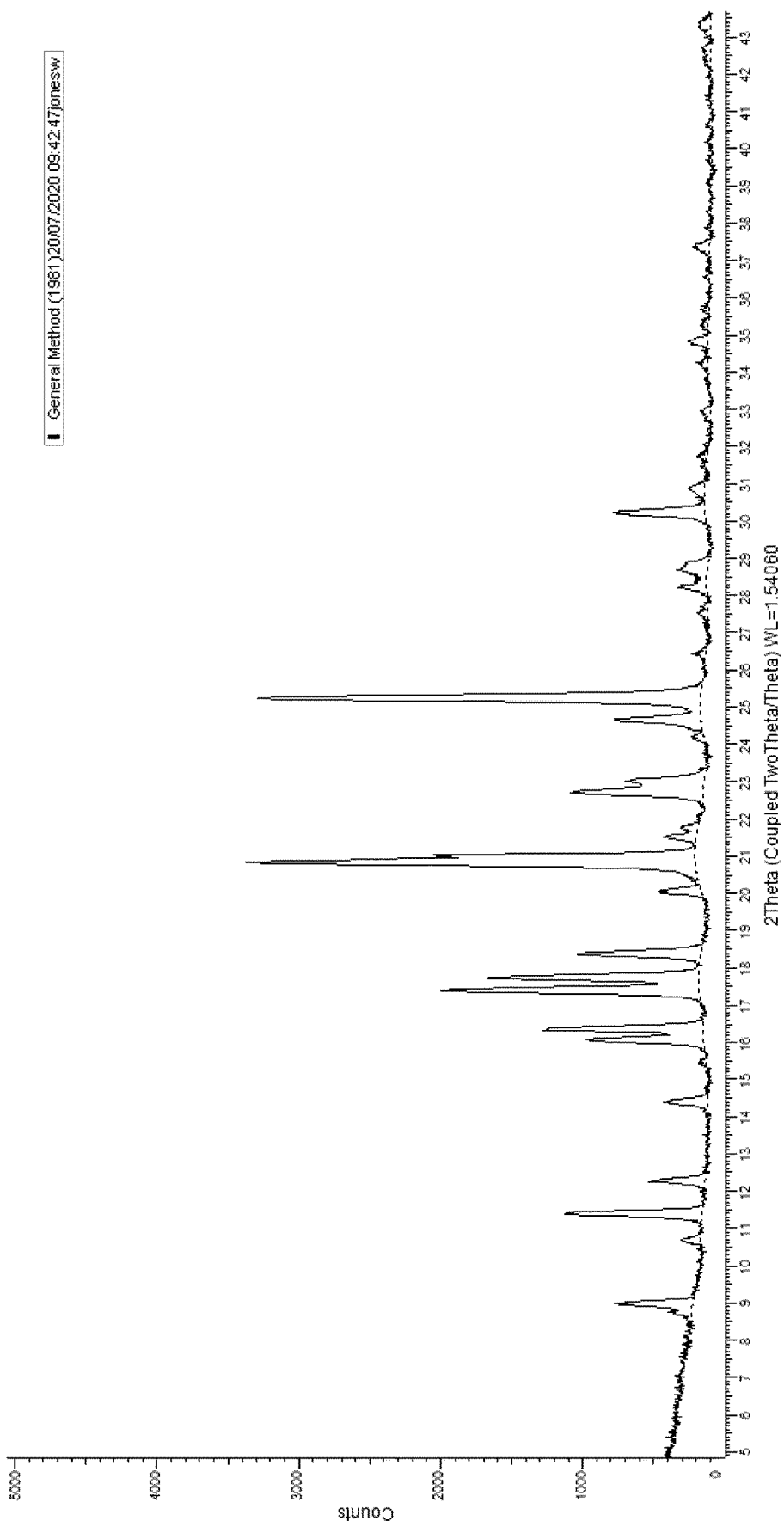
FIG. 7 shows an XRPD diffractogram of 5MeODMT benzoate following particle size reduction.
Figure 8:
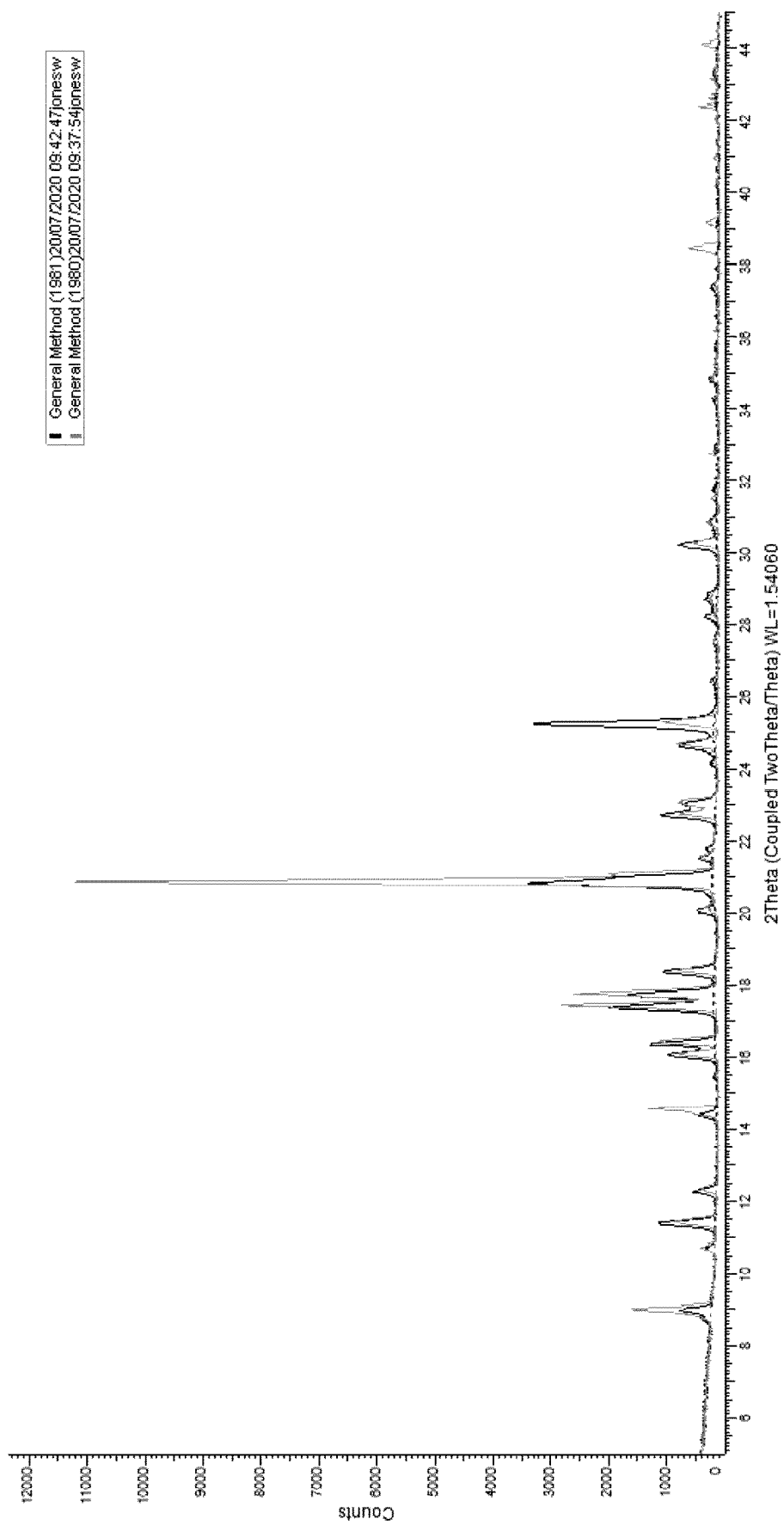
FIG. 8 shows the XRPD diffractograms of FIGS. 6 and 7 overlaid on one another.

In an embodiment, there is provided crystalline 5MeODMT benzoate, characterised by peaks in an XRPD diffractogram as substantially illustrated in FIG. 6, 7 or 8.

In an embodiment, there is provided crystalline 5MeODMT benzoate, characterised by peaks in an XRPD diffractogram as substantially illustrated in FIG. 6.

In an embodiment, there is provided crystalline 5MeODMT benzoate, characterised by peaks in an XRPD diffractogram as substantially illustrated in FIG. 7.

In an embodiment, there is provided crystalline 5MeODMT benzoate, characterised by peaks in an XRPD diffractogram as substantially illustrated in FIG. 8.

In an embodiment, there is provided crystalline 5MeODMT benzoate, characterised by one or more of:
Peaks in an XRPD diffractogram as previously or subsequently described;
An endothermic event in a DSC thermograph as previously or subsequently described;
An onset of decomposition in a TGA thermograph as previously or subsequently described;
A DVS isotherm profile as previously or subsequently described; and
A crystalline structure as previously or subsequently described.

Example 18: Thermal Analysis of 5MeODMT Benzoate

The differential scanning calorimetry (DSC) thermograph of 5MeODMT benzoate salt, contained one endotherm with an onset of 123.34° C., peak of 124.47° C. and an enthalpy of 134.72 J/g. There were no other thermal events. The DSC thermograph, acquired at 10° C./min, can be seen in FIG. 9.

In an embodiment, there is provided crystalline 5MeODMT benzoate, characterised by an endothermic event in a DSC thermograph having an onset temperature of between 120 and 130° C.

Figure 9:
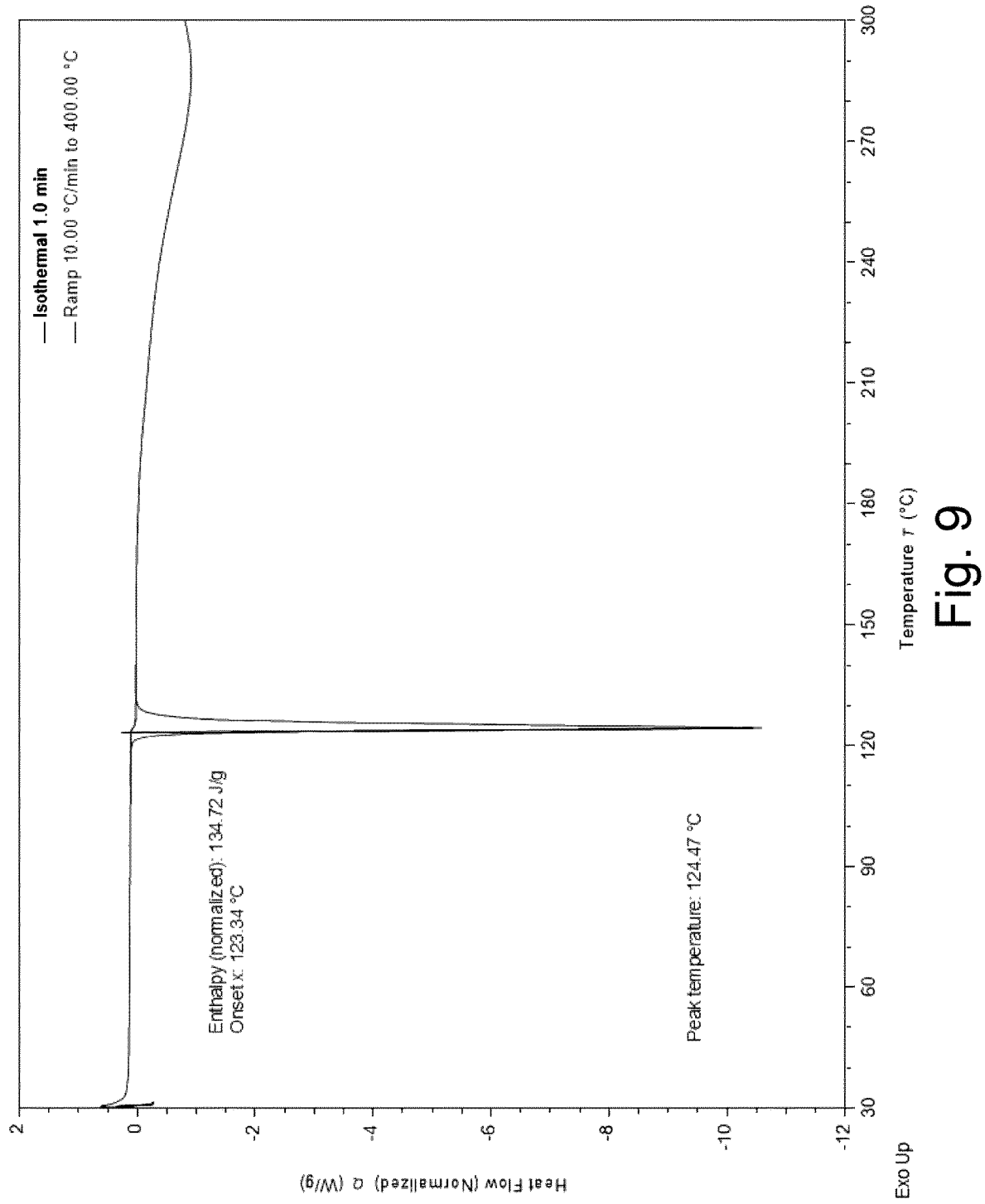
FIG. 9 shows a DSC thermograph of 5MeODMT benzoate.

In an embodiment, there is provided crystalline 5MeODMT benzoate, characterised by an endothermic event in a DSC thermograph having an onset temperature of between 120 and 130° C. as substantially illustrated in FIG. 9.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., between 124 and 126° C.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., between 124 and 126° C. as substantially illustrated in FIG. 9.

In an embodiment, there is provided crystalline 5MeODMT benzoate, characterised by an endothermic event in a DSC thermograph having an onset temperature of 123° C.

In an embodiment, there is provided crystalline 5MeODMT benzoate, characterised by an endothermic event in a DSC thermograph having an onset temperature of 123° C. a substantially illustrated in FIG. 9.

In an embodiment, there is provided crystalline 5MeODMT benzoate, characterised by an endothermic event in a DSC thermograph having an onset temperature of 124° C.

In an embodiment, there is provided crystalline 5MeODMT benzoate, characterised by an endothermic event in a DSC thermograph having an onset temperature of 124° C. as substantially illustrated in FIG. 9.

In an embodiment, there is provided crystalline 5MeODMT benzoate, characterised by an endothermic event in a DSC thermograph having an onset temperature of between 120 and 130° C. and a peak of between 122 and 128° C.

In an embodiment, there is provided crystalline 5MeODMT benzoate, characterised by an endothermic event in a DSC thermograph having an onset temperature of between 120 and 130° C. and a peak of between 122 and 128° C. as substantially illustrated in FIG. 9.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C. and a peak of between 124 and 126° C.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C. and a peak of between 124 and 126° C. as substantially illustrated in FIG. 9.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., and a peak of between 124 and 126° C. and an enthalpy of between −130 and −140 J/g.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., and a peak of between 124 and 126° C. and an enthalpy of between −130 and −140 J/g as substantially illustrated in FIG. 9.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., and a peak of between 124 and 126° C. and an enthalpy of between −130 and −135 J/g.

In an embodiment, there is provided crystalline 5MeODMT benzoate, characterised by an endothermic event in a DSC thermograph having an onset temperature of between 120 and 130° C., between 121 and 129° C., between 122 and 128° C., between 123 and 127° C., and a peak of between 124 and 126° C. and an enthalpy of between −130 and −135 J/g as substantially illustrated in FIG. 9.

The thermogravimetric analysis (TGA) thermograph of 5MeODMT benzoate salt, revealed that the onset of decomposition was ca 131° C., which is past the melt at ca 125° C. The TGA thermograph, acquired at 10° C./min, can be seen in FIG. 10.

In an embodiment, there is provided crystalline 5MeODMT benzoate, characterised by an onset of decomposition in a TGA thermograph of between 128 and 135° C., between 129 and 134° C., between 130 and 133° C. or between 130 and 132° C.

Figure 10:
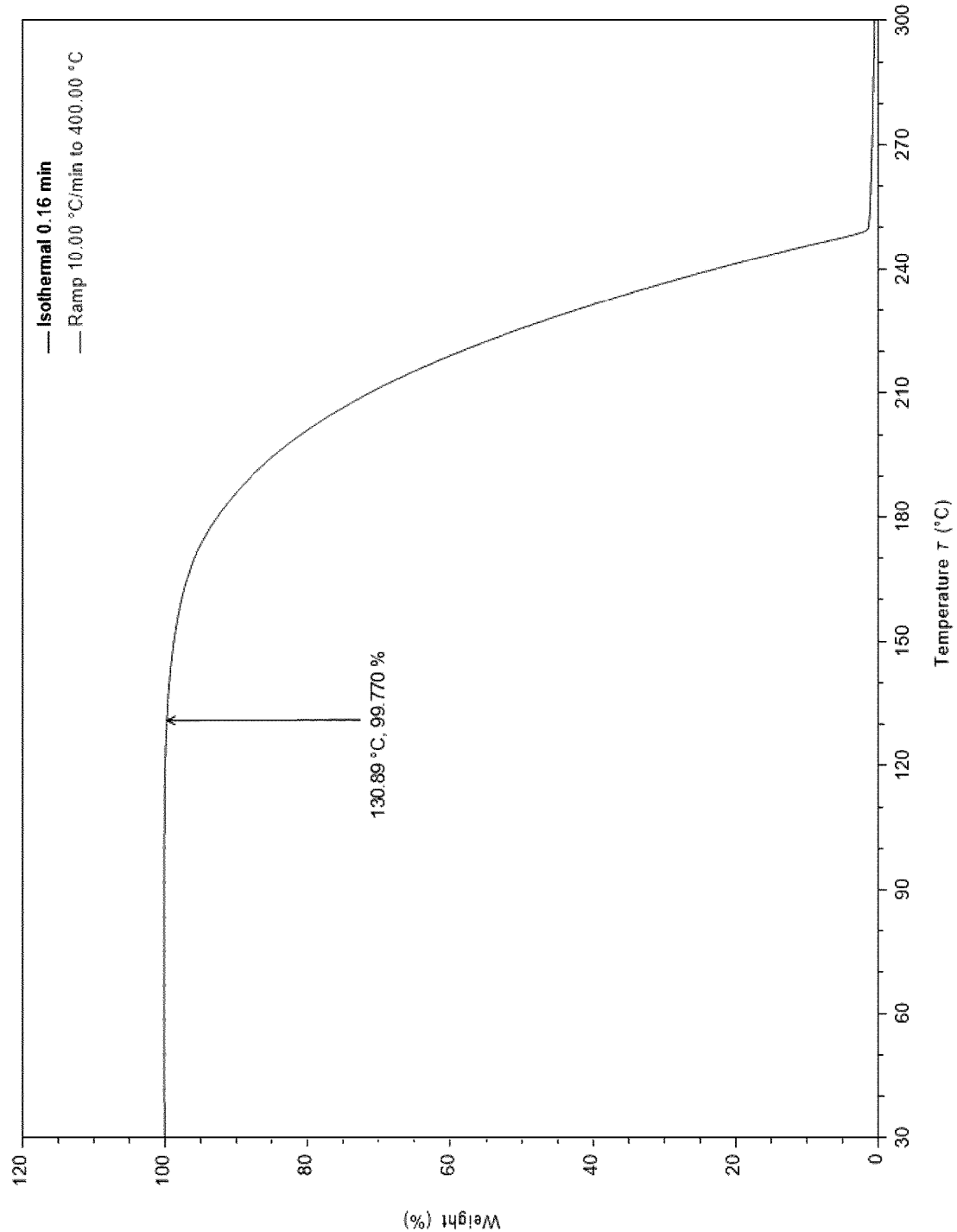
FIG. 10 shows a TGA thermograph of 5MeODMT benzoate.

In an embodiment, there is provided crystalline 5MeODMT benzoate, characterised by an onset of decomposition in a TGA thermograph of between 128 and 135° C., between 129 and 134° C., between 130 and 133° C. or between 130 and 132° C. as substantially illustrated in FIG. 10.

In an embodiment, there is provided crystalline 5MeODMT benzoate, characterised by an onset of decomposition in a TGA thermograph of 131° C.

In an embodiment, there is provided crystalline 5MeODMT benzoate, characterised by an onset of decomposition in a TGA thermograph of 131° C. as substantially illustrated in FIG. 10.

In an embodiment, there is provided crystalline 5MeODMT benzoate, characterised by one or more of:
    an endothermic event in a DSC thermograph having an onset temperature of between 120 and 130° C., between 121 and 129° C., between 122 and 128° C., between 123 and 127° C., between 124 and 126° C.; and
    an onset of decomposition in a TGA thermograph of between 128 and 135° C., between 129 and 134° C., between 130 and 133° C. or between 130 and 132° C.

In an embodiment, there is provided crystalline 5MeODMT benzoate, characterised by one or more of:
    an endothermic event in a DSC thermograph having an onset temperature of between 120 and 130° C., between 121 and 129° C., between 122 and 128° C., between 123 and 127° C., between 124 and 126° C. as substantially illustrated in FIG. 9; and
    an onset of decomposition in a TGA thermograph of between 128 and 135° C., between 129 and 134° C., between 130 and 133° C. or between 130 and 132° C. as substantially illustrated in FIG. 10.

In an embodiment, there is provided crystalline 5MeODMT benzoate, characterised by one or more of:
    an endothermic event in a DSC thermograph having an onset temperature of 123° C.; and
    an onset of decomposition in a TGA thermograph of 131° C.

In an embodiment, there is provided crystalline 5MeODMT benzoate, characterised by one or more of:
    an endothermic event in a DSC thermograph having an onset temperature of between 120 and 130° C., between 121 and 129° C., between 122 and 128° C., between 123 and 127° C., between 124 and 126° C. and a peak of between 124 and 126° C.; and
    an onset of decomposition in a TGA thermograph of between 128 and 135° C., between 129 and 134° C., between 130 and 133° C. or between 130 and 132° C.

In an embodiment, there is provided crystalline 5MeODMT benzoate, characterised by one or more of:
    an endothermic event in a DSC thermograph having an onset temperature of between 120 and 130° C., between 121 and 129° C., between 122 and 128° C., between 123 and 127° C., between 124 and 126° C. and a peak of between 124 and 126° C. as substantially illustrated in FIG. 9; and
    an onset of decomposition in a TGA thermograph of between 128 and 135° C., between 129 and 134° C., between 130 and 133° C. or between 130 and 132° C. as substantially illustrated in FIG. 10.

In an embodiment, there is provided crystalline 5MeODMT benzoate, characterised by one or more of:
    an endothermic event in a DSC thermograph having an onset temperature of 123° C., a peak of 124° C.; and
    an onset of decomposition in a TGA thermograph of 131° C.

In an embodiment, there is provided crystalline 5MeODMT benzoate, characterised by one or more of:
    an endothermic event in a DSC thermograph having an onset temperature of 123° C., a peak of 124° C. as substantially illustrated in FIG. 9; and
    an onset of decomposition in a TGA thermograph of 131° C. as substantially illustrated in FIG. 10.

In an embodiment, there is provided crystalline 5MeODMT benzoate, characterised by one or more of:
    an endothermic event in a DSC thermograph having an onset temperature of between 120 and 130° C., between 121 and 129° C., between 122 and 128° C., between 123 and 127° C., between 124 and 126° C., a peak of between 124 and 126° C. and an enthalpy of between −130 and −140 J/g; and
    an onset of decomposition in a TGA thermograph of between 128 and 135° C., between 129 and 134° C., between 130 and 133° C. or between 130 and 132° C.

In an embodiment, there is provided crystalline 5MeODMT benzoate, characterised by one or more of:
- an endothermic event in a DSC thermograph having an onset temperature of between 120 and 130° C., between 121 and 129° C., between 122 and 128° C., between 123 and 127° C., between 124 and 126° C., a peak of between 124 and 126° C. and an enthalpy of between −130 and −140 J/g as substantially illustrated in FIG. 9; and
- an onset of decomposition in a TGA thermograph of between 128 and 135° C., between 129 and 134° C., between 130 and 133° C. or between 130 and 132° C. as substantially illustrated in FIG. 10.

In an embodiment, there is provided crystalline 5MeODMT benzoate, characterised by one or more of:
- an endothermic event in a DSC thermograph having an onset temperature of 123° C., a peak of 124° C. and an enthalpy of −135° C.; and
- an onset of decomposition in a TGA thermograph of 131° C.

In an embodiment, there is provided crystalline 5MeODMT benzoate, characterised by one or more of:
- an endothermic event in a DSC thermograph having an onset temperature of 123° C., a peak of 124° C. and an enthalpy of −135° C. as substantially illustrated in FIG. 9; and
- an onset of decomposition in a TGA thermograph of 131° C. as substantially illustrated in FIG. 10.

Figure 11:
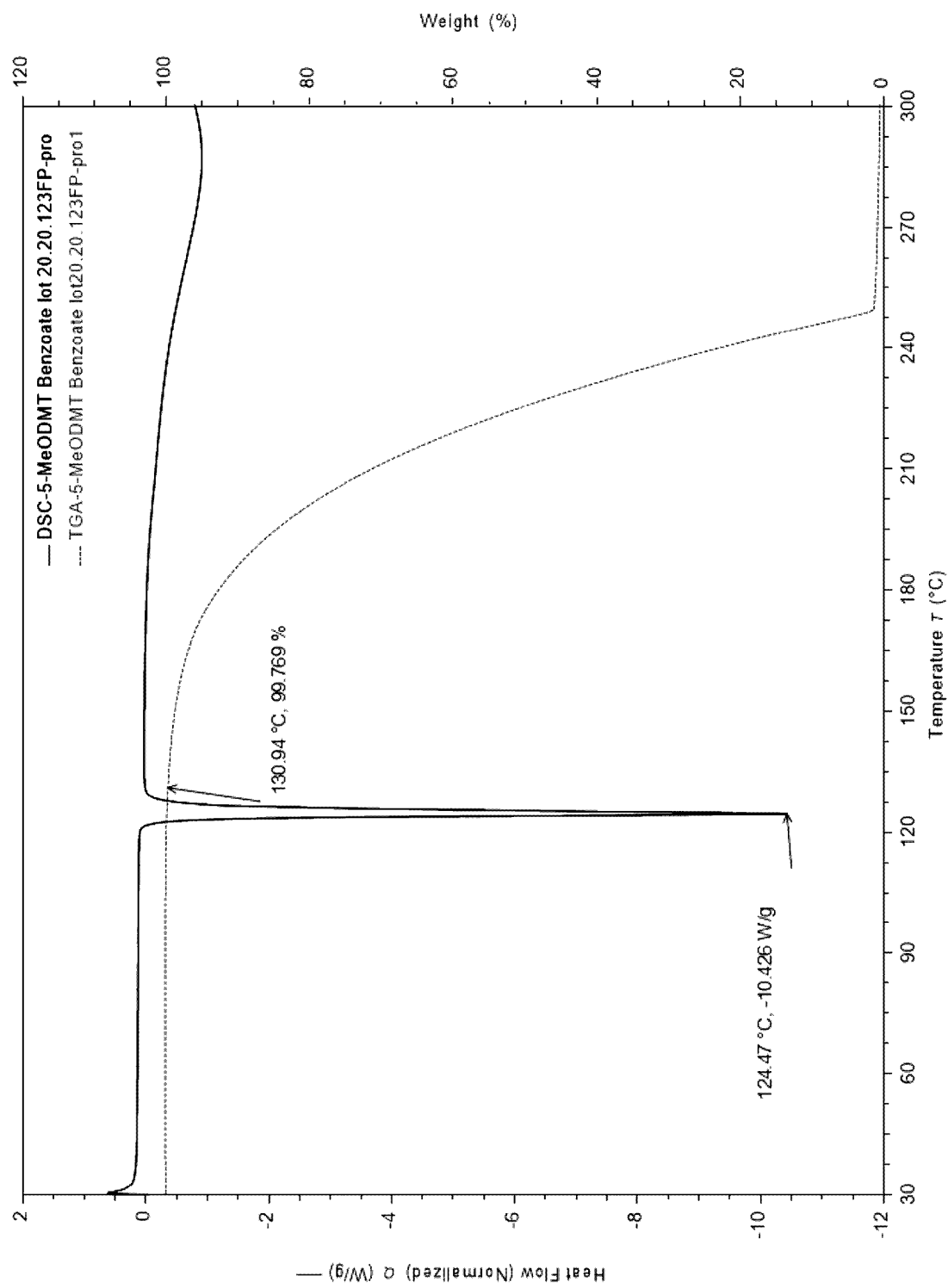
FIG. 11 shows a combined TGA/DSC thermograph of 5MeODMT benzoate.

A combined TGA/DSC thermograph, acquired at 10° C./min, can be seen in FIG. 11.

Example 19: Dynamic Vapour Sorption (DVS) of 5MeODMT Benzoate

The DVS profile for 5MeODMT benzoate salt, revealed reversible water uptake/loss over the humidity range and no hysteresis. The water uptake/loss from 0 to 90% was gradual and amounted to a maximum of ca 0.20% and was a consequence of wetting of the solid. There was no evidence of form/version modification as a consequence of exposure of 5MeODMT benzoate salt to variable humidity. The DVS isotherm can be seen in FIG. 12.

Figure 17:
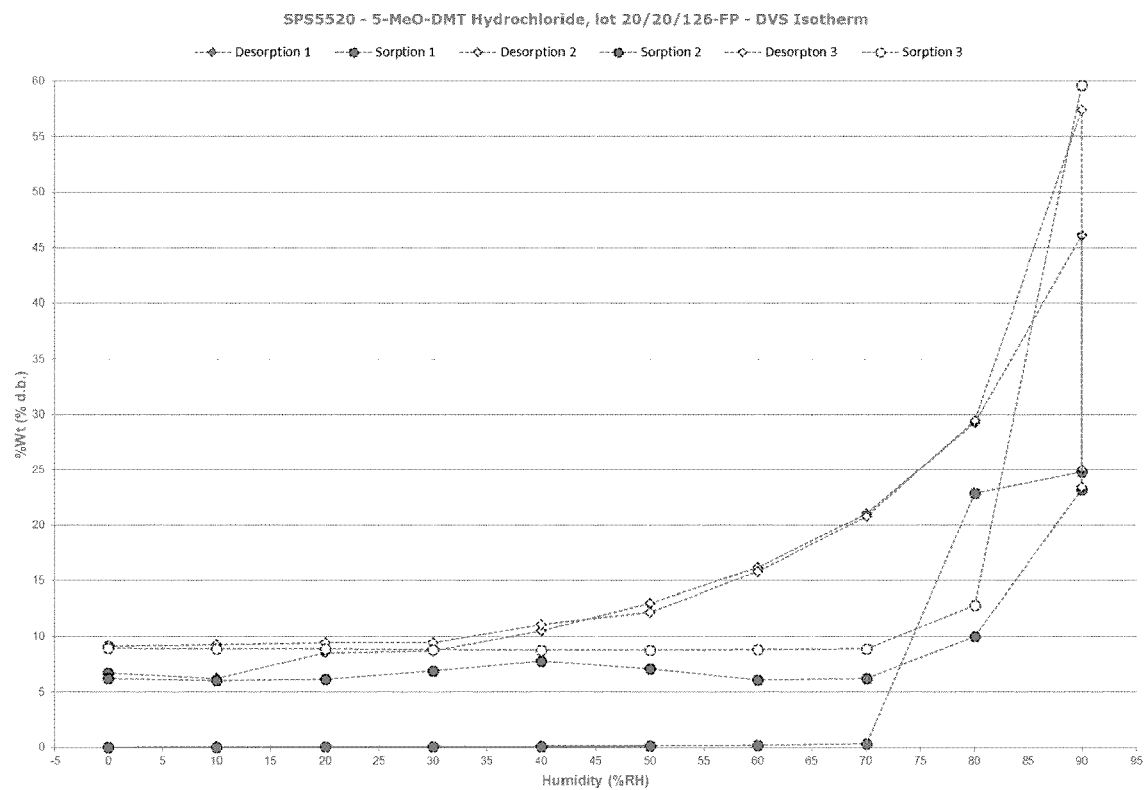
FIG. 17 shows a DVS isotherm of 5MeODMT hydrochloride (lot 20/20/126-FP).

The DVS isotherm of a 5MeODMT Hydrochloride, lot 20/20/126-FP (FIG. 17) was found to undergo significant moisture uptake upon the first sorption cycle from 70% RH. Approximately 23% $^w/_w$, uptake is observed between 70-80% RH, whereas less than 0.3% $^w/_w$ moisture uptake from 0-70% RH was observed. A further 20% $^w/_w$ moisture uptake is observed up to and when held at 90% RH before commencement of the second desorption cycle. Subsequent sorption and desorption cycles follow a similar profile with some observed hysteresis between operations that do not match the original desorption step. These return to ca. 6-9% $^w/_w$ above the minimum mass recorded at 0% RH, which indicates significant retention of moisture. Upon completion of the DVS cycle, the input material was noted to have completed deliquesced.

A modified DVS isotherm of lot 20/45/006-FP (the same crystalline version) was undertaken to examine material behaviour from 60% RH and above. A 2 cycle DVS with desorption beginning from 40-0% RH with sorption from 0-60% RH in 10% RH intervals, followed by incremental 5% RH increases to 65, 70, 75, 80 and finally 85% RH. This is to obtain in-depth profiling of the material towards humidity at these elevated levels.

Figure 18:
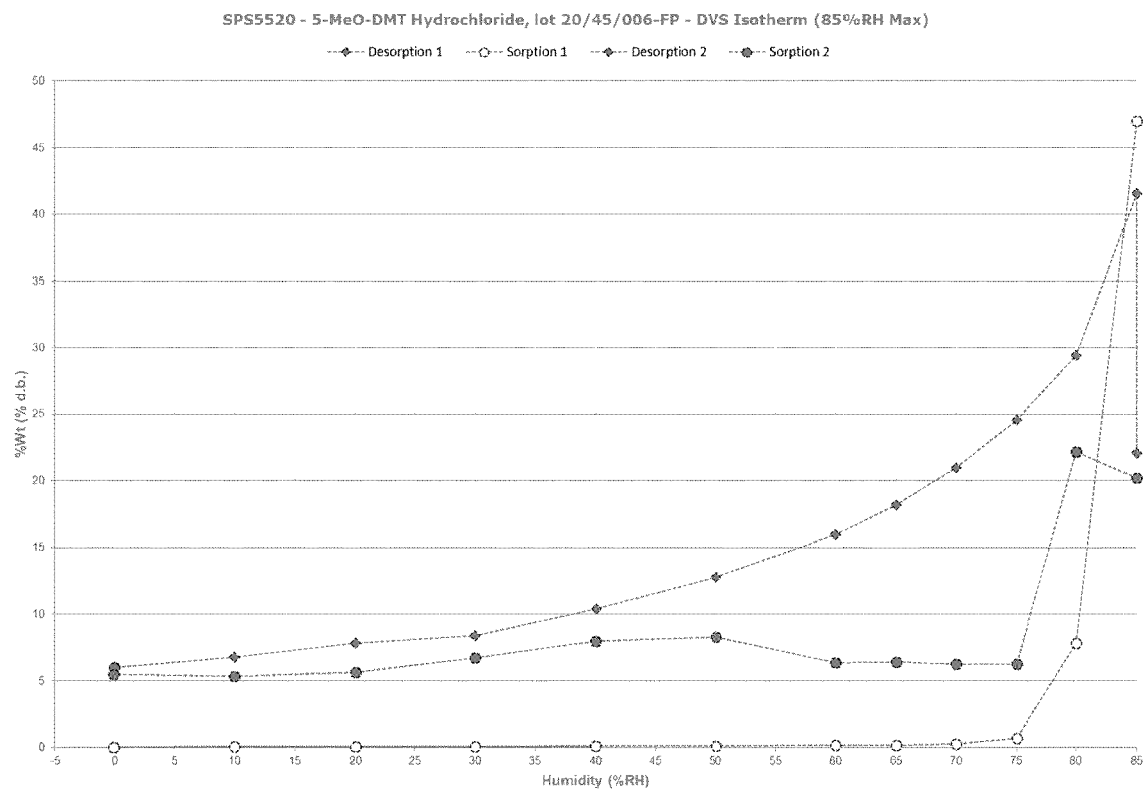
FIG. 18 shows a DVS isotherm of 5MeODMT hydrochloride (lot 20/45/006-FP).

No significant moisture uptake/loss in first desorption-sorption profile between 0-70% RH was noted (FIG. 18) followed by a ca. 0.46% w/w increase from 70-75% RH. A further ca. 7% uptake is observed from 75-80% RH, then ca. 40% from 80-85% RH w/w. Complete deliquescence of the solids was observed upon isolation of the material post DVS analysis, which has likely occurred above 80% RH.

Temperature and humidity are important factors in the processing and storage of pharmaceuticals. DVS provides a versatile and sensitive technique for evaluating the stability of pharmaceutical formulations.

The DVS profiles show that the stability of the benzoate salt of 5MeODMT is significantly higher than that of the hydrochloride salt and is therefore a more promising salt for development as a pharmaceutical composition.

There is thus provided in an embodiment of the invention an increased stability composition of 5MeODMT wherein the composition comprises the benzoate salt. There is further provided a composition of 5MeODMT having an increased stability wherein the composition comprises the benzoate salt.

In an embodiment there is thus provided a pharmaceutical composition of 5MeODMT benzoate having an increased shelf-life compared to a pharmaceutical composition of 5MeODMT hydrochloride.

In an embodiment, there pharmaceutical composition may be a nasal inhalation composition.

It is advantageous that the 5MeODMT benzoate salt retains a low/consistent moisture content over its shelf-life preserving its ability to be consistently formulated, and preserving its ability to be inhaled in a free flowing powder form.

Figure 12:
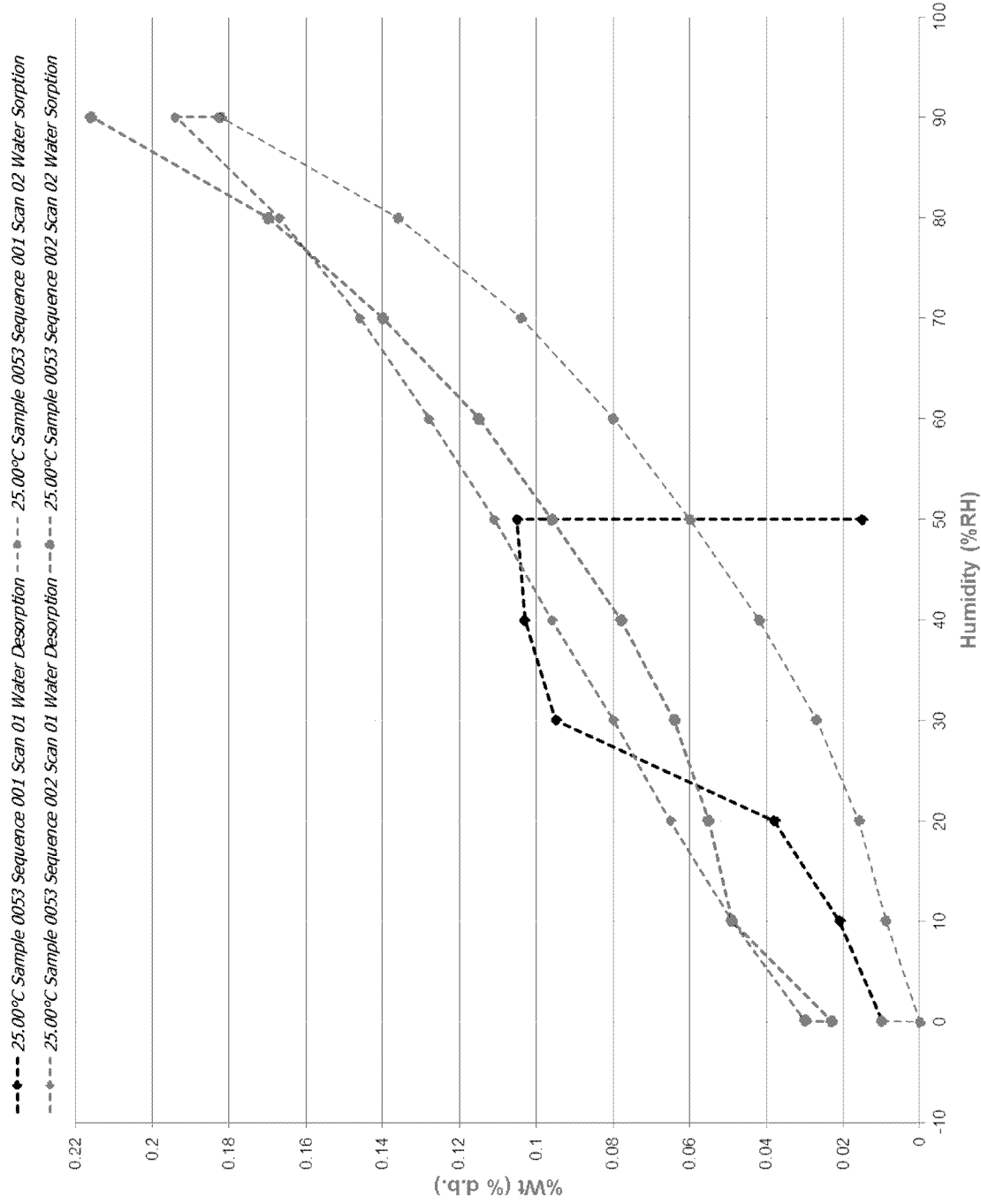
FIG. 12 shows a DVS isotherm of 5MeODMT benzoate.

In an embodiment, there is provided crystalline 5MeODMT benzoate, characterised by a DVS isotherm profile as substantially illustrated in FIG. 12.

In an embodiment, there is provided crystalline 5MeODMT benzoate, characterised by one or more of:
- an endothermic event in a DSC thermograph having an onset temperature of between 120 and 130° C., between 121 and 129° C., between 122 and 128° C., between 123 and 127° C., between 124 and 126° C., optionally a peak of between 124 and 126° C. and optionally an enthalpy of between −130 and −140 J/g as substantially illustrated in FIG. 9;
- an onset of decomposition in a TGA thermograph of between 128 and 135° C., between 129 and 134° C., between 130 and 133° C. or between 130 and 132° C. as substantially illustrated in FIG. 10; and
- a DVS isotherm profile as substantially illustrated in FIG. 12.

In an embodiment, there is provided crystalline 5MeODMT benzoate, characterised by one or more of:
- an endothermic event in a DSC thermograph having an onset temperature of 123° C., optionally a peak of 124° C. and optionally an enthalpy of −135° C. as substantially illustrated in FIG. 9;
- an onset of decomposition in a TGA thermograph of 131° C. as substantially illustrated in FIG. 10; and
- a DVS isotherm profile as substantially illustrated in FIG. 12.

The person skilled in the art will appreciate the defining characteristics of one of more of the previously or subsequently described embodiments may be interchanged with those of one or more other embodiments.

Example 20: Microscopy, Optical of 5MeODMT Benzoate

Optical microscopy examination was undertaken using an Olympus BX53M polarised light microscope and an Olympus SC50 digital video camera for image capture using imaging software Olympus Stream Basic, V2.4. The image scale bar was verified against an external graticule, 1.5/0.6/0.01 mm DIV, on a monthly basis.

A small amount of each sample was placed onto a glass slide and dispersed using mineral dispersion oil if required. The samples were viewed with appropriate magnification and various images recorded.

Optical micrographs of 5MeODMT benzoate salt, were acquired. The material is composed of large rhombohedral/trigonal crystals, ranging from 400 to 1000 microns. There are also small crystals adhering to the large crystals. Some of the small crystals, from 10 microns, are a consequence of mechanical attrition, but others have formed by crystallisation. There are also large aggregates composed of various habits. FIGS. 13 to 16 show various optical micrographs of 5MeODMT benzoate at various magnifications.

Example 21: Further Characterisation of 5MeODMT Benzoate

The propensity of 5MeODMT benzoate to polymorphism was investigated and is considered low with solids isolated with two different XRPD patterns.

The equilibration of 5MeODMT benzoate in solvents with thermal modulation induced a form or version change which are not considered to be solvates.

The anti-solvent mediated crystallisation investigation of 5MeODMT benzoate did not afford any solids indicating form or version change.

The controlled cooling crystallisation investigation of 5MeODMT benzoate did not afford any solids indicating form or version change.

The reverse anti-solvent mediated crystallisation investigation of 5MeODMT benzoate did induce a form or version change.

Two versions of 5MeODMT benzoate have been identified, the Pattern A form (see Example 17, hereafter this form is referred to as Pattern A) version and a second, Pattern B form, believed to be meta-stable.

The equilibration investigation of 5MeODMT benzoate in a range of solvents with thermal modulation returned Pattern A by XRPD from most solvents. The equilibration solvents toluene, chlorobenzene, and anisole induced a form or version change in the 5MeODMT benzoate and is defined as Pattern B by XRPD. Solvate formation can be excluded based upon TGA.

The anti-solvent mediated crystallisation investigation of 5MeODMT benzoate afforded solids which were concordant Pattern A by XRPD indicating no form or version change.

The controlled cooling crystallisation investigation of 5MeODMT benzoate afforded solids which were concordant Pattern A by XRPD indicating no form or version change.

The reverse anti-solvent mediated crystallisation investigation of 5MeODMT benzoate returned Pattern A form from most mixtures. The methanol:toluene and IPA:toluene mixtures produced material which is considered to be Pattern B form with improved characteristics compared to the Pattern B form solids isolated via solvent equilibration.

Figure 19:
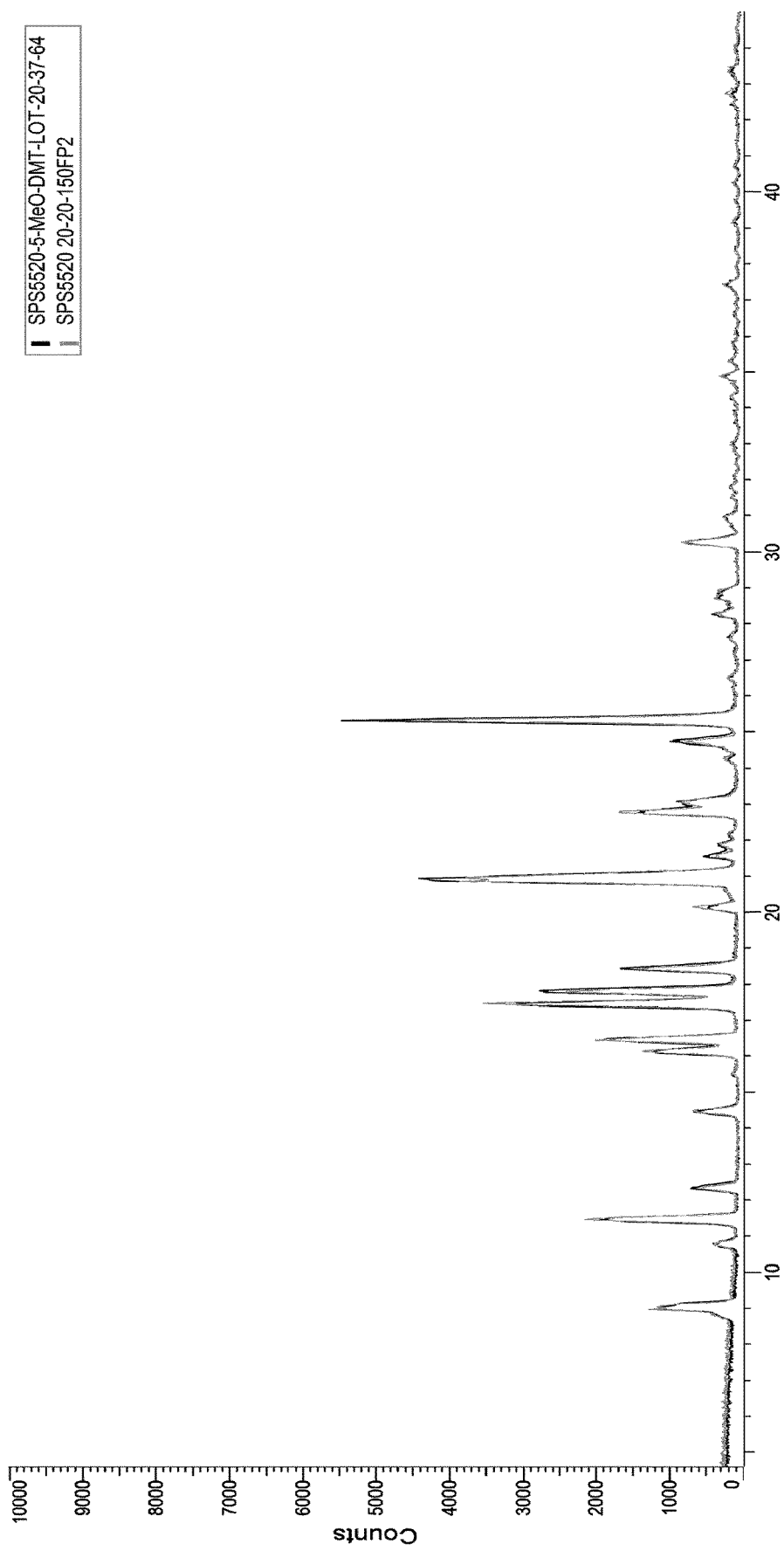
FIG. 19 shows XRPD pattern comparison of two different lots of 5MeODMT benzoate.

XRPD examination (FIG. 19) revealed a powder pattern of 5MeODMT benzoate that was concordant with that found in previous XRPD examinations (see Example 17, Pattern A form).

Figure 20:
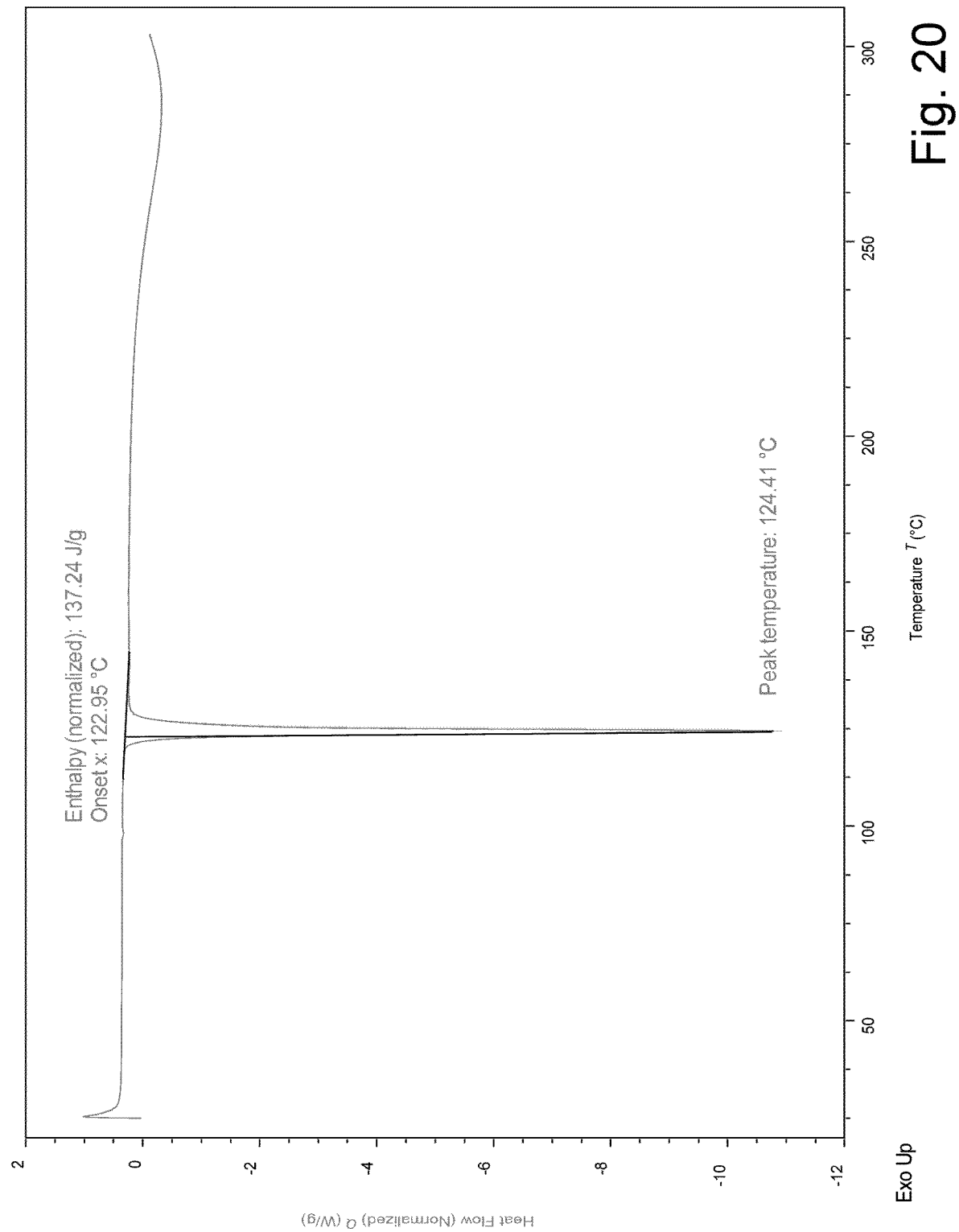
FIG. 20 shows a DSC thermograph of another lot of 5MeODMT benzoate.

DSC examination (FIG. 20) revealed one sharp endotherm with an onset of 122.95° C. and a peak at 124.41° C. which was a match with Pattern A form (see Example 18 wherein the onset is 123.34° C. and the peak at 124.47° C.).

Figure 21:
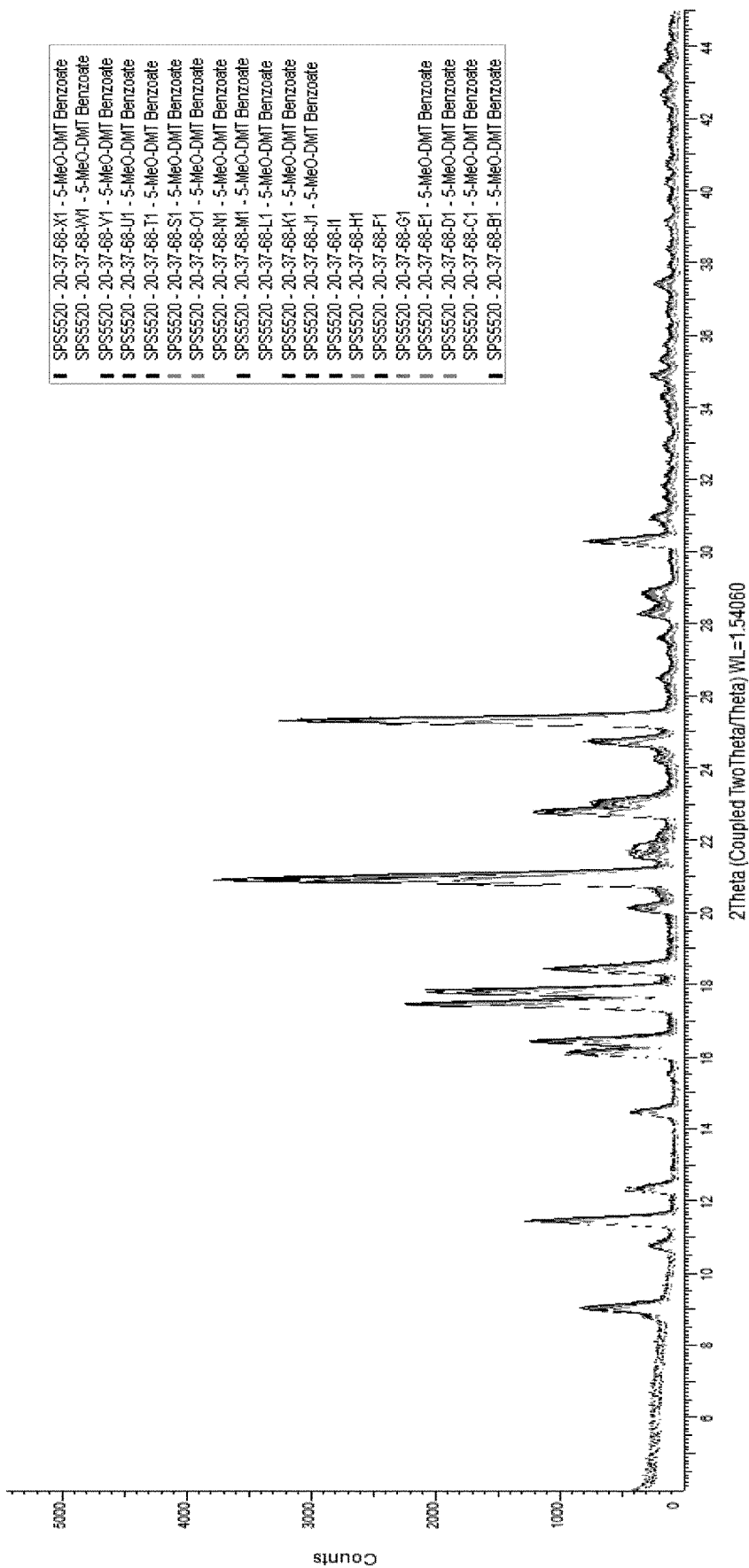
FIG. 21 shows additional XRPD characterisation of multiple lots of 5MeODMT benzoate.

Additional XRPD examination of multiple lots of 5MeODMT benzoate can be seen in FIG. 21, matching Pattern A.

Figure 22:
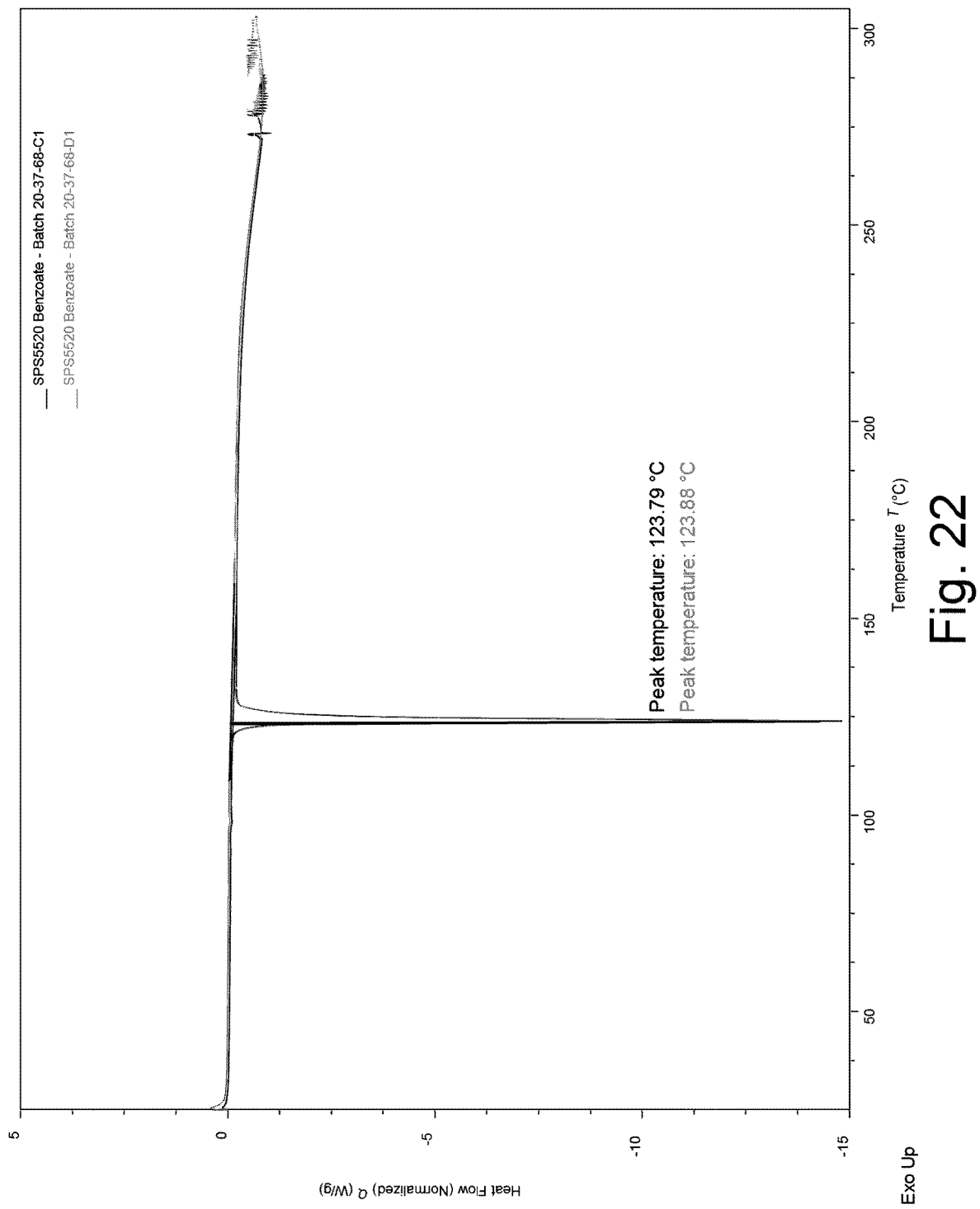
FIG. 22 shows DSC thermograph results for 5MeODMT benzoate lots C1, D1 and E1.
Figure 23:
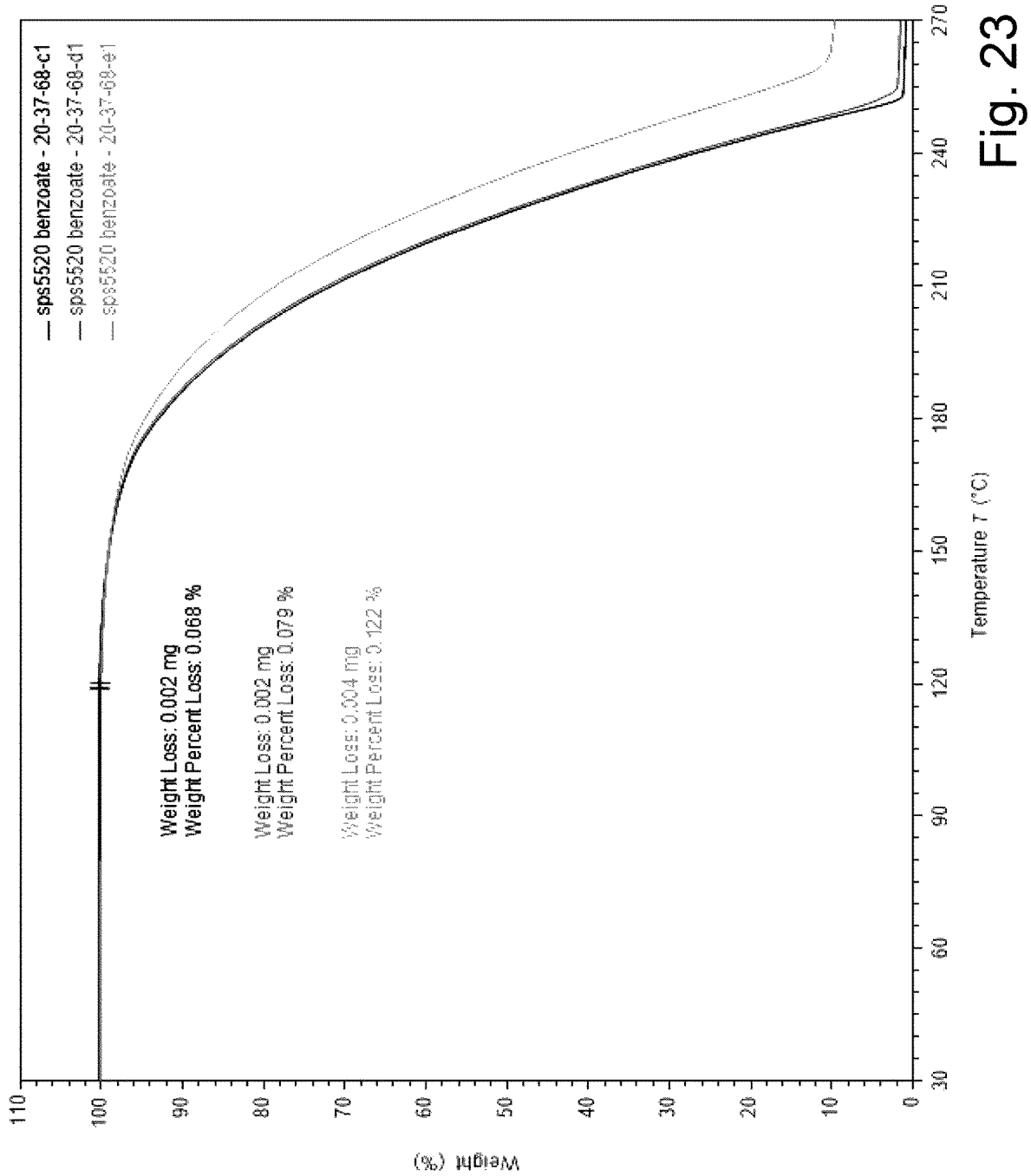
FIG. 23 shows TGA thermograph results for 5MeODMT benzoate lots C1, D1 and E1 at 10° C.·min$^{-1}$.

DSC examination of 5MeODMT benzoate lots C1, D1 and E1 revealed a common endothermic event with a peak temperature of 123.76° C. to 123.88° C. (FIG. 22). TGA analysis of C1, D1 and E1 revealed a negligible weight loss before major decomposition (FIG. 23).

Figure 24:
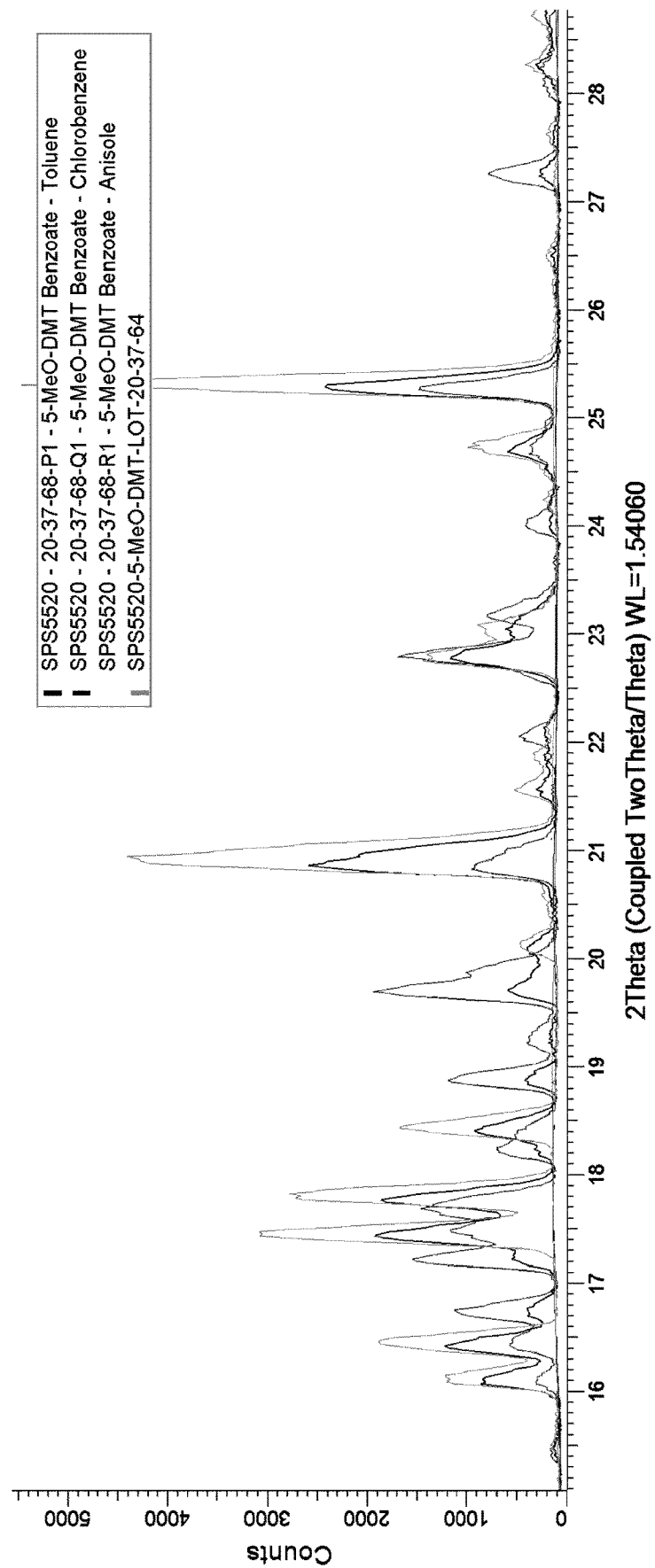
FIG. 24 shows XRPD pattern comparison of 5MeODMT benzoate P1 (Toluene), Q1 (Chlorobenzene), and R1 (Anisole) against the XRPD pattern of Pattern A.

The XRPD patterns of P1 (Toluene), 01 (Chlorobenzene), and R1 (Anisole) revealed a new diffraction pattern referred to as 'Pattern B'. These samples contained 3 common diffractions between 18.5 and 20° 2θ (FIG. 24).

A selection of samples of Pattern A form: C1 (IPA:Heptane [1:1]), D1 (3-Methyl-1-butanol:Heptane [1:1], and E1 (TBME) were thermally characterised.

DSC examination of samples P1, Q1, and R1 revealed a major common endothermic event with a peak temperature of 123.73° C. to 124.40° C. and a minor common endothermic-exothermic event between 113.01 and 115.27° C.

Sample R1 contained a unique endothermic event between the minor endothermic-exothermic event and the major endotherm with a peak temperature of 117.24° C.

Figure 25:
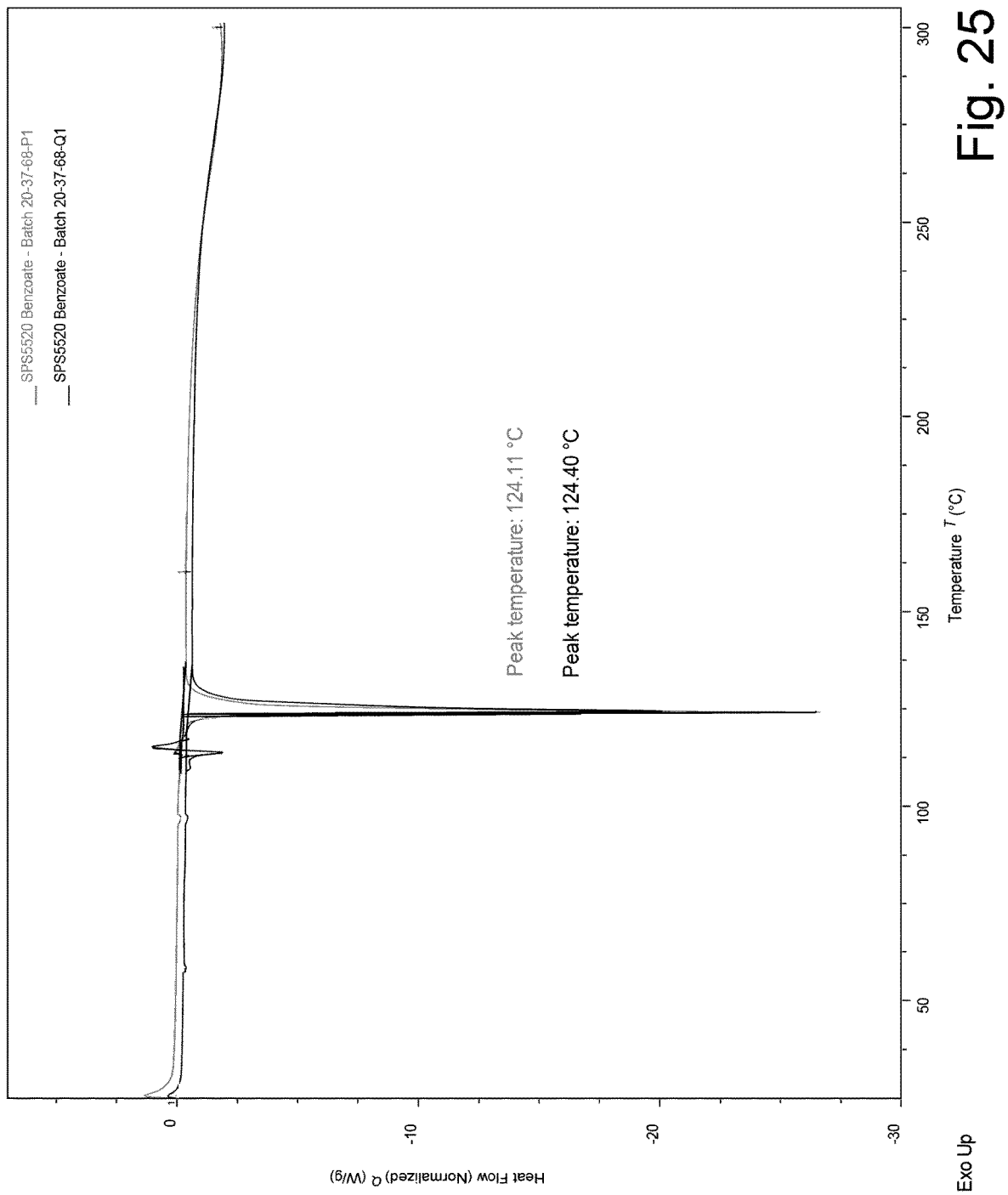
FIG. 25 shows DSC thermographs of 5MeODMT lots P1, Q1 and R1 at 10° C.·min$^{-1}$.
Figure 26:
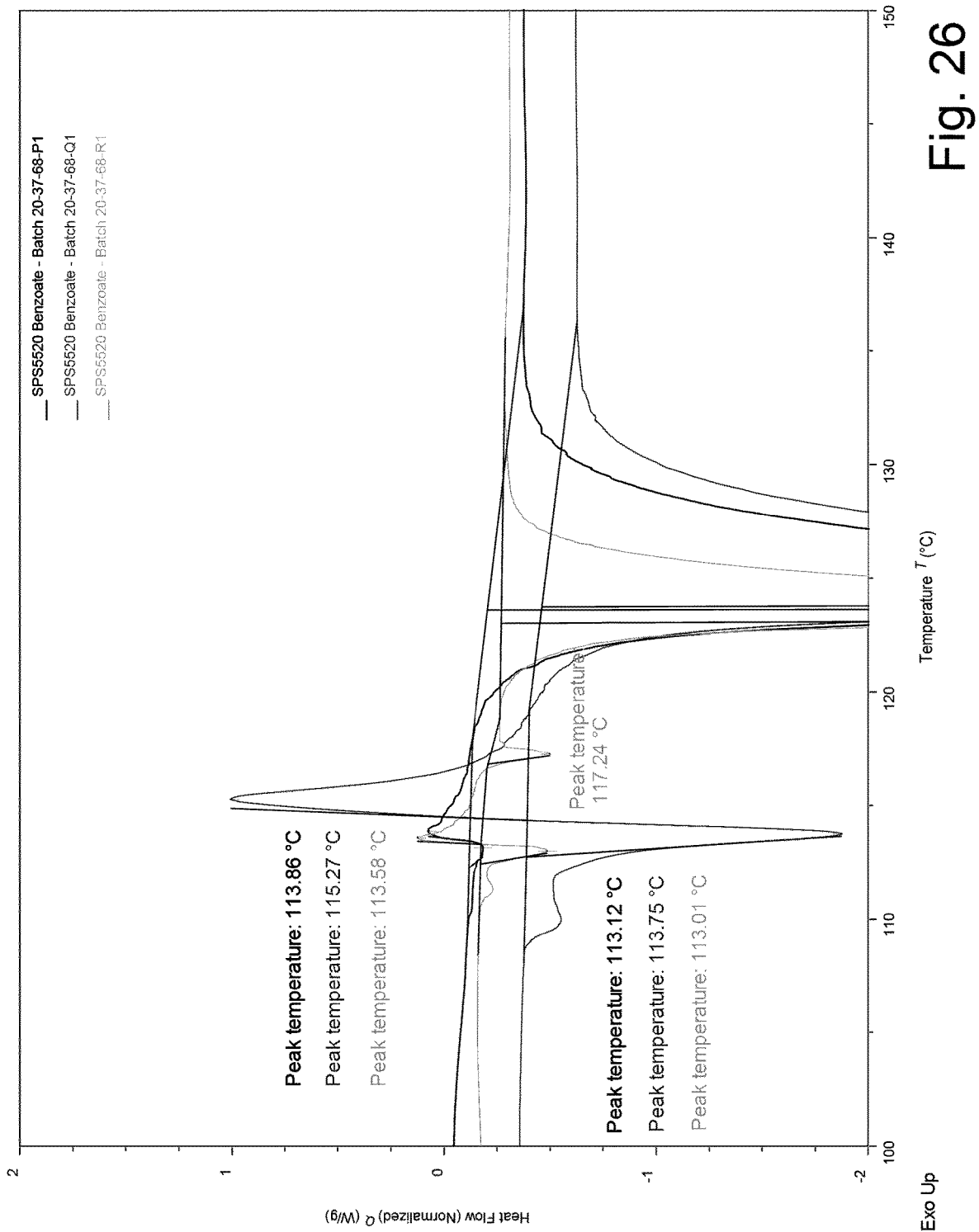
FIG. 26 shows DSC thermograph expansions of 5MeODMT lots P1, Q1 and R1 at 10° C.·min$^{-1}$.
Figure 27:
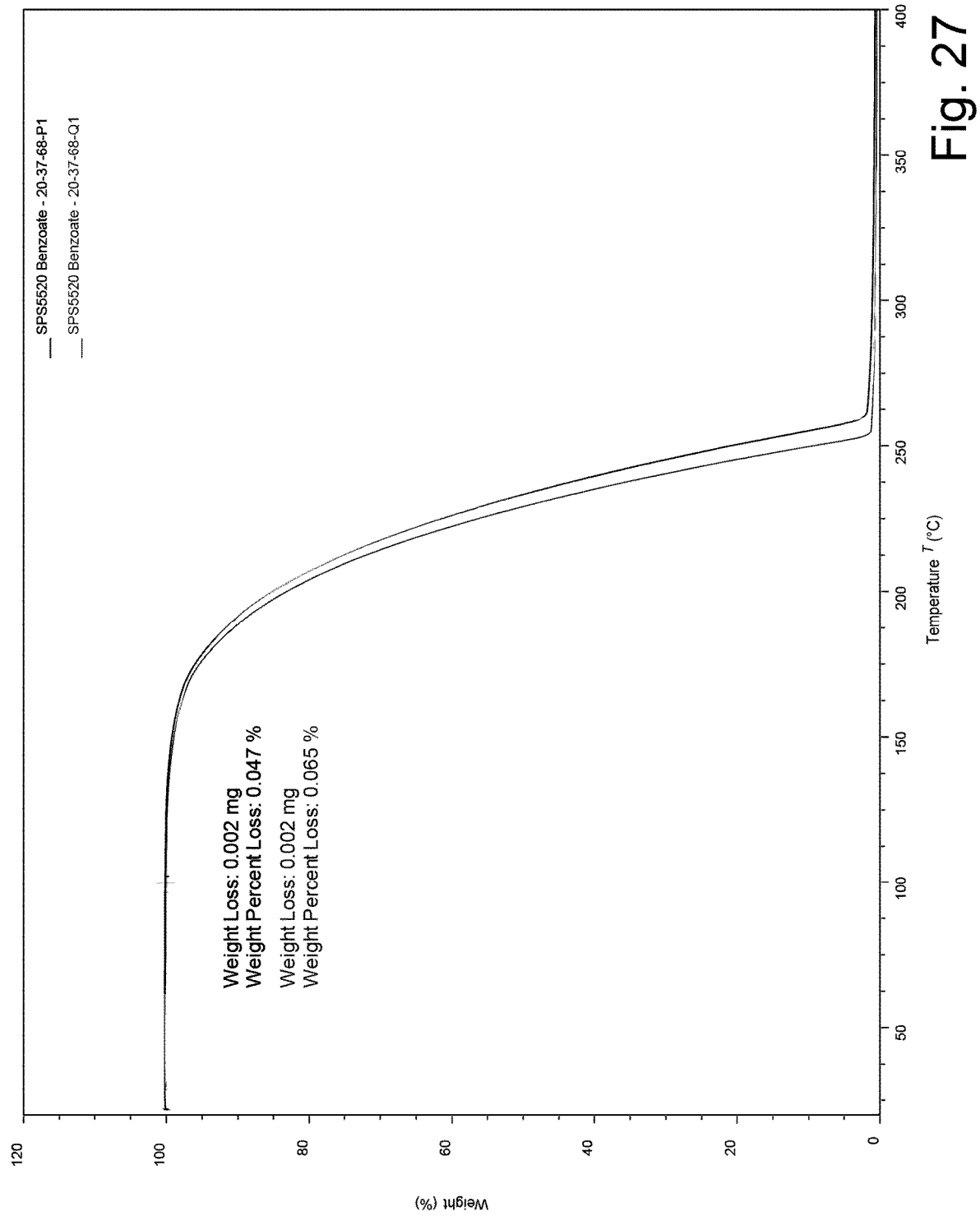
FIG. 27 shows TGA thermographs of 5MeODMT lots P1, Q1 and R1 at 10° C.·min$^{-1}$.

TGA examination revealed a negligible weight loss for samples P1 and Q1. For sample R1 there was a weight reduction of 0.293% weight before decomposition. DSC thermographs of P1, 01 and R1 at 10° C.·min$^{-1}$ can be seen in FIG. 25. DSC thermograph expansions of 5MeODMT benzoate lots P1, 01 and R1 at 10° C.·min$^{-1}$ can be seen in FIG. 26. TGA thermographs of 5MeODMT benzoate lots P1, 01 and R1 at 10° C.·min$^{-1}$ can be seen in FIG. 27.

Figure 28:
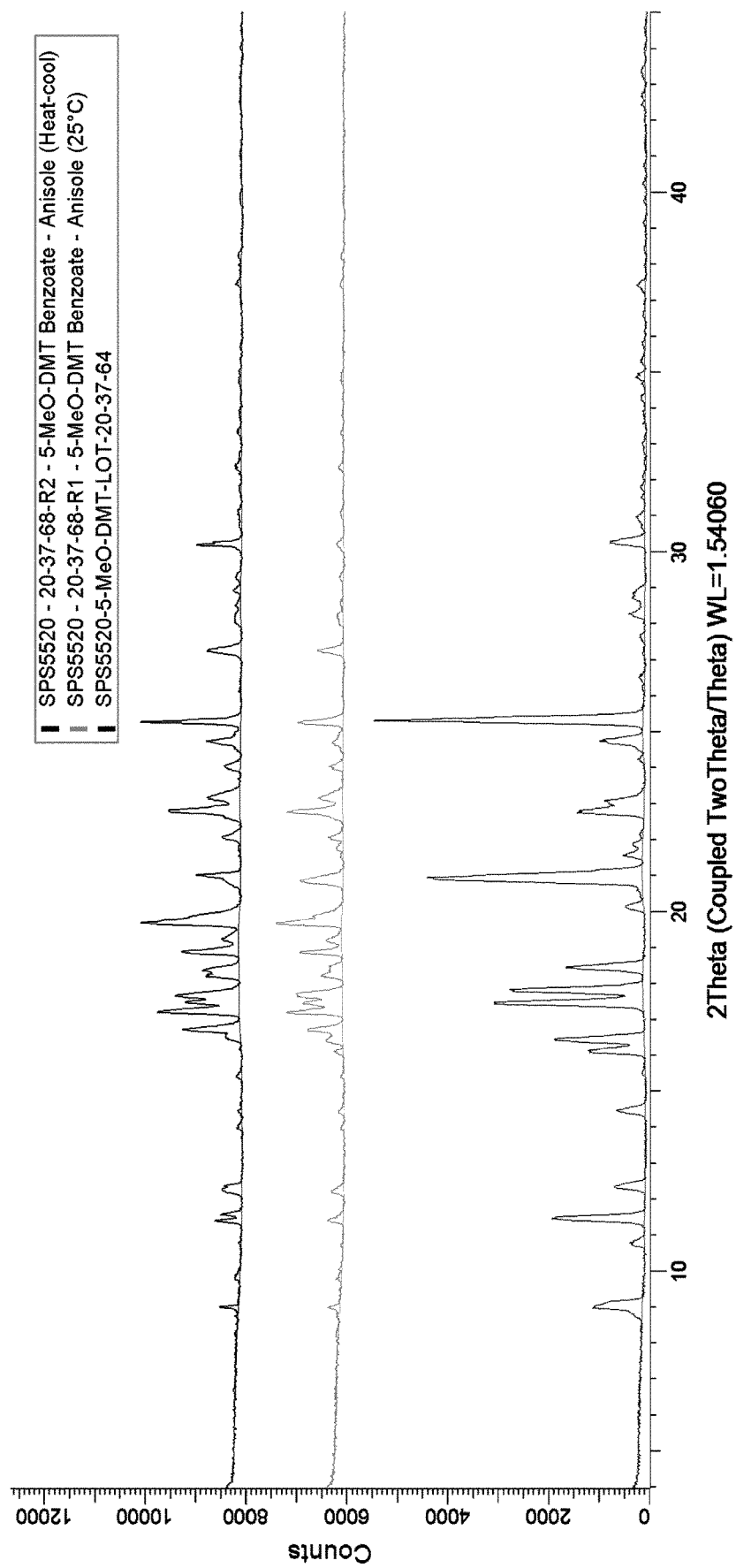
FIG. 28 shows XRPD pattern comparison of 5MeODMT benzoate lots R1 and R2 (thermally cycled suspensions) compared with a reference Pattern A XRPD diffractogram.

XRPD examination of samples P2, Q2, and R2 (thermally cycled suspensions) revealed P2 and Q2 had converted to Pattern A form. However, R2 remained as Pattern B form but with larger diffractions concordant with Pattern B. The XRPD diffractogram of lots R1 and R2 (thermally cycled suspensions) compared with a reference Pattern A XRPD diffractogram can be seen in FIG. 28.

DSC examination of P2 revealed only the major endothermic event characteristic of the Pattern A form was present with a peak temperature of 124.48° C. (FIGS. 29-31).

DSC revealed the minor endo-exotherm was smaller for sample 02 with peak temperatures of 113.41 and 114.32° C. but the major endotherm was unaffected with a peak temperature of 124.23° C. (FIGS. 29-31).

Figure 29:
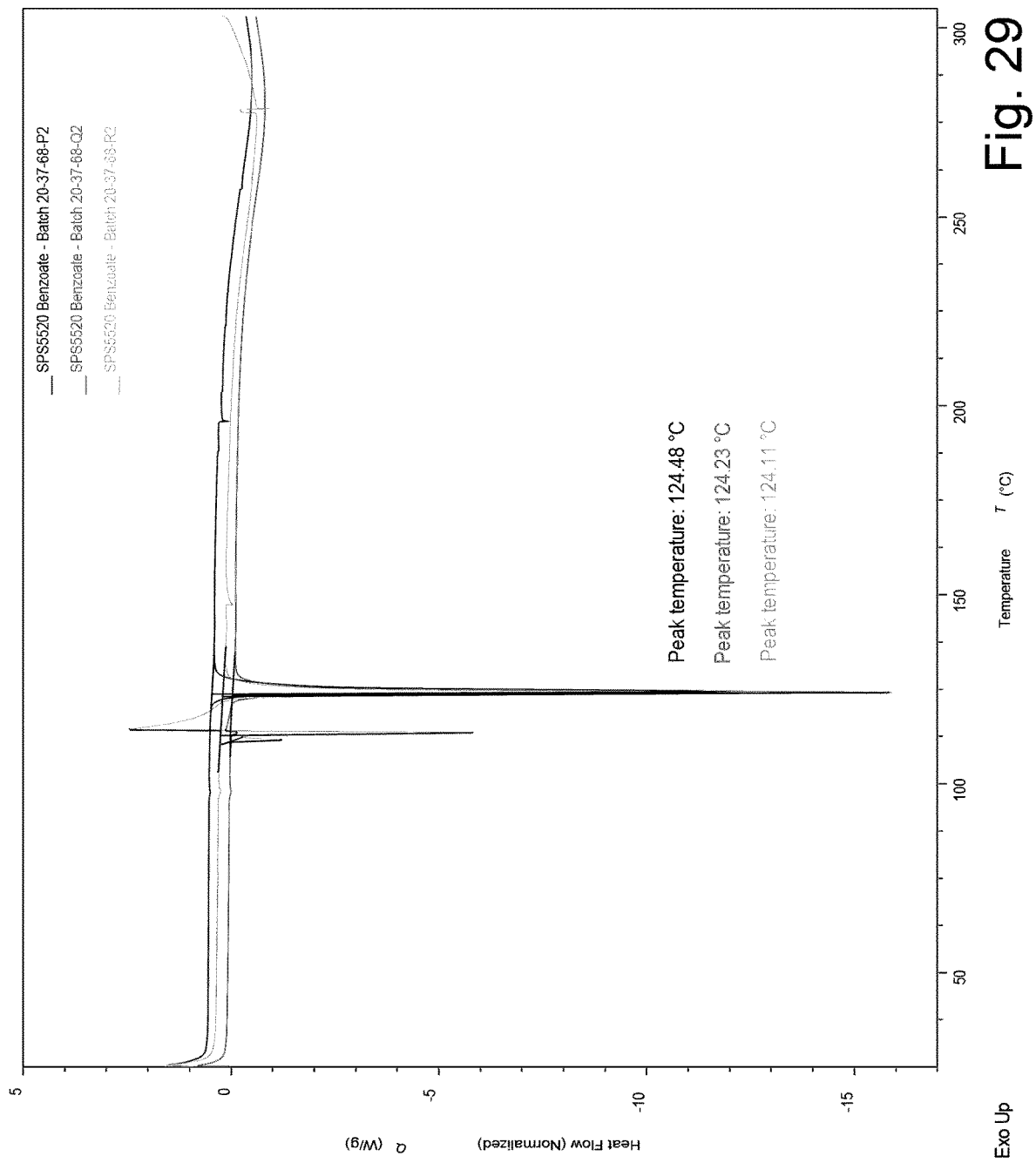
FIG. 29 shows DSC thermographs of 5MeODMT benzoate lots P2, Q2 and R2 at 10° C.·min$^{-1}$.
Figure 30:
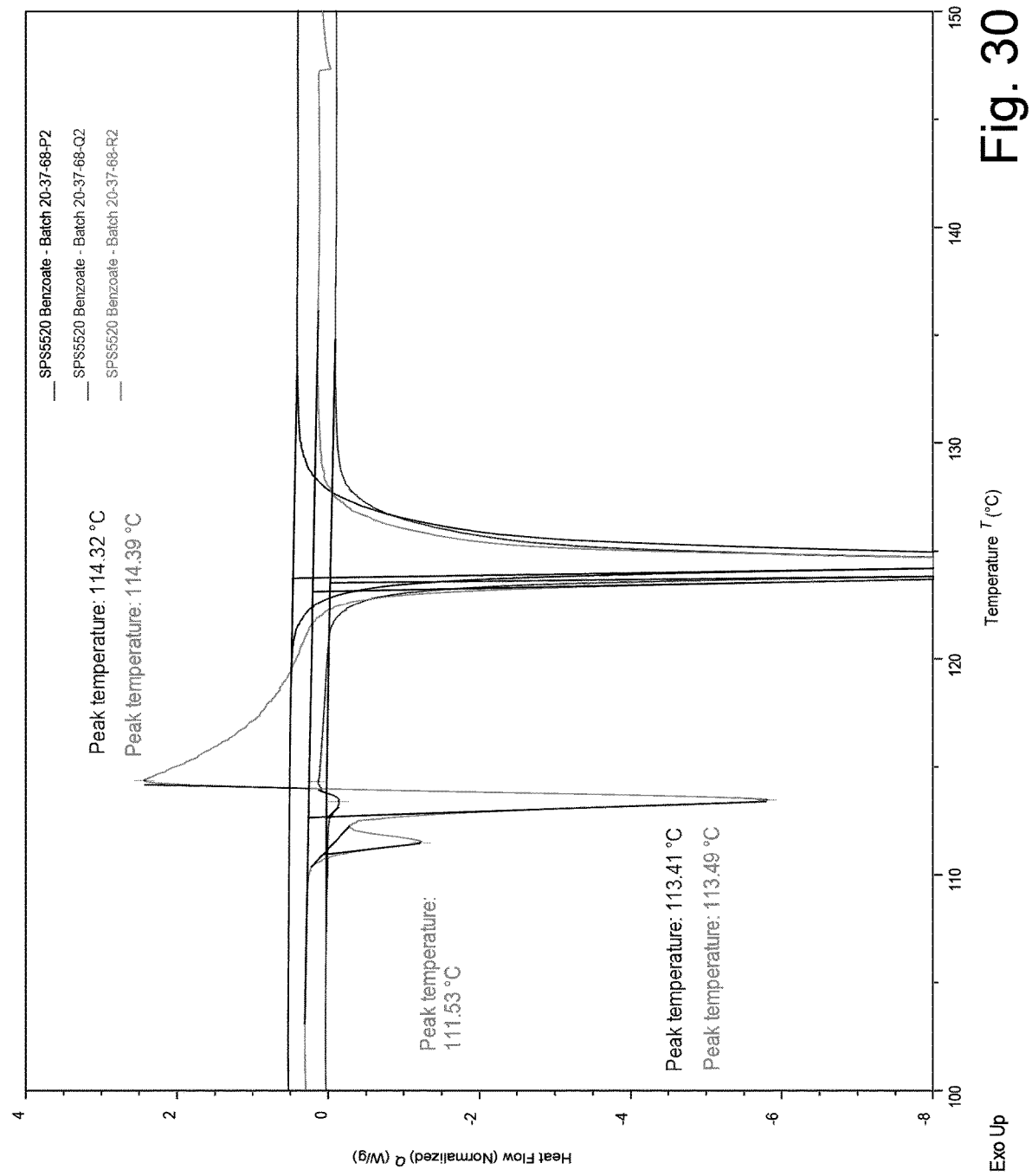
FIG. 30 shows DSC thermograph expansions of 5MeODMT benzoate lots P2, Q2 and R2 at 10° C.·min$^{-1}$.
Figure 31:
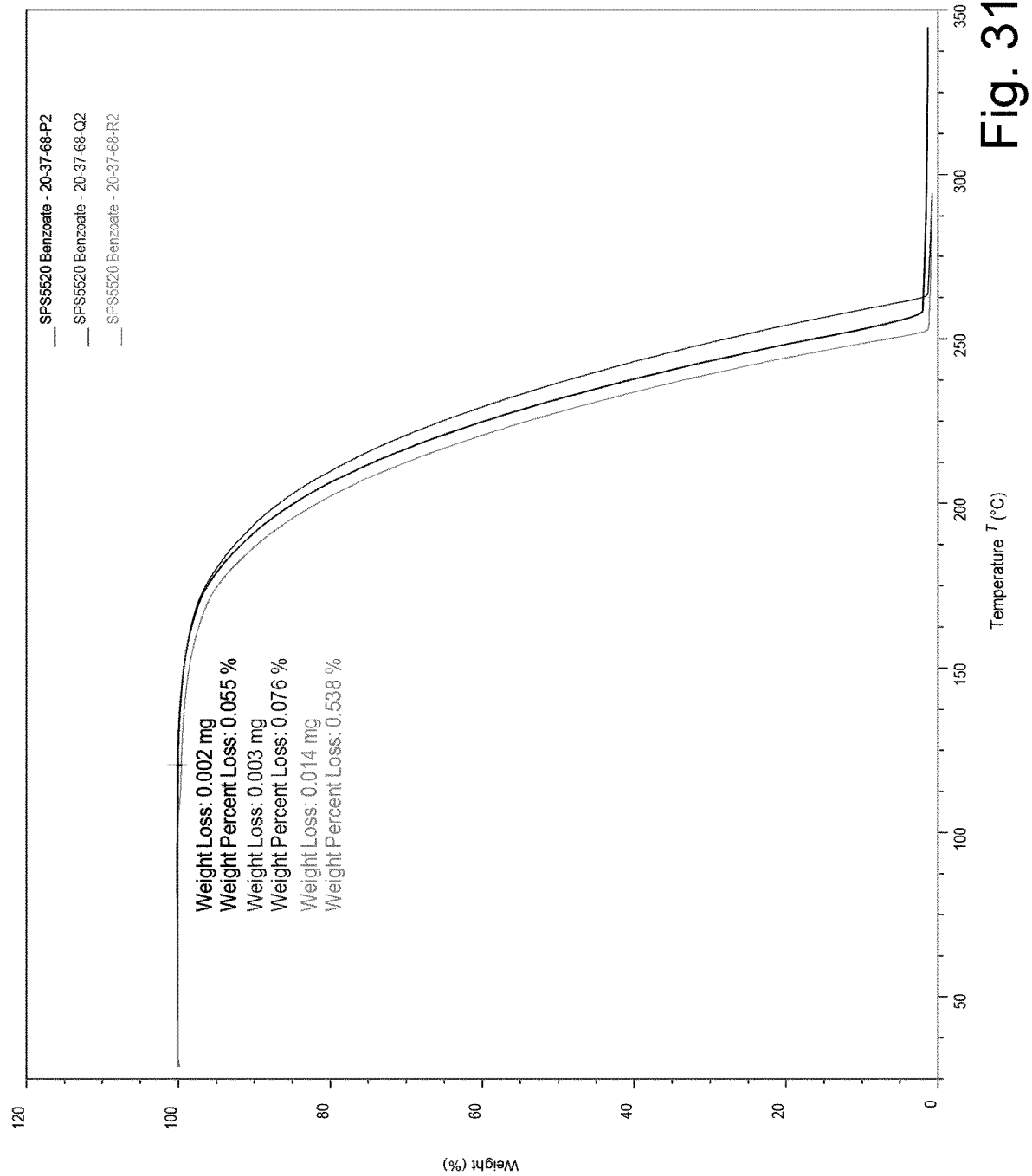
FIG. 31 shows TGA thermographs of 5MeODMT benzoate lots P2, 02 and R2 at 10° C.·min$^{-1}$.

DSC examination of sample R2 revealed the endothermic event in the minor endo-exotherm had two peaks of 111.53 and 113.49° C. followed by the exotherm with a peak temperature of 114.39° C., the minor events were much larger compared to R1 and the second minor endothermic event was not present (FIGS. 29-31).

TGA examination revealed a negligible weight loss for samples P2 and Q2. For sample R2 there was a weight reduction of 0.583% before decomposition. The increase in weight loss corresponds to the increase in the magnitude of the minor events revealed by DSC (FIGS. 29-31).

The solvent mediated equilibration of 5MeODMT benzoate with temperature modulation revealed the salt to be stable to version or form change except for the solvents toluene, chlorobenzene, and anisole. Solids isolated from these solvents had different XRPD patterns and thermal events indicating a version of form change of the salt. Solvate formation can be excluded based upon TGA.

In an embodiment, there is provided crystalline 5MeODMT benzoate as described above.

Anti-Solvent Addition Driven Crystallisation of 5MeODMT Benzoate

Equilibration of Pattern A form in a variety of solvents and solvent mixtures with thermal modulation identified a range of potentially suitable solvents and anti-solvents. An investigation of the anti-solvent driven crystallisation of 5MeODMT benzoate from solution was conducted.

5MeODMT benzoate, 6×220 mg, was dissolved in six solvents at 50° C. (detailed in the Table below) and the stock solutions clarified through 0.45 μm syringe filters. Aliquots of each solution containing 50 mg of 5MeODMT benzoate were charged to 4 crystallisation tubes.

The THF and Acetonitrile solutions of 5MeODMT benzoate crystallised post-clarification. All crystallisation tubes were heated to 55° C. to afford solutions and cooled to 50° C. Samples were agitated via stirrer bead at 400 rpm for the duration of the experiment.

Various anti-solvents (detailed in the Table below), 2.5 vol., were charged to the solutions and the mixtures, then equilibrated at 50° C. for 30 minutes and the anti-solvent addition repeated.

The mixtures were cooled to 25° C. over ca. 1.5 hours and equilibrated for 17 hours.

Suspensions were isolated via isolutes and vacuum dried for 1 minute to remove excess solvent. The isolutes were transferred to a vacuum oven at 50° C. for 24 hours.

The remaining solutions were heated to 50° C. and anti-solvent, 5 vol. charged. The mixtures were equilibrated for 30 minutes and then repeated. Additional anti-solvent, 10 vol., was charged, equilibrated for 30 minutes, cooled to 25° C. over 1.5 hours and equilibrated for 30 minutes.

Suspensions were isolated via isolutes and vacuum dried to remove excess solvent and then dried in a vacuum oven at 50° C. for 24 hours.

The remaining solutions were reduced to ca. 0.25 mL volume under $N_2$ flow at 25° C. Anti-solvent, 20 vol., was charged and the mixtures equilibrated for 30 minutes.

In an embodiment, there is provided crystalline 5MeODMT benzoate as described above.

Despite the initial suggestion that water was a potentially suitable anti-solvent, the utilisation of water as an anti-solvent failed to afford suspensions.

All THF, Acetone and MeCN containing mixtures (excluding water) afforded suspensions by cooling to 25° C. with 10 volumes of anti-solvent. All other mixtures (excluding water) either required an increased anti-solvent charge or significant solution volume reduction and anti-solvent addition to afford suspensions.

Figure 32:
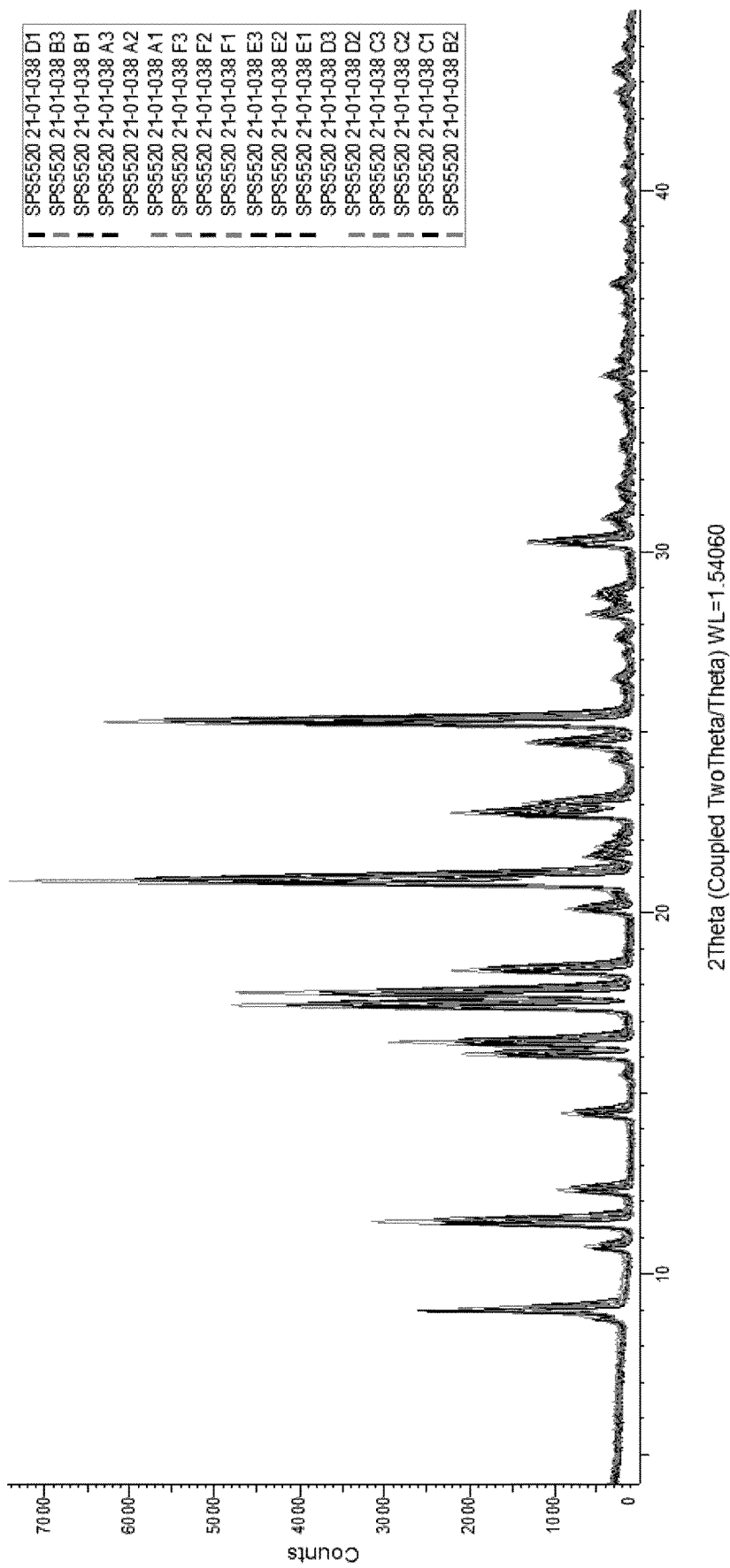
FIG. 32 shows XRPD pattern overlay of samples isolated via anti-solvent mediated crystallisation 5MeODMT benzoate.
Figure 33:
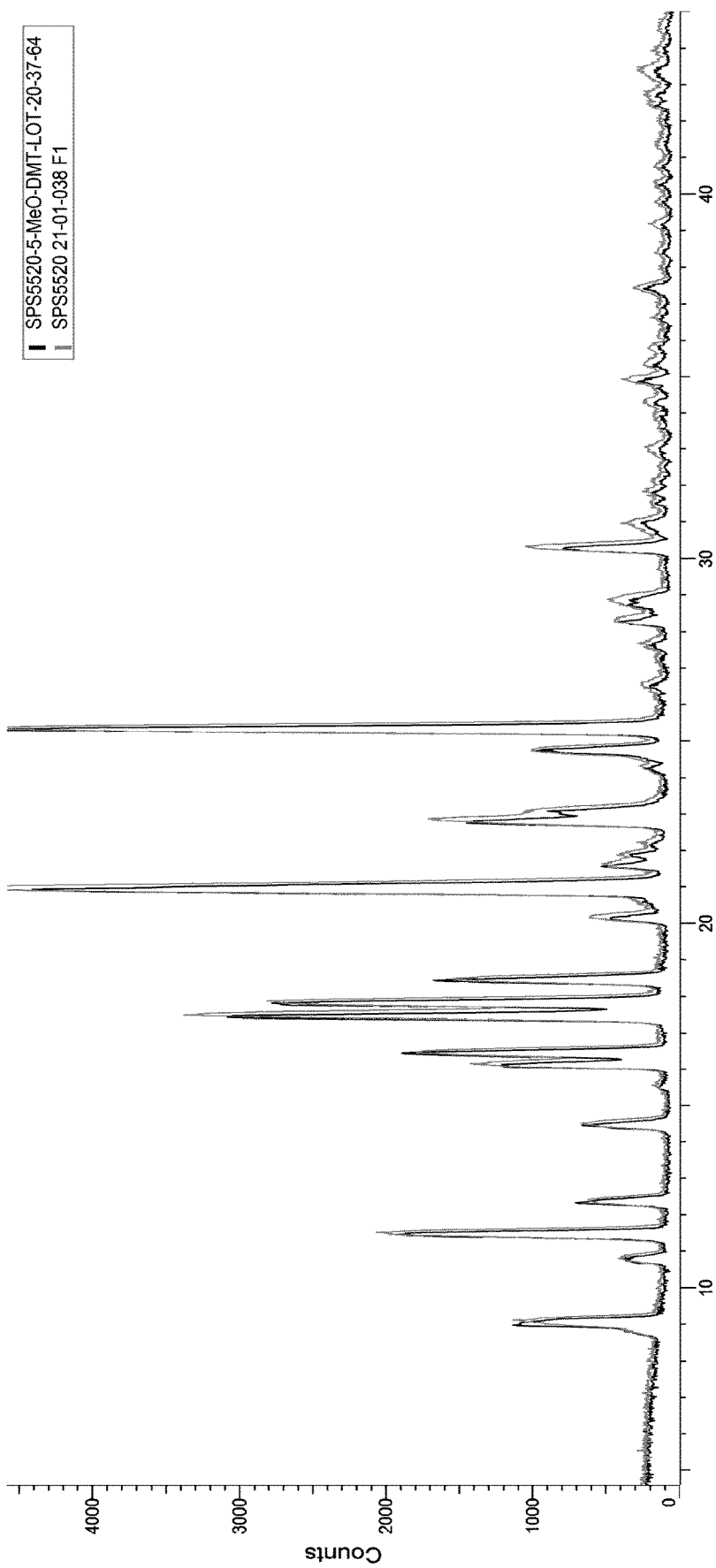
FIG. 33 shows XRPD pattern overlay of 5MeODMT benzoate lot F1 and a reference Pattern A form/material.

The XRPD examination of all isolated and dried solid samples were Pattern A as shown in FIGS. 32 and 33. The XRPD characterisation of the 5MeODMT benzoate solids isolated from anti-solvent mediated crystallisation are concordant with Pattern A. This implies that there is no form/version modification of 5MeODMT benzoate under the conditions investigated.

Controlled Cooling Crystallisation Investigation of 5MeODMT Benzoate

Observations from both the initial equilibration investigation and the first anti-solvent based investigations of 5MeODMT benzoate identified potentially suitable solvents for the dissolution of 5MeODMT benzoate at temperature to afford saturated solutions that could then be subject to a controlled gradual cooling operation.

5MeODMT benzoate, 25±0.5 mg, was dissolved in the minimal volume of solvent at 50° C. (detailed in the Table below). The solutions were clarified through a 0.45 μm Teflon syringe filter into pre-heated crystallisation tubes and cooled from 50° C. to −10° C. over 60 hours (1° C. Hr-1 cooling rate) and held at −10° C. for 50 hours (no agitation).

Several crystallisations contained large off-white crystals on the base of the crystallisation tube (detailed in the Table below). The crystals were directly transferred from the crystallisation tube to the XRPD sample holder and were left open to the atmosphere for ca. 1 hour prior to analysis.

The remaining mixtures were agitated at 400 rpm at ambient temperature, open to the atmosphere to allow partial solvent evaporation, over 18 hours.

Observations with anti-solvent addition and temperature equilibration

| ID | Solvent | Anti-solvent | 2.5 vol.; 50° C.; 30 mins | 5 vol.; 50° C.; 30 mins | 25° C.; 18 hours | 10 vol.; 50° C.; 30 mins | 20 vol.; 50° C.; 30 mins | 20 vol.; 25° C.; 30 mins | Reduced; 20 vol.; 30 mins |
|---|---|---|---|---|---|---|---|---|---|
| A1 | MeOH | Toluene | Solution | Solution | Solution | Solution | Solution | Solution | Suspension |
| A2 | 200.07 | Heptane | Solution | Solution | Solution | Solution | Solution | Solution | Suspension |
| A3 | mg/mL | TBME | Solution | Solution | Solution | Solution | Solution | Solution | Suspension |
| A4 | | DI Water | Solution | Solution | Solution | Solution | Solution | Solution | Solution |
| B1 | IPA | Toluene | Solution | Solution | Solution | Solution | Solution | Solution | Suspension |
| B2 | 50.08 | Heptane | Solution | Solution | Suspension | N/a | N/a | N/a | N/a |
| B3 | mg/mL | TBME | Solution | Solution | Solution | Solution | Solution | Solution | Suspension |
| B4 | | DI Water | Solution | Solution | Solution | Solution | Solution | Solution | Solution |
| C1 | THF | Toluene | Suspension | Suspension | Suspension | N/a | N/a | N/a | N/a |
| C2 | 200.35 | Heptane | Suspension | Suspension | Suspension | N/a | N/a | N/a | N/a |
| C3 | mg/mL | TBME | Suspension | Suspension | Suspension | N/a | N/a | N/a | N/a |
| C4 | | DI Water | Solution | Solution | Solution | Solution | Solution | Solution | Solution |
| D1 | 2-MeTHF | Toluene | Solution | Solution | Solution | Solution | Solution | Solution | Suspension |
| D2 | 50.02 | Heptane | Solution | Solution | Solution | Solution | Suspension | Suspension | N/a |
| D3 | mg/mL | TBME | Solution | Solution | Solution | Solution | Solution | Suspension | N/a |
| D4 | | DI Water | Solution | Solution | Solution | Solution | Solution | Solution | Solution |
| E1 | Acetone | Toluene | Solution | Solution | Suspension | N/a | N/a | N/a | N/a |
| E2 | 100.22 | Heptane | Suspension | Suspension | Suspension | N/a | N/a | N/a | N/a |
| E3 | mg/mL | TBME | Solution | Solution | Suspension | N/a | N/a | N/a | N/a |
| E4 | | DI Water | Solution | Solution | Solution | Solution | Solution | Solution | Solution |
| F1 | MeCN | Toluene | Solution | Solution | Suspension | N/a | N/a | N/a | N/a |
| F2 | 100.25 | Heptane | Solution | Solution | Suspension | N/a | N/a | N/a | N/a |
| F3 | mg/mL | TBME | Solution | Solution | Suspension | N/a | N/a | N/a | N/a |
| F4 | | DI Water | Solution | Solution | Solution | Solution | Solution | Solution | Solution |

| ID | Solvent | Solubility (mg · mL⁻¹) | −10° C.; 50 hours | Volume reduced; 25° C.; 18 hours | XRPD |
|---|---|---|---|---|---|
| A | MeOH | 250 | Solution | Solution | N/a |
| B | IPA | 42 | Crystallites | N/a | Pattern A |
| C | THF | 83 | Solution | Suspension | TBD |
| D | 2-MeTHF | 31.25 | Crystallites | N/a | Pattern A |
| E | Acetone | 62.5 | Crystallites | N/a | Pattern A |
| F | MeCN | 50 | Crystallites | N/a | Pattern A |
| G | MEK | 62.5 | Crystallites | N/a | Pattern A |
| H | Nitromethane | 125 | Crystallites | N/a | Pattern A |
| I | 3-methyl-1-butanol | 31.25 | Crystallites | N/a | Pattern A |
| J | Chlorobenzene | 12.5 | Solution | Suspension | — |
| K | iPrOAc | 12.5 | Solution | Suspension | — |
| L | MeOH:TBME (1:1) | 125 | Solution | Solid | — |

Figure 34:
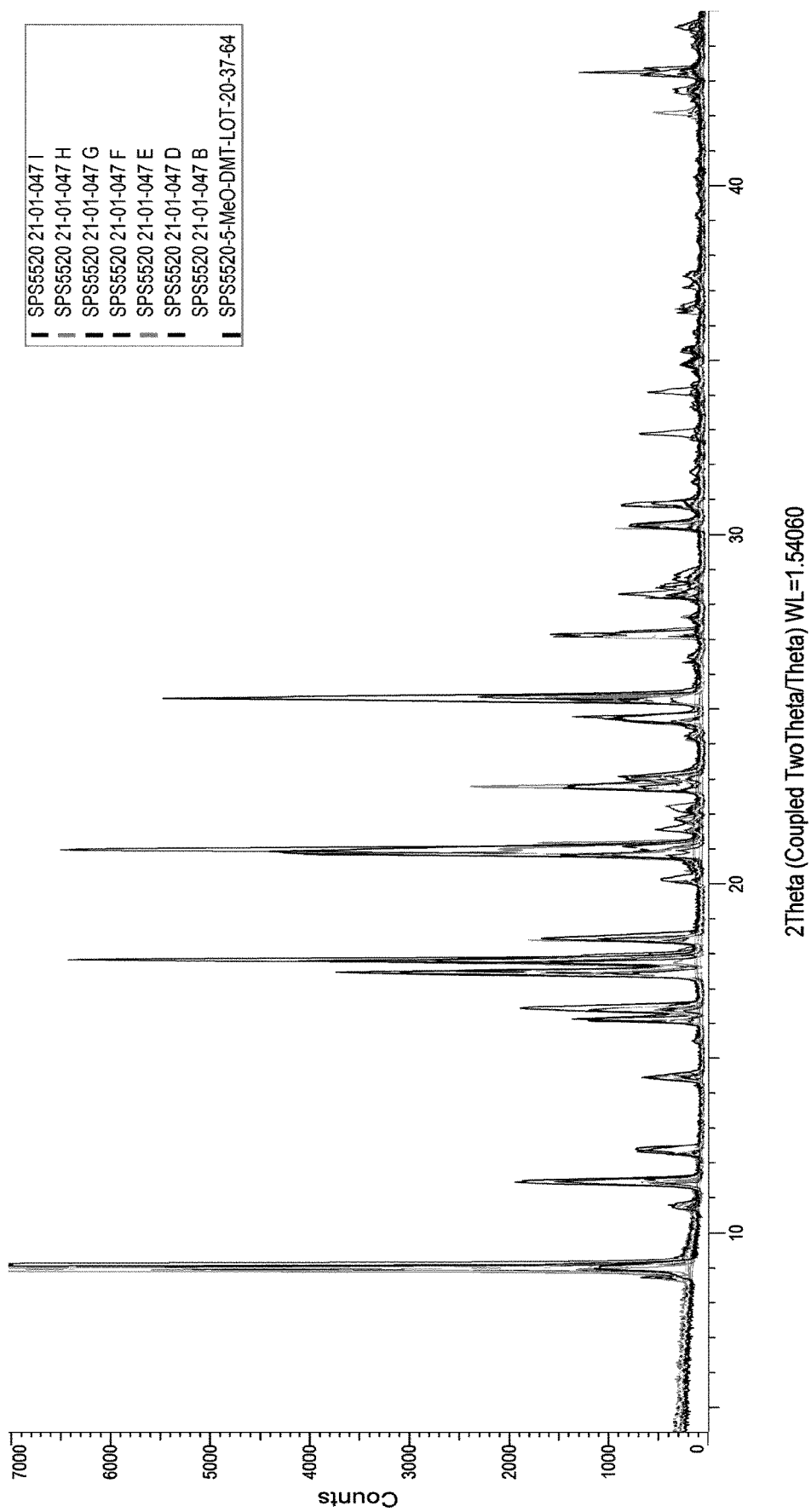
FIG. 34 shows XRPD pattern overlay of 5MeODMT benzoate samples isolated from cooling and a Pattern A reference.

XRPD examination of the solid samples isolated following cooling of the solutions (observed as relatively large particles) revealed evidence of preferred orientation (FIG. 34).

Figure 35:
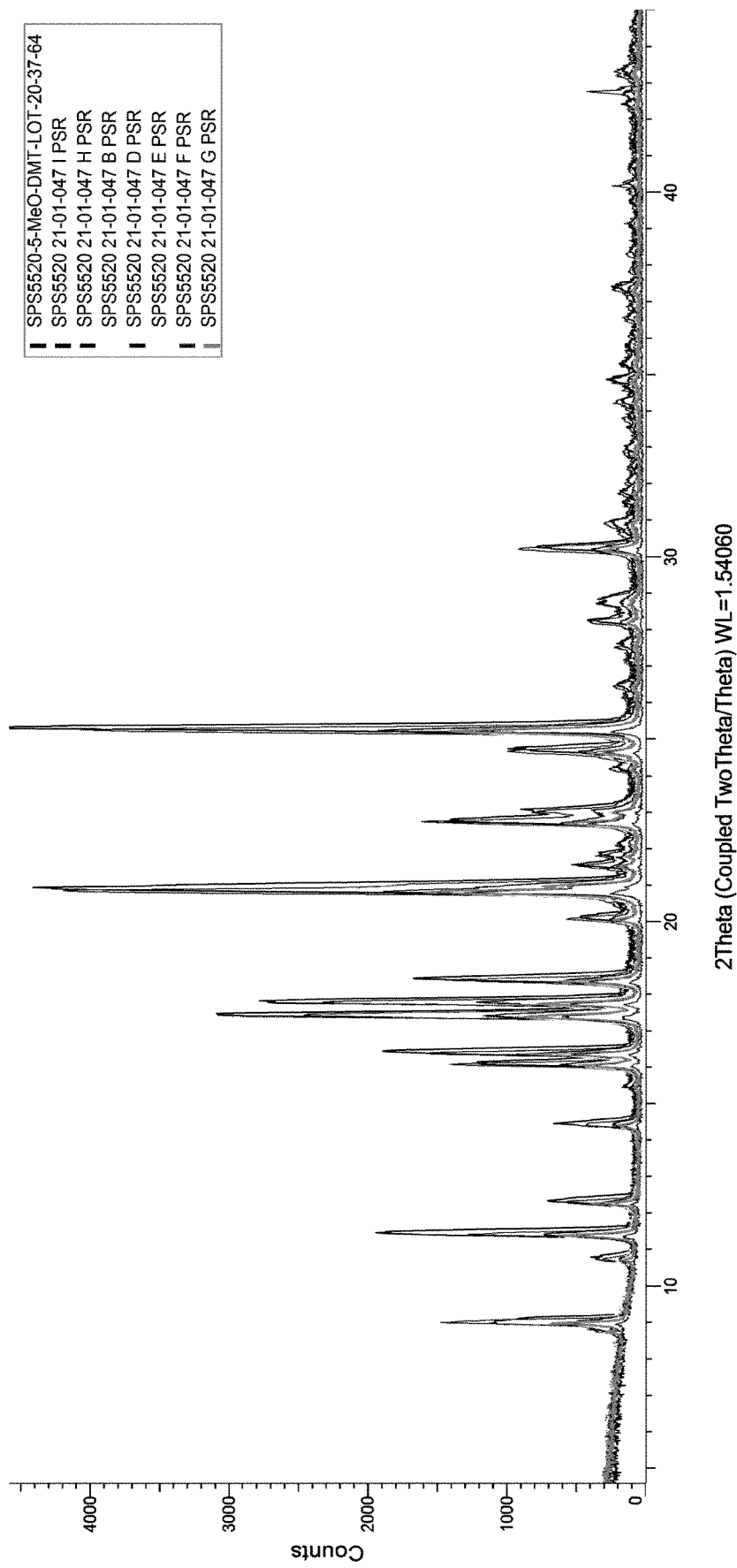
FIG. 35 shows XRPD pattern overlay of 5MeODMT benzoate samples isolated from cooling post-particle size reduction and Pattern A reference.

The particle size of the samples was reduced via particle size reduction with a mortar and pestle. Subsequent reexamination by XRPD revealed all solids to be Pattern A (FIG. 35).

The XRPD characterisation of the 5MeODMT benzoate solids isolated to date from the single solvent mediated crystallisation of 5MeODMT benzoate are concordant with Pattern A. This implies that there is no form or version modification 5MeODMT benzoate under the conditions investigated.

In an embodiment, there is provided crystalline 5MeODMT benzoate as described above.

Reverse Addition Anti-Solvent Driven Crystallisation of 5MeODMT Benzoate

The first anti-solvent-driven crystallisation of 5MeODMT benzoate, revealed a selection of suitable solvent/anti-solvent mixtures. Utilising relatively gradual anti-solvent addition and cooling from elevated temperature afforded only solids classed as Pattern A by XRPD. The suitable solvent/anti-solvent mixtures were re-examined with reverse addition of hot stock solution to cold anti-solvent to potentially rapidly precipitate a new and/or meta-stable solid form version of 5MeODMT benzoate.

5MeODMT benzoate, 165±0.5 mg, was charged to vials A to F and dissolved in the minimal amount of solvent at 50° C. as detailed in the Table below.

Anti-solvent, 1 ml, was charged to crystallisation tubes then cooled to −10° C. and agitated at 400 rpm.

Aliquots of the stock solutions of 5MeODMT benzoate, ca. 50 mg, were charged directly to the anti-solvents.

All crystallisation tubes afforded suspensions within 5 minutes of addition of the 5MeODMT benzoate solution.

Suspensions were isolated immediately in vacua via isolute then transferred to vacuum oven and dried at 50° C. for 18 hours.

TABLE

Summary of solvents, anti-solvents and observations

| ID | Solvent | Anti-solvent | Observations upon charging warm saturated solutions to cold anti-solvent | XRPD |
|---|---|---|---|---|
| A1 | MeOH | Toluene | suspension within 1 minute. | Pattern B |
| A2 | | Heptane | suspension within 1 minute. | N/a |
| A3 | | TBME | suspension within 1 minute. | Pattern A |
| B1 | IPA | Toluene | suspension within 5 minutes. | Pattern B |
| B2 | | Heptane | suspension within 1 minute. | Pattern A |
| B3 | | TBME | suspension within 5 minutes. | Pattern A |
| C1 | THF | Toluene | suspension within 1 minute. | Pattern A |
| C2 | | Heptane | Suspension upon addition | Pattern A |
| C3 | | TBME | suspension within 1 minute. | Pattern A |
| D1 | 2-MeTHF | Toluene | suspension within 1 minute. | Pattern A |
| D2 | | Heptane | Suspension upon addition | Pattern A |
| D3 | | TBME | suspension within 1 minute. | Pattern A |
| E1 | Acetone | Toluene | suspension within 1 minute. | Pattern A |
| E2 | | Heptane | suspension within 1 minute. | Pattern A |
| E3 | | TBME | suspension within 1 minute. | Pattern A |
| F1 | MeCN | Toluene | suspension within 1 minute. | Pattern A |
| F2 | | Heptane | Precipitate upon addition | Pattern A |
| F3 | | TBME | suspension within 1 minute. | Pattern A |

Figure 36:
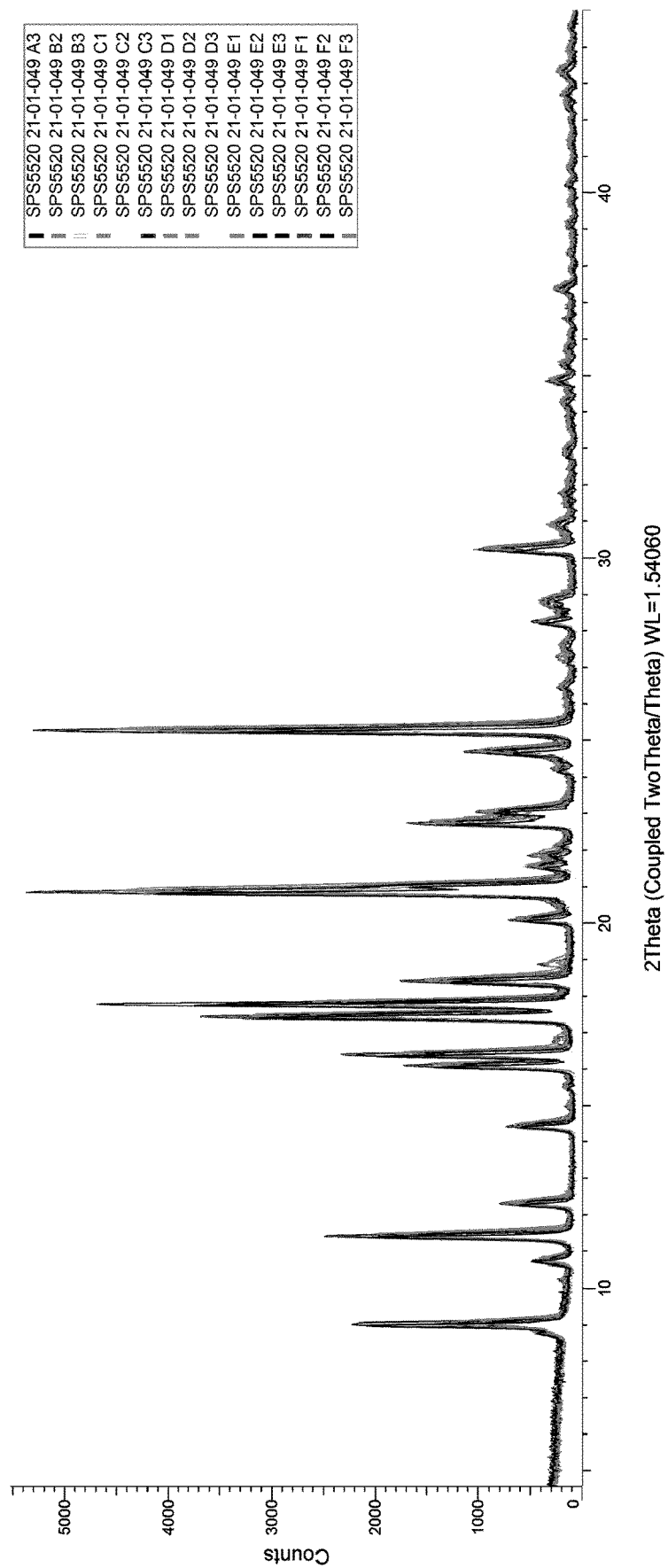
FIG. 36 shows XRPD pattern comparison for all samples from the reverse addition anti-solvent driven crystallisation of 5MeODMT benzoate except for A1 and B1.
Figure 37:
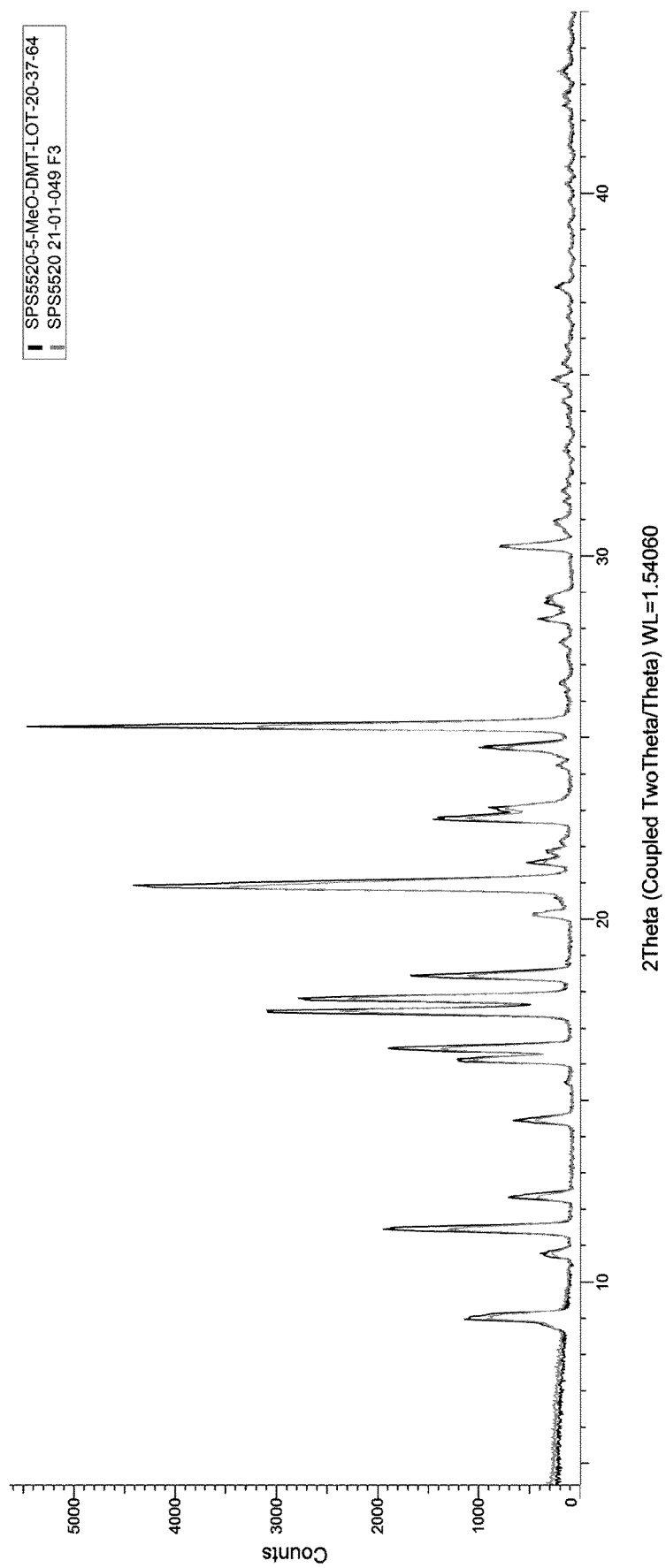
FIG. 37 shows XRPD pattern comparison for 5MeODMT benzoate F3 with a known Pattern A reference.

XRPD examination of most isolated solids (except for A1 and B1) were concordant with Pattern A (see FIGS. 36 and 37).

Figure 38:
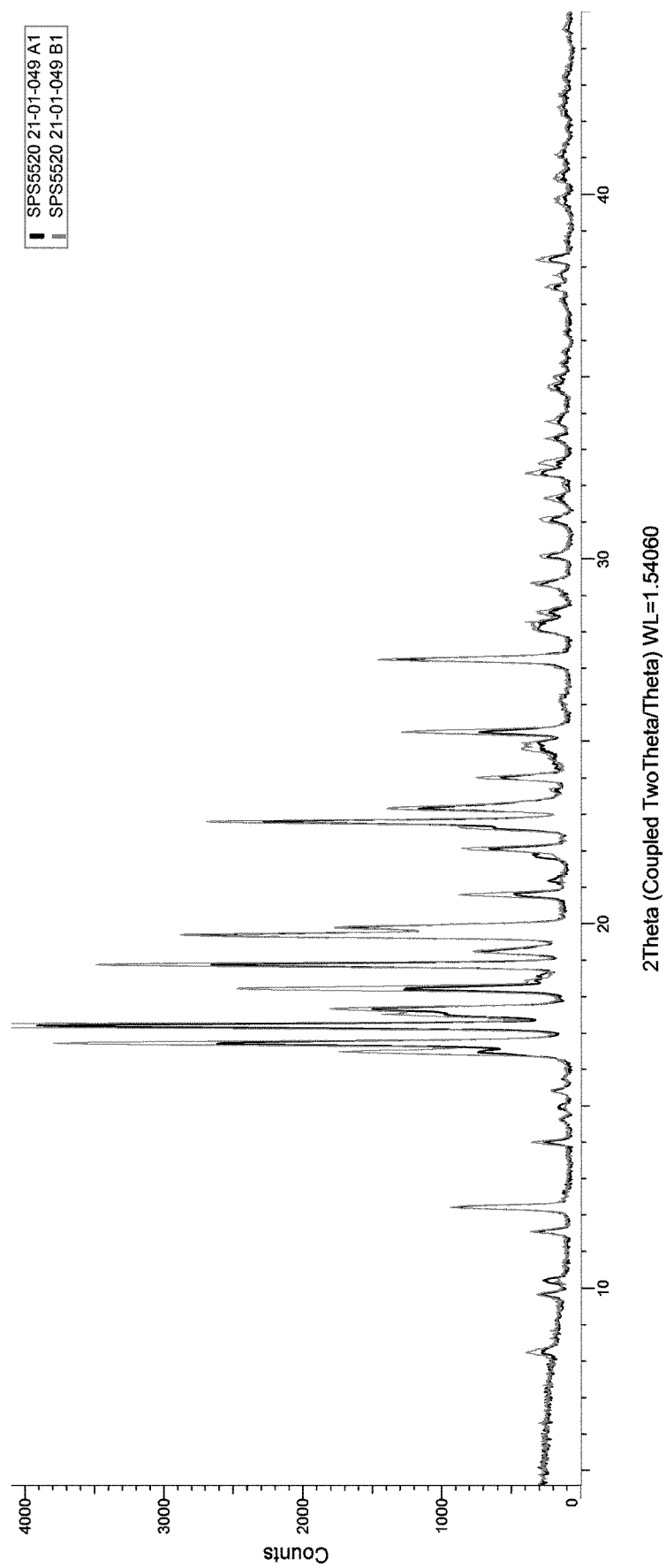
FIG. 38 shows XRPD pattern comparison of 5MeODMT benzoate A1 and B1.
Figure 39:
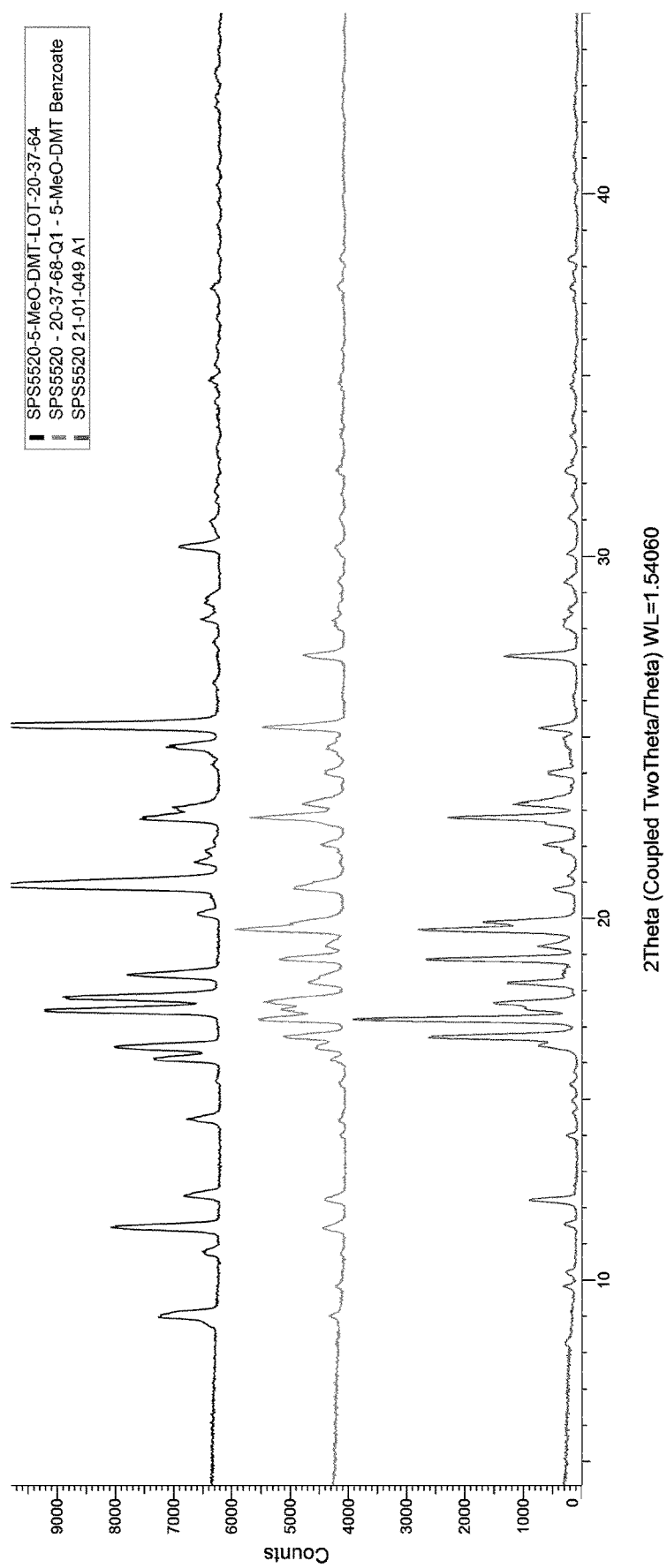
FIG. 39 shows XRPD patterns for 5MeODMT benzoate A1, Q1 and a reference Pattern A pattern.
Figure 40:
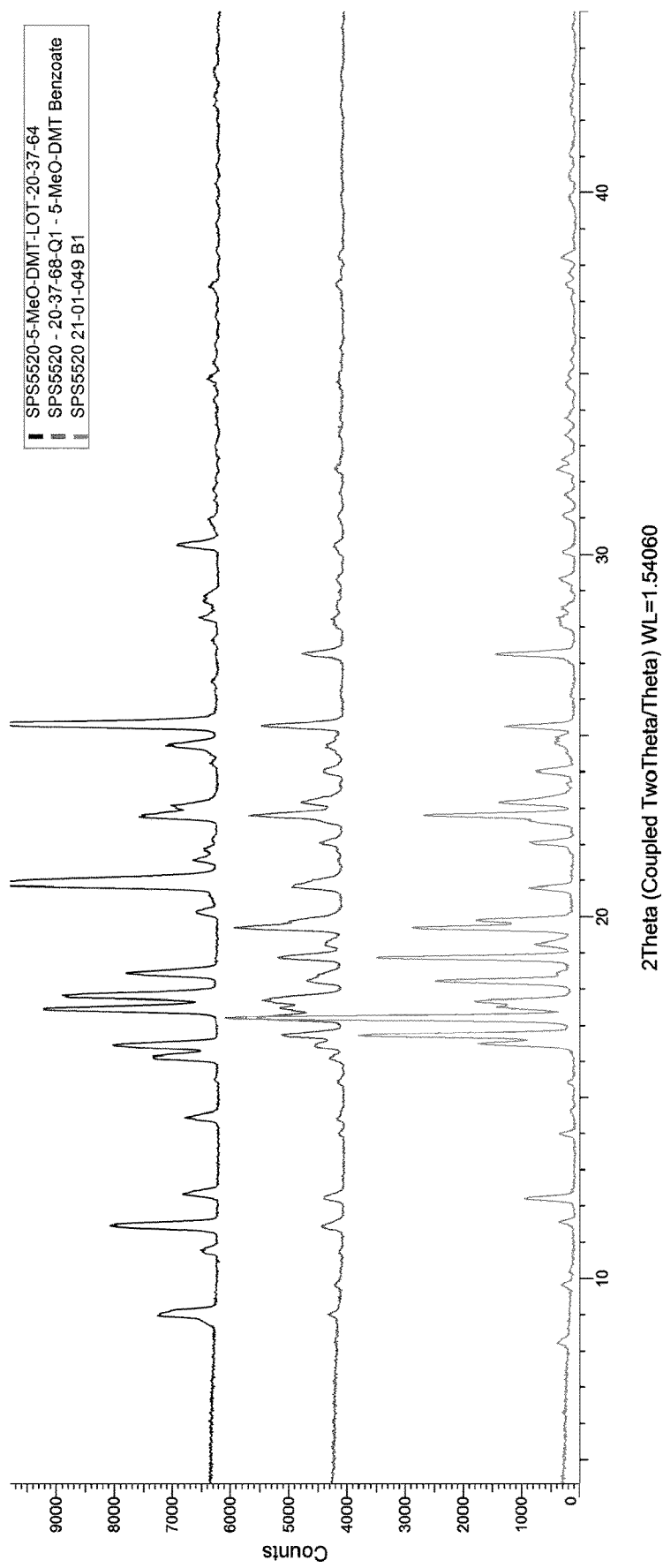
FIG. 40 shows XRPD patterns for 5MeODMT benzoate B1, Q1 and a reference Pattern A pattern.

XRPD examination of solids A1 and 81 were concordant with one another but not Pattern A (FIGS. 38, 39)

Lots A1 and B1 shared diffractions with 5MeODMT benzoate lot Q1 (a pattern previously identified as Form B). However, on closer inspection, Q1 was observed to share diffractions with Pattern A. As lot Q1 shared diffractions with both lots A1 and 81 and Pattern A.

The diffraction patterns for lots A1 and B1 were considered to be characteristic of Pattern B.

Figure 41:
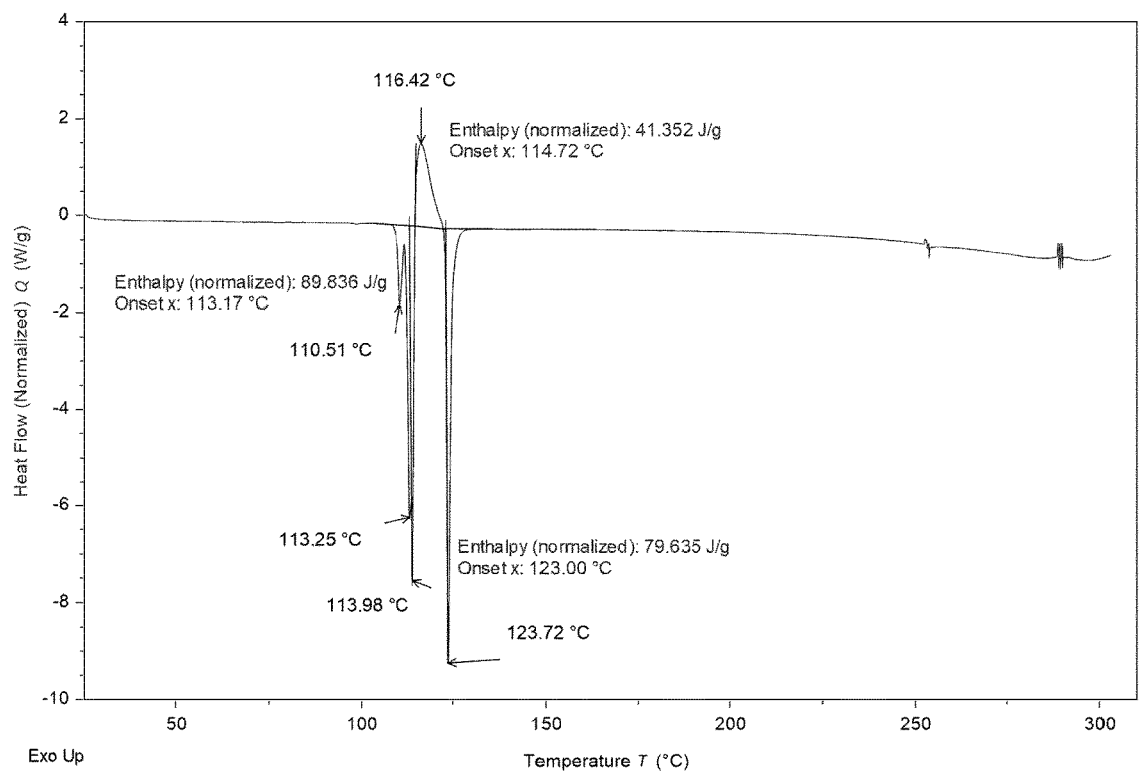
FIG. 41 shows a DSC thermograph of 5MeODMT benzoate sample A1 at 10° C.·min$^{-1}$ isolated from methanol and toluene.

The DSC thermograph of sample A1 (FIG. 41) revealed an endothermic event with onset ca. 110° C. and major peak at 113.98° C., followed by an exotherm with onset 114.72° C. and peak at 116.42° C., followed by a second endotherm with an onset of 123.00° C. and peak at 123.72° C.

Figure 42:
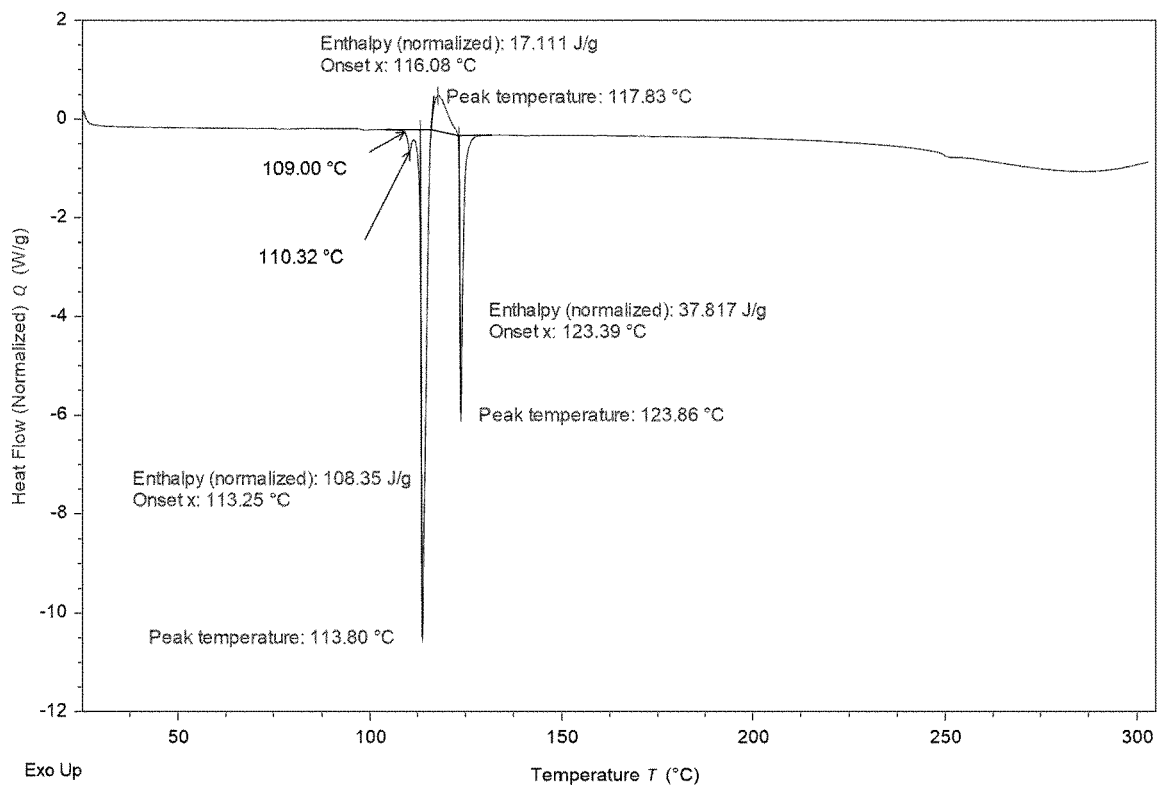
FIG. 42 shows a DSC thermograph of 5MeODMT benzoate B1 at 10° C.·min-1 isolated from isopropanol and toluene.
Figure 43:
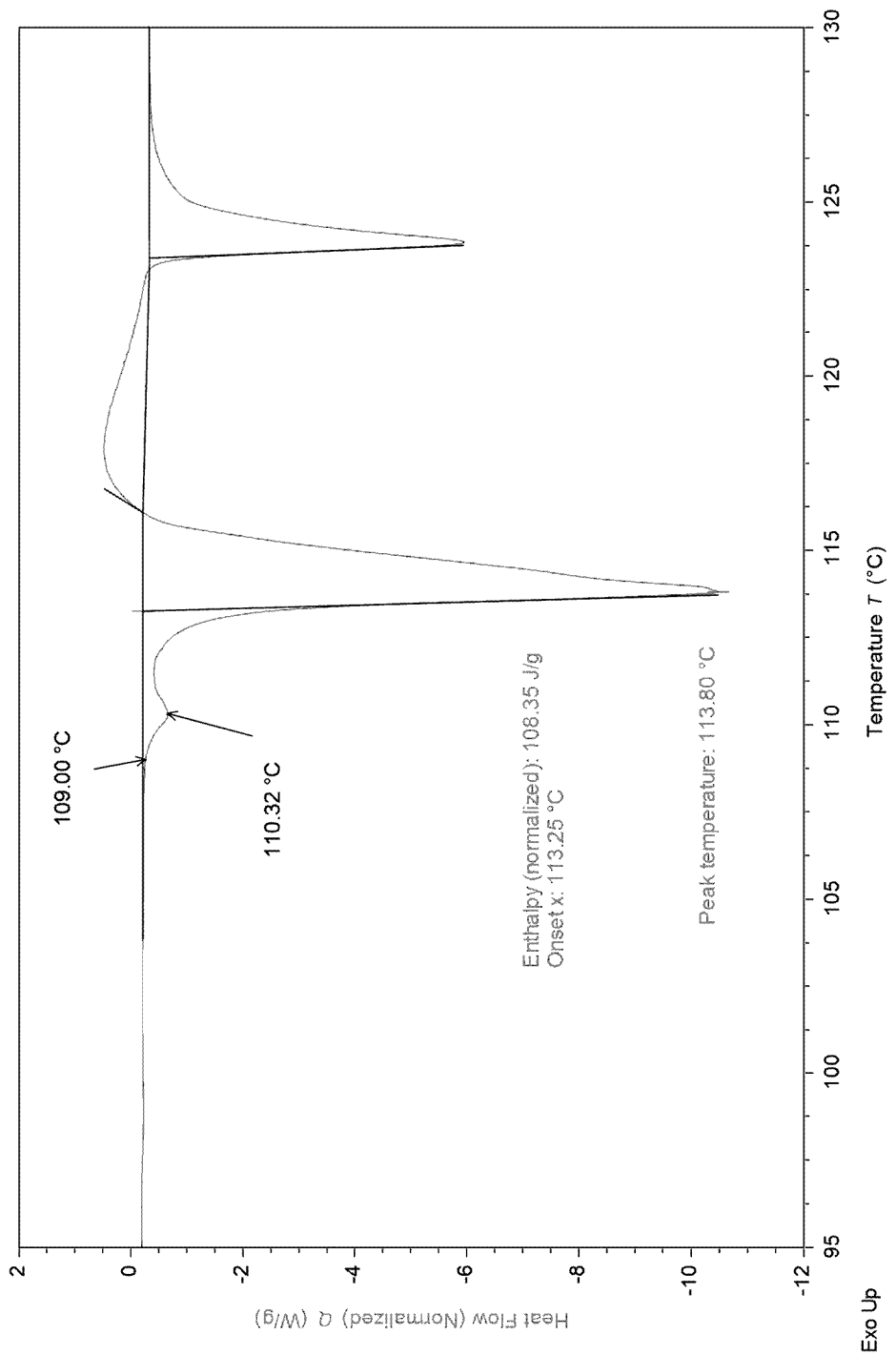
FIG. 43 shows a DSC thermograph expansion of 5MeODMT benzoate. B1 at 10° C.·min-1 isolated from isopropanol and toluene.

DSC examination of sample B1 (FIG. 42 and FIG. 43) revealed a similar DSC thermograph to A1 but the first endothermic event was larger, 108 J·g⁻¹ compared 90 J·g⁻¹ and only contained 2 peak temperatures of 109.00 and 110.32° C. instead of the 3 present in A1. The exothermic event that immediately followed was smaller, 17 J·g⁻¹ compared to 41 J·g⁻¹. The second main endotherm was also smaller for 81 at 38 J·g⁻¹ compared to 80 J·g⁻¹ for A1.

In an embodiment, there is provided crystalline 5MeODMT benzoate as described above.

In an embodiment, there is provided crystalline 5MeODMT salt, characterised by an endothermic or exothermic event in a DSC thermograph as substantially illustrated in any one of the Figures.

In an embodiment, there is provided a composition comprising 5MeODMT benzoate Pattern A form.

In an embodiment, there is provided a composition comprising 5MeODMT benzoate Pattern B form.

In an embodiment, there is provided a composition comprising a mixture of 5MeODMT benzoate Pattern A form and Pattern B form.

Example 22: Generation of the Amorphous 5MeODMT Benzoate

Rapid in Vacuo Concentration

5MeODMT benzoate, 101.55 mg, was dissolved in THF, 4 mL and clarified into a 100 mL round bottom flask. The solution was concentrated in vacuo 40° C. at 200 rpm. The liquid evaporated from the flask, yielding a concentrated clear colourless liquid residue around the flask.

The residue was dissolved in acetone, 4 ml, concentrated in vacuo at 40° C. at 200 rpm. The liquid evaporated from the flask, yielding a concentrated clear colourless liquid residue around the flask. Small crystals were visible on the inside of the flask, these were isolated after 18 hours affording 21-01-051 A.

Quench of Melt

5MeODMT benzoate was held at 125° C. for 5 minutes by TGA then cooled to ambient over 3 minutes affording 21-01-051 B. The sample was analysed immediately and after 20 hours held in a sealed container.

Lyophilisation

5MeODMT benzoate, 200 mg, was dissolved in deionised water, 10 ml, and clarified through a 0.45 µm nylon filter into a 500 mL round bottom flask, then frozen into a thin layer. The flask was transferred to a vacuum and equilibrated to ambient temperature affording a fluffy white solid, 21-01-051 C.

The solid transformed into gum over ca. 1 hour. The sample was analysed immediately and after 20 hours held in a sealed container.

Lyophilisation for Amorphous Solid Equilibration

Lyophilisation was repeated as described above with 5MeODMT benzoate, 800 mg, dissolved in 25 ml, affording 21-01-051 D. The solid was heated to 60° C. for 10 minutes then cooled yielding 21-01-051 E. The sample was analysed immediately.

Figure 44:
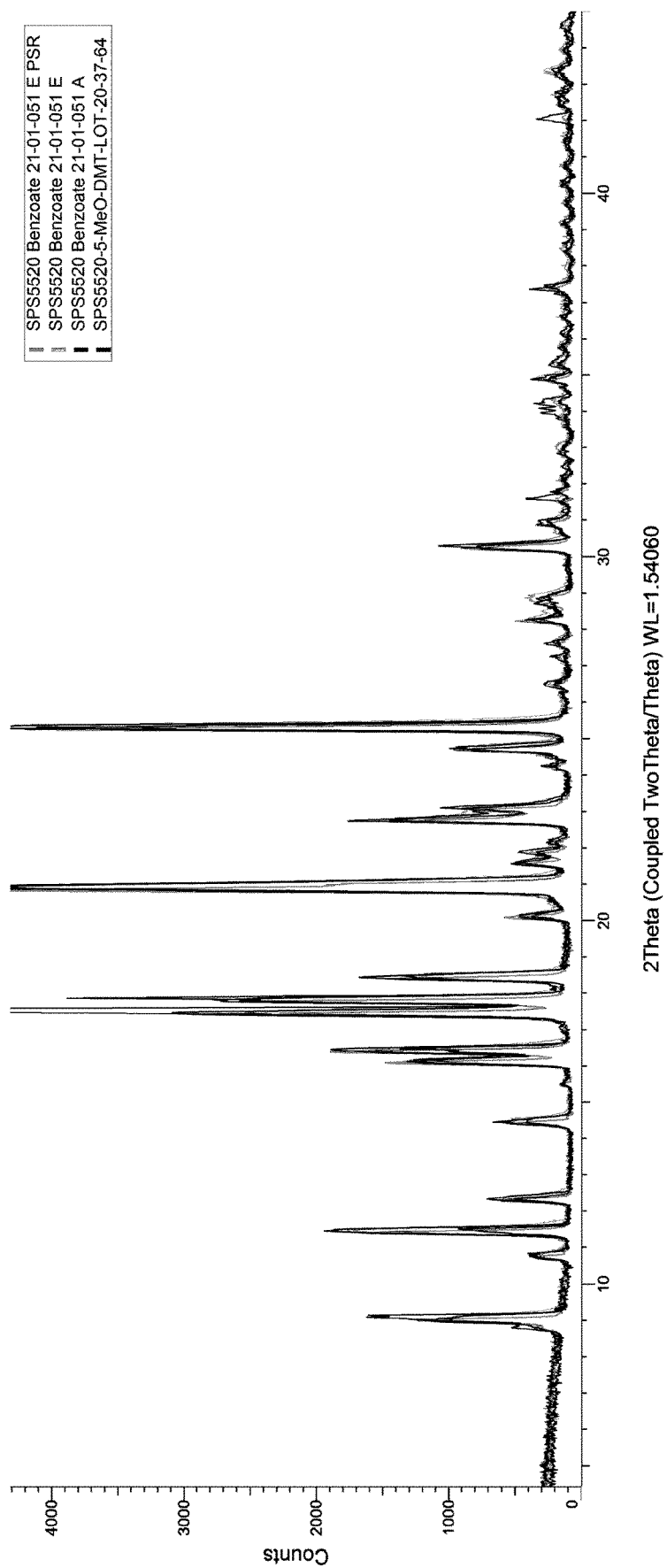
FIG. 44 shows XRPD comparison of 5MeODMT benzoate lot 21-01-051 A, E; E Particle size reduced and Pattern A reference.

FIG. 44 shows XRPD comparison of 5MeODMT benzoate lot 21-01-051 A, E, E Particle size reduced and Pattern A reference.

Figure 45:
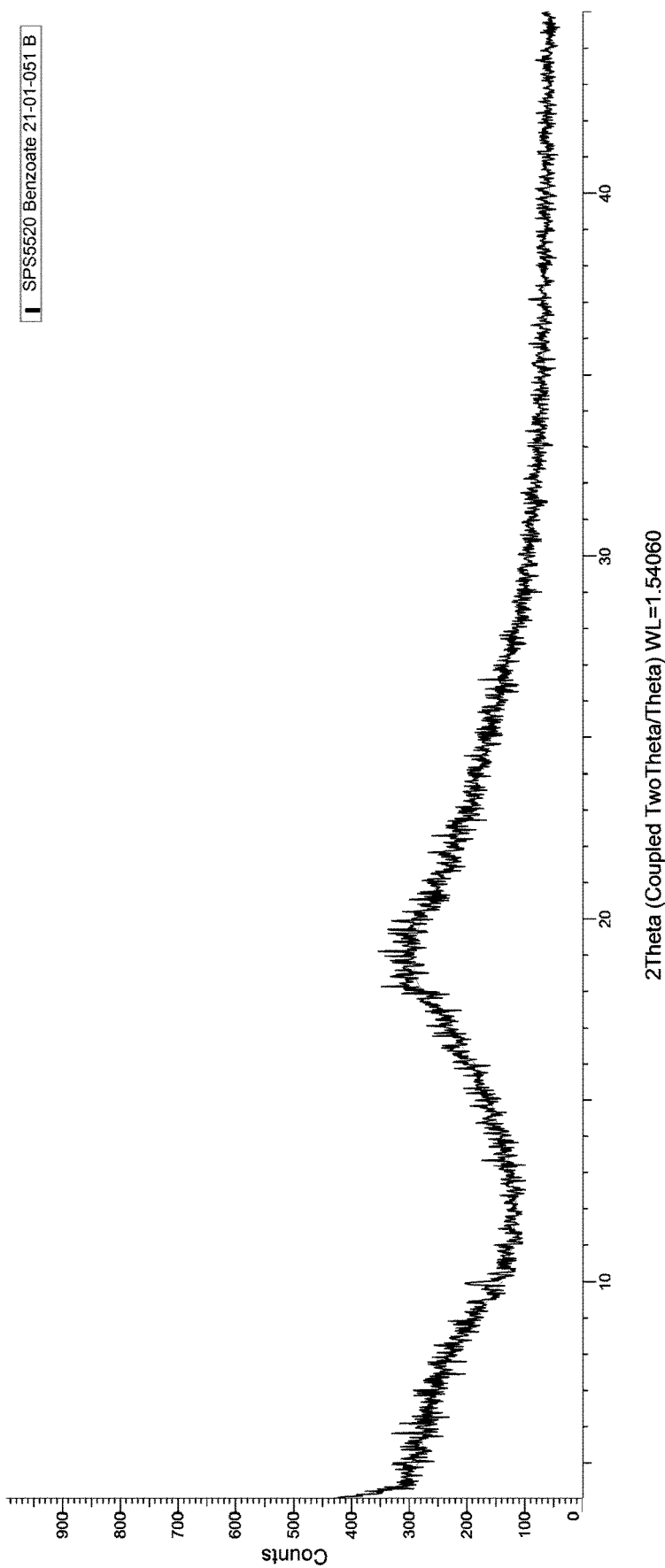
FIG. 45 shows XRPD of 5MeODMT benzoate lot 21-01-051 B, obtained from quenching the melt.

FIG. 45 shows XRPD of 5MeODMT benzoate lot 21-01-051 B, obtained from quenching the melt.

Figure 46:
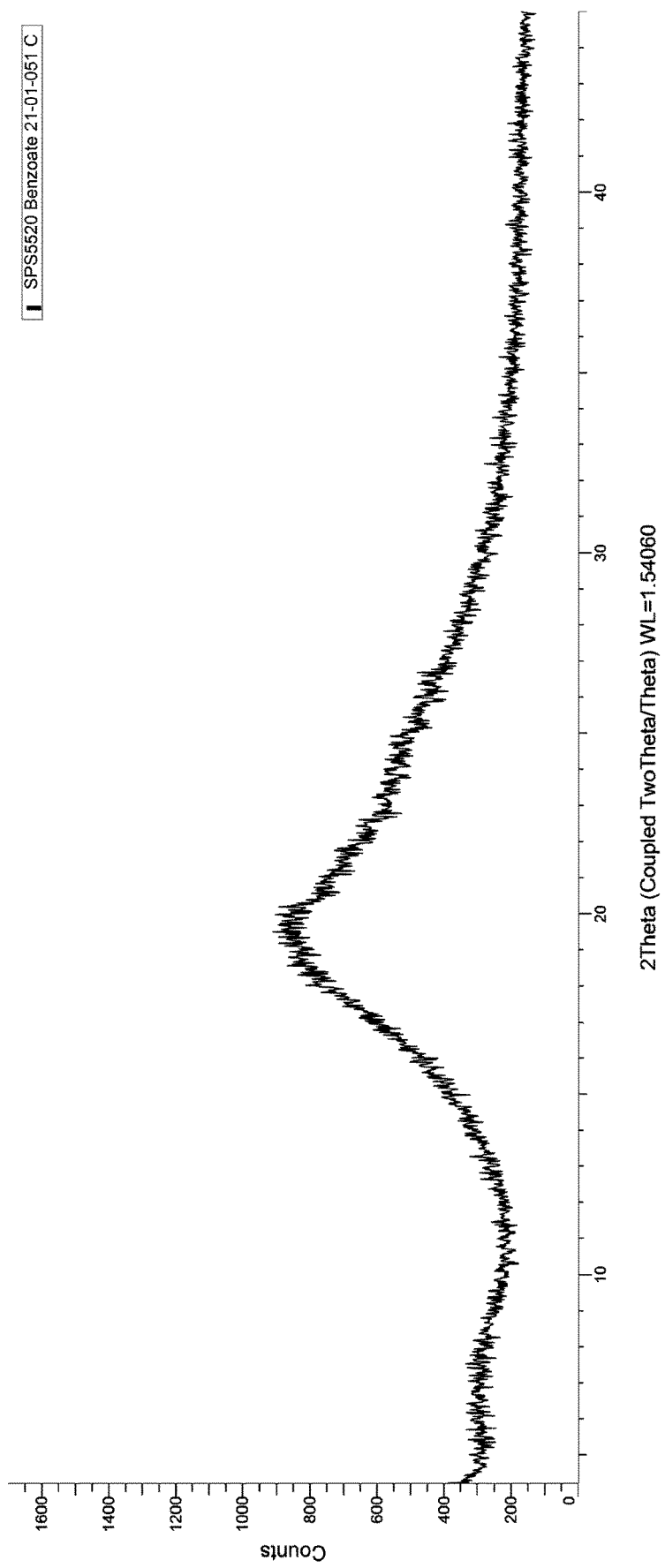
FIG. 46 shows XRPD of 5MeODMT benzoate lot 21-01-051 C, obtained by lyophilisation.

FIG. 46 shows XRPD of 5MeODMT benzoate lot 21-01-051 C, obtained by lyophilisation.

The XRPD patterns of 5MeODMT benzoate 21-01-051 B and C were concordant with Pattern A, indicating that the amorphous form converts to Pattern A form in a sealed container at ambient temperature and pressure.

The XRPD pattern of 5MeODMT benzoate 21-01-051 A, the solid isolated by acetone concentration, was concordant with Pattern A form. Rapid in vacuo concentration did not produce the amorphous version.

The XRPD patterns revealed 5MeODMT benzoate 21-01-051 B and C to have an amorphous 'halo', indicating quenching molten material and lyophilisation produced amorphous 5MeODMT benzoate.

Figure 47:
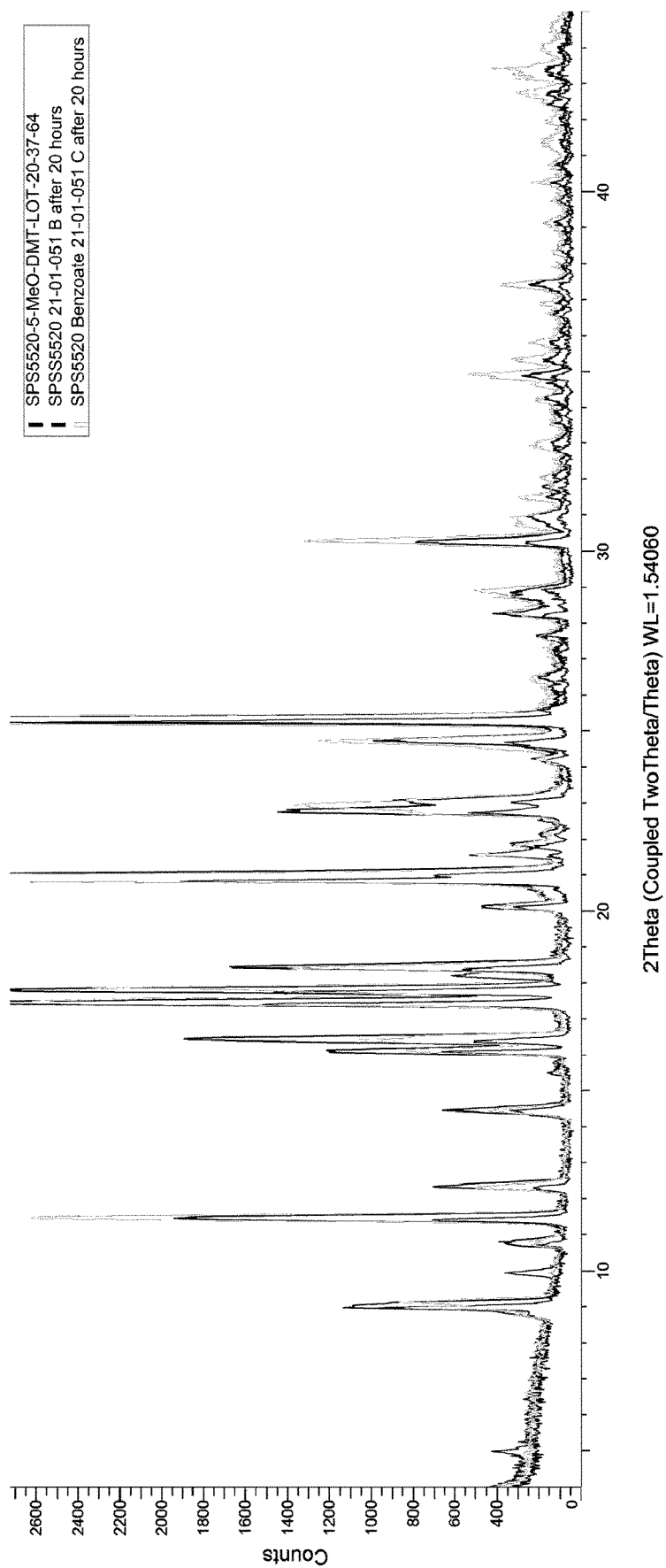
FIG. 47 shows XRPD comparison of 5MeODMT benzoate lot 21-01-051 B after 20 hours, C after 20 hours, and Pattern A reference.

FIG. 47 shows XRPD comparison of 5MeODMT benzoate lot 21-01-051 B after 20 hours, C after 20 hours, and Pattern A reference.

The XRPD pattern of 5MeODMT benzoate 21-01-051 E were concordant with Pattern A, indicating that the amorphous form converts to Pattern A form at 60° C. for 10 minutes.

Figure 48:
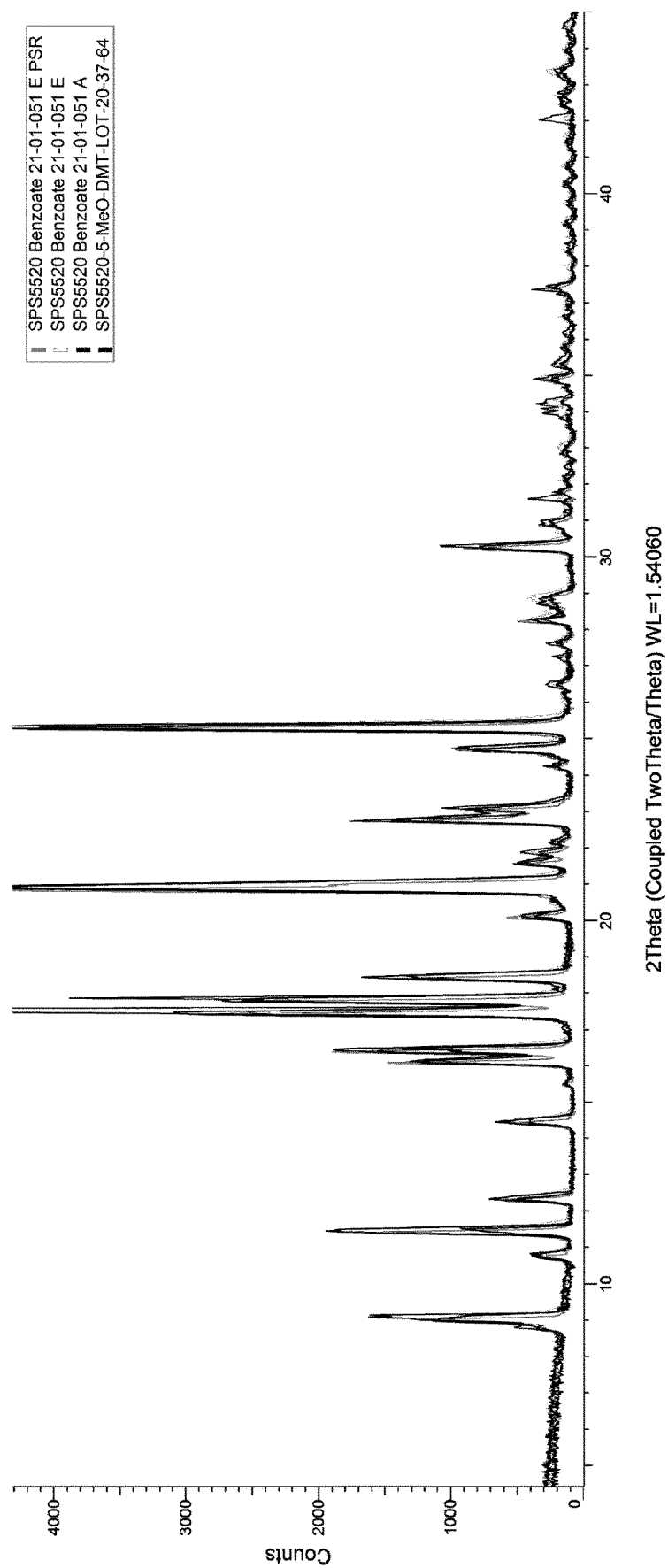
FIG. 48 shows XRPD comparison of 5MeODMT benzoate lot 21-01-051 A, E; E particle size reduced, and Pattern A reference.

FIG. 48 shows XRPD comparison of 5MeODMT benzoate lot 21-01-051 A, E, E particle size reduced, and Pattern A reference.

DSC examination revealed amorphous 5MeODMT benzoate 21-01-051 C and D obtained by lyophilisation, contained an exothermic event with a peak temperature between 65.63 and 70.84° C., followed by a broad endothermic shoulder leading into a endothermic event with a peak temperature between 120.20 and 121.22° C. The major endothermic event is ca. 3° C. lower compared to Pattern A form material.

Figure 49:
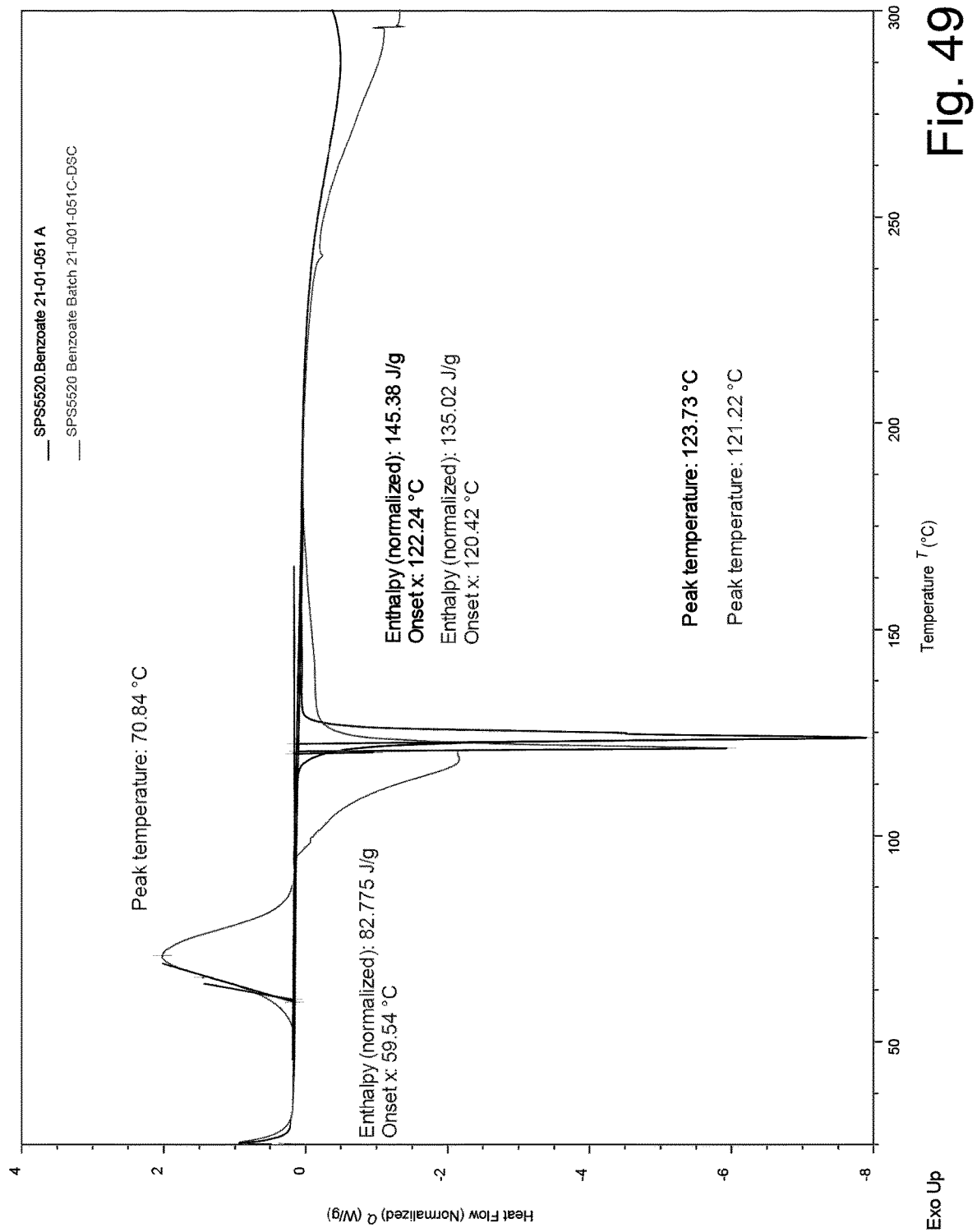
FIG. 49 shows DSC thermograph comparison of 5MeODMT benzoate lot 21-01-051 A, C, and D at 10° C.·min$^{-1}$, isolated from acetone concentrate, 051 A, and lyophilisation, 051 C and 051 D.

FIG. 49 shows DSC thermograph comparison of 5MeODMT benzoate lot 21-01-051 A, C, and D at 10° C.·min$^{-1}$, isolated from acetone concentrate, 051 A, and lyophilisation, 051 C and 051 D.

DSC examination revealed 5MeODMT benzoate 21-01-051 C post 20 hours no longer contained an exothermic event and the endothermic event at ca. 123° C. was sharper and concordant with Pattern A form.

Figure 50:
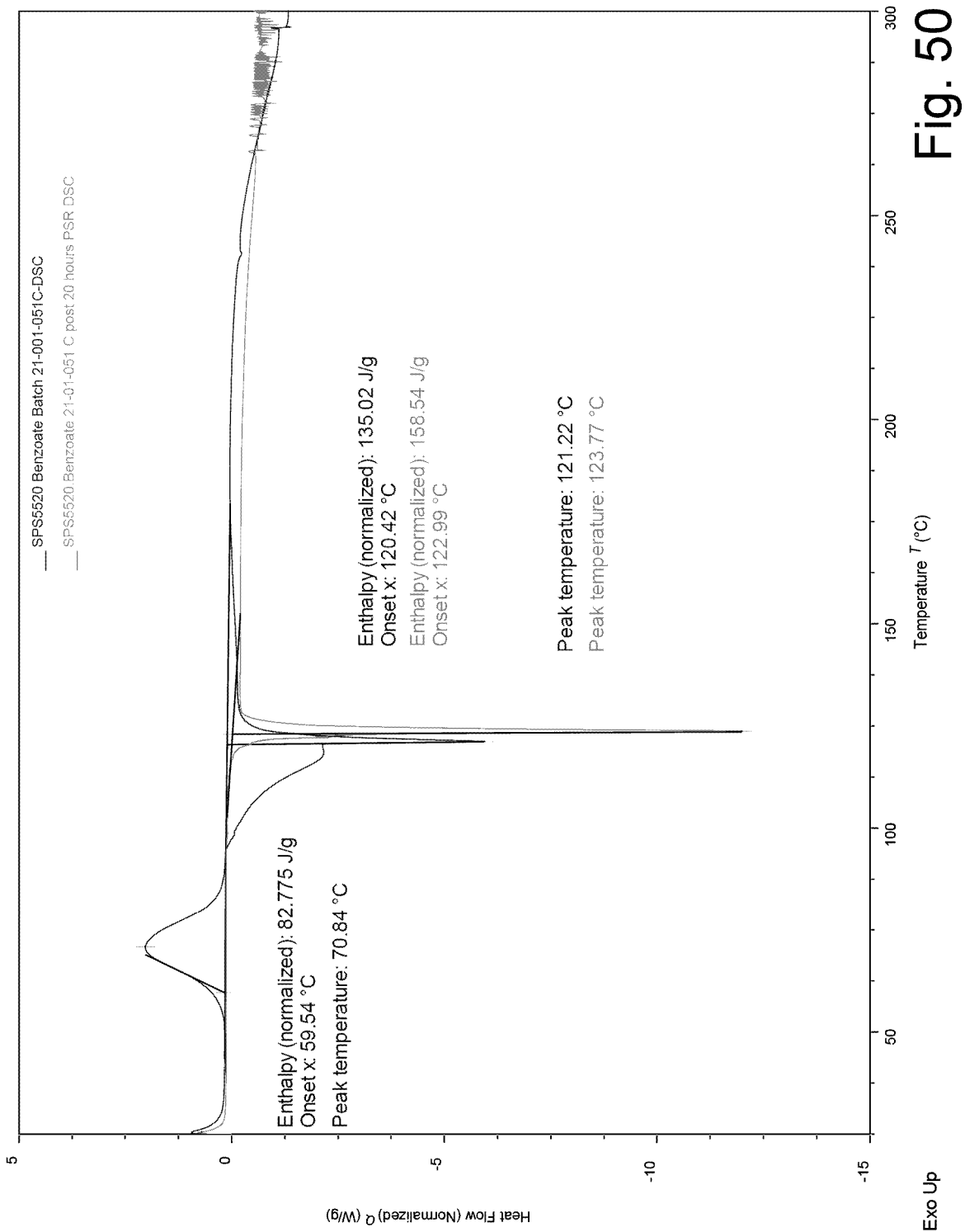
FIG. 50 shows DSC thermograph comparison of 5MeODMT benzoate lot 21-01-051 C and C post 20 hours at 10° C.·min$^{-1}$.

FIG. 50 shows DSC thermograph comparison of 5MeODMT benzoate lot 21-01-051 C and C post 20 hours at 10° C.·min$^{-1}$.

Amorphous 5MeODMT benzoate can be generated by lyophilisation of an aqueous solution and the quenched melt.

The amorphous 5MeODMT benzoate will convert to Pattern A form material on standing.

In one embodiment, there is provided an amorphous 5MeODMT benzoate. In one embodiment, there is provided a composition comprising an amorphous 5MeODMT benzoate.

In one embodiment, there is provided a composition comprising an amorphous 5MeODMT benzoate salt produced as detailed above or below.

Example 23: Further Characterisation of Amorphous 5MeODMT Benzoate

The thermal examination of amorphous 5MeODMT benzoate by DSC and hot stage microscopy revealed a crystallisation event and endothermic melt. The endothermic melt is not consistent with the DSC thermograph of Pattern A form.

The solvent mediated equilibration of amorphous 5MeODMT benzoate with thermal modulation afforded Pattern A by XRPD and DSC from all solvents except anisole. New variations were generated.

Amorphous 5MeODMT benzoate generated by lyophilisation, 21-01-051 D (21-01-051) was examined by hot-stage microscopy at a heating rate of 5° C.·min-1 for corroboration with the DSC thermograph of the amorphous solid.

Figure 52:
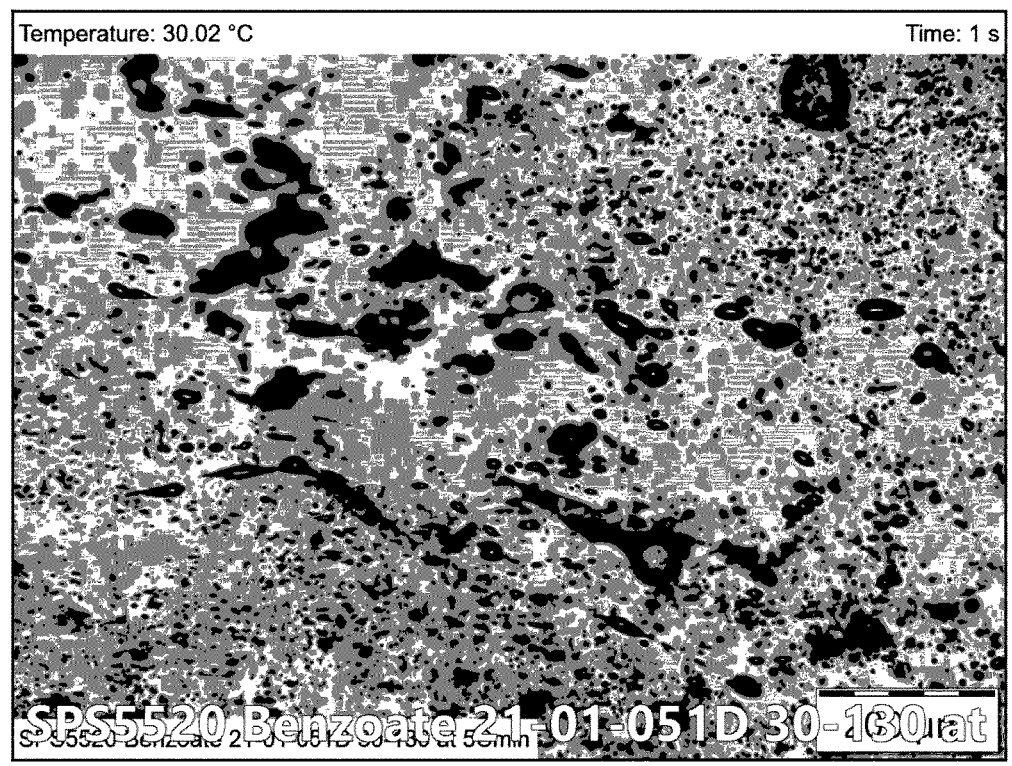
FIG. 52 shows Micrograph image of 5MeODMT benzoate lot 21-01-051 D at 30.02° C.
Figure 53:
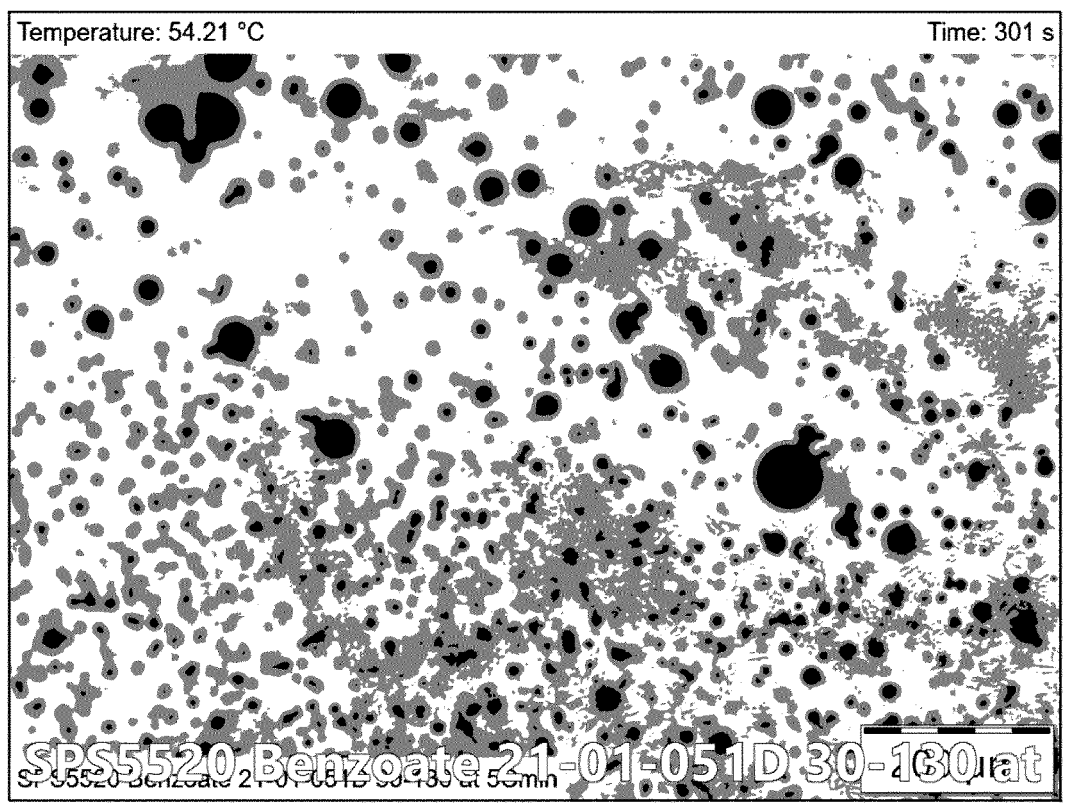
FIG. 53 shows Micrograph image of 5MeODMT benzoate lot 21-01-051 D at 54.21° C.
Figure 54:
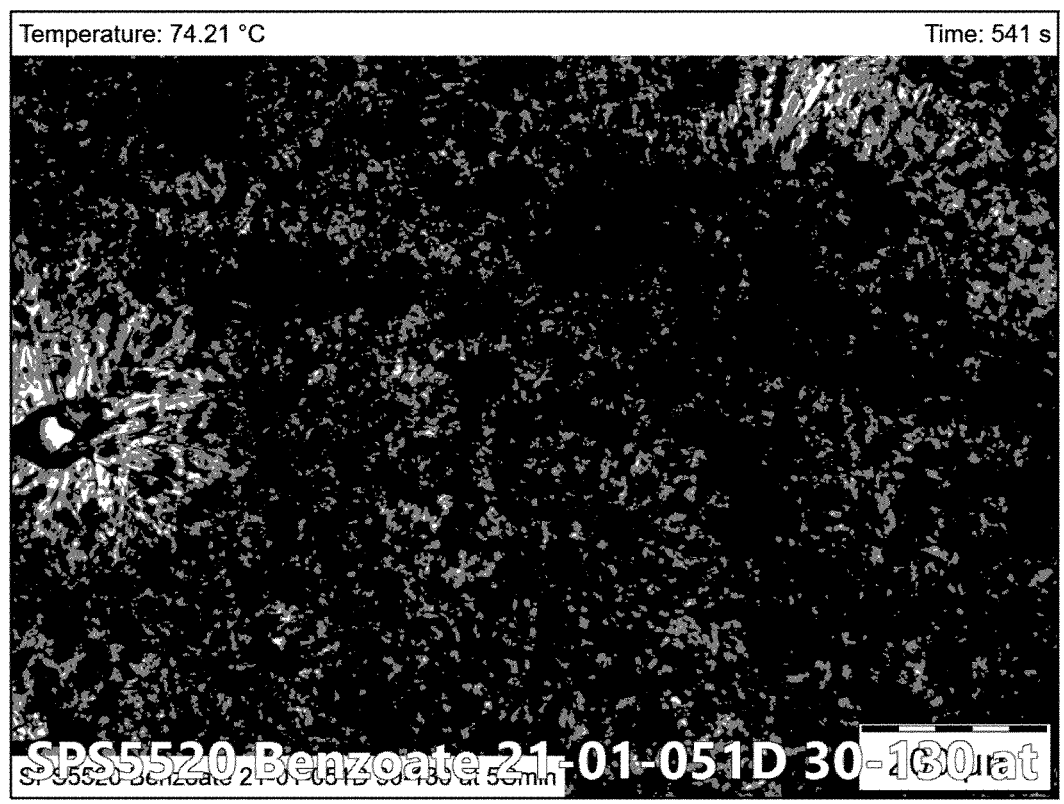
FIG. 54 shows Micrograph image of 5MeODMT benzoate lot 21-01-051 D at 74.21° C.

Initially, 5MeODMT benzoate was a sticky translucent gum (FIG. 52) that upon heating to 54.21° C. reduced in viscosity and spread out into a thinner uniform layer (FIG. 53). At 54.21° C. the liquid began to crystallise (FIG. 53) which neared completion by 74.21° C. (FIG. 54). The newly formed crystals began to melt at 114.24° C. (FIG. 55) which neared completion by 120.14° C. (FIG. 56).

The hot stage microscopy examination corroborated with events in the DSC thermograph (FIG. 51); the crystallisation exotherm at ca. 65° C. and the melt endotherm at ca. 115° C.

Figure 51:
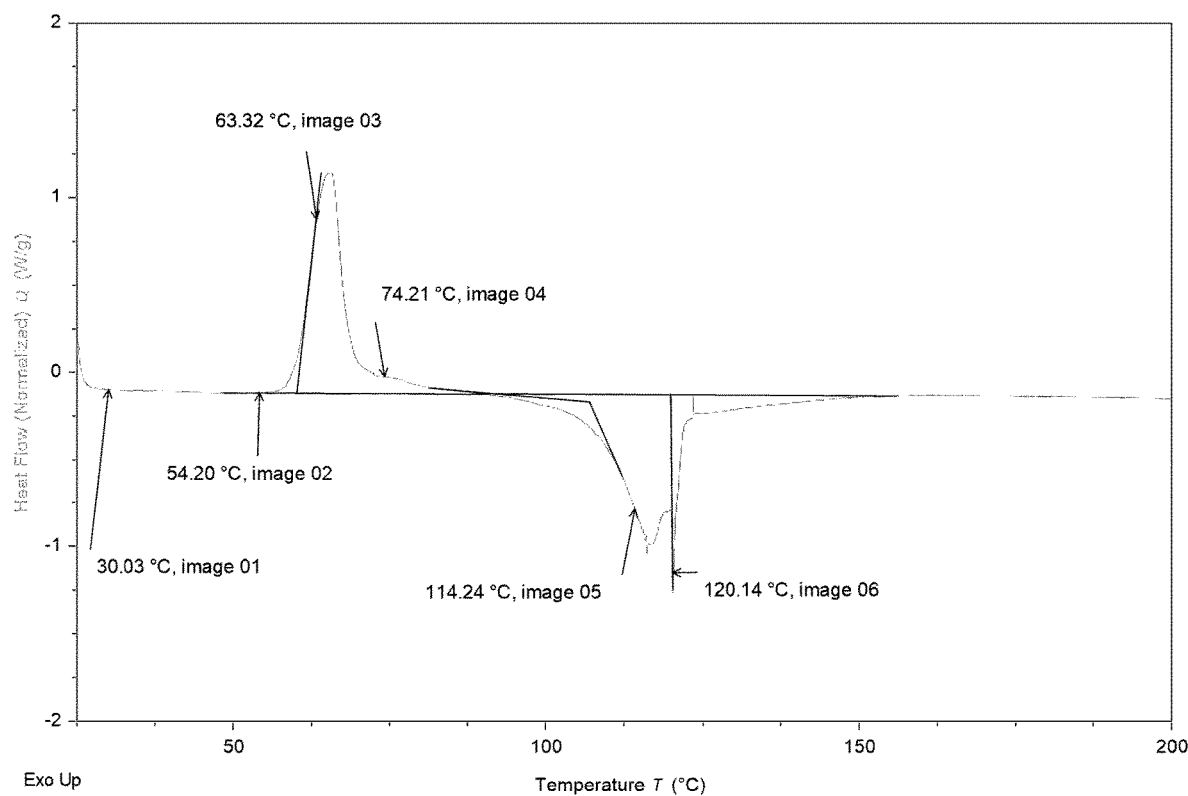
FIG. 51 shows DSC thermograph of 5MeODMT benzoate lot 21-01-051 D, large scale lyophilised material, with temperature stamps corresponding to hot-stage microscopy images.

FIG. 51 shows DSC thermograph of 5MeODMT benzoate lot 21-01-051 D, large scale lyophilised material, with temperature stamps corresponding to hot-stage microscopy images.

FIG. 52 shows Micrograph image of 5MeODMT benzoate lot 21-01-051 D at 30.02° C.

FIG. 53 shows Micrograph image of 5MeODMT benzoate lot 21-01-051 D at 54.21° C.

FIG. 54 shows Micrograph image of 5MeODMT benzoate lot 21-01-051 D at 74.21° C.

Figure 55:
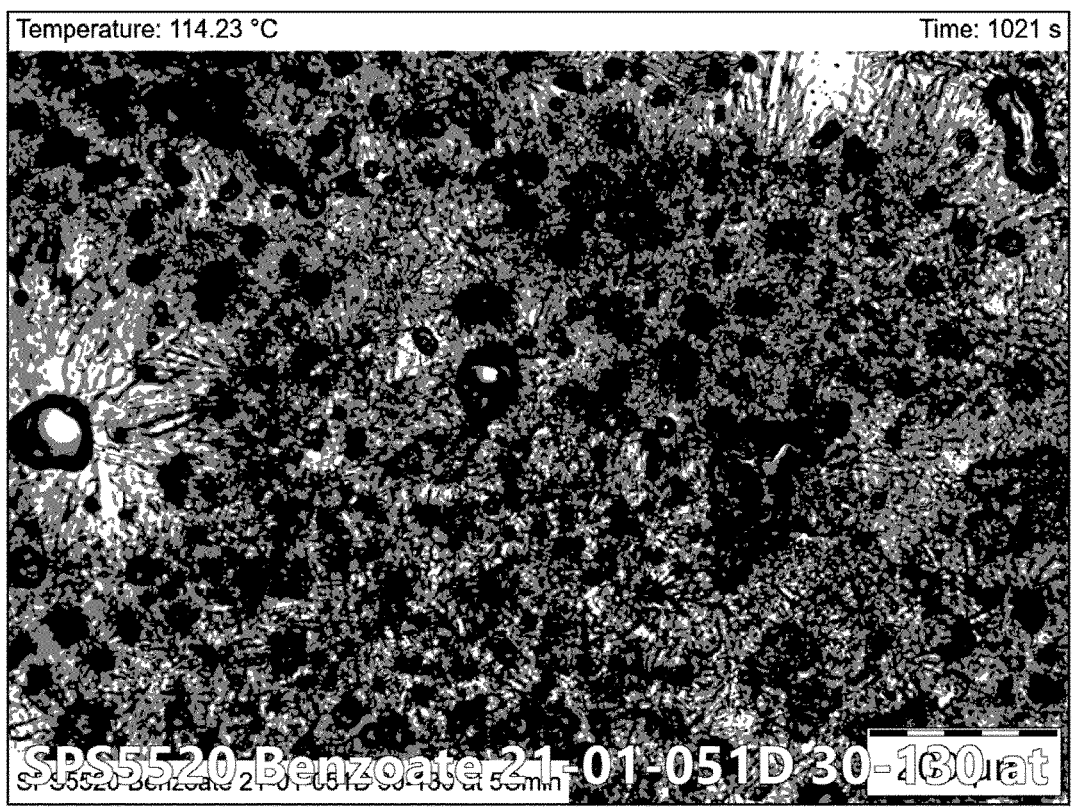
FIG. 55 shows Micrograph image of 5MeODMT benzoate lot 21-01-051 D at 114.23° C.
Figure 56:
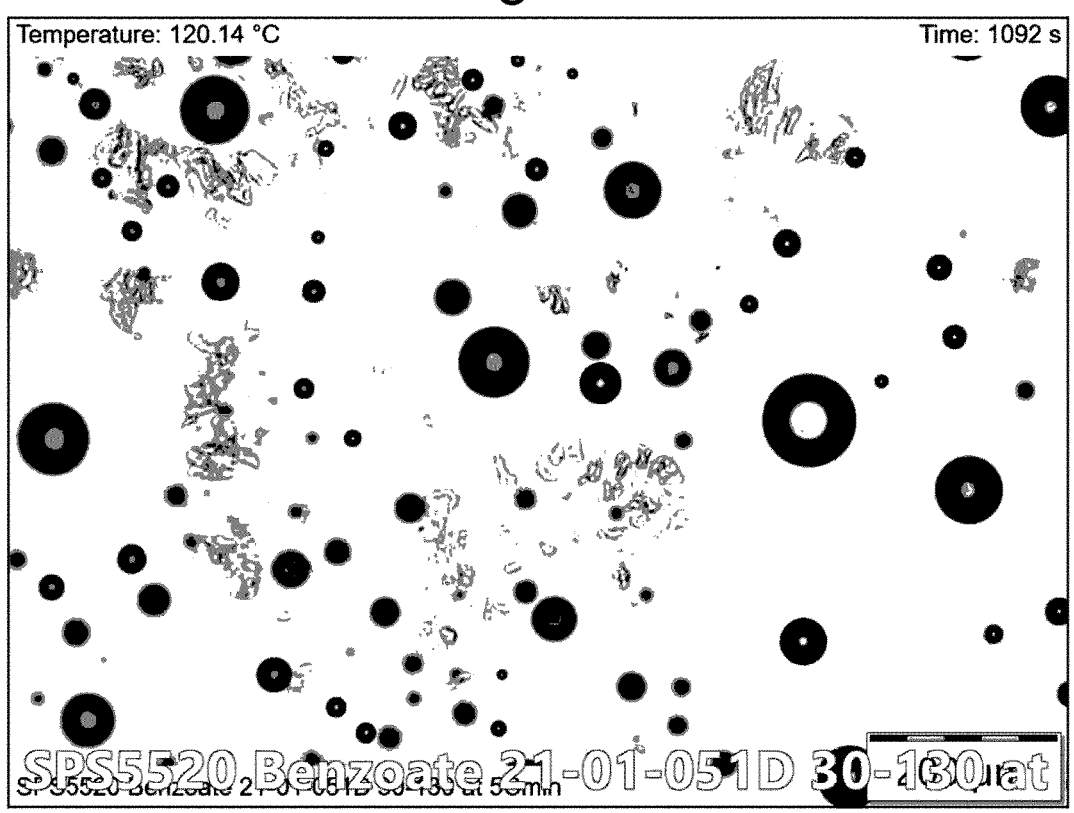
FIG. 56 shows Micrograph image of 5MeODMT benzoate lot 21-01-051 D at 120.14° C.

FIG. 55 shows Micrograph image of 5MeODMT benzoate lot 21-01-051 D at 114.23° C.

FIG. 56 shows Micrograph image of 5MeODMT benzoate lot 21-01-051 D at 120.14° C.

Solvent Mediated Equilibration of Amorphous 5MeODMT Benzoate with Thermal Manipulation The action of agitating the amorphous version of a solid in a series of solvents can lead to dissolution and crystallisation to more ordered and energetically stable solids. In this manner, alternate crystal forms of a solid can be potentially generated for comparison and evaluation.

Amorphous 5MeODMT benzoate 21-01-51 D, 24×25±2 mg was transferred to crystallisation tubes and solvent, 0.125 mL charged as detailed in the Table below. The mixtures were agitated at 300 rpm at 25° C. for 30 minutes. Solvent, 0.125 mL, was charged to relevant mixtures and equilibrated for 18 hours.

Mixtures were heated to 55° C. for 8 hours then cooled to 25° C. over 1 hour then equilibrated for 18 hours at 300 rpm, observations following each manipulation is detailed in the Table below.

Suspensions were transferred to Isolute tubes for isolation and dried under vacuum for 2 mins then dried in vacuo at 50° C. for 24 hours.

Figure 57:
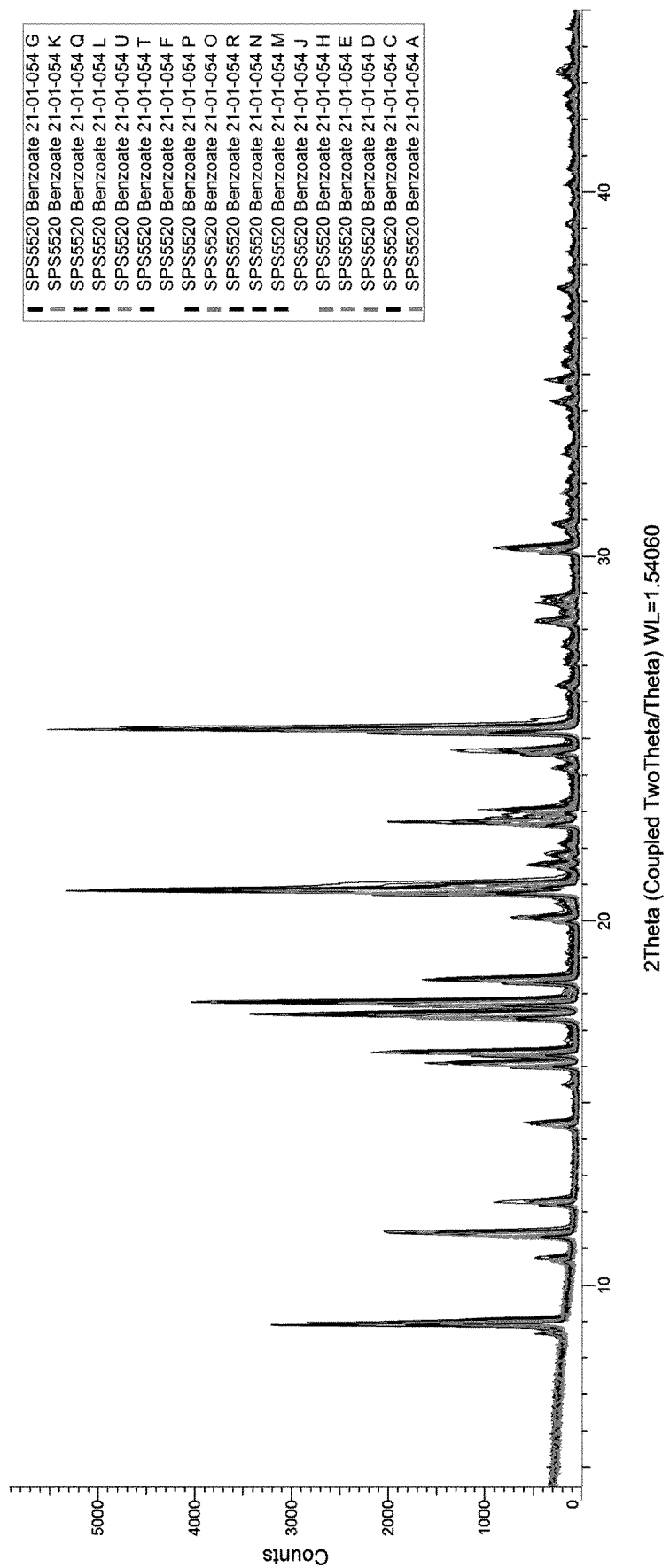
FIG. 57 shows XRPD pattern comparison of 5MeODMT benzoate lot 21-01-054 solids isolated from the equilibration of amorphous 5MeODMT benzoate with thermal modulation.
Figure 58:
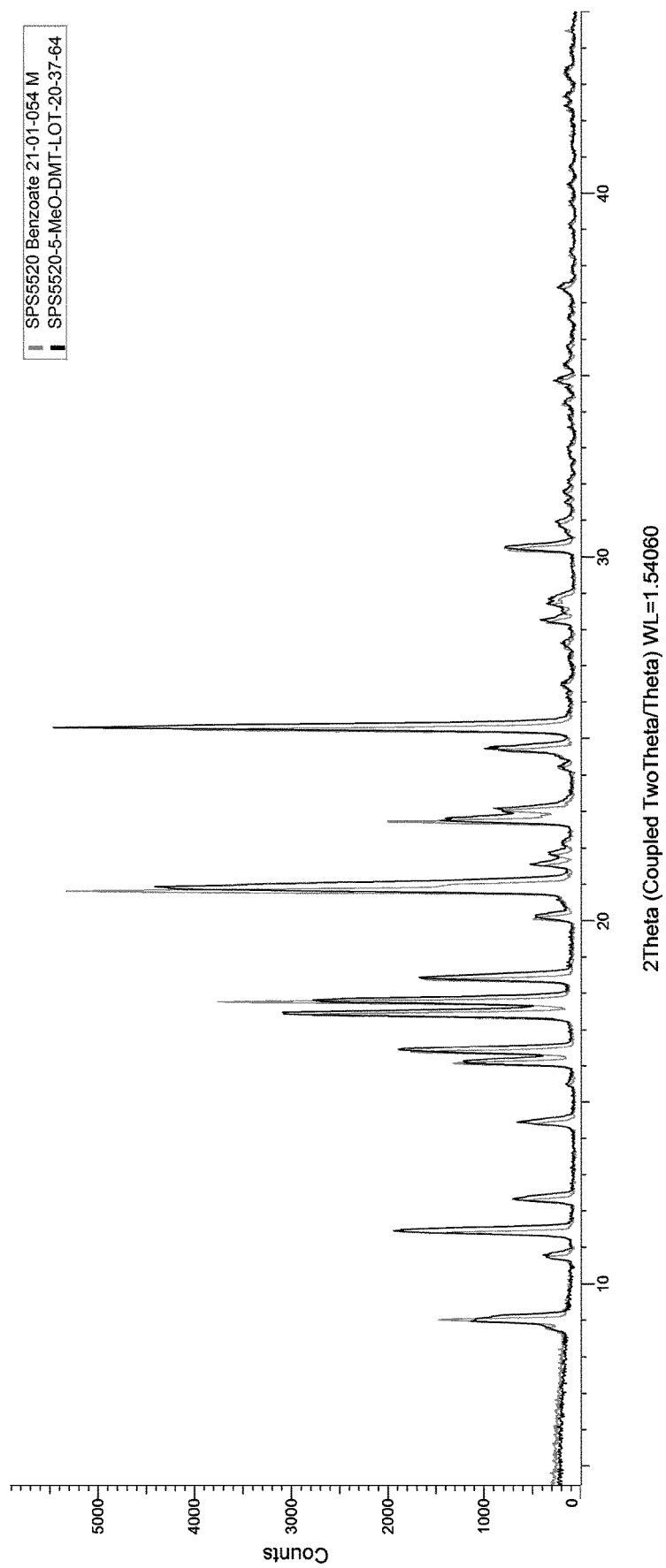
FIG. 58 shows XRPD pattern comparison of 5MeODMT benzoate lot 21-01-054 M isolated from the equilibration of amorphous 5MeODMT benzoate in α,α,α-trifluorotoluene with thermal modulation with lot 20-37-64 (Pattern A).

XRPD examination of the solids isolated from the equilibration of amorphous 5MeODMT benzoate with thermal modulation revealed all powder patterns to be concordant with Pattern A (FIG. 57 and FIG. 58).

FIG. 57 shows XRPD pattern comparison of 5MeODMT benzoate lot 21-01-054 solids isolated from the equilibration of amorphous 5MeODMT benzoate with thermal modulation.

FIG. 58 shows XRPD pattern comparison of 5MeODMT benzoate lot 21-01-054 M isolated from the equilibration of amorphous 5MeODMT benzoate in α,α,α-trifluorotoluene with thermal modulation with lot 20-37-64 (Pattern A).

The DSC examination of a selection of 5MeODMT benzoate solids classified as Pattern A revealed a major endothermic event with onset temperatures between 121.88 and 123.39° C. and peak temperatures between 123.66 and 124.11° C. This endotherm is characteristic of Pattern A form (FIG. 59).

Figure 60:
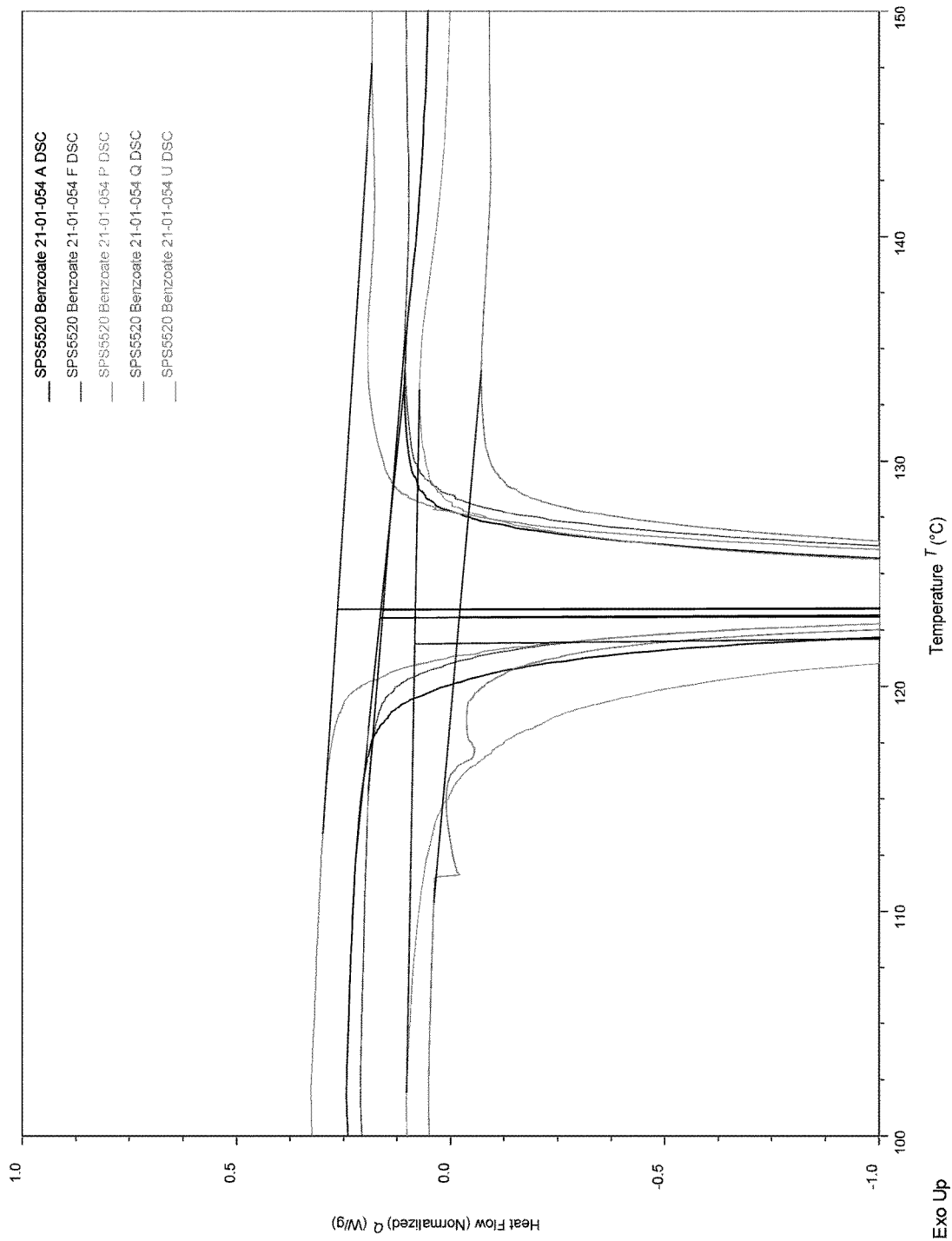
FIG. 60 shows DSC thermograph expansion comparison of 5MeODMT benzoate lot 21-01-054 solids isolated from the equilibration of amorphous 5MeODMT benzoate with thermal modulation classified as Pattern A, highlighting an event in lot 21-01-054 Q, solid isolated from anisole.
Figure 61:
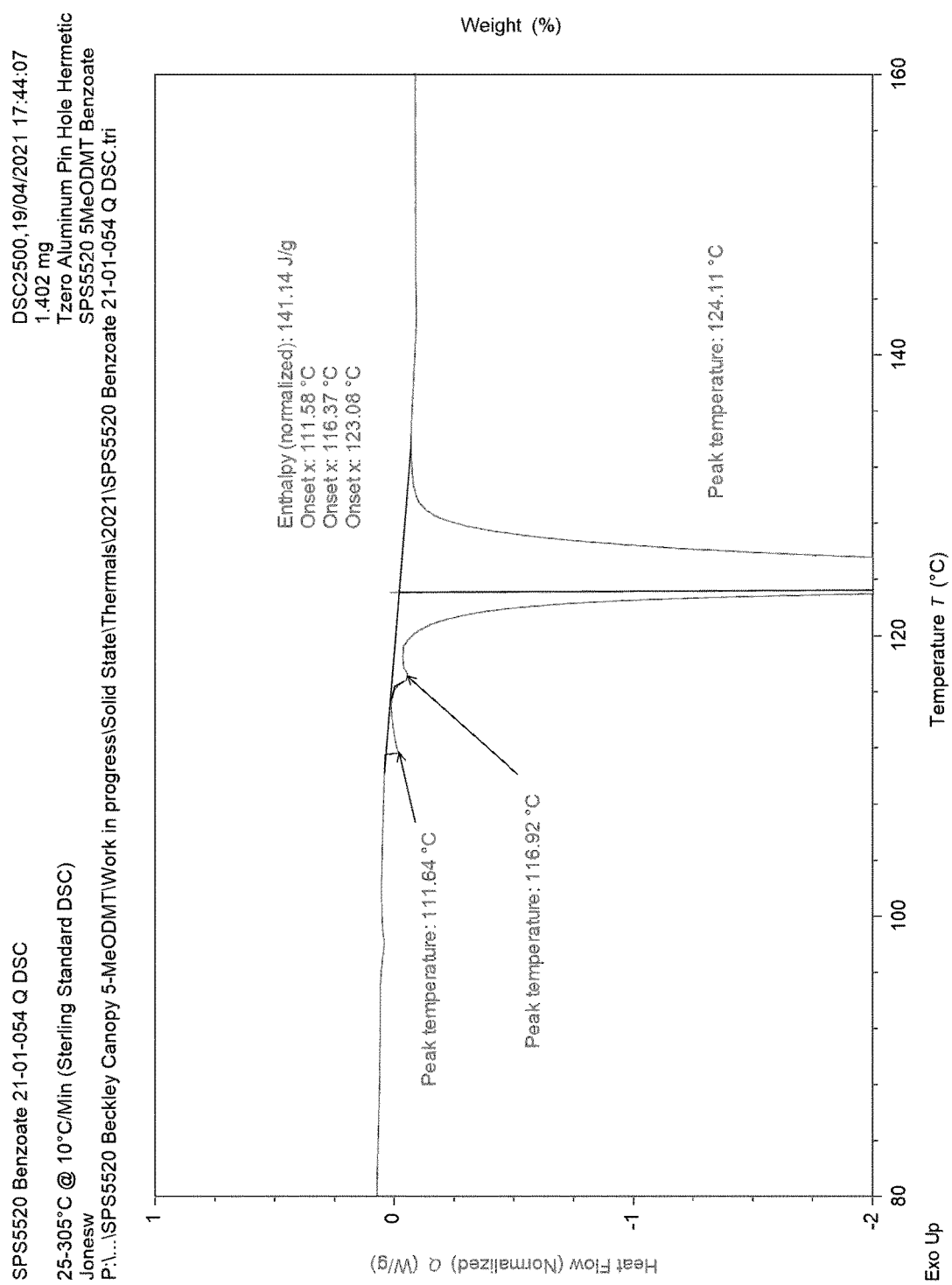
FIG. 61 shows Expanded DSC thermograph expansion highlighting an event in lot 21-01-054 Q, isolated from anisole.

5MeODMT benzoate 21-01-054 Q, solid isolated from anisole, contained events within the major endothermic event with peak temperatures of 111.64° C. and 116.92° C. (FIG. 60, FIG. 61). This is in line with the DSC thermograph of 5MeODMT benzoate isolated following equilibration in anisole, 20-37-64-R1, although less pronounced.

Figure 59:
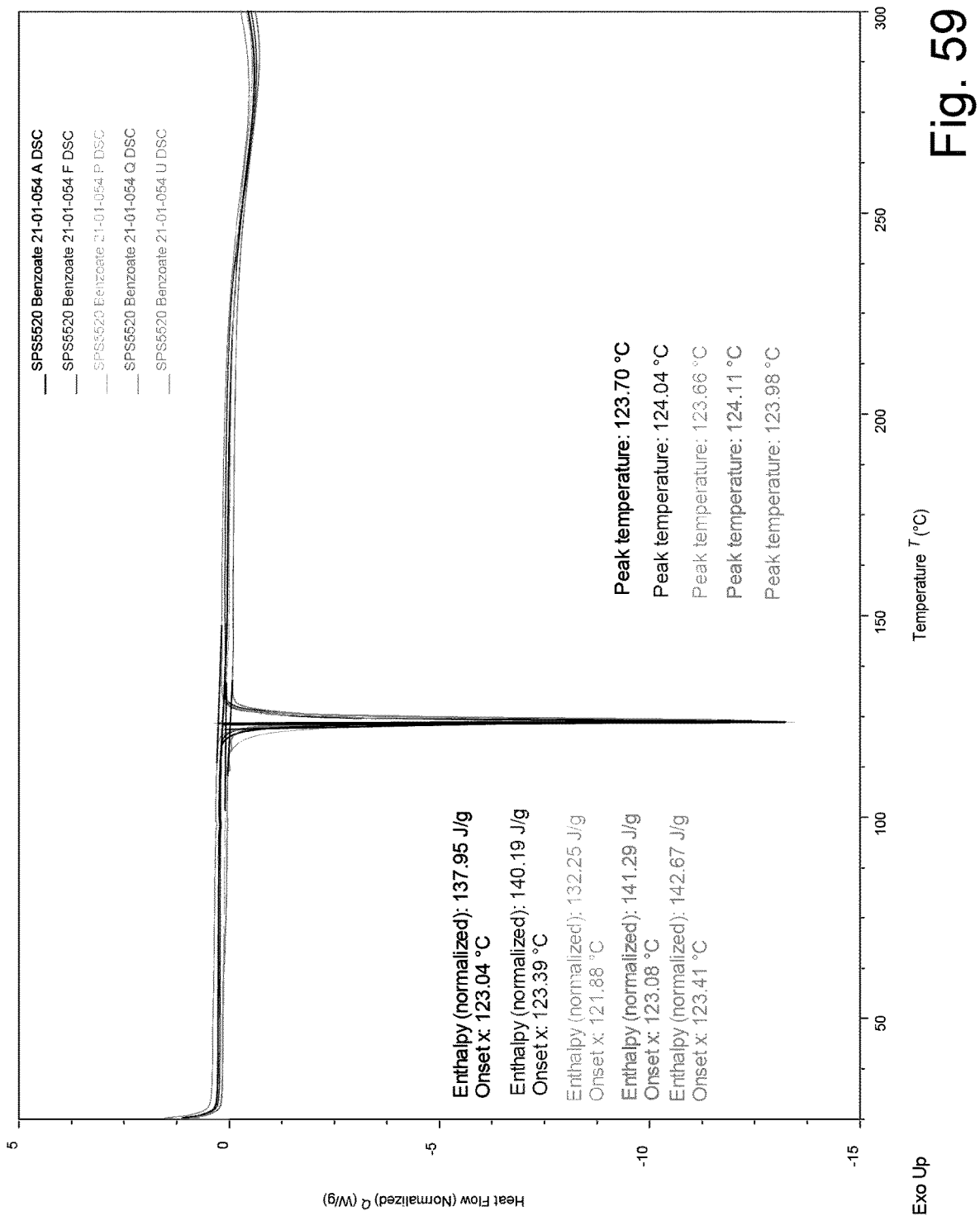
FIG. 59 shows DSC thermograph comparison of a selection of 5MeODMT benzoate lot 21-01-054 solids isolated from the equilibration of amorphous 5MeODMT benzoate with thermal modulation classified as Pattern A.

FIG. 59 shows DSC thermograph comparison of a selection of 5MeODMT benzoate lot 21-01-054 solids isolated from the equilibration of amorphous 5MeODMT benzoate with thermal modulation classified as Pattern A form.

FIG. 60 shows DSC thermograph expansion comparison of a selection of 5MeODMT benzoate lot 21-01-054 solids isolated from the equilibration of amorphous 5MeODMT benzoate with thermal modulation classified as Pattern A form, highlighting an event in lot 21-01-054 Q, solid isolated from anisole.

FIG. 61 shows Expanded DSC thermograph expansion highlighting an event in lot 21-01-054 Q, isolated from anisole.

Example 24: Pattern C

Additional 5MeODMT benzoate Pattern B form material was required for further characterisation. The procedure of charging 5MeODMT benzoate/IPA solution to cold toluene was employed.

5MeODMT benzoate 20/20/150FP2, 250 mg, was dissolved in IPA, 5 ml, and heated to 50° C. and clarified. The clarified solution, 2×2 ml, 100 mg of 5MeODMT benzoate, was charged to toluene, 4 ml, at −10° C. and agitated at 750 rpm.

Upon addition, both mixtures remained as clear colourless solutions.

After 30 minutes a solid had formed in tube A. The solid, 21-01-060 A, was isolated immediately via isolute and dried in vacuo for 2 minutes. A portion, 21-01-060 A1 was removed for XRPD analysis, a portion was dried in vacua at 50° C. for 20 hours, 21-01-060 A2.

After 50 minutes a solid had formed in tube B and was allowed to equilibrate at −10° C. and agitated at 750 rpm for 3 hours. The solid, 21-01-060 B, was isolated immediately via isolute and dried in vacuo for 2 minutes. A portion 21-01-060 B1 was removed for XRPD analysis, the remainder was dried in vacuo at 50° C. for 20 hours, 21-01-060 B2.

| Sample | 5MeODMT benzoate 21-01-060 A1 and A2 | 5MeODMT benzoate 21-01-060 B1 and B2 |
|---|---|---|
| Tube | 21-01-060 A | 21-01-060 B |
| Origin | Reverse anti-solvent addition of salt/IPA solution to toluene at −10° C. | |
| Time to form suspension | 30 minutes | 50 minutes |
| Time left as suspension | ca. 0 minutes | 3 hours |
| Analysis | XRPD pattern collected taken after 0 hours air dried XRPD pattern and DSC thermograph None collected after 1 hour air dried XRPD pattern and DSC thermograph collected after 20 hours air drying XRPD pattern and DSC thermograph collected after 20 hours drying in vacuo at 50° C. | |

Samples 21-01-060 A1 and 21-01-060 B1 were air dried under ambient conditions for 20 hours and assessed by XRPD and DSC.

Immediately following isolation, 21-01-060 A1 was analysed by XRPD. This revealed a new diffraction pattern that was not concordant with Pattern A or Pattern B. This is referred to as Pattern C.

Figure 62:
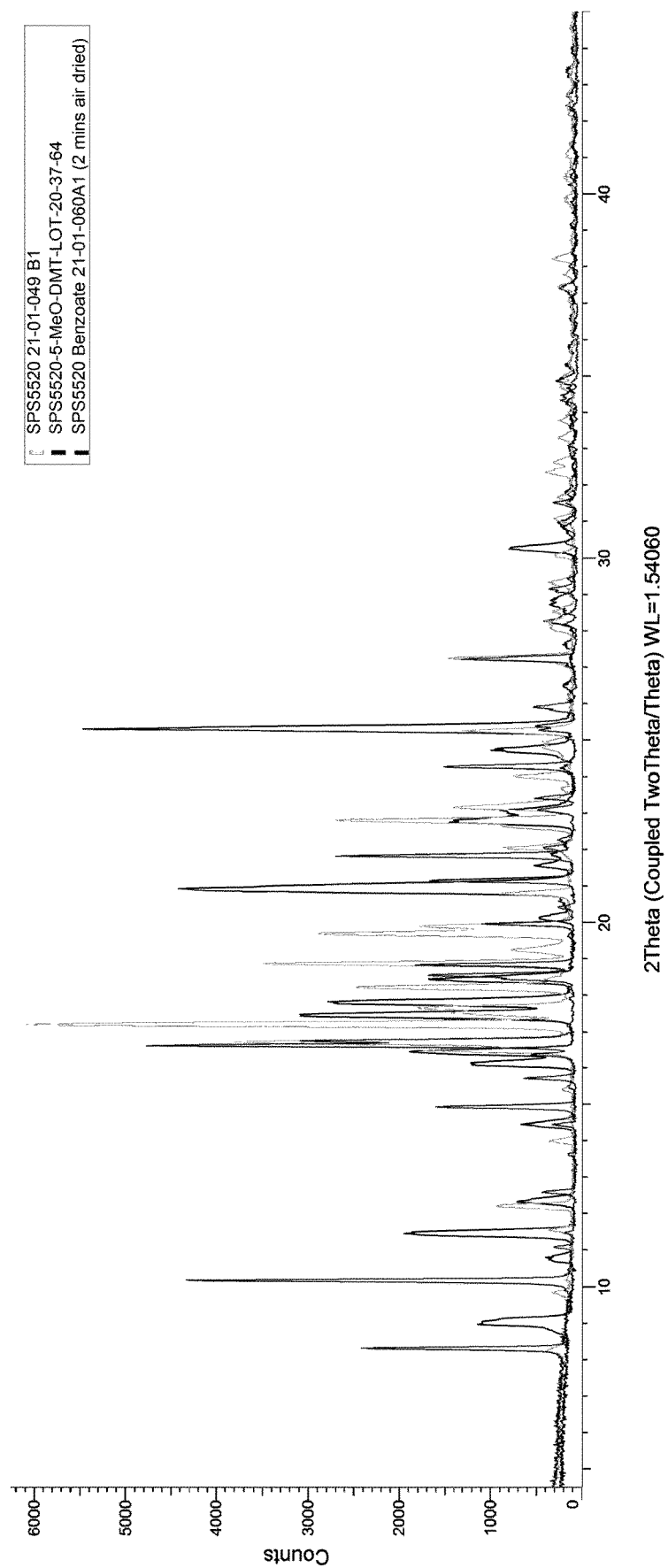
FIG. 62 shows XRPD pattern comparison of 5MeODMT benzoate lot 21-01-060 A1 air dried 2 minutes, lot 21-01-049 B1, Pattern B, and lot 20-37-64, Pattern A.

The XRPD pattern of 21-01-060 A1 (2 mins air dried) was reacquired following a further 1 hour of air drying under ambient conditions (FIG. 62). Additional diffractions were present in the XRPD of 21-01-060 A1 (air dried 1 hour) compared to 21-01-060 A1 (2 mins air dried), which suggests conversion to Pattern B form (FIG. 63).

FIG. 62 shows XRPD pattern comparison of 5MeODMT benzoate lot 21-01-060 A1 air dried 2 minutes, lot 21-01-049 B1, Pattern B, and lot 20-37-64, Pattern A.

Figure 63:
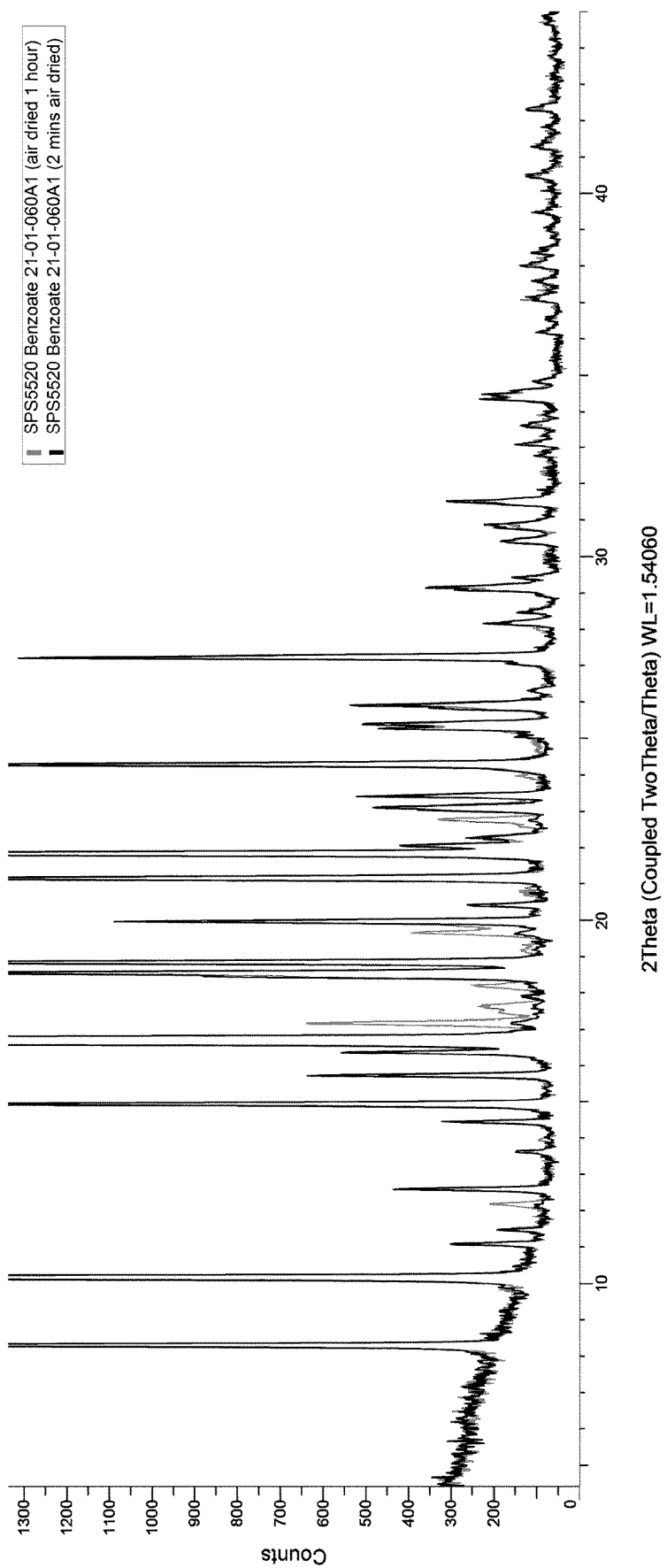
FIG. 63 shows XRPD pattern comparison of 5MeODMT benzoate lot 21-01-060 A1-air dried 1 hour and lot 21-01-060 A1-air dried 2 minutes.

FIG. 63 shows XRPD pattern comparison of 5MeODMT benzoate lot 21-01-060 A1-air dried 1 hour and lot 21-01-060 A1-air dried 2 minutes.

Figure 64:
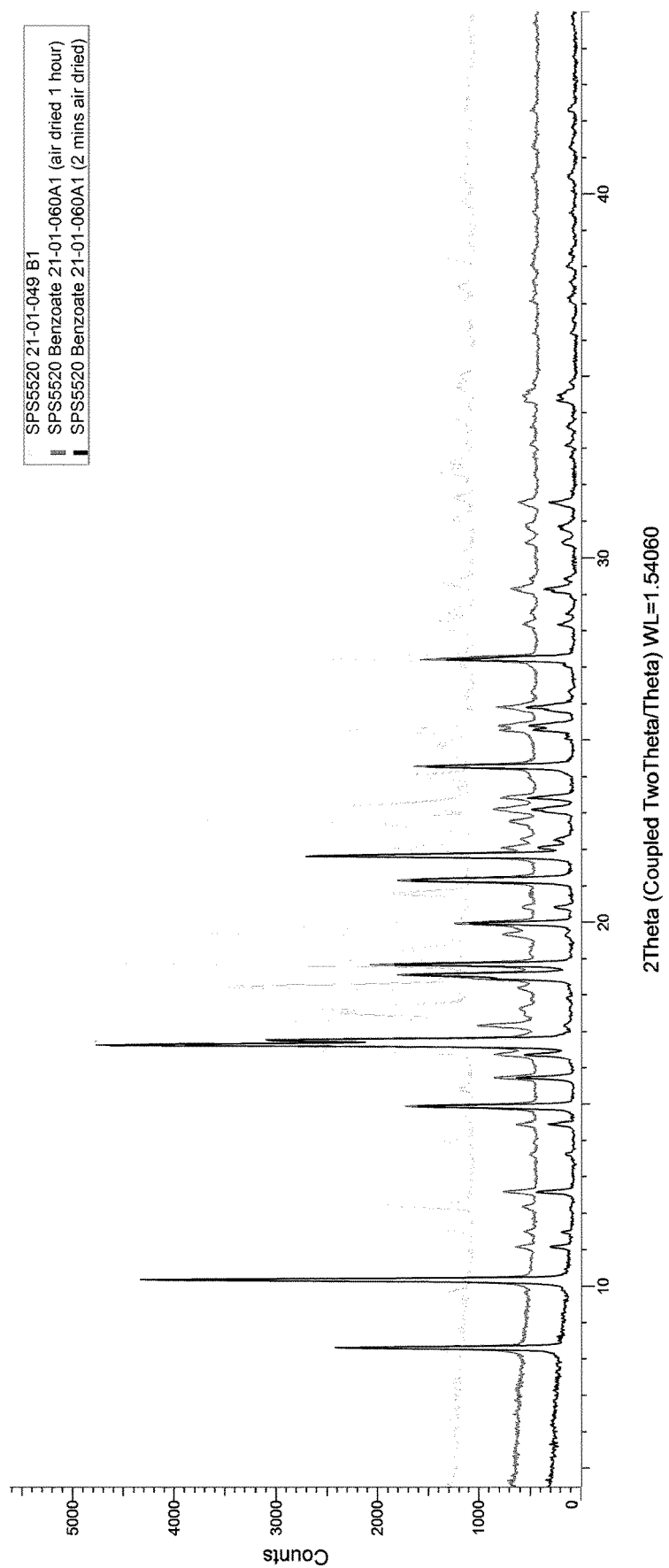
FIG. 64 shows XRPD pattern comparison of 5MeODMT benzoate lot 21-01-060 A1-air dried 2 minutes, lot 21-01-060 A1-air dried 1 hour, and lot 21-01-049 B1, Pattern B.

FIG. 64 shows XRPD pattern comparison of 5MeODMT benzoate lot 21-01-060 A1-air dried 2 minutes, lot 21-01-060 A1-air dried 1 hour, and lot 21-01-049 B1, Pattern B.

The DSC thermograph of 5MeODMT benzoate 21-01-060 A1 (air dried 1 hour) (FIG. 65 and FIG. 66) revealed a minor broad endotherm with a peak temperature of 108° C. which is considered characteristic of Pattern C form solid. This is followed by an exotherm with a peak temperature of 112.35° C. which is considered to be the conversion of Pattern C form to Pattern A form, since the main endotherm has a peak temperature of 124.12° C., which is characteristic of Pattern A form.

Figure 65:
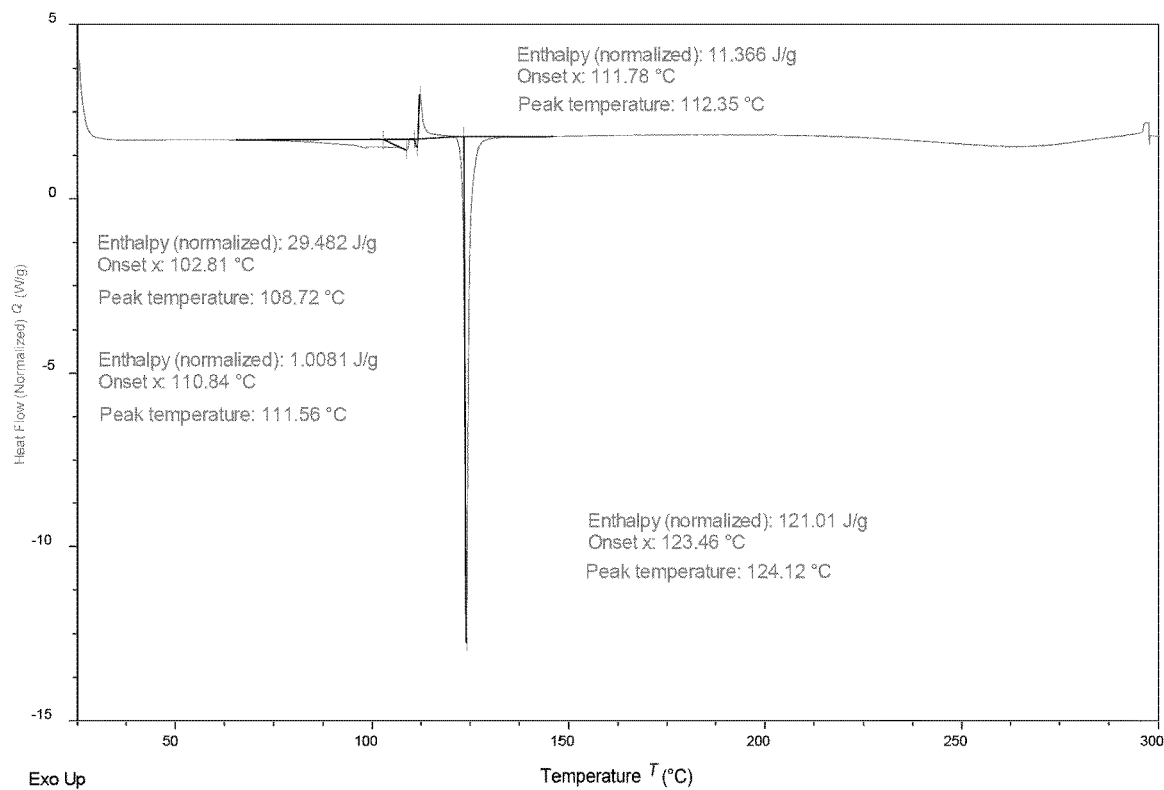
FIG. 65 shows DSC thermograph of 5MeODMT benzoate lot 21-01-060 A1, isolated immediately from IPA/toluene and air dried for 1 hour.

FIG. 65 shows DSC thermograph of 5MeODMT benzoate lot 21-01-060 A1, isolated immediately from IPA/toluene and air dried for 1 hour.

Figure 66:
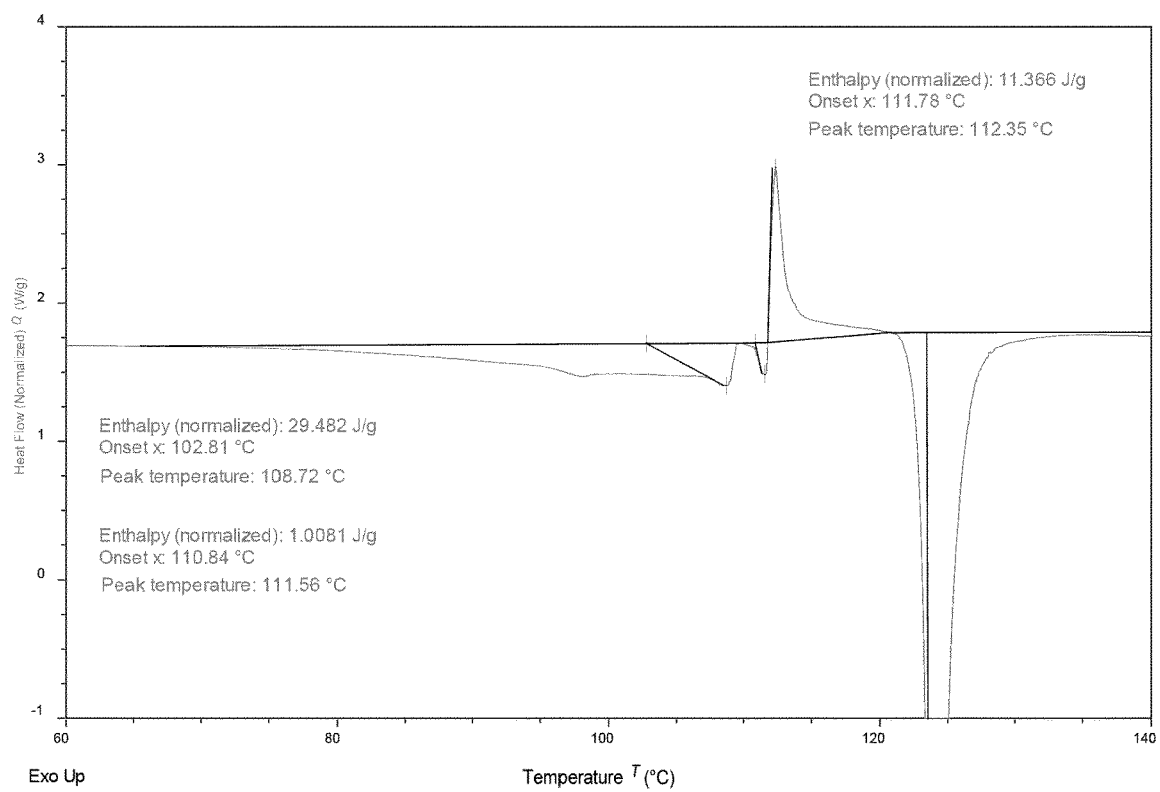
FIG. 66 shows DSC thermograph expansion of 5MeODMT benzoate lot 21-01-060 A1, isolated immediately from IPA/toluene and air dried for 1 hour.

FIG. 66 shows DSC thermograph expansion of 5MeODMT benzoate lot 21-01-060 A1, isolated immediately from IPA/toluene and air dried for 1 hour.

An XRPD pattern of 5MeODMT benzoate lot 21-01-060 A1 was acquired following a total of 20 hours air drying. This revealed the pattern (FIG. 67) to be concordant with SP55520 21-01-049 B1, Pattern B, but contained diffractions indicative of Pattern C such as 10.3° 2θ (FIG. 67).

Figure 67:
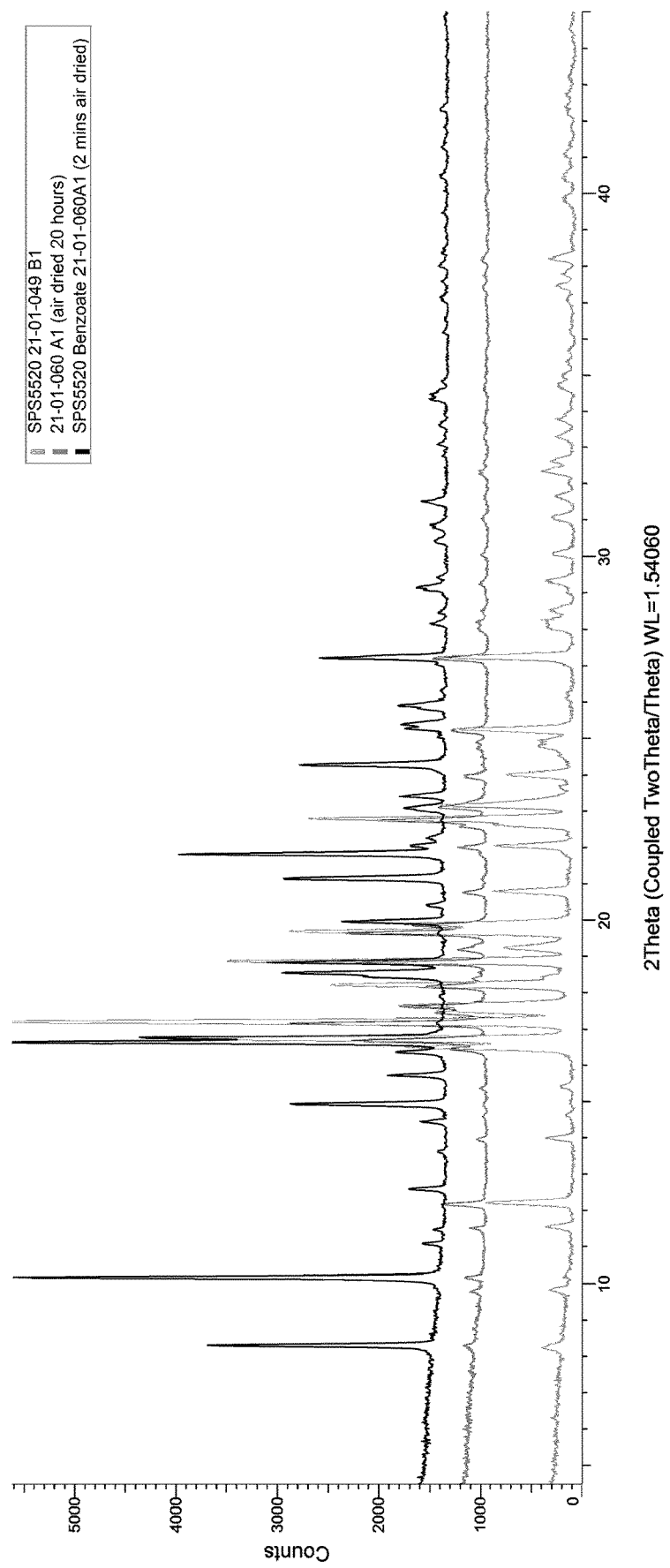
FIG. 67 shows XRPD pattern comparison of 5MeODMT benzoate lot 21-01-060 A1 air dried 20 hours, lot 21-01-060 A1 air dried 2 minutes, and lot 21-01-049 B1, Pattern B reference.

FIG. 67 shows XRPD pattern comparison of 5MeODMT benzoate lot 21-01-060 A1 air dried 20 hours, lot 21-01-060 A1 air dried 2 minutes, and lot 21-01-049 B1, Pattern B ref. 5MeODMT Benzoate 21-01-060 B1 Produced from Reverse Anti-Solvent Addition, Equilibrated for 3 Hours, then Isolated and Air Drying at Ambient Temperature Immediately following isolation, the solid was analysed by XRPD. This revealed a diffraction pattern concordant with 21-01-060 A1, Pattern C (FIG. 68).

The XRPD pattern (FIG. 69) was reacquired following 20 hours air drying and revealed the solid was still Pattern C but contained diffractions at 17.2° and 19.5 2θ indicative of Pattern B.

Figure 68:
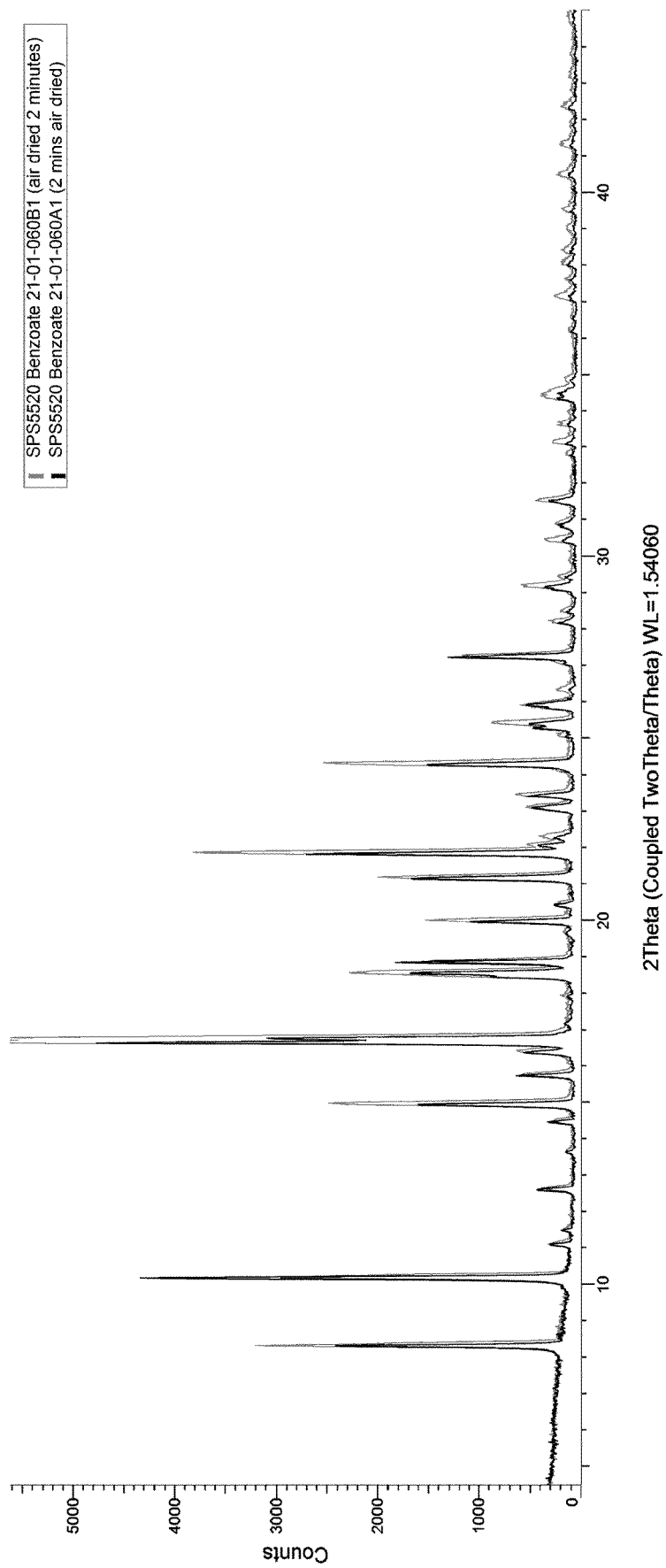
FIG. 68 shows XRPD pattern comparison of 5MeODMT benzoate lot 21-01-060 B1, isolated after 3 hours equilibration then air dried for 2 mins and A1 isolated immediately then air dried for 2 minutes.

FIG. 68 shows XRPD pattern comparison of 5MeODMT benzoate lot 21-01-060 B1, isolated after 3 hours equilibration then air dried for 2 mins and A1 isolated immediately then air dried for 2 minutes.

Figure 69:
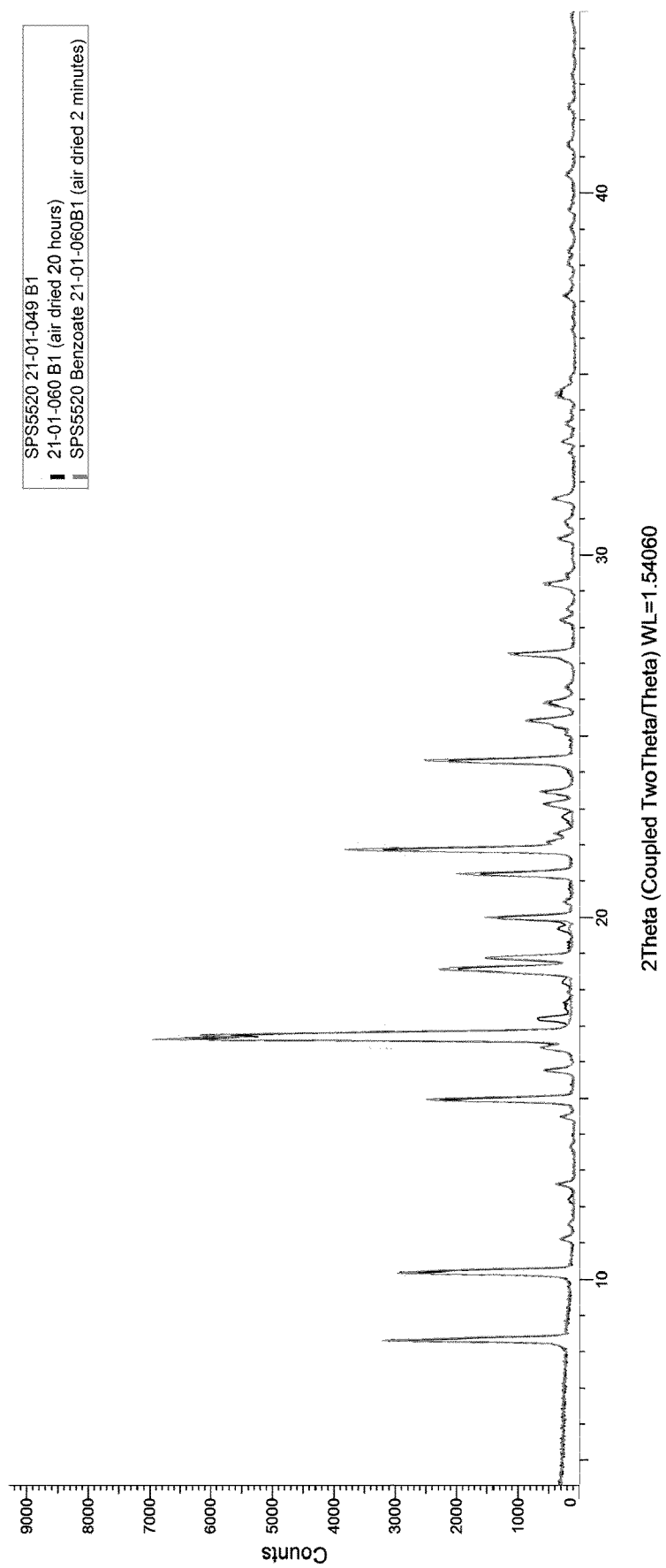
FIG. 69 shows XRPD pattern comparison of 5MeODMT benzoate lot 21-01-060 B1, isolated after 3 hours equilibration then air dried for 20 hours and B1 isolated after 3 hours equilibration then air dried for 2 minutes, and lot 21-01-049 B1, Pattern B.

FIG. 69 shows XRPD pattern comparison of 5MeODMT benzoate lot 21-01-060 B1, isolated after 3 hours equilibration then air dried for 20 hours and B1 isolated after 3 hours equilibration then air dried for 2 minutes, and lot 21-01-049 B1, Pattern B.

Example 25: Investigation of the Impact of Solvent Vapour Diffusion Upon Amorphous 5MeODMT Benzoate Subjecting an amorphous solid to solvent vapour is considered to be a low energy process for inducing form or version change of the solid in order to generate meta stable versions and/or solvates from the amorphous solid for comparison and evaluation.

5MeODMT benzoate, 497.44 mg, was dissolved in deionised water, 10 mL, and clarified into a 500 mL round bottom flask and lyophilised as detailed previously. The fluffy white solid produced, 12×25 mg, was charged to HPLC vials and placed in a sealed container with ca. 2 mL of solvent. The solvents employed and observations are detailed in the Table below.

Following equilibration for 7 days, solids were transferred to XRPD sample holder directly and analysed by XRPD. DSC was collected for all notable samples by XRPD and a selection of Pattern A form solids.

| | | Observations | | |
|---|---|---|---|---|
| ID | Solvent | Upon charge | Post 1 day | Post 7 days |
| A | Methanol | Off-white gum | White Opaque solid | Yellow solution |
| B | Ethyl acetate | Off-white gum | Off-white gum | Off-white agglomerate |
| C | Acetone | Off-white gum | White Opaque solid | Solids adhered to glass above a clear solution |
| D | Anisole | Off-white gum | Off-white gum | Off-white agglomerate |
| E | TBME | Off-white gum | Off-white gum | Off-white agglomerate |
| F | THF | Off-white gum | Off-white gum | Off-white agglomerate |
| G | Toluene | Off-white gum | Off-white gum | Off-white agglomerate |
| H | 1,4-Dioxane | Off-white gum | Off-white gum | Off-white agglomerate |
| I | DCM | Off-white gum | Off-white gum | Solids adhered to glass above a clear solution |
| J | Heptane | Off-white gum | Off-white gum | Off-white agglomerate |
| K | Acetonitrile | Off-white gum | Off-white gum | Off-white agglomerate |
| L | Water | Off-white gum | Off-white gum | Off-white agglomerate |

Figure 70:
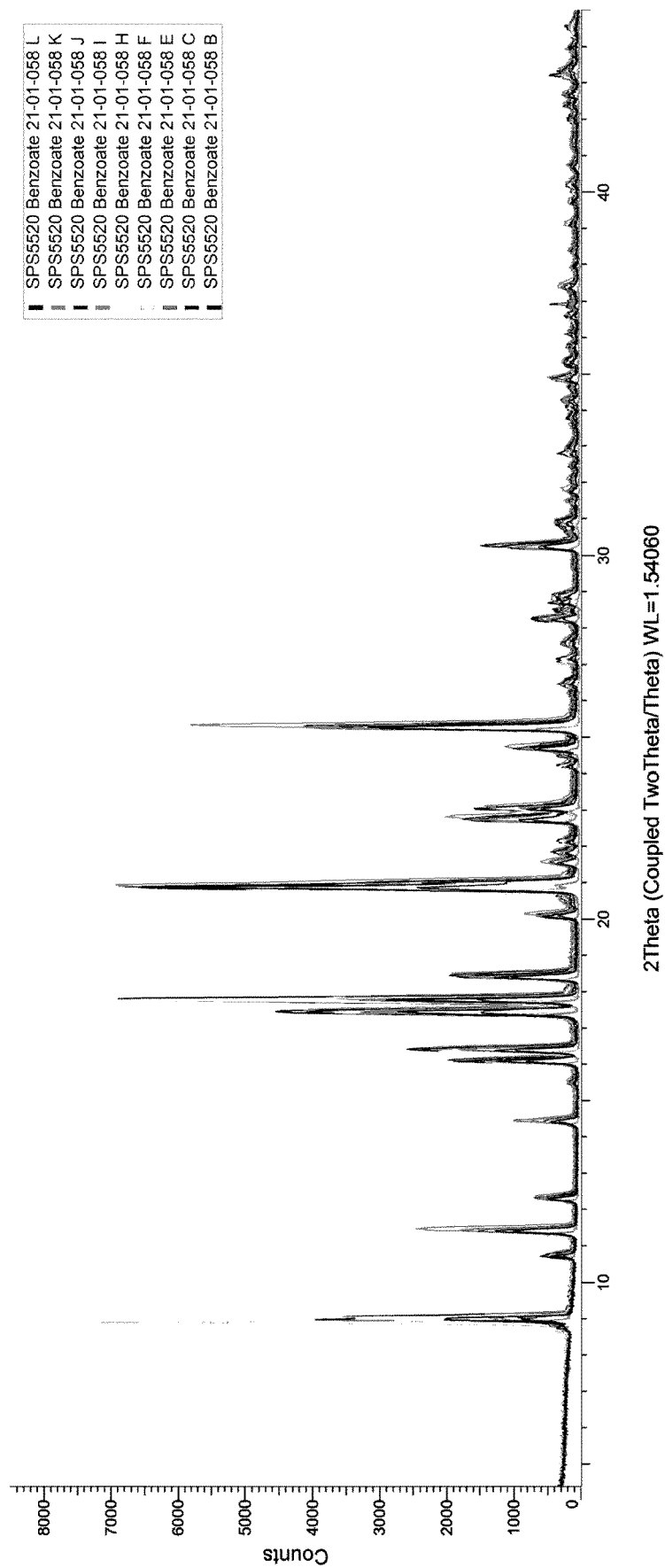
FIG. 70 shows XRPD pattern comparison of 5MeODMT benzoate lot 21-01-058 solids isolated from amorphous 5MeODMT benzoate exposed to solvent vapour.
Figure 71:
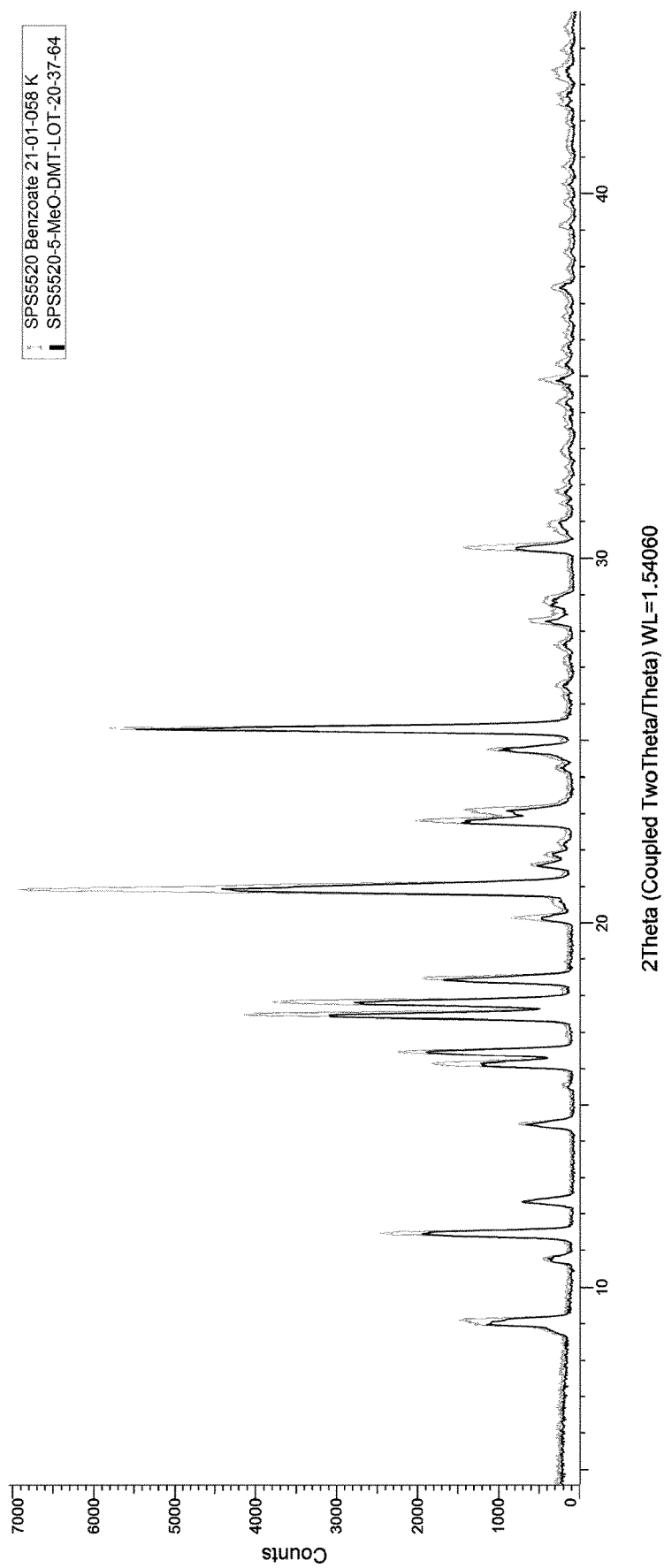
FIG. 71 shows XRPD pattern comparison of 5MeODMT benzoate lot 21-01-058 K, isolated from amorphous 5MeODMT benzoate exposed to solvent vapour, with lot 20-37-64, Pattern A.

XRPD pattern for all samples (FIG. 70) except for 21-01-058 D and 21-01-058 G, isolated from anisole and toluene respectively, were concordant with Pattern A form material (FIG. 71).

FIG. 70 shows XRPD pattern comparison of 5MeODMT benzoate lot 21-01-058 solids isolated from amorphous 5MeODMT benzoate exposed to solvent vapour.

FIG. 71 shows XRPD pattern comparison of 5MeODMT benzoate lot 21-01-058 K, isolated from amorphous 5MeODMT benzoate exposed to solvent vapour, with lot 20-37-64, Pattern A.

The DSC thermograph comparison of a selection of Pattern A form solids (FIG. 72) revealed an endothermic event with peak temperatures between 123.69° C. and 124.14° C. which is indicative of Pattern A form and corroborates the XRPD data.

The DSC thermograph of lot 21-01-058 G (not Pattern A form, by XRPD) demonstrates a minor endothermic event prior to the main endotherm and is elaborated on below.

Figure 72:
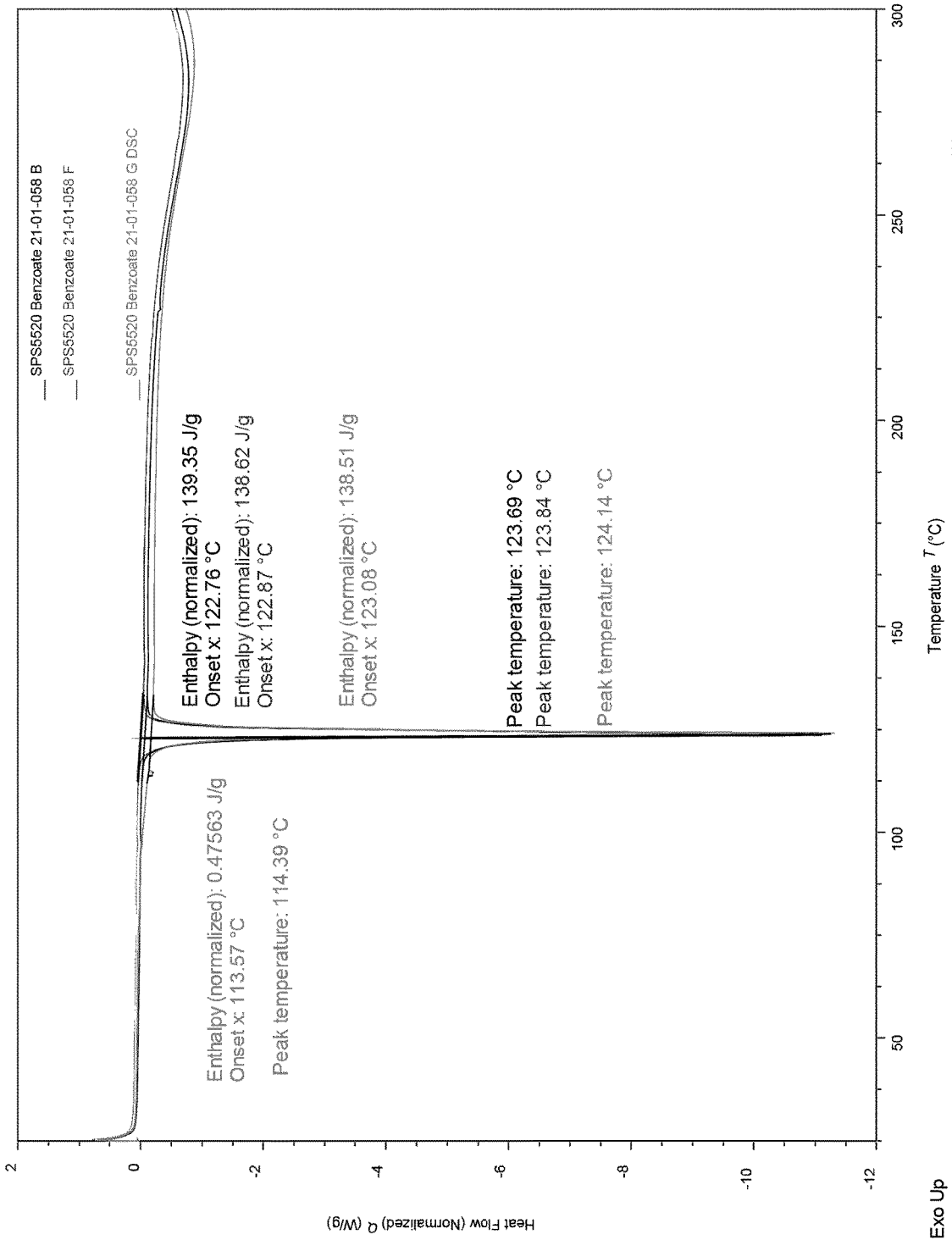
FIG. 72 shows DSC thermograph comparison of 5MeODMT benzoate lot 21-01-058 B, lot 21-01-058 F, lot 21-01-058 K, and lot 21-01-062 G.

FIG. 72 shows DSC thermograph comparison of 5MeODMT benzoate lot 21-01-058 B, lot 21-01-058 F, lot 21-01-058 K, and lot 21-01-062 G.

Example 26: Pattern D

Figure 73:
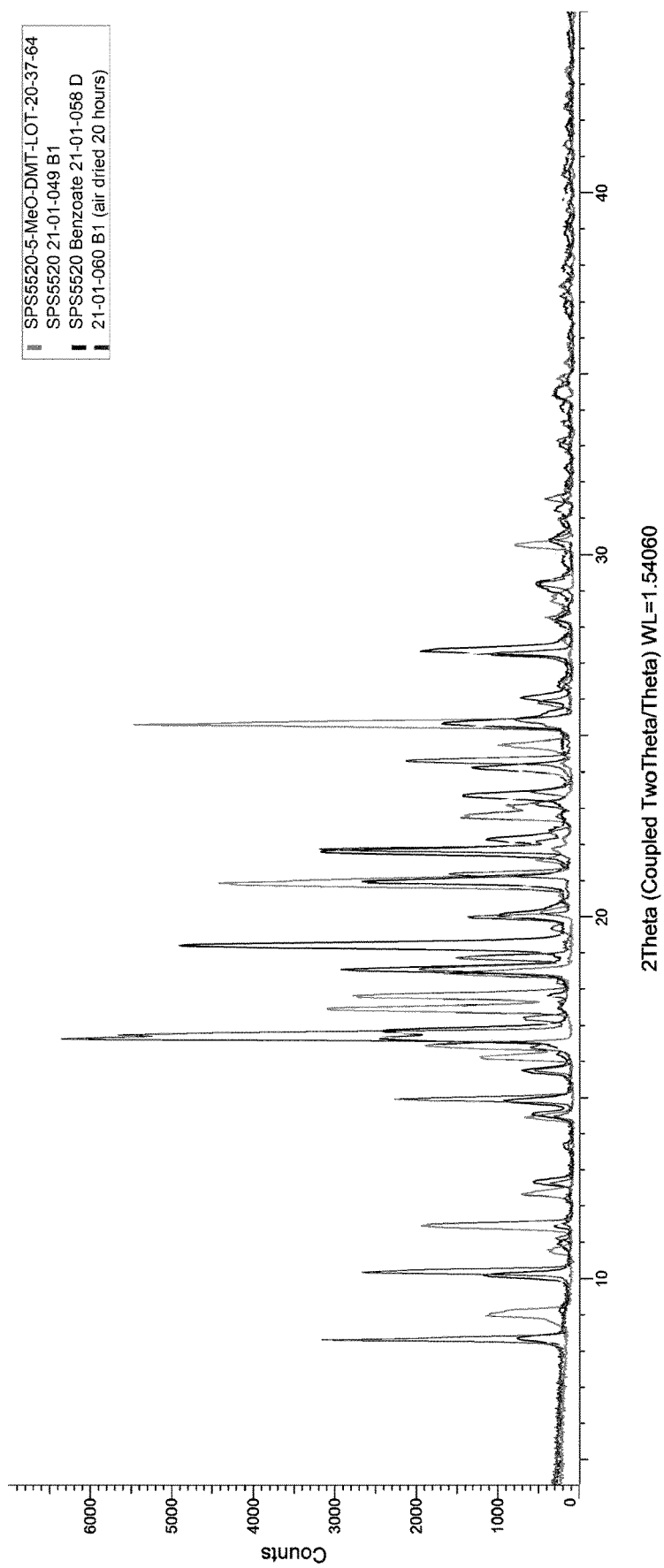
FIG. 73 shows XRPD pattern comparison of 5MeODMT benzoate lot 21-01-058 D, lot 20-37-64, Pattern A, lot 21-01-049 B1, Pattern B, and lot 21-01-060 B1, Pattern C (air dried 20 hours).
Figure 74:
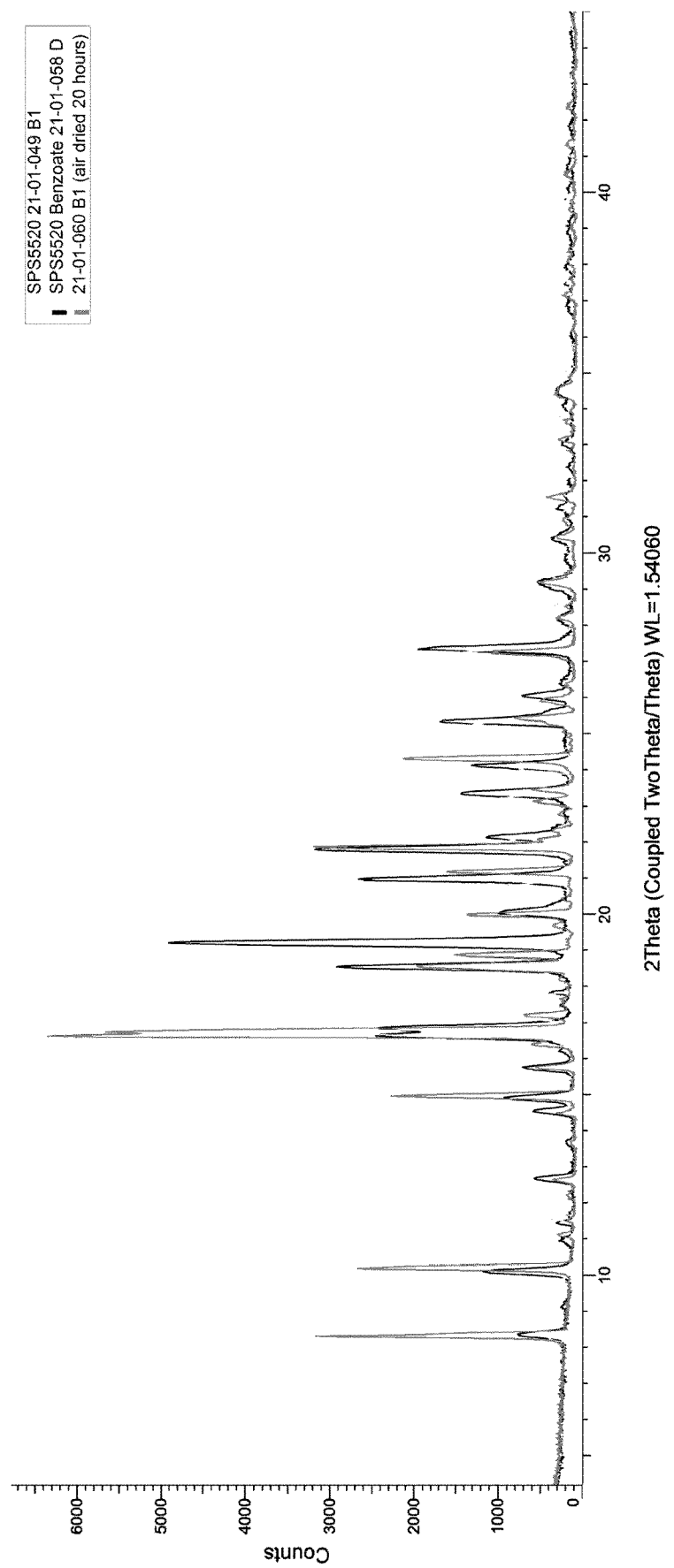
FIG. 74 shows XRPD pattern comparison of 5MeODMT benzoate lot 21-01-058 D, lot 21-01-049 B1, Pattern B, and lot 21-01-060 B1, Pattern C (air dried 20 hours).

5MeODMT Benzoate 21-01-058 D, Solid Isolated from Exposure of Amorphous 5MeODMT Benzoate to Anisole Vapour for 7 Days XRPD of 5MeODMT benzoate lot 21-01-058 D, isolated from amorphous 5MeODMT benzoate exposed to anisole vapour, revealed a unique powder pattern (FIG. 73 and FIG. 74). The diffractions of 21-01-058 D are similar to Pattern C but vary in intensity and position (FIG. 75).

FIG. 73 shows XRPD pattern comparison of 5MeODMT benzoate lot 21-01-058 D, lot 20-37-64, Pattern A, lot 21-01-049 B1, Pattern B, and lot 21-01-060 B1, Pattern C (air dried 20 hours).

FIG. 74 shows XRPD pattern comparison of 5MeODMT benzoate lot 21-01-058 D, lot 21-01-049 B1, Pattern B, and lot 21-01-060 B1, Pattern C (air dried 20 hours).

Figure 75:
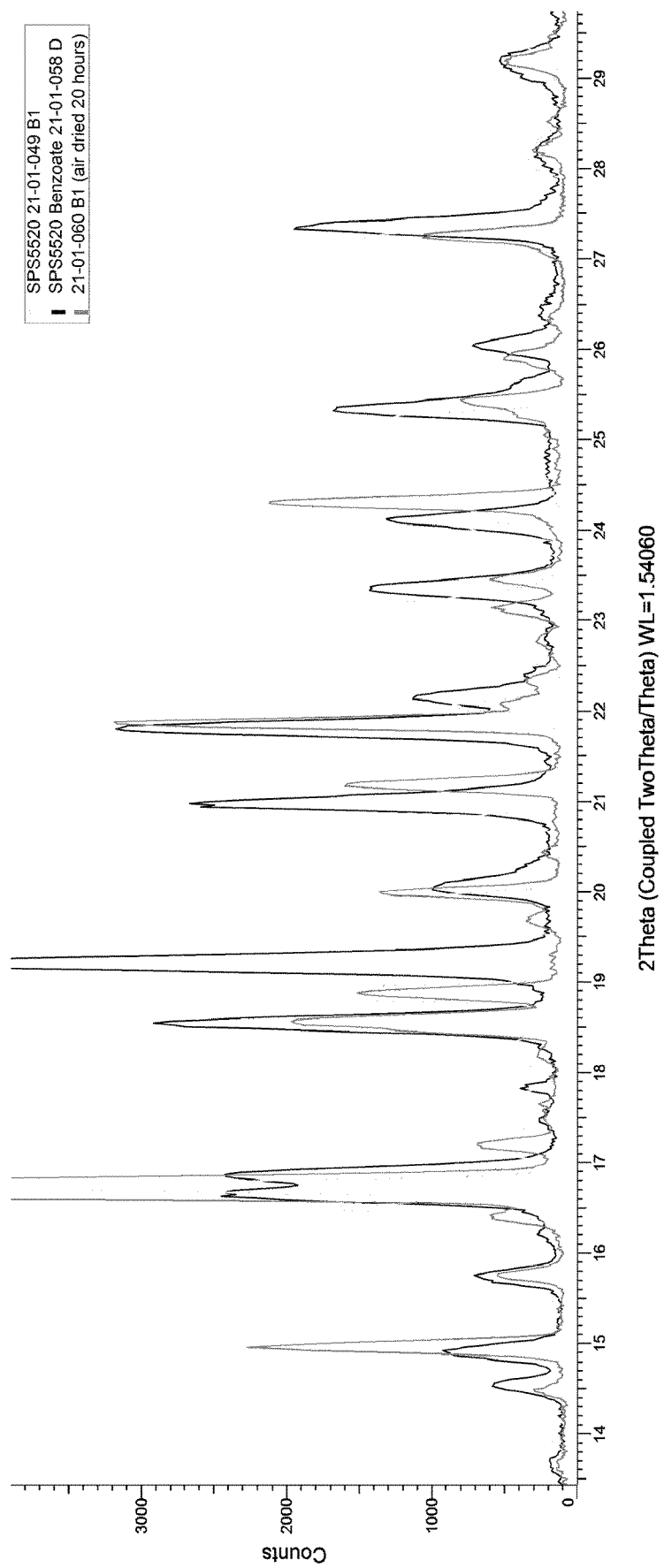
FIG. 75 shows XRPD pattern expansion comparison of 5MeODMT benzoate lot 21-01-058 D, lot 21-01-049 B1, Pattern B, and lot 21-01-060 B1, Pattern C (air dried 20 hours).

FIG. 75 shows XRPD pattern expansion comparison of 5MeODMT benzoate lot 21-01-058 D, lot 21-01-049 B1, Pattern B, and lot 21-01-060 B1, Pattern C (air dried 20 hours).

The DSC thermograph of 5MeODMT benzoate lot 21-01-058 D (FIG. 76), isolated from amorphous 5MeODMT benzoate exposed to anisole vapour revealed an endothermic event with a peak temperature of 118.58° C. This corroborates the XRPD data, confirming a new version has been isolated.

Figure 76:
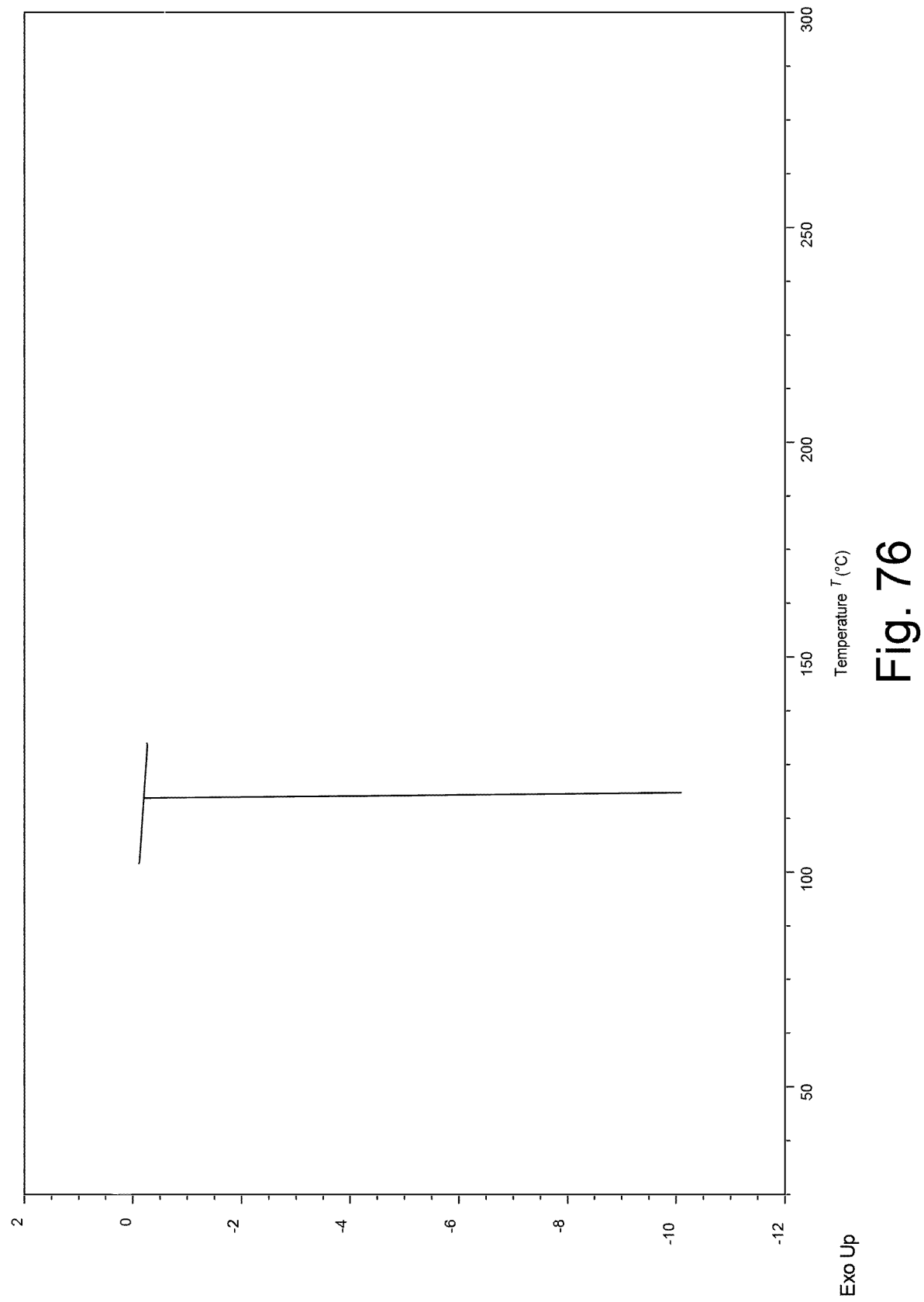
FIG. 76 shows DSC thermograph of 5MeODMT benzoate lot 21-01-058 D, isolated from exposure of anisole vapour to amorphous form.

FIG. 76 shows DSC thermograph of 5MeODMT benzoate lot 21-01-058 D, isolated from exposure of anisole vapour to amorphous form.

Amorphous 5MeODMT benzoate exposed to anisole vapour afforded an anisole hemi-solvate, nominated herein as Pattern D form. The XRPD pattern of Pattern D form is similar to Pattern C, the toluene hemi-solvate, but with variance in peak position.

Amorphous 5MeODMT benzoate exposed to toluene vapour afforded a mixed form version that was predominantly Pattern A form with some evidence of Pattern C form, the toluene hemi-solvate, observed by XRPD and DSC.

Amorphous 5MeODMT benzoate exposed to all other solvent vapours returned exclusively Pattern A by XRPD and DSC.

| Sample | Solvent | XRPD | DSC | 1H NMR |
|---|---|---|---|---|
| A | Methanol | N/A - solution by day 7 | | |
| B | Ethyl acetate | Pattern A | Endo at 123.69° C. | NC |
| C | Acetone | Pattern A | NC | NC |
| D | Anisole | Pattern D | Endo at 118.58° C. | Salt to anisole ratio of 1:0.47 |
| E | TBME | Pattern A | NC | NC |
| F | THF | Pattern A | Endo at 123.84° C. | NC |
| G | Toluene | Predominantly Pattern A and some Pattern C | Endo at 114.39° C. Endo at 124.14° C. | Salt to toluene ratio of 1:0.04 |
| H | 1,4-Dioxane | Pattern A | NC | NC |
| I | DCM | Pattern A | NC | NC |
| J | Heptane | Pattern A | NC | NC |
| K | Acetonitrile | Pattern A | Endo at 123.85° C. | NC |
| L | Water | Pattern A | NC | NC |

Example 27: Pattern E

5MeODMT benzoate Pattern C form was isolated via reverse anti-solvent addition of isopropanol solution of 5MeODMT benzoate to toluene, this solid is believed to be a hemi-solvate which when desolvated afforded Pattern B form. Pattern B form has been accessed by equilibration of 5MeODMT benzoate in anisole and chlorobenzene. Pattern B form may be accessed from anisole and chlorobenzene hemi-solvates, consequently reverse anti-solvent addition to chlorobenzene and anisole is believed to afford a hemi-solvate as with toluene.

5MeODMT benzoate 20/20/150FP2, 650 mg, was charged to sample vial with IPA, 13 ml, and heated to 50° C. The clear solution was clarified through a 0.45 μm nylon syringe filter.

Anti-solvent, 4 ml, was charged to crystallisation tubes and cooled to −10° C. with agitation via stirrer bead at 750 rpm as detailed in the Table below.

IPA stock solution at 50° C., 2 ml, was charged to cold anti-solvent, 4 ml, at −10° C.

Observations are detailed in the Table below, with B, D, and F isolated immediately.

Tubes A, C, and E were equilibrated for 3 hours then isolated.

Suspensions were transferred to isolute cartridge and dried in vacuo for NMT 60 seconds and analysed immediately, following 4 hours, and 44 hours open to atmosphere.

5MeODMT benzoate 21-01-064 E was damp after air drying for 60 seconds.

| Tube | Anti-solvent | Time to form a suspension | Equilibration period after suspension formed |
|---|---|---|---|
| A | Toluene | 3.5 hours | 3 hours |
| B | Toluene | 3 hours | 0 hours |
| C | Chlorobenzene | 3.5 hours | 3 hours |
| D | Chlorobenzene | 3.5 hours | 0 hours |
| E | Anisole | 3.5 hours | 3 hours |
| F | Anisole | 3 hours | 0 hours |

5MeODMT benzoate 21-01-064 D was isolated immediately following the formation of the suspension afforded by the addition of concentrated IPA solution to chlorobenzene at −10° C.

Figure 77:
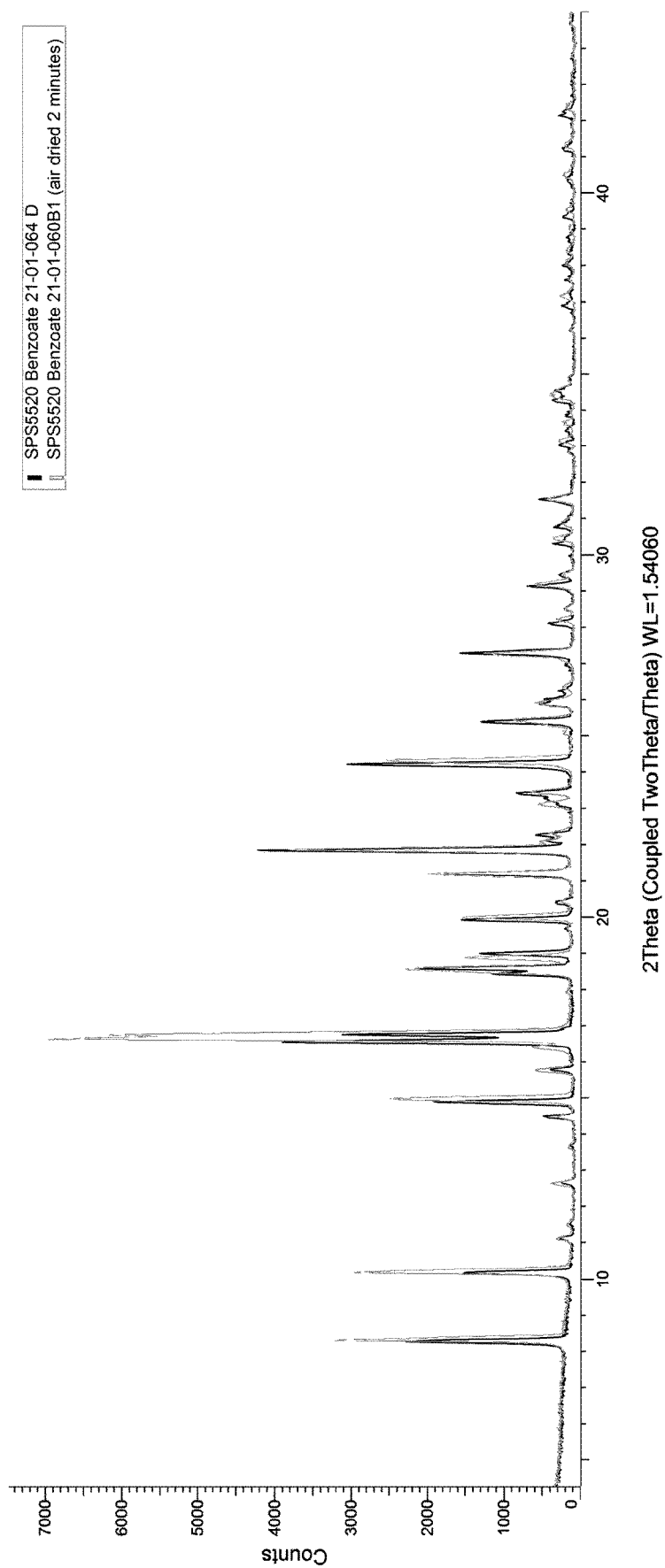
FIG. 77 shows XRPD pattern comparison of 5MeODMT benzoate lot 21-01-064 D, and 21-01-060 B1 (air dried 2 minutes).

The XRPD revealed the diffraction pattern of 5MeODMT benzoate lot 21-01-064 D was similar to 21-01-060 B1 (air dried 2 minutes), Pattern C (FIG. 77). Several diffractions including 19 and 20° 2θ are slightly higher and lower compared to Pattern C which are not consequences of the sample presentation (FIG. 78).

5MeODMT benzoate lot 21-01-064 D is a new diffraction pattern, and defined herein as Pattern E.

FIG. 77 shows XRPD pattern comparison of 5MeODMT benzoate lot 21-01-064 D, and 21-01-060 B1 (air dried 2 minutes).

Figure 78:
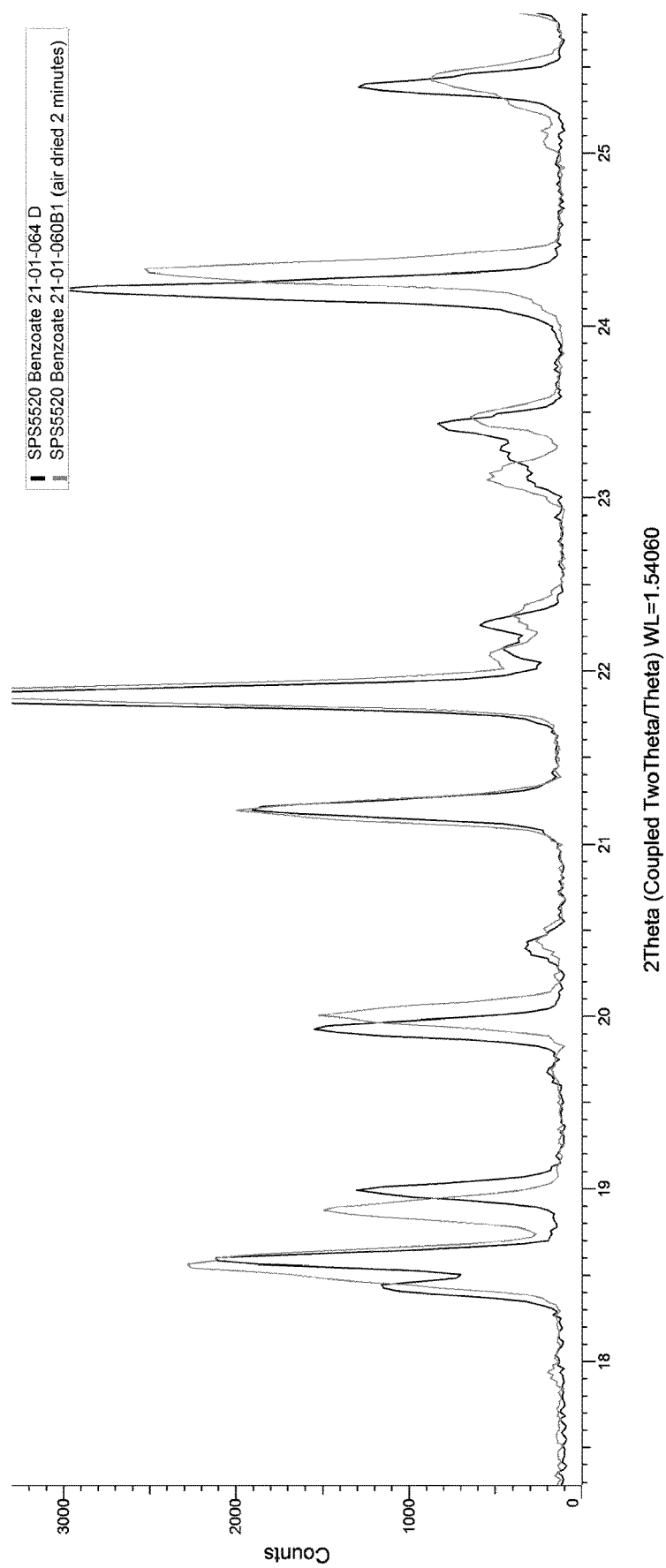
FIG. 78 shows XRPD pattern expansion comparison of 5MeODMT benzoate lot 21-01-064 D, and 21-01-060 B1 (air dried 2 minutes).

FIG. 78 shows XRPD pattern expansion comparison of 5MeODMT benzoate lot 21-01-064 D, and 21-01-060 B1 (air dried 2 minutes).

The DSC thermograph of 5MeODMT benzoate lot 21-01-064 D revealed a major bimodal endothermic event with peak temperatures of 110.31° C. and 113.13° C. (FIG. 79), followed by a minor endothermic event with a peak temperature of 119.09° C.

Figure 79:
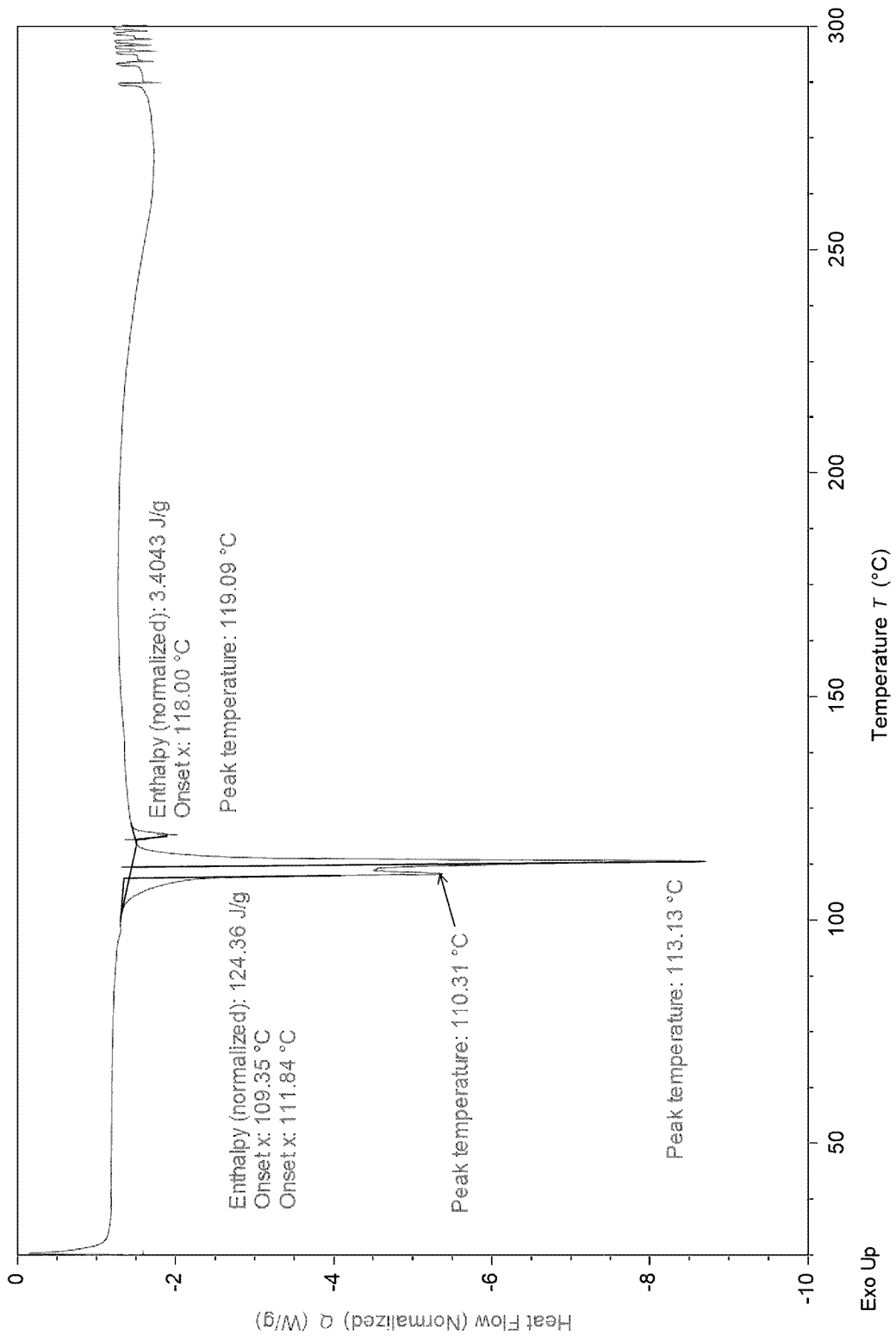
FIG. 79 shows DSC thermograph of 5MeODMT benzoate lot 21-01-064 D at 10° C.·min-1.

FIG. 79 shows DSC thermograph of 5MeODMT benzoate lot 21-01-064 D at 10° C.·min-1.

The 1H NMR spectrum of 5MeODMT benzoate lot 21-01-064 D isolated immediately following equilibration revealed the stoichiometry of the salt to be 1:1 and also revealed a salt to solvent ratio for chlorobenzene of 1:0.512 and a salt to solvent ratio for IPA of 1:0.013.

The isolated salt is a chlorobenzene hemi-solvate.

There is no evidence of a Pattern A form endothermic at ca. 123° C. in the DSC thermograph, 21-01-064 D (FIG. 79) since it is considered that the residual chlorobenzene is inhibiting crystallisation of 5MeODMT benzoate.

5MeODMT benzoate 21-01-064 C was isolated following a 3 hour equilibration of the suspension afforded by the addition of concentrated IPA solution to chlorobenzene at −10° C.

Figure 80:
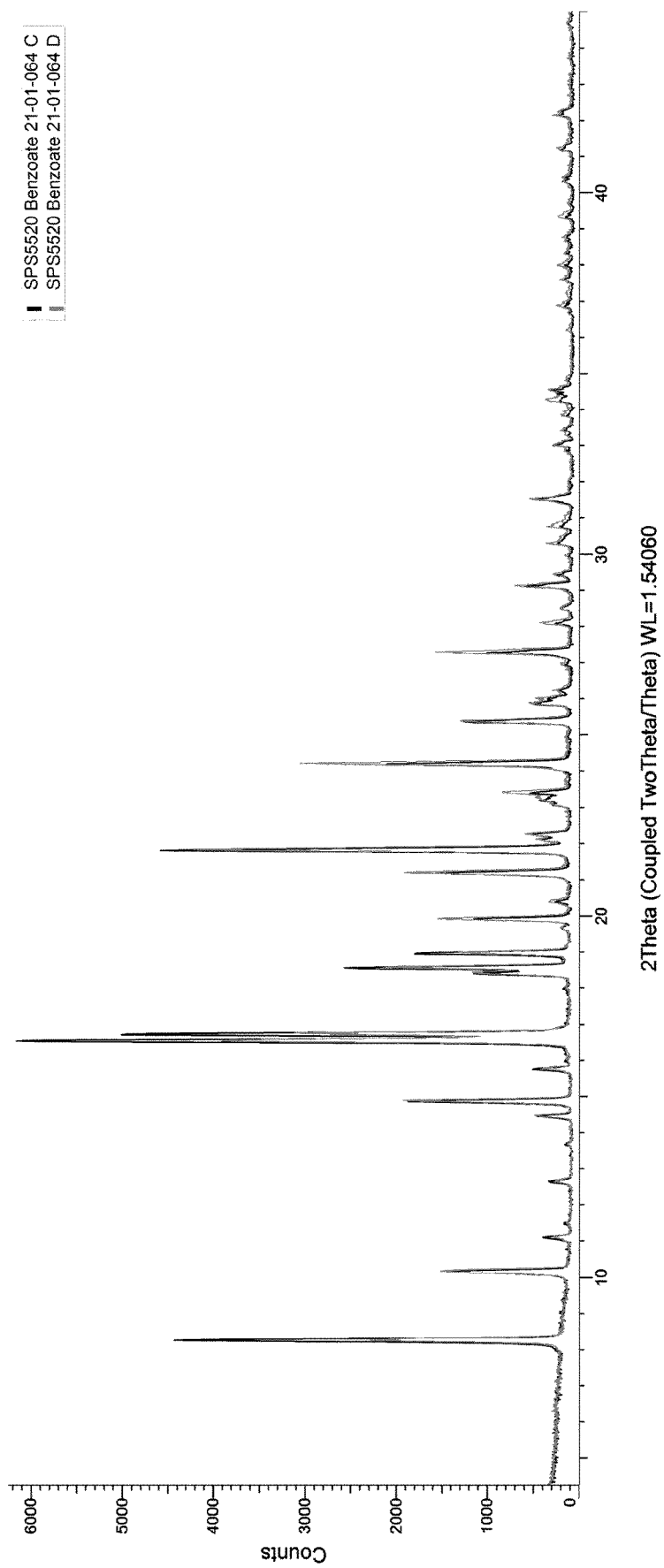
FIG. 80 shows XRPD pattern comparison of 5MeODMT benzoate lot 21-01-064 C, and 21-01-064 D.

The XRPD revealed the diffraction pattern of 5MeODMT benzoate lot 21-01-064 C was concordant with 21-01-064 D, Pattern E (FIG. 80).

FIG. 80 shows XRPD pattern comparison of 5MeODMT benzoate lot 21-01-064 C, and 21-01-064 D.

Figure 81:
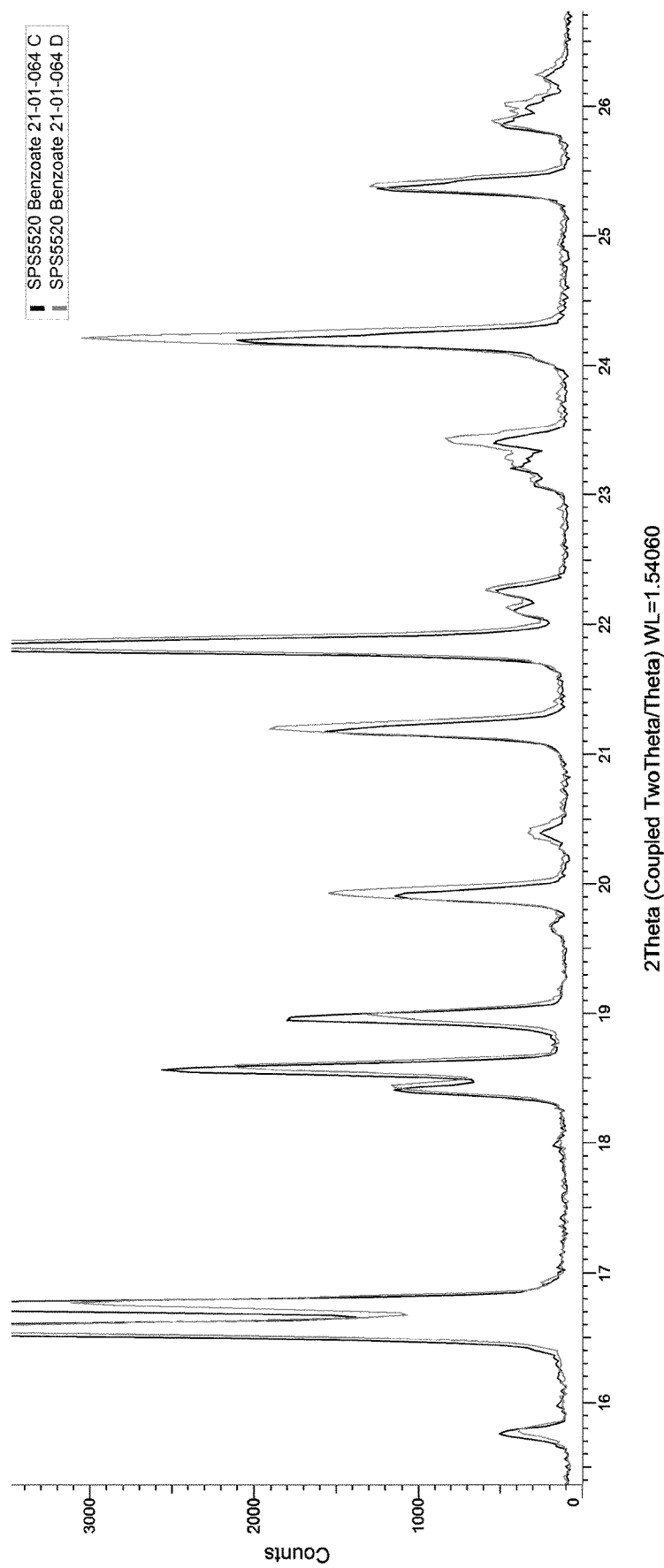
FIG. 81 shows XRPD pattern expansion comparison of 5MeODMT benzoate lot 21-01-064 C, and 21-01-064 D.

FIG. 81 shows XRPD pattern expansion comparison of 5MeODMT benzoate lot 21-01-064 C, and 21-01-064 D.

The DSC thermograph of 5MeODMT benzoate lot 21-01-064 C revealed a major endothermic event with peak temperatures of 111.39° C., 113.22° C., and 114.35° C. (FIG. 82).

The DSC thermograph of 21-01-064 C is similar to that of the thermograph of 21-01-064 D.

Figure 82:
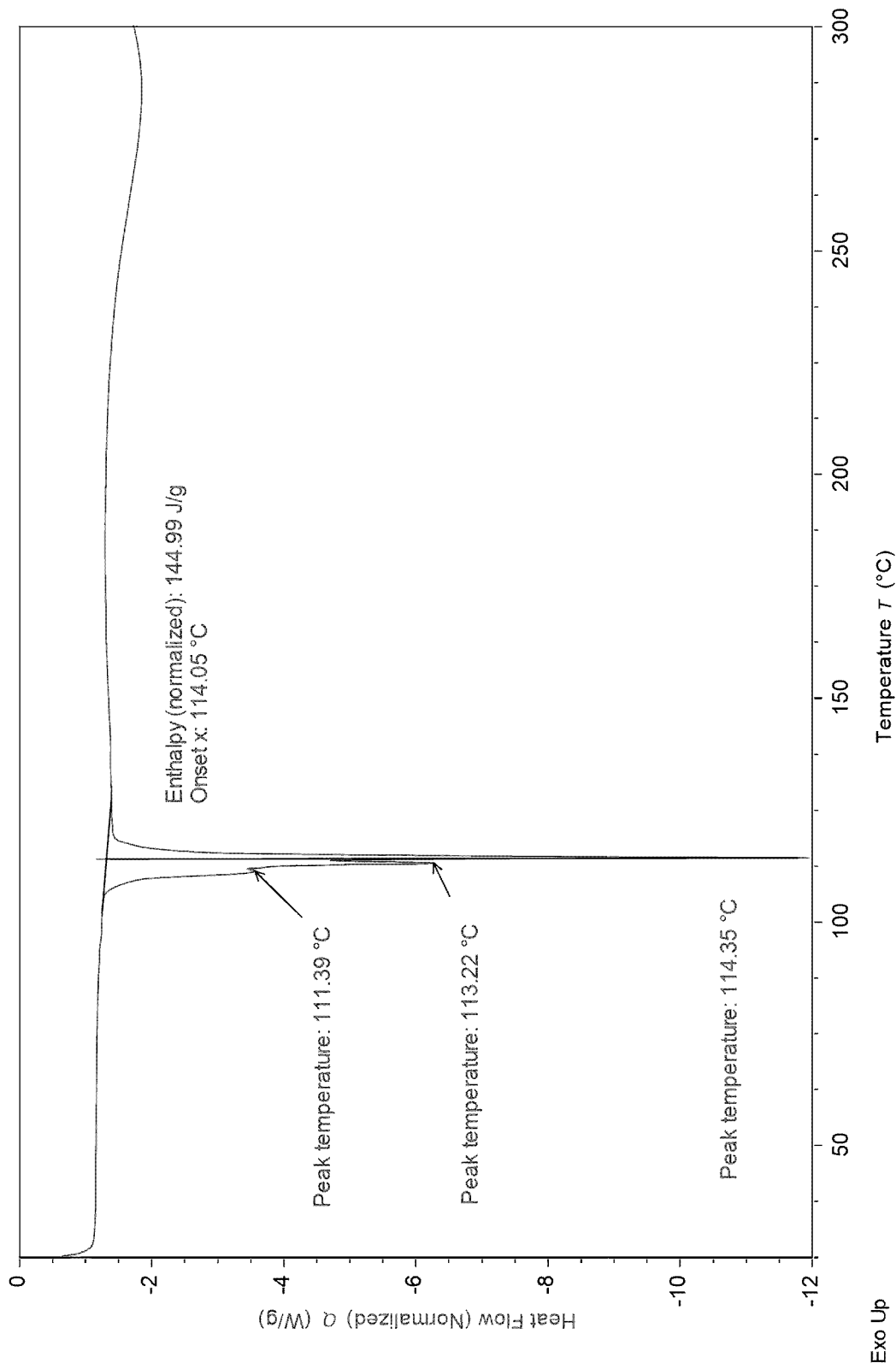
FIG. 82 shows DSC thermograph of 5MeODMT benzoate lot 21-01-064 C at 10° C.·min-1.

FIG. 82 shows DSC thermograph of 5MeODMT benzoate lot 21-01-064 C at 10° C.·min-1.

The 1H NMR spectrum of 5MeODMT benzoate lot 21-01-064 C isolated following a 3 hour equilibration revealed the stoichiometry of the salt to be 1:1 and also revealed a salt to solvent ratio for chlorobenzene of 1:0.506 and a salt to solvent ratio for IPA of 1:0.004.

The isolated salt is a chlorobenzene hemi-solvate.

The XRPD of 5MeODMT benzoate lot 21-01-064 C (4 hours air dried) revealed a diffraction pattern concordant with 21-01-064 C, Pattern E.

The XRPD of 5MeODMT benzoate lot 21-01-064 C (44 hours air dried) revealed a diffraction pattern concordant with 21-01-064 C and 21-01-064 C (4 hours air dried), Pattern E.

The XRPD of 5MeODMT benzoate lot 21-01-064 F revealed a diffraction pattern concordant with 21-01-058 D, Pattern D from the vapour diffusion investigation of amorphous 5MeODMT benzoate in anisole, but more crystalline and does not contain minor diffractions characteristic of Pattern A.

The XRPD of 5MeODMT benzoate 21-01-064 E revealed a diffraction pattern concordant with 21-01-064 F, Pattern D.

The XRPD of 5MeODMT benzoate 21-01-064 E (air dried 4 hours) revealed a diffraction pattern concordant with 21-01-064 E, Pattern D.

The XRPD of 5MeODMT benzoate 21-01-064 E (air dried 44 hours) revealed a diffraction pattern concordant with 21-01-064 E, Pattern D but with an additional diffraction at 18.3° 2θ, which is believed to be an indication of Pattern B.

Example 28: Further Discussion of Patterns B to E

Pattern B

Below is a Table which summarises lots of 5MeODMT benzoate with predominantly Pattern B form compositional and crystallographic characteristics.

| Sample name | Comments | Crystalline character | Composition by 1H NMR |
|---|---|---|---|
| 5MeODMT benzoate 21-01-049 A1 | Addition of methanol solution to cold toluene then isolated and dried in vacuo at 50° C. | Pattern B and C | 1:0.03 toluene 0 MeOH |
| 5MeODMT benzoate 21-01-049 B1 | Addition of IPA solution to cold toluene then isolated and dried in vacuo at 50° C. | Pattern B | 1:0.01 toluene 0 IPA |
| 5MeODMT benzoate 21-01-047 J | Crystallised from cooling a saturated solution of chlorobenzene and dried in vacuo at 50° C. | Pattern B and A | |
| 5MeODMT benzoate 21-01-060 A1 (air dried 20 hours) | Addition of IPA solution to cold toluene then isolated immediately and air dried for 20 hours | Pattern B and C | 1:0.04 toluene 1:0.20 IPA |
| 5MeODMT benzoate 21-01-060 A2 | Addition of IPA solution to cold toluene then isolated immediately and dried in vacuo at 50° C. | Pattern B | 1:0.007 toluene 1:0.09 IPA |
| 5MeODMT benzoate 21-01-060 B2 | Addition of IPA solution to cold toluene, equilibrated for 3 hours, then isolated and dried in vacuo at 50° C. | Pattern B and C | 1:0.05 toluene 1:0.07 IPA |

Below is a Table which summarises predominantly Pattern B thermal characteristics.

| Sample name | Broad exo at 101° C. | Endo at 109.5° C. | Endo at 110.5° C. | Endo at 113° C. | Exo at 113.4° C. | Endo at 114° C. | Exo at 114.1° C. | Exo at 117.8° C. | Endo at 124° C. |
|---|---|---|---|---|---|---|---|---|---|
| 5MeODMT benzoate 21-01-049 A1 | | | Y | Y | | Y | | Y | Y |
| 5MeODMT benzoate 21-01-049 B1 | | | Y | | | Y | | Y | Y |
| 5MeODMT benzoate 21-01-047 J | | Y | | Y | | | Y | | Y |
| 5MeODMT benzoate 21-01-060 A1 (air dried 20 hours) | Y | | | | Y | | | | Y |
| 5MeODMT benzoate 21-01-060 A2 | | | Y | | | Y | | Y | Y |
| 5MeODMT benzoate 21-01-060 B2 | | Y | | | | | | Y | Y |
| | | | Characteristic of Pattern B | | | | | | Characteristic of Pattern A |

5MeODMT benzoate lot 21-01-049 B1 was produced via reverse anti-solvent addition of an IPA solution to toluene, isolated immediately, then dried in vacuo at 50° C. XRPD revealed a diffraction pattern that was defined as Pattern B. DSC examination identified an endothermic event at 110° C. which coincides with the boiling point of toluene, this is followed by an endothermic event immediately followed by an exothermic event indicating the melt-crystallisation of Pattern B form to Pattern A form then the endothermic event indicating the melt of Pattern A form material. 1H NMR revealed low amounts of residual toluene and no IPA.

5MeODMT benzoate lot 21-01-060 A2 was produced by the same methodology as 049 B1 except on a larger scale and afforded an identical product by XRPD and DSC but contained residual IPA by 1H NMR.

5MeODMT benzoate lot 21-01-049 A1 was produced by the same methodology as 049 B1 except it was initially dissolved in methanol, XRPD revealed a powder pattern concordant with Pattern B with some Pattern C. 1H NMR revealed a salt to toluene ratio of 1:0.03. DSC examination revealed a similar thermograph to 049 B1 but the first endothermic event at 110° C. was larger and the subsequent endothermic melt of Pattern B form is bimodal and peaks at a lower temperature. Following the melt of Pattern B form, Pattern A form crystallises, and melts as expected.

5MeODMT benzoate lot 21-01-060 B2 was produced by the same methodology as 060 A2 but equilibrated for 3 hours before isolation and drying in vacuo. XRPD revealed a mixture of Pattern B with some Pattern C. 1H NMR revealed a salt to toluene ratio of 1:0.05. DSC examination revealed a similar thermograph to 049 A1 (a mixture of Pattern B and C forms) but the Pattern B form melt endothermic event is not bimodal. The endothermic event at 110° C. is considered to be a consequence of a slightly increased amount of toluene in the sample in the form of the toluene hemi-solvate.

5MeODMT benzoate lot 21-01-060 A1 (air dried 20 hours) was produced by the same methodology as 060 A2 but was air dried instead of at 50° C. in vacuo. XRPD revealed a mixture of Pattern B and C. 1H NMR revealed a salt to toluene ratio of 1:0.04. However, 060 A1 contained a significant amount more IPA than other samples (1:0.2 instead of 1:0.05). This may have modified the endothermic events during the DSC examination of the sample, but the Pattern A form melt endothermic event is present.

5MeODMT benzoate lot 21-01-047 J was produced by crystallisation from chlorobenzene at 50° C. and dried in vacuo at 50° C. XRPD revealed the sample to be a mixture of Pattern B and some Pattern A. DSC examination revealed an endothermic event similar to the endothermic event considered to be loss of toluene, which is believed to indicate the loss of chlorobenzene. The melting endotherm of Pattern B form occurs earlier than for 049 B1 but the crystallisation of Pattern A form is very exothermic and is accompanied by a melt of Pattern A form.

5MeODMT benzoate Pattern B form material contains a characteristic endo-exothermic event as it melts then crystallises as Pattern A form, Pattern B form is produced by the desolvation of hemi-solvates, therefore an endothermic event characteristic of the residual hemi-solvate is present in all samples isolated.

For those solids that contain toluene at low levels, which is believed to be the hemi-solvate version of the salt, the thermal characteristics will be modified by the loss of toluene.

Pattern C

Below is a Table which summarises lots of 5MeODMT benzoate with predominantly Pattern C compositional and crystallographic characteristics.

| Sample name | Comments | Crystalline character | Composition by 1H NMR |
|---|---|---|---|
| 5MeODMT benzoate 21-01-060 A1 (air dried 1 hour) | Addition of IPA solution to cold toluene then isolated and air dried for 1 hour | Pattern C and B | |
| 5MeODMT benzoate 21-01-060 B1 (air dried 20 hours) | Addition of IPA solution to cold toluene, equilibrated for 3 hours, then isolated and air dried for 20 hours | Pattern C and B | 1:0.43 toluene 1:0.12 IPA |
| 5MeODMT benzoate 21-01-064 A | Addition of IPA solution to cold toluene, equilibrated for 3 hours, then isolated | Pattern C | 1:0.49 toluene 1:0.004 IPA |
| 5MeODMT benzoate 21-01-064 A (air dried 4 hours) (DSC at 2.5° C. min$^{-1}$) | Addition of IPA solution to cold toluene, equilibrated for 3 hours, then isolated and air dried for 4 hours | Pattern C and B | |
| 5MeODMT benzoate 21-01-064 A (air dried 44 hours) | Addition of IPA solution to cold toluene, equilibrated for 3 hours, then isolated and air dried for 44 hours | Pattern C and B | |
| 5MeODMT benzoate 21-01-064 B | Addition of IPA solution to cold toluene then isolated | Pattern C | 1:0.5 toluene 1:0.006 IPA |

Below is a Table which summarises predominantly Pattern C form thermal characteristics.

| Sample name | Exo between 105 and 113° C. | Endo at 110.0° C. | Endo at 111.3° C. | Endo at 112.1° C. | Exo at 112.4° C. | Endo at 113.3° C. |
|---|---|---|---|---|---|---|
| 5MeODMT benzoate 21-01-060 A1 (air dried 1 hour) | P | | | | Y | |
| 5MeODMT benzoate 21-01-060 B1 (air dried 20 hours) | | | Y | | | |
| 5MeODMT benzoate 21-01-064 A | | | Y | | | Y |

-continued

| Sample name | Exo between 105 and 113° C. | Endo at 110.0° C. | Endo at 111.3° C. | Endo at 112.1° C. | Exo at 112.4° C. | Endo at 113.3° C. |
|---|---|---|---|---|---|---|
| 5MeODMT benzoate 21-01-064 A (air dried 4 hours) (DSC at 2.5° C. · min⁻¹) | Y | | | | | Y |
| 5MeODMT benzoate 21-01-064 A (air dried 44 hours) | | | Y | Y | | |
| 5MeODMT benzoate 21-01-064 B | | | | Y | Y | |
| | | | | Characteristic of Pattern B | | |

| Sample name | Exo at 113.6° C. | Endo at 115.0° C. | Endo at 115.5° C. | Endo at 117.8° C. | Endo at 120.2° C. | Endo at 122.0° C. | Endo at 124° C. |
|---|---|---|---|---|---|---|---|
| 5MeODMT benzoate 21-01-060 A1 (air dried 1 hour) | | | | | | | Y |
| 5MeODMT benzoate 21-01-060 B1 (air dried 20 hours) | | | Y | Y | Y | | |
| 5MeODMT benzoate 21-01-064 A | | Y | Y | | Y | | |
| 5MeODMT benzoate 21-01-064 A (air dried 4 hours) (DSC at 2.5° C. · min⁻¹) | Y | | | | | | Y |
| 5MeODMT benzoate 21-01-064 A (air dried 44 hours) | | Y | | | | Y | |
| 5MeODMT benzoate 21-01-064 B | Y | Y | | | | Y | |
| | Characteristic of Pattern B | | | | | Characteristic of Pattern A | |

5MeODMT benzoate lot 21-01-064 B was produced by reverse anti-solvent addition of an IPA solution to toluene. XRPD revealed Pattern C which was supported by a ratio of 1:0.5 of salt to toluene by 1H NMR indicating a toluene hemi-solvate. DSC examination revealed a bimodal endothermic event with peak temperatures of 111.3° C. and 112.1° C., this indicates the endothermic event at 111° C. in the Pattern B mixtures was a result of residual Pattern C. There were endothermic events indicative of Pattern B form, which suggested transformation to Pattern B form then Pattern A form.

5MeODMT benzoate lot 21-01-064 A was produced by the same methodology as 064 B but was equilibrated for 3 hours before isolation. XRPD and 1H NMR revealed identical characteristics as 064 B. However, DSC examination revealed a different major multi-modal endothermic event with a peak temperature of 115.0° C.

5MeODMT benzoate lot 21-01-064 A (air dried 44 hours) and 21-01-060 B1 air dried (20 hours) were produced similarly to 064 A but air dried for longer. XRPD revealed a mixture of Pattern C and Pattern B for both, 1H NMR revealed less toluene in 060 B1 than for 064 A, which is believed to be a result of air drying which supports the presence of Pattern B form in the sample by XRPD. DSC examination revealed an endothermic event with a peak temperature of 111.3° C. for both, followed by multiple unique endothermic events.

5MeODMT benzoate lot 21-01-064 A (air dried 4 hours) was produced by air drying 064 A. XRPD revealed a mixture of Pattern C with some Pattern B. DSC examination revealed a broad exothermic event between 105 and 113° C. followed by a weak endothermic event indicative of Pattern C form and endothermic events indicative of Pattern B form.

The change to the heating rate is the cause of the change to thermal behaviour, as the DSC thermograph of 21-01-064 A (44 hour air dried) sample is similar to 21-01-064 A the transformation of Pattern C form occurred in situ during the examination.

5MeODMT benzoate 21-01-060 A1 (air dried 1 hour) was produced by the same methodology as 064 A but isolated immediately. XRPD revealed a mixture of Pattern C and some Pattern B. DSC examination revealed a thermograph indicative of Pattern B form with a minor exothermic event at ca 109° C.

5MeODMT benzoate Pattern C form is a toluene hemi-solvate it has no characteristic endothermic event except for a melt between 110° C. and 115° C. The XRPD pattern of the toluene hemi-solvate of 5MeODMT benzoate is distinct to 5MeODMT benzoate. Desolvation may occur under ambient conditions and it is considered that Pattern B form is produced.

The thermal characteristics will be influenced by the loss of toluene during DSC examination.

Pattern D

The Table below is a summary of predominantly Pattern D form compositional and crystallographic characteristics.

| Sample name | Comments | Crystalline character | Composition by 1H NMR |
| --- | --- | --- | --- |
| 5MeODMT benzoate 21-01-058 D | Exposure of amorphous form to anisole vapours | Pattern D and A | 1:0.47 anisole |
| 5MeODMT benzoate 21-01-064 E | Addition of IPA solution to cold anisole, equilibrated for 3 hours, then isolated | Pattern D | 1:1.04 anisole 1:0.11 IPA |
| 5MeODMT benzoate 21-01-064 E (air dried 4 hours) | Addition of IPA solution to cold anisole, equilibrated for 3 hours, then isolated and air dried for 4 hours | Pattern D | |
| 5MeODMT benzoate 21-01-064 E (air dried 44 hours) | Addition of IPA solution to cold anisole, equilibrated for 3 hours, then isolated and air dried for 44 hours | Pattern D and B | |
| 5MeODMT benzoate 21-01-064 F | Addition of IPA solution to cold anisole then isolated | Pattern D | 1:0.503 anisole 1:0.01 IPA |

The table below shows a summary of predominantly Pattern D form thermal characteristics.

| Sample name | Endo at 111.2° C. | Endo at 117.8° C. | Endo at 118.6° C. | Endo at 119.2° C. |
| --- | --- | --- | --- | --- |
| 5MeODMT benzoate 21-01-058 D | | | Y | |
| 5MeODMT benzoate 21-01-064 E | | Y | | |
| 5MeODMT benzoate 21-01-064 E (air dried 4 hours) | Y | Y | | |
| 5MeODMT benzoate 21-01-064 E (air dried 44 hours) | Y | Y | Y | |
| 5MeODMT benzoate 21-01-064 F | | | Y | Y |

5MeODMT benzoate lot 21-01-064 F was produced by reverse anti-solvent addition of an IPA solution to anisole and isolated immediately. XRPD revealed a diffraction pattern concordant with Pattern D, which was supported by a ratio of 1:0.503 for anisole by 1H NMR indicating a hemi-solvate. DSC examination revealed a bimodal endothermic event with peak temperatures of 118.61° C. and 119.21° C.

5MeODMT benzoate lot 21-01-064 E was produced by reverse anti-solvent addition of an IPA solution to anisole, then equilibrated for 3 hours before isolation. XRPD revealed Pattern D but this was not supported by 1H NMR which revealed a ratio of salt to anisole of 1:1.04, the isolated solid was damp after isolation. DSC examination revealed very poorly defined broad endothermic events with peak temperatures of 113.51° C. and 161.93° C., the endothermic event at 113.51° C. is believed to be a result of the melting of the hemi-solvate present by XRPD followed by evaporation of anisole. The DSC thermograph is not considered representative of Pattern D form due to the solvent content.

5MeODMT benzoate lot 21-01-058 D was produced by exposure of the amorphous form to anisole vapour. XRPD revealed a mixture of Pattern D and some Pattern A diffractions which was supported by 1H NMR which revealed a ratio of salt to anisole of 1:0.47 indicating an anisole hemi-solvate. DSC examination revealed an endothermic event with a peak temperature of 118.6° C., which is concordant with the data collected from 064 F. However, the melt of Pattern A form is not revealed in the DSC thermograph, this could be modified by the liberated anisole solvent present in the sample.

5MeODMT benzoate lot 21-01-064 E (air dried 4 hours) was produced by air drying 064 E for 4 hours. XRPD revealed Pattern D. DSC examination was performed at 2.5° C.·min-1 with the aim to resolve the bimodal endothermic event observed in the thermograph of 064 E. DSC examination revealed a minor endothermic event with a peak temperature of 111.24° C., this endothermic event is concordant with the broad endothermic event observed in 064 E. The better resolution of this endothermic is believed to be a result of the slower heating rate, or due to removal of residual anisole by air drying. This was followed by a major endothermic event with a peak temperature of 117.90° C. which is concordant with 058 D and 064 F.

5MeODMT benzoate lot 21-01-064 E (air dried 44 hours) was produced by air drying 064 E (air dried 4 hours) for a further 40 hours. XRPD revealed a mixture of Pattern D with some Pattern B diffractions. DSC examination revealed a thermograph concordant with 064 E (4 hours air dried). The Pattern B form content was not evident in the DSC thermograph this is believed to be caused by the liberated anisole solvent present in the sample, similar to 058 D.

5MeODMT benzoate Pattern D form is an anisole hemi-solvate and has been produced directly from exposure of the amorphous form to anisole vapour as well as reverse anti-solvent addition from an IPA solution to cold anisole. No characteristic thermal behaviour has been identified although, endothermic events near 118° C. are common and the lack of recrystallisation to Pattern B or A forms is believed to be due to the presence of residual anisole.

Pattern E

The Table below is a summary of predominantly Pattern E form compositional and crystallographic characteristics.

| Sample name | Comments | Crystalline character | Composition by 1H NMR |
|---|---|---|---|
| 5MeODMT benzoate 21-01-064 C | Addition of IPA solution to cold chlorobenzene, equilibrated for 3 hours, then isolated | Pattern E | 1:0.506 chlorobenzene 1:0.04 IPA |
| 5MeODMT benzoate 21-01-064 C (air dried 4 hours) | Addition of IPA solution to cold chlorobenzene, equilibrated for 3 hours, then isolated and air dried for 4 hours | Pattern E | |
| 5MeODMT benzoate 21-01-064 C (air dried 44 hours) | Addition of IPA solution to cold chlorobenzene, equilibrated for 3 hours, then isolated and air dried for 44 hours | Pattern E | |
| 5MeODMT benzoate 21-01-064 D | Addition of IPA solution to cold chlorobenzene then isolated | Pattern E | 1:0.512 chlorobenzene 1:0.01 IPA |

The table below is a summary of predominantly Pattern E form thermal characteristics, the endothermic event at 123.7° C. is characteristic of Pattern A.

| Sample name | Exo between 105 and 115° C. | Endo at 110.3° C. | Endo at 111.3° C. | Endo at 113.1° C. | Endo at 114.3° C. | Endo at 115.1° C. | Endo at 115.8° C. | Endo at 119.1° C. | Endo at 123.7° C. |
|---|---|---|---|---|---|---|---|---|---|
| 5MeODMT benzoate 21-01-064 C | | | Y | Y | Y | | | | |
| 5MeODMT benzoate 21-01-064 C (air dried 4 hours) | Y | | | | Y | | | | Y |
| 5MeODMT benzoate 21-01-064 C (air dried 44 hours) | | | | | | Y | Y | | |
| 5MeODMT benzoate 21-01-064 D | | Y | | Y | | | | Y | |

5MeODMT benzoate lot 21-01-064 D was produced by reverse anti-solvent addition of an IPA solution to chlorobenzene. XRPD revealed Pattern E, this was supported by 1H NMR which revealed a ratio of salt to chlorobenzene of 1:0.506 indicating a chlorobenzene hemi-solvate. DSC examination revealed a bimodal endothermic event with peak temperatures of 111.3° C. and 113.1° C., followed by a minor endothermic event with a peak temperature of 119.1° C.

5MeODMT benzoate lot 21-01-064 C was produced by reverse anti-solvent addition of an IPA solution to cold chlorobenzene, then equilibrated for 3 hours before isolation. XRPD revealed Pattern E, this was supported by 1H NMR which revealed a ratio of salt to chlorobenzene of 1:0.512 indicating a hemi-solvate. DSC examination revealed a trimodal endothermic event with peak temperatures of 111.3° C., 113.1° C., and 114.3° C. There are similarities between DSC thermographs of 064 D and C but the endothermic event at 119.1° C. is not present in 064 C and 064 D did not reveal a trimodal endothermic event. The differences in the DSC thermograph are of note since the XRPD patterns were identical and 1H NMR revealed hemi-solvates.

5MeODMT benzoate lot 21-01-064 C (air dried 4 hours) was produced by air drying 064 C for 4 hours. XRPD revealed Pattern E. DSC examination was performed at 2.5° C.·min$^{-1}$ and revealed a broad exothermic event followed by a minor endothermic event at 114.3° C. but much weaker in comparison to the same endothermic event in 064 C. This was followed by the major endothermic event at 123.7° C. which is indicative of Pattern A form. The DSC thermograph is similar to the previous 2.5° C.·min$^{-1}$ DSC examination and is generating Pattern A form during the DSC examination.

5MeODMT benzoate lot 21-01-064 C (air dried 44 hours) was produced by air drying 064 C (air dried 4 hours) for a further 40 hours. XPRD revealed Pattern E. DSC examination revealed a bimodal endothermic event with peak temperatures of 115.1° C. and 115.8° C. The endothermic event of 064 C (air dried 44 hours) is similar to 064 C but peaks at a slightly higher temperature.

5MeODMT benzoate Pattern E form is a chlorobenzene hemi-solvate with no defined thermal characteristics except for a multi-modal endothermic event between 110 and 117° C. Similarly, to the anisole hemi-solvate, Pattern A and B forms do not recrystallise from the melt. Chlorobenzene hemi-solvate appears to not desolvate when open to ambient conditions and did not desolvate over 44 hours.

Example 29: Hemi-Solvates

Equilibration of suspensions in anti-solvent (toluene, anisole, and chlorobenzene) at −10° C. afforded the expected hemi-solvate by XRPD and 1H NMR spectroscopy and TGA.

The partial desolvation of hemi-solvates is considered to afford multi-modal endothermic events observed in the DSC thermographs, a consequence of changing composition and the applied heating rate.

Desolvation of hemi-solvates in vacuo at 50° C. for 22 hours afforded Pattern B form material by XRPD, DSC, however, some residual hemi-solvate remained in all samples.

The DSC thermograph of the hemi-solvates were similar to those isolated from IPA/antisolvent but with minor differences which are considered to be a consequence of how they were prepared.

Drying 5MeODMT benzoate toluene hemi-solvate and chlorobenzene hemi-solvate in vacua at 50° C. for 67 hours afforded Pattern A form, but the anisole hemi-solvate afforded predominantly Pattern B form.

Addition of 5MeODMT benzoate/IPA solution to toluene at −10° C. then air dried for 5 minutes afforded the toluene hemi-solvate when performed on a 1 g input.

Drying 5MeODMT benzoate toluene hemi-solvate at 50° C. for 24 hours afforded Pattern B form.

5MeODMT benzoate batches 20/53/057-FP and 20/20/123FP demonstrated similar particle habits of large hexagonal/rhombus plates (ca. 500 μm to 1 mm in length) and some smaller plates that demonstrated accretion on the plate surfaces and significant evidence of broken fine particles and plates, potentially due to attrition.

This was different to batches 20/20/150FP2 T=0 and 20/20/154FP which demonstrated similar particle habits of accreted, jagged clusters of irregular plates, (ca. 250 to 600 μm in length) and broken, irregular plates and crystallites (some <20 μm in length) that were indicative of particle attrition.

The significant difference in particle size and habit between the batches is believed to have an impact on isolation, flowability and kinetic dissolution rate of the solids, highlighting the importance of a controlled crystallisation.

Example 30: Patterns F and G

5MeODMT benzoate methyl benzoate hemi-solvate (Pattern F form) has been isolated from controlled cooling of a clarified 5MeODMT benzoate methyl benzoate solution from 50° C. to −10° C.

5MeODMT benzoate 2-chlorotoluene hemi-solvate (Pattern G form) has been isolated from controlled cooling of a clarified 5MeODMT benzoate 2-chlorotoluene solution from 80° C. to −10° C.

Equilibration in α,α,α-trifluorotoluene did not afford a hemi-solvate as anticipated from a monosubstituted aromatic solvent. Equilibration in cumene afforded Pattern B form, which indicated a cumene hemi-solvate.

DVS examination of amorphous 5MeODMT benzoate revealed a weight loss of ca. 2% indicating the elimination of a component and confirming that a stable hydrate of 5MeODMT benzoate was not isolated.

Pattern A form is the most stable version of 5MeODMT benzoate and is the thermodynamically favoured product except when isolated from a small selection of solvents, which afforded the respective hemi-solvate.

Stability studies revealed conversion of all patterns to Pattern A form when dried in vacuo at 50° C. However, Pattern B form has been shown to be stable when open to atmosphere at ca. 20° C. for up to 12 days. Pattern C form underwent partial conversion to Pattern B form within 24 hours when open to atmosphere at ca. 20° C., but failed to convert any further from a Pattern B/C mixed version over an additional 11 days.

FTIR spectra for Patterns A, B and C were overall similar though there were some unique bands in Pattern A form and absent bands that were otherwise present and shared by Patterns B and C forms.

Controlled Cooling Crystallisation Investigation with an Expanded Solvent Selection Initial cooling crystallisation investigation of 5MeODMT benzoate revealed Pattern A form was isolated from most solvents except chlorobenzene which was consistent with Pattern B form. The range of solvents was expanded, with an emphasis on esters and aromatics.

5MeODMT benzoate lot 20/20/150FP2, 50 mg±1 mg, was charged to crystallisation tubes A-L. Minimal solvent at 50° C. was charged to afford a clear solution as detailed in the Table below. Crystallisation tubes I, J, K, and L remained as suspensions at 12.5 mg·ml-1 at 50° C. and so were heated to 80° C. to afford clear solutions.

Solutions were clarified into crystallisation tubes at 50° C. and were cooled to −10° C. at a rate of 10° C.·hr-1, then equilibrated at −10° C. for 12 hours, then agitated at −10° C. at 400 rpm for 30 minutes which afforded a mobile suspension for all samples except Sample I which remained a solution. Further equilibration with agitation at −10° C. at 400 rpm for 3 hours afforded a thin suspension. All samples were isolated via isolute cartridge and air dried for 5 minutes before characterisation.

Sample F isolated from methyl benzoate was a thick white paste after air drying for 5 minutes and was left to air dry on the XRPD sample holder for a further 30 minutes which then afforded a dry powder.

| Cryst. tube | Solvent | Solubility mg·ml$^{-1}$ at ° C. | Observations |
|---|---|---|---|
| A | Methyl acetate | 33.3 at 50 | Crystals grew during controlled cooling, then agitated to form a mobile suspension |
| B | n-Propyl acetate | 20 at 50 | Clear solution post equilibration that afforded a mobile suspension following brief agitation |
| C | Iso-Propyl acetate | 16.7 at 50 | Crystals grew during controlled cooling, then agitated to form a mobile suspension |
| D | Iso-Butyl acetate | 12.5 at 50 | Clear solution post equilibration that afforded a mobile suspension following brief agitation |
| E | Ethyl formate | 40 at 50 | Crystals grew during controlled cooling, then agitated to form a mobile suspension |
| F | Methyl benzoate | 50 at 50 | Clear solution post equilibration that afforded a mobile suspension following brief agitation |
| G | Methyl propionate | 40 at 50 | Crystals grew during controlled cooling, then agitated to form a mobile suspension |
| H | 4-Methyl-2-pentanone | 25 at 50 | Clear solution post equilibration that afforded a mobile suspension following brief agitation |
| I | Cumene | 12.5 at 80 | Clear solution post equilibration that afforded a mobile suspension following agitation for 3 hours |
| J | Toluene | 12.5 at 80 | Crystals grew during controlled cooling, then agitated to form a mobile suspension |
| K | 2-Chlorotoluene | 12.5 at 80 | Crystals grew during controlled cooling, then agitated to form a mobile suspension |
| L | α,α,α-Trifluorotoluene | 12.5 at 80 | Crystals grew during controlled cooling, then agitated to form a mobile suspension |

5MeODMT benzoate lots 21-01-073 B, C, D, E, G, H, and L were isolated from n-propyl acetate, isopropyl acetate, iso-butyl acetate, ethyl formate, methyl propionate, 4-methyl-2-pentanone, and α,α,α-trifluorotoluene respectively.

The XRPD of these samples revealed powder patterns concordant with 5MeODMT benzoate lot 20-37-64, Pattern A.

The DSC thermograph of a selection of pattern A material revealed a common endothermic event with a peak temperature ranging from 123.07° C. to 124.17° C. with an enthalpy of ca. 140 J·g-1, which is characteristic of Pattern A form. The $^1$H NMR spectra of 5MeODMT benzoate lots 21-01-073 B, E, H, and L isolated following controlled cooling, then air dried for 5 minutes revealed the stoichiometry of the salts to be 1:1 and also revealed a salt to solvent ratio ranging from 1:0.0155 to 1:0.027.

5MeODMT benzoate lot 21-01-073 A was isolated from controlled cooling of a methyl acetate solution from 50° C. to −10° C., then air dried for 5 minutes.

The XRPD of 5MeODMT benzoate lot 21-01-073 A revealed the diffraction pattern was concordant with 5MeODMT benzoate lot 20-37-64, Pattern A (FIG. 83), but featured diffractions at 21 and 24.6° 2θ that were more intense. The difference in intensity was likely a result of preferred orientation.

Figure 83:
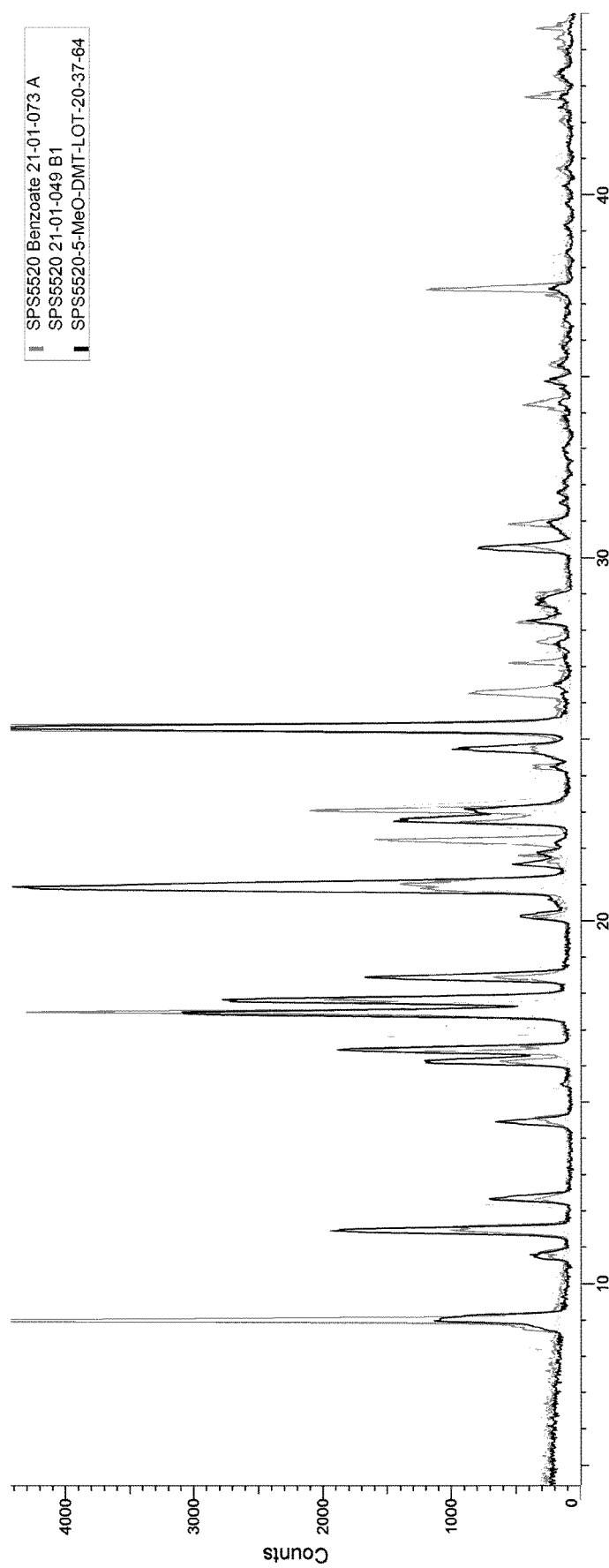
FIG. 83 shows XRPD pattern comparison of 5MeODMT benzoate lot 21-01-073 A, 21-01-049 B1, Pattern B, and 20-37-64, Pattern A.

FIG. 83 shows XRPD pattern comparison of 5MeODMT benzoate lot 21-01-073 A, 21-01-049 B1, Pattern B, and 20-37-64, Pattern A.

The DSC thermograph of 5MeODMT benzoate lot 21-01-073 A revealed an endothermic event with a peak temperature of 123.58° C., this is characteristic of Pattern A form.

The 1H NMR spectrum of 5MeODMT benzoate lots 21-01-073 A isolated following controlled cooling, then air dried for 5 minutes revealed the stoichiometry of the salts to be 1:1 and also revealed a salt to solvent ratio of methyl acetate of 1:0.033. 5MeODMT benzoate lot 21-01-073 F was isolated from controlled cooling of a methyl benzoate solution from 50° C. to −10° C., then air dried for 5 minutes. After air drying for 5 minutes the sample was a paste, air drying further for 30 minutes afforded a damp powder.

Figure 84:
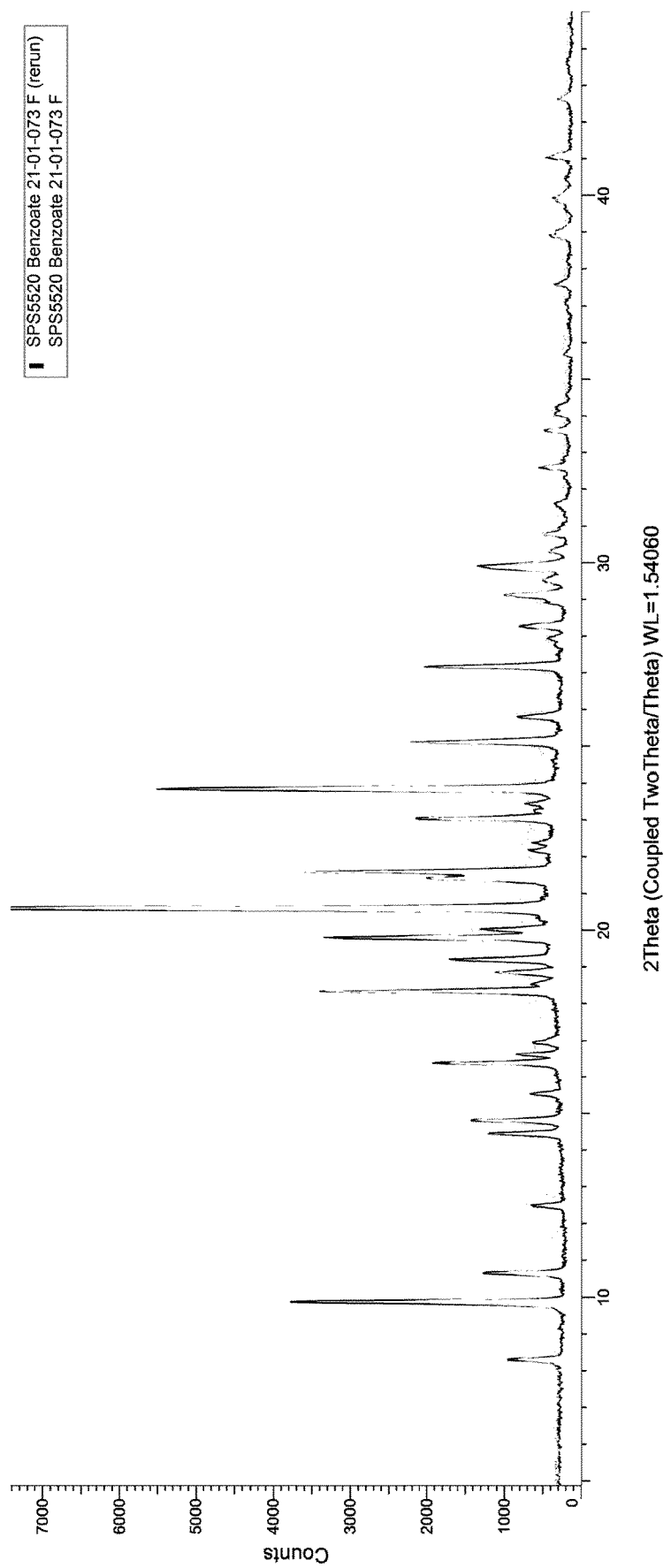
FIG. 84 shows XRPD pattern comparison of 5MeODMT benzoate lot 21-01-073 F and 21-01-073 F rerun.
Figure 85:
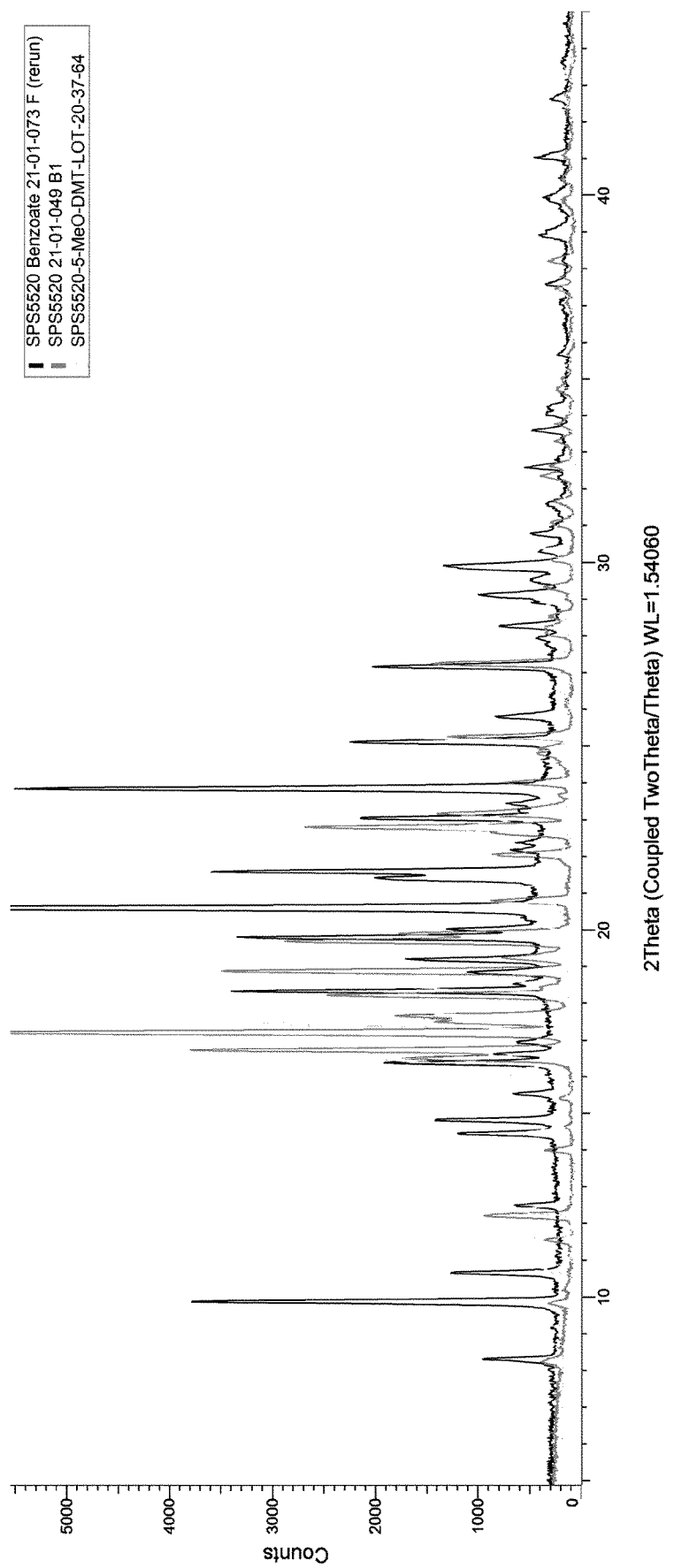
FIG. 85 shows XRPD pattern comparison of 5MeODMT benzoate lot 21-01-073 F rerun, 21-01-049 B1, Pattern B, and 20-37-64, Pattern A.

The XRPD of 5MeODMT benzoate lot 21-01-073 F revealed an XRPD pattern with an amorphous halo (FIG. 84). The sample was re-run after further air drying. The XRPD of 5MeODMT benzoate 21-01-073 F (re-run) revealed a diffraction pattern concordant with the initial measurement but with a reduced amorphous halo (FIG. 85). The diffraction pattern demonstrated some similarities with both Pattern A and B (FIG. 86) but the presence of unique diffractions and absence of characteristic Pattern A and Pattern B diffractions indicate this material to be a unique solid form version, identified herein as Pattern F form.

FIG. 84 shows XRPD pattern comparison of 5MeODMT benzoate lot 21-01-073 F and 21-01-073 F rerun.

FIG. 85 shows XRPD pattern comparison of 5MeODMT benzoate lot 21-01-073 F rerun, 21-01-049 B1, Pattern B, and 20-37-64, Pattern A.

Figure 86:
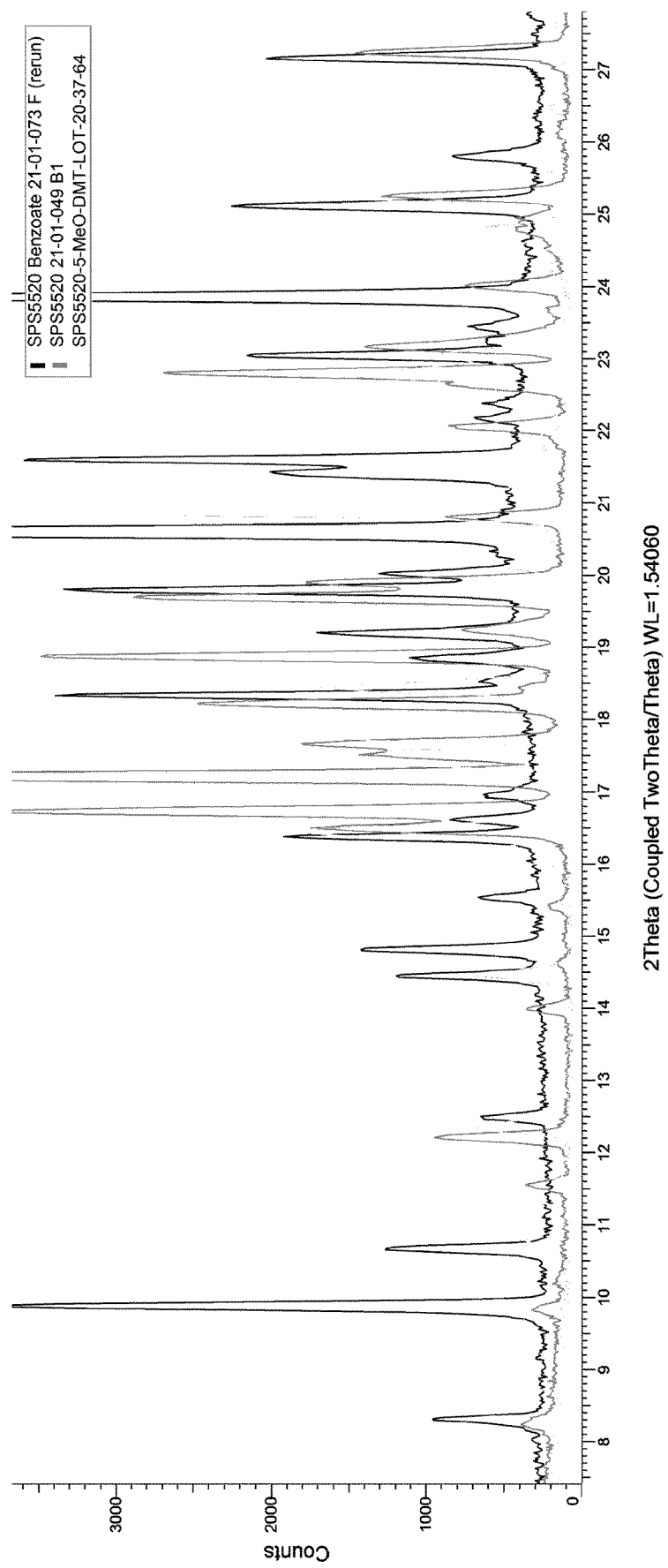
FIG. 86 shows XRPD pattern expansion comparison of 5MeODMT benzoate lot 21-01-073 F rerun, 21-01-049 B1, Pattern B, and 20-37-64, Pattern A.

FIG. 86 shows XRPD pattern expansion comparison of 5MeODMT benzoate lot 21-01-073 F rerun, 21-01-049 B1, Pattern B, and 20-37-64, Pattern A.

The DSC thermograph of 5MeODMT benzoate lot 21-01-073 F (re-run) revealed a broad endothermic event with a peak temperature of 90.50° C., this was followed by a small endothermic event with a peak temperature of 106.65° C. This was followed by a broad and shallow endothermic event with a peak temperature of 180.35° C.

DSC examination was repeated after the sample was stored in a sealed container for 24 hours. The DSC thermograph revealed a major endothermic event with a peak temperature of 95.33° C., followed by an exothermic event with a peak temperature of 102.70° C. This was followed by an endothermic event with a peak temperature of 113.77° C.

The 1H NMR spectrum of 5MeODMT benzoate lots 21-01-073 F isolated following controlled cooling, then air dried for 5 minutes, revealed the stoichiometry of the salts to be 1:1 and also revealed a salt to solvent ratio of 1:0.59.

After air drying, the paste-like consistency indicated the presence of methyl benzoate, the visually damp powder following 30 minutes of air drying, indicates that residual methyl benzoate was still present. However, due to the unique diffraction pattern and DSC thermograph, combined with the stoichiometry close to 1:0.5 and the propensity of the 5MeODMT benzoate salt to form hemi-solvates with aromatic solvents, this sample is believed to be a methyl benzoate hemi-solvate.

5MeODMT benzoate lot 21-01-073 I was isolated from controlled cooling of a 5MeODMT benzoate cumene solution from 50° C. to −10° C., then air dried for 5 minutes.

The XRPD of 5MeODMT benzoate lot 21-01-073 I revealed the diffraction pattern was concordant with SPS5520 21-01-049 B1, Pattern B.

The DSC thermograph of 5MeODMT benzoate lot 21-01-073 I revealed an endothermic event with a peak temperature of 109.24° C. with a broad shoulder at ca. 100° C. This was followed by an exothermic event with a peak temperature of 111.35° C., then an endothermic event with a peak temperature of 120.31° C. This was followed by a broad exothermic event with a peak temperature of 146.19° C. This thermal profile resemble historic Pattern B samples, although the post-final melt exotherm was known.

The 1H NMR spectrum of 5MeODMT benzoate lots 21-01-073 I isolated following controlled cooling, then air dried for 5 minutes revealed the stoichiometry of the salts to be 1:1 and also revealed a salt to solvent ratio of 1:0.035.

5MeODMT benzoate lot 21-01-073 J was isolated from controlled cooling of an 5MeODMT benzoate toluene solution from 50° C. to −10° C., then air dried for 5 minutes.

The XRPD of 5MeODMT benzoate lot 21-01-073 J revealed the diffraction pattern was concordant with 5MeODMT benzoate lot 21-01-064 A, Pattern C.

The DSC thermograph of 5MeODMT benzoate lot 21-01-073 J revealed an endothermic event with peak temperatures of 110.00° C., 115.03° C., and 120.60° C. The DSC thermograph is similar to 5MeODMT benzoate lot 21-01-071 C1, previously isolated Pattern C form material, although the minor peaks are different which is believed to be a consequence of sample preparation.

The 1H NMR spectrum of 5MeODMT benzoate lots 21-01-073 J isolated following controlled cooling, then air dried for 5 minutes revealed the stoichiometry of the salts to be 1:1 and also revealed a salt to solvent ratio of 1:0.473, confirming the isolation of the Pattern C form toluene hemi-solvate.

5MeODMT benzoate lot 21-01-073 K was isolated from controlled cooling of an 5MeODMT benzoate 2-chlorotoluene solution from 50° C. to −10° C., then air dried for 5 minutes.

The XRPD of 5MeODMT benzoate lot 21-01-073 K revealed a diffraction pattern that was unique (FIG. 87) and is herein identified as Pattern G.

Figure 87:
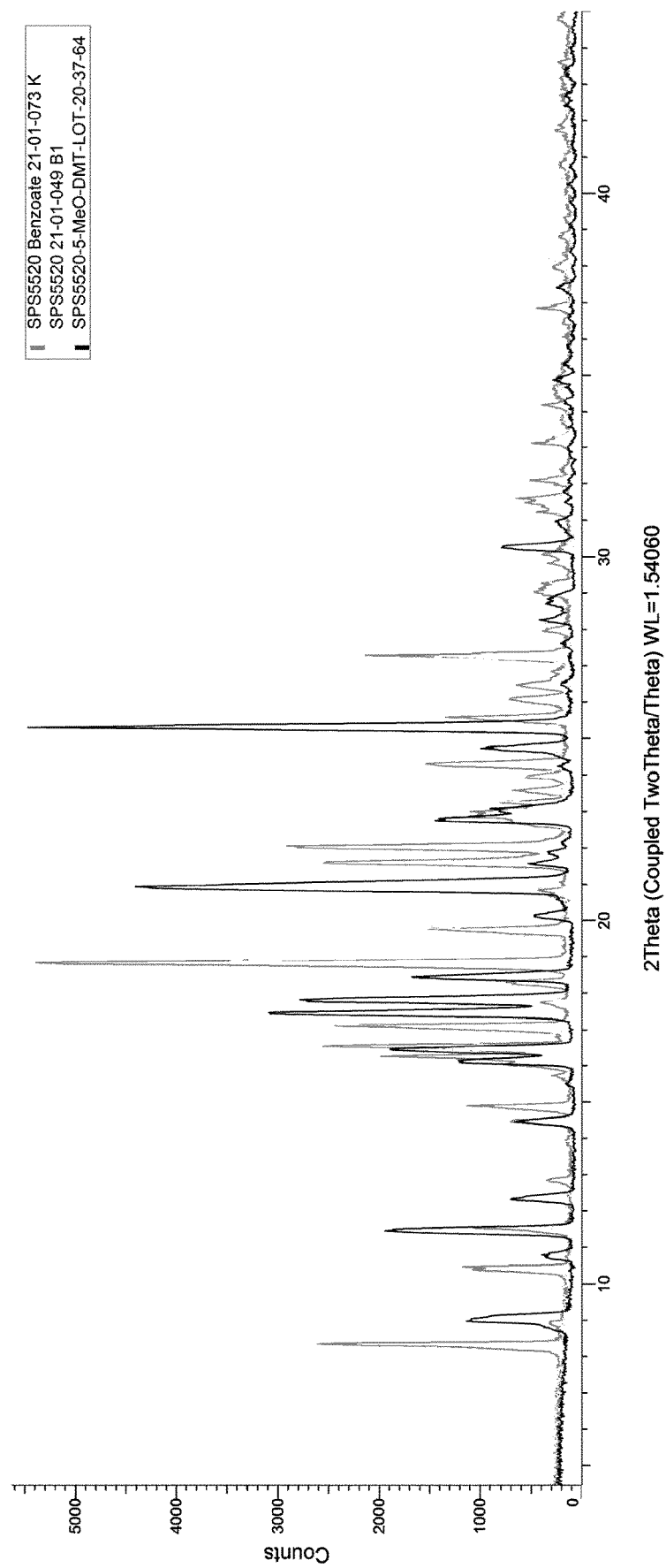
FIG. 87 shows XRPD pattern comparison of 5MeODMT benzoate lot 21-01-073 K, 21-01-049 B1, Pattern B, and 20-37-64.

FIG. 87 shows XRPD pattern comparison of 5MeODMT benzoate lot 21-01-073 K, 21-01-049 B1, Pattern 8, and 20-37-64.

The DSC thermograph of 5MeODMT benzoate lot 21-01-073 K revealed an endothermic event with peak temperatures of 111.28° C. and 119.61° C.

The 1H NMR spectrum of 5MeODMT benzoate lots 21-01-073 K isolated following controlled cooling, then air dried for 5 minutes revealed the stoichiometry of the salts to be 1:1 and also revealed a salt to solvent ratio of 1:0.516, thus Pattern G form is believed to correspond to a 2-Chlorotoluene hemi-solvate.

The Table below is a summary of samples isolated from this controlled cooling experiment and the XRPD patterns afforded.

| Sample | Solvent | XRPD pattern | DSC | Composition by ¹H NMR |
|---|---|---|---|---|
| A | Methyl acetate | A | N/C | 1:0.033 solvent |
| B | n-Propyl acetate | A | A | 1:0.027 solvent |
| C | Iso-Propyl acetate | A | N/C | N/C |
| D | Iso-Butyl acetate | A | N/C | N/C |
| E | Ethyl formate | A | A | 1:0.016 solvent |
| F | Methyl benzoate | F | 95.33° C. | 1:0.59 solvent |
| G | Methyl propionate | A | N/C | N/C |
| H | 4-Methyl-2-pentanone | A | A | 1:0.016 solvent |
| I | Cumene | B | 109.24° C. + 120.31° C. | 1:0.035 solvent |
| J | Toluene | C | 120.60° C. | 1:0.473 solvent |
| K | 2-Chlorotoluene | G | 119.61° C. | 1:0.516 solvent |
| L | α,α,α-Trifluorotoluene | A | A | Obscured |

Example 31: DVS Examination of Amorphous 5MeODMT Benzoate Produced Via Lyophilisation 5MeODMT benzoate 20/20/150FP2, 150 mg, was dissolved in deionised (DI) water, 5 ml affording a clear solution. The solution was clarified into a 500 ml round bottom flask, the round bottom flask was rotated in an acetone/dry ice bath to freeze the solution in a thin layer around the flask. The ice was sublimed in vacuo at ambient temperature affording a fluffy white solid. The solid was removed from the round bottom flask and transferred to the DVS instrument. During this transfer, the solid collapsed to a sticky gum.

The sample was examined by DVS from 40% RH and cycled between 0% RH and 90% RH twice.

XRPD was collected on a portion of the sample post-lyophoilisation and post-DVS examination.

Figure 88:
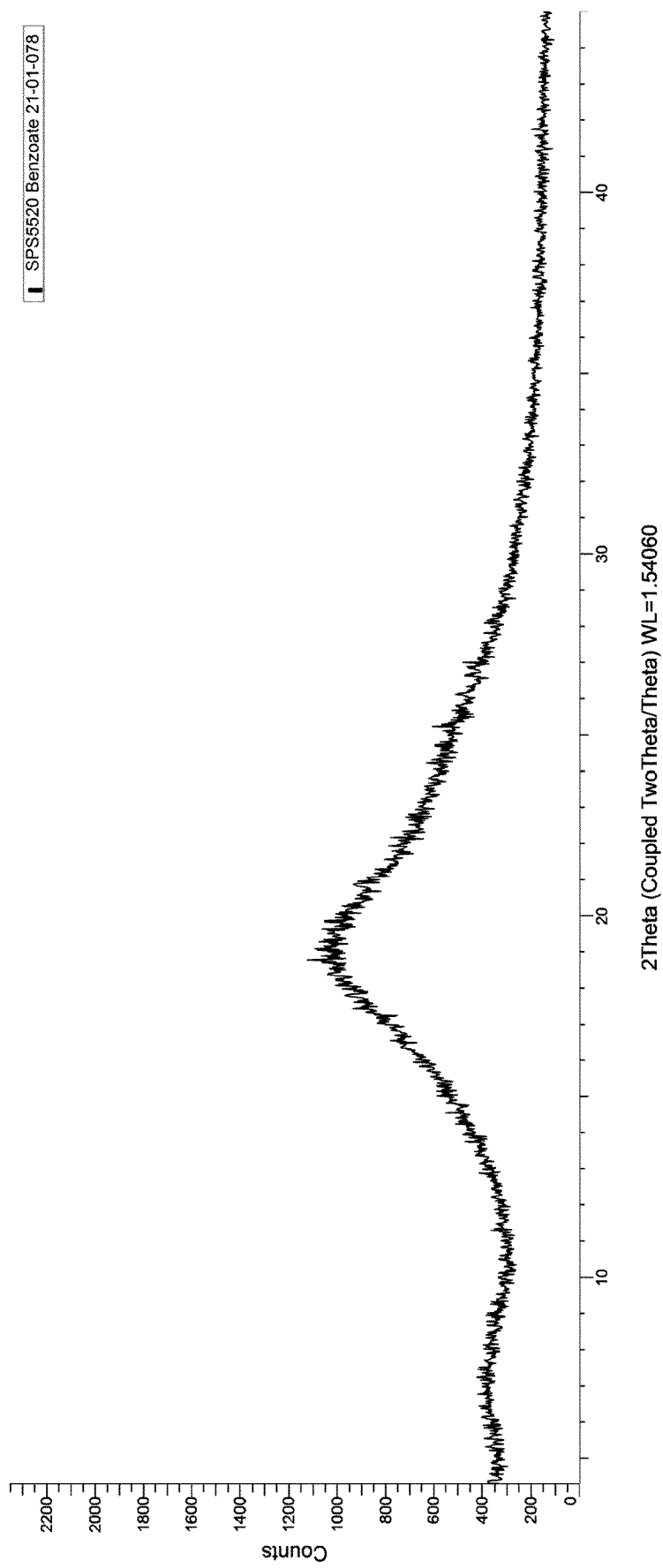
FIG. 88 shows XRPD of 5MeODMT benzoate lot 21-01-078.

The XRPD of 5MeODMT benzoate before DVS analysis revealed an amorphous diffraction pattern which was expected (FIG. 88). FIG. 88 shows XRPD of 5MeODMT benzoate lot 21-01-078.

The DVS examination demonstrates an initial weight reduction of ca. 1.4% from the start of the investigation during the first desorption cycle (FIG. 89) which was much lower than the 5 wt % required for a 5MeODMT benzoate monohydrate. Weight reduction continues despite the RH increasing to 70% RH during the first sorption. At 80 and 90% RH on the first sorption cycle, there is a small increase in weight. Following this there is a weight reduction to the minimum on the second desorption cycle, on the subsequent sorption cycle there is no change in weight until 50% RH, between 50% RH and 90% RH there is a weight increase of 0.2%.

Figure 89:
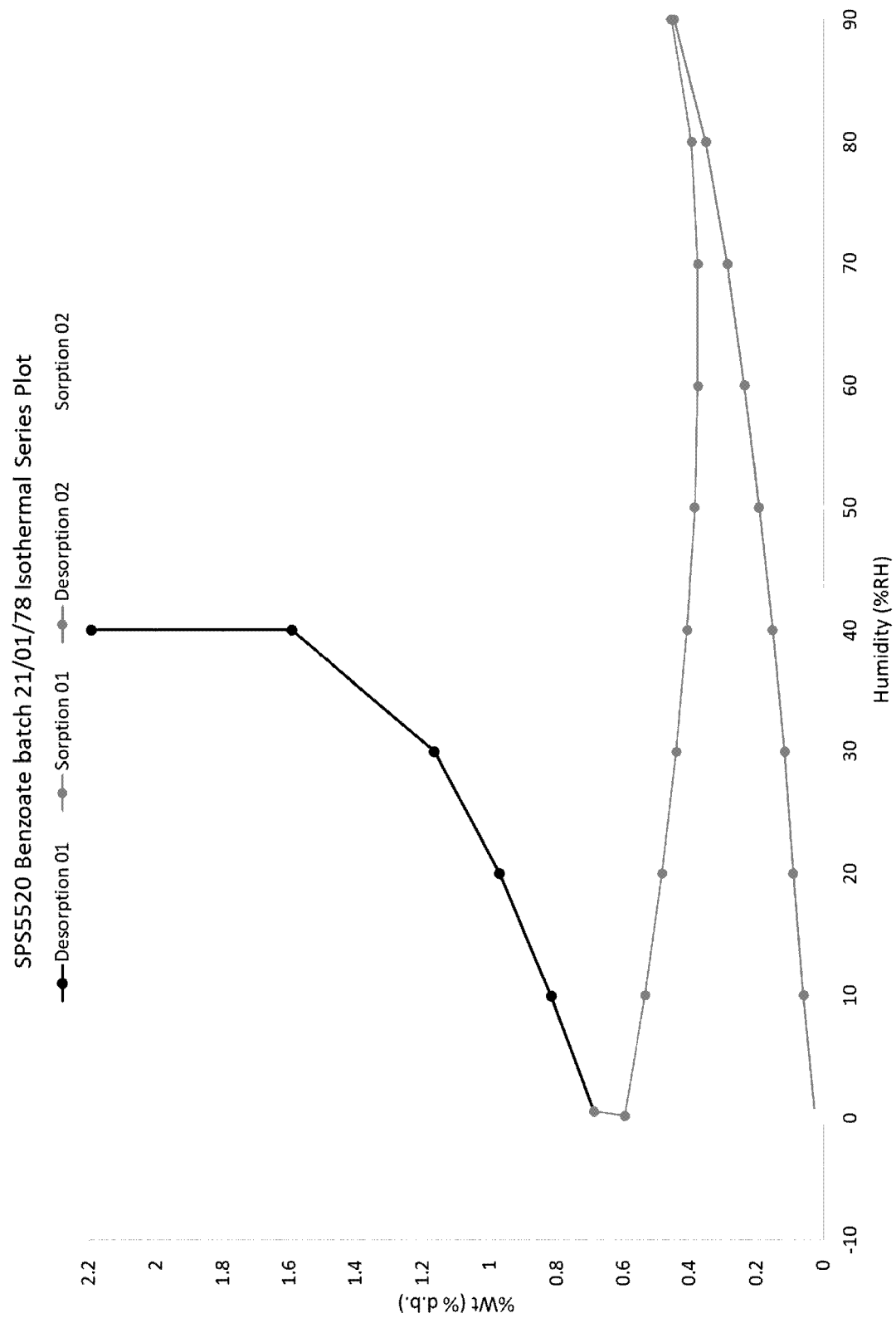
FIG. 89 shows DVS isothermal plot of 5MeODMT benzoate lot 21-01-078.

FIG. 89 shows DVS isothermal plot of 5MeODMT benzoate lot 21-01-078.

Figure 90:
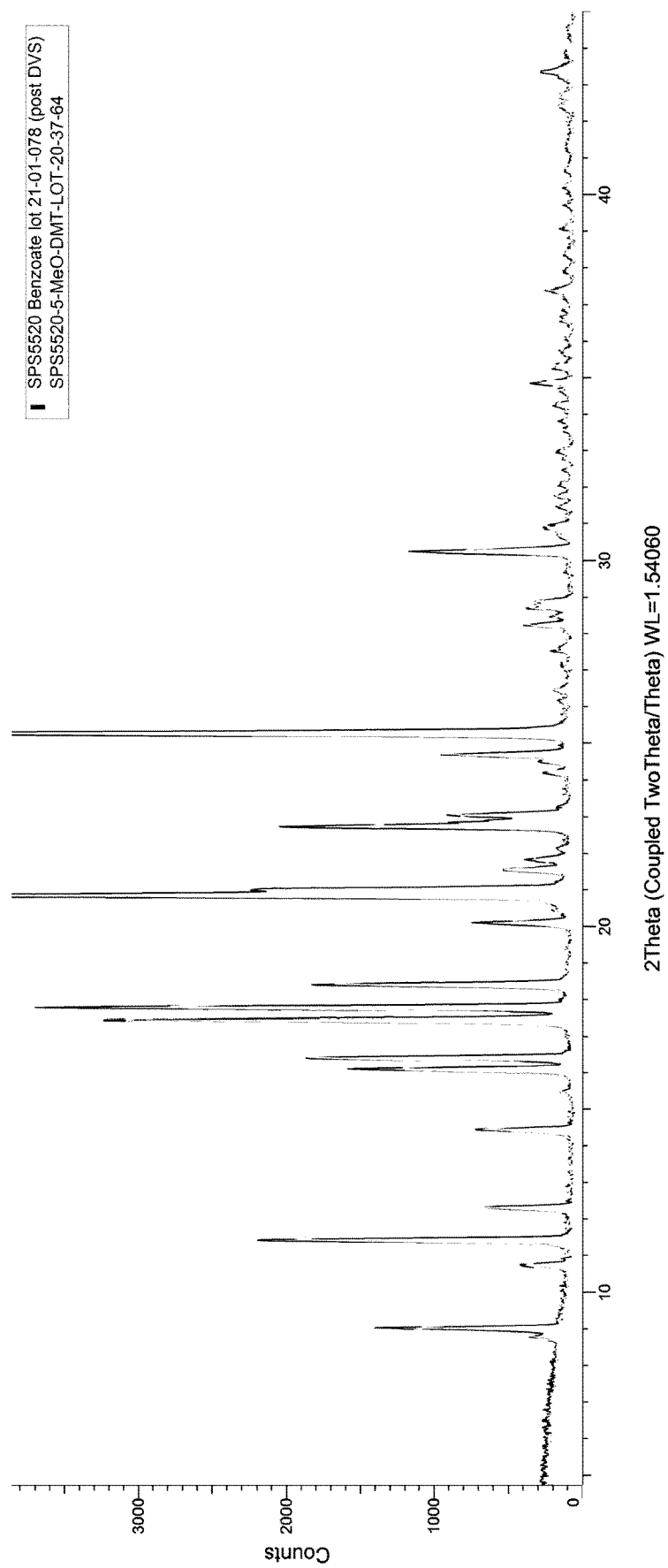
FIG. 90 shows XRPD pattern comparison of 5MeODMT benzoate lot 21-01-078 (post-DVS) and 20-37-64.

The XRPD of 5MeODMT benzoate lot 21-01-078 after DVS examination at 90% RH revealed a diffraction pattern concordant with Pattern A (FIG. 90).

FIG. 90 shows XRPD pattern comparison of 5MeODMT benzoate lot 21-01-078 (post-DVS) and 20-37-64.

Amorphous 5MeODMT benzoate is unstable and undergoes transformation to Pattern A form under all conditions studied. Under ambient conditions it is believed that the amorphous version uptakes moisture from the atmosphere which is eliminated from the sample following conversion to Pattern A form. Such a conversion is not considered to be via a hydrate as there has been no observed evidence of a 5MeODMT benzoate hydrate. Alternatively, the process of lyophilisation could seem complete when in fact some moisture remains bound to the solid. Upon evacuation of the lyophilisation vessel to atmospheric pressure, the low density, voluminous solid contracts, entrapping the moisture to afford the gum that is then ejected as the amorphous gum and converts to the more stable, ordered Pattern A form version.

Example 32: FTIR Spectroscopy of 5MeODMT Benzoate Patterns a, B and C

Figure 91:
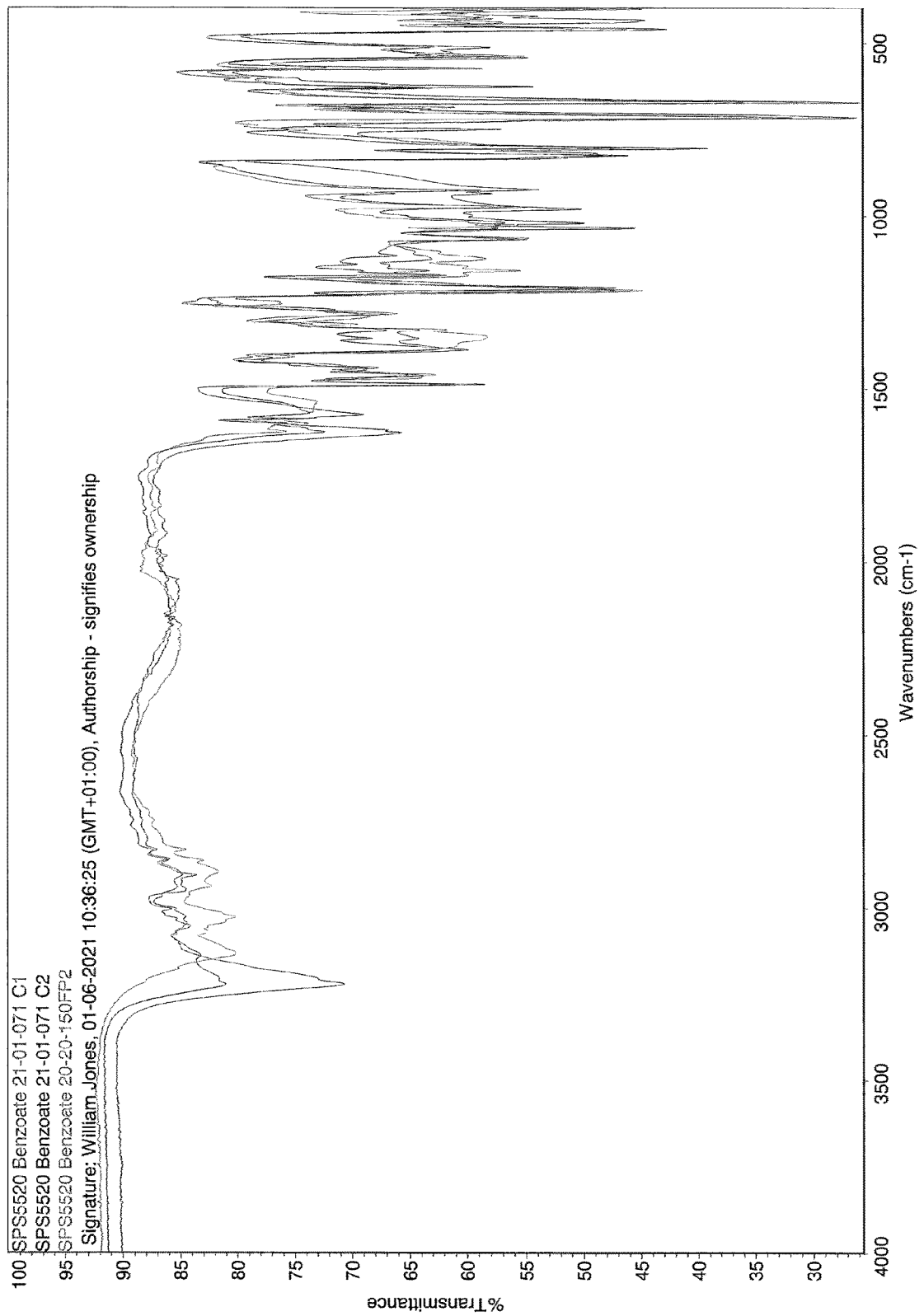
FIG. 91 shows FTIR overlay of 5MeODMT benzoate Pattern A form (20-20-150FP2), Pattern B form (21-01-071 C2) and Pattern C form (21-010071 C1).

FIG. 91 shows FTIR overlay of 5MeODMT benzoate Pattern A form (20-20-150FP2), Pattern B form (21-01-071 C2) and Pattern C form (21-010071 C1).

Figure 92:
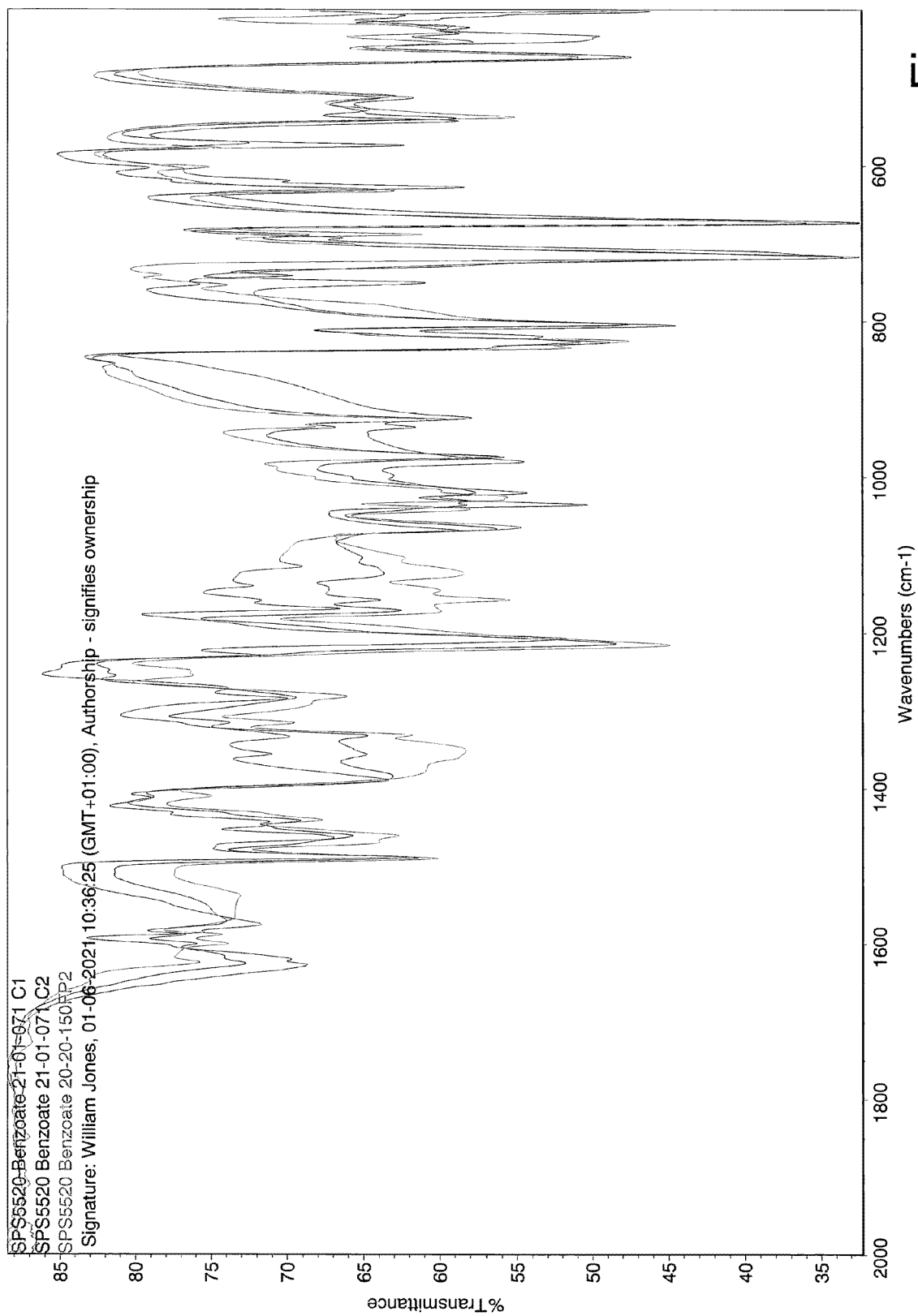
FIG. 92 shows FTIR overlay of 5MeODMT benzoate Pattern A form (20-20-150FP2), Pattern B form (21-01-071 C2) and Pattern C form (21-010071 C1) at 450 to 2000 cm-1.

FIG. 92 shows FTIR overlay of 5MeODMT benzoate Pattern A form (20-20-150FP2), Pattern B form (21-01-071 C2) and Pattern C form (21-010071 C1) at 450 to 2000 cm-1.

Figure 93:
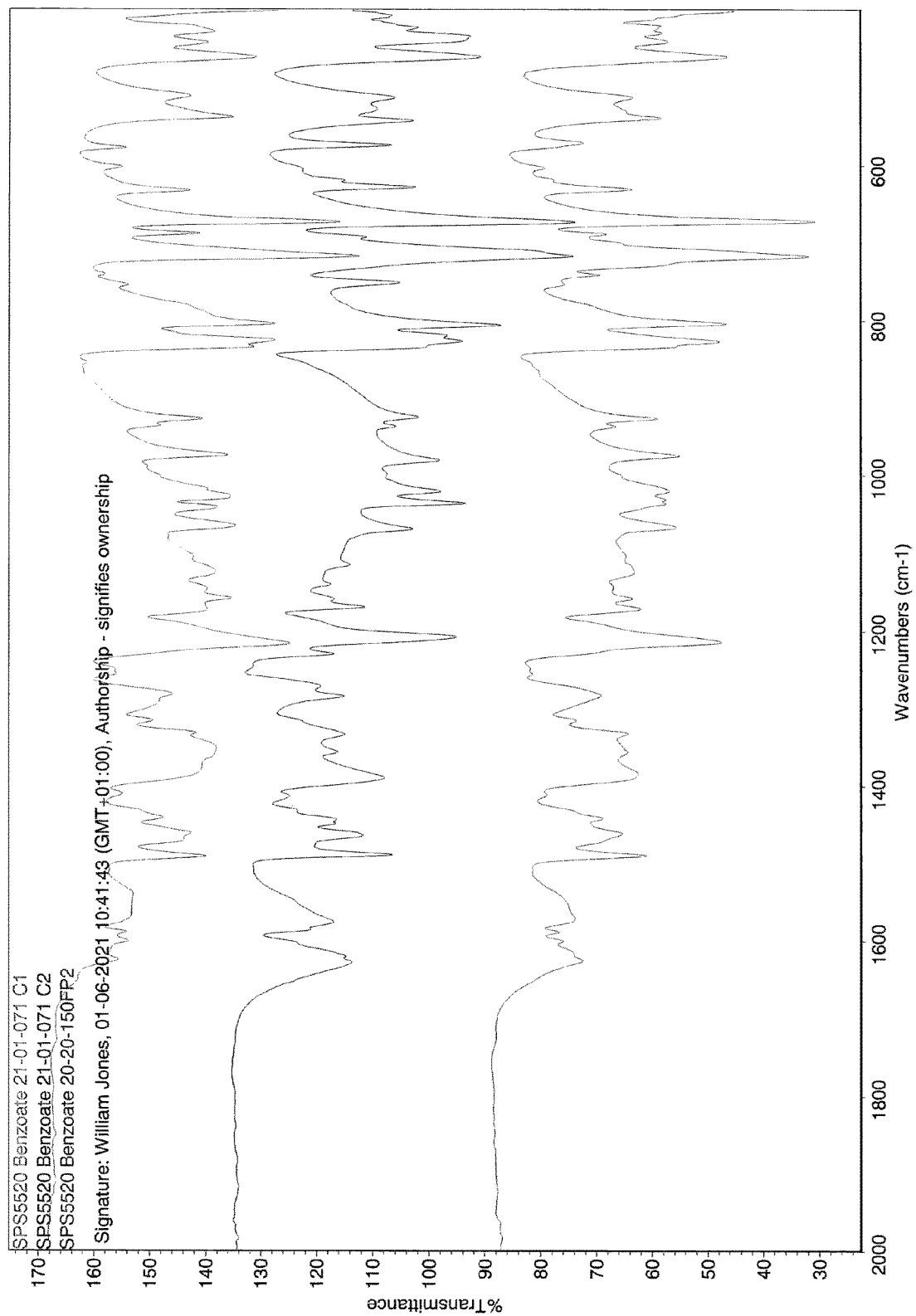
FIG. 93 shows FTIR overlay of 5MeODMT benzoate Pattern A form (20-20-150FP2), Pattern B form (21-01-071 C2) and Pattern C form (21-010071 C1) at 450 to 2000 cm-1; spectra separated.

FIG. 93 shows FTIR overlay of 5MeODMT benzoate Pattern A form (20-20-150FP2), Pattern B form (21-01-071 C2) and Pattern C form (21-010071 C1) at 450 to 2000 cm-1; spectra separated.

Inspection of FTIRs reveals the Pattern A form demonstrates a number of bands of significantly different intensity compared to Patterns B form and C form. Such notable bands were observed at ca. 3130, 1540, 1460, 1160 and 690 cm-1, whilst key absent (or significantly reduced intensity) bands present in Patterns B and C included those observed at ca. 3230 and 1640 cm-1.

Patterns B and C forms demonstrated far fewer differences in their FTIRs to one another, as when compared to the FTIR of the Pattern A form.

This was anticipated when it is considered that the Pattern C form hemi-solvate desolvates somewhat readily to afford the Pattern B form, resulting in a relatively small change to the crystal lattice compared to the energy required (i.e.; drying in vacua at elevated temperature) to induce conversion of Pattern B form to Pattern A form, restructuring the crystal lattice to a greater extent than facile desolvation.

Example 33: Stability of Patterns B and C

Drying 5MeODMT benzoate Pattern C form in vacua at 50° C. for 24 hours historically often afforded Pattern B form and Pattern B form is known to transform to Pattern A form at 90° C. as observed by hot stage microscopy. The stability of Pattern A form and Pattern B form under both atmospheric conditions and in vacua at 50° C. was investigated to determine the relationship between the forms.

5MeODMT benzoate lot 21-01-071 C1, Pattern C form, and lot 21-01-071 C2, Pattern B form, were charged to XRPD sample holders and sample vials and left open to the atmosphere for 12 days.

5MeODMT benzoate lot 21-01-071 C1, Pattern C form, was dried in vacua at 50° C. for 5 days.

XRPD was performed regularly. DSC and 1H NMR spectroscopy were performed on samples where significant differences to the diffraction patterns were observed.

The Table below shows a summary of solid form conversion by XRPD during the stability tests.

| Sample | Drying method | XRPD pattern throughout drying | | | | | | | | |
|---|---|---|---|---|---|---|---|---|---|---|
| | | Day 0 | Day 1 | Day 2 | Day 3 | Day 4 | Day 5 | Day 6 | Day 8 | Day 12 |
| 21-01-071 C1, Pattern C | Open to atmosphere at 20 ± 2° C. | C | C + B | n/c | n/c | C + B | n/c | C + B | C + B | C + B |
| 21-01-071 C2, Pattern B | Open to atmosphere at 20 ± 2° C. | B | B | n/c | n/c | B | n/c | B | B | B |
| 21-01-071 C1, Pattern C | In vacuo at 50° C. | C | B | B + A | A + B | n/c | A | n/c | n/c | n/c |

Example 34: Competitive Equilibration of 5MeODMT Benzoate Pattern a, B, and C Forms in Solvents The relationship between 5MeODMT benzoate Pattern A, B, and C forms was investigated to determine the thermodynamically stable version and hierarchy. Competitive equilibration was conducted between Pattern A and B forms, and Pattern A and C forms in a variety of solvents including IPA and toluene. Pattern A form was expected to be the most stable form given its melting point of 124° C. and prevalence during most investigations performed.

5MeODMT benzoate 20/20/150FP2, Pattern A form, 15 mg, was charged to all crystallisation tubes. 5MeODMT benzoate lot 21-01-071 C2, Pattern B form, 30 mg, was charged to AB crystallisation tubes. 5MeODMT benzoate toluene hemi-solvate lot 21-01-071 C1, Pattern C form, 30 mg, was charged to AC crystallisation tubes. Solvent, 0.5 ml, was charged to crystallisation tubes as detailed in the Table below. Suspensions were agitated at 100 rpm at 20±2° C. for 24 hours. Suspensions were isolated via isolute cartridge and air dried for 5 minutes and characterised by XRPD and DSC.

| Solid mixture | Solvent | Summary of solid form characterisation | | |
|---|---|---|---|---|
| | | ID | XRPD | DSC |
| Pattern A (15 mg) + Pattern B (30 mg) | IPA | AB1 | Pattern A | Endotherm at 124° C. |
| | Toluene | AB2 | Pattern C | Endotherm at 122° C. |
| | iPrOAc | AB3 | Pattern A | Endotherm at ca. 124° C. + minor events |
| | MeCN | AB4 | Pattern A | Endotherm at 124° C. |
| | MEK | AB5 | Pattern A | Endotherm at 124° C. |
| | 2-MeTHF | AB6 | Pattern A | Endotherm at 124° C. |
| Pattern A (15 mg) + Pattern B (30 mg) | IPA | AC1 | Pattern A | Endotherm at 124° C. |
| | Toluene | AC2 | Pattern C | Endotherm at 123° C. + minor events |
| | iPrOAc | AC3 | Pattern A | Endotherm at 124° C. |
| | MeCN | AC4 | Pattern A | Endotherm at 124° C. |
| | MEK | AC5 | Defined Pattern A | Endotherm at 124° C. |
| | 2-MeTHF | AC6 | Pattern A | Endotherm at 124° C. |

The XRPD of all samples revealed the majority gave Pattern A.

Sample AC5 isolated from MEK revealed an additional diffraction at 8.8° 2θ however this was considered to be caused by the splitting of the diffraction at 9° 2θ due to better resolution between diffractions of this sample.

The DSC thermograph of most Pattern A form samples revealed an endothermic event with peak temperatures ranging from 123.74° C. to 124.22° C. which is indicative of Pattern A form.

The DSC thermograph of 5MeODMT benzoate lot 21-01-079 AB3, isolated from isopropyl acetate, revealed a series of events between 109° C. and 115° C., then a minor endothermic event with a peak temperature of 115.69° C. This was followed by a major endothermic event with a peak temperature of 123.85° C. indicative of the Pattern A form.

The minor endothermic events are believed to be due to the incomplete conversion of Pattern B form to Pattern A form via equilibration.

The XRPD of 5MeODMT benzoate lot 21-01-079 AB2 and AC2, both equilibrated in toluene, revealed a diffraction pattern concordant with 5MeODMT benzoate lot 21-01-064 A toluene hemi-solvate, Pattern C form.

The DSC thermograph of 5MeODMT benzoate lot 21-01-079 AB2 revealed a bimodal endothermic event with peak temperatures of 114.96° C. and 121.92° C. The thermal characteristics are similar to previously isolated pattern C samples, including 5MeODMT benzoate lot 21-01-073 J.

The DSC thermograph of 5MeODMT benzoate lot 21-01-079 AC2 revealed a minor endothermic event with a peak temperature of 110.11° C., followed by overlapping endothermic and exothermic events between 110.73° C. and 113.23° C. This was followed by an endothermic event with a peak temperature of 122.82° C., this endothermic event is comparable to the melt of Pattern A form when recrystallised from Pattern B form.

Competitive equilibration of both Pattern A/B form mixtures and Pattern A/C form mixtures in solvents that were not previously observed to produce hemi-solvates demonstrated conversion to the Pattern A form. It is anticipated that all other hemi-solvates will convert to the Pattern A form in these solvents.

Competitive equilibration of both Pattern A/B forms and Pattern A/C forms in toluene demonstrated conversion to the Pattern C form. It is anticipated that equilibration of 5MeODMT benzoate in a solvent (typically an aromatic solvent) that has the propensity to form a hemi-solvate will afford that particular 5MeODMT benzoate hemi-solvate over the otherwise thermodynamically stable Pattern A form solid form version.

Example 35: Administration of a 5MeODMT Salt

The physical surroundings of the participant/patient/subject are of high importance in the character of many psychedelic experiences. The space should be private, meaning that there should be no chance of intrusion by others. Ideally, sound from outside (e.g. the hallway, the street, etc.) will be minimal. The dosing sessions should take place in rooms that feel like a living room or den rather than a clinical setting. Artwork, plants, flowers, soft furniture, soft lighting, and related décor should be employed in creating a cozy and relaxing aesthetic. Artwork with any specific religious iconography, ideological connotation, or tendency to evoke negative emotions should be avoided. The dosing room may also provide comfortable furniture for the participant and the therapists, who may sit on either side of the participant. Participants under the effect of 5MEODMT may exhibit spontaneous movement or slide off of the bed or couch in their prone position. It is therefore important to make sure no sharp or hard objects are nearby that the participant may fall on. Additionally, pillows may be useful to physically support participants who are mobile during the experience. A therapist can provide physical support to the participant by placing a pillow between their hands and the participant's body.

Music may accompany the experience, so the dosing room should be equipped with a stereo. The room should shield the participant from sights and sounds of the world beyond the room, and the participant should not have any cause for concern of observation or interruption by anyone other than the therapists.

The space may also contain:
The tools for safety procedures and medical devices necessary to respond in the unlikely event of a medical complication. The participant should be made aware of these procedures and the equipment, but as much as possible they should be hidden from view.
A secured and locked space for study materials and documentation in the session room or nearby.
An approved safe for storing the 5MEODMT in the session room or nearby.
Audio and video-recording equipment: If allowed in the study protocol the participant will have already consented to being recorded, and should be made aware of the equipment, but it should be placed to be as unobtrusive as possible. Participants may request the cessation of recording at any time.

Physical Space

The space may be large enough to accommodate chairs for two therapists, the stereo equipment and cabinet for storage of the participant's belongings and any extra supplies the therapists may need during the day. The space may accommodate a bed or couch on which the participant can either sit up or lie down with a comfortable surroundings of pillows. The space may be at least $100^2$ feet or $10^2$ meters so that participants do not feel cramped or too physically close to therapists. Participants should have room to explore a variety of positions including sitting on the floor or stretch their bodies without restriction. A bathroom should be either accessible directly from the session room or nearby.

Music

5MEODMT sessions may use a pre-set playlist of nature sounds for creating a calm atmosphere. These nature sounds are considered to be a background element, helping drown out any noise from outside the room, and keep the participant focused on their experience. Participants are not instructed to listen to the sounds in any particular way, but may be asked to focus on it as a way of grounding their senses and relaxing before or after session.

Medication Discontinuation

Medication discontinuation can be challenging for participants. Participants are to have discontinued all contraindicated medications and completed washout periods prior to Prep-1 with the therapist. The study team members, including the therapist, may provide supportive check-in calls with the participant prior to this, as-needed during the washout period, but should not start Prep-1 until washout is complete and the participant confirms intention to continue with the therapy.

Preparatory Sessions

This treatment model includes three, 60-90 minute preparatory sessions with the therapist. These take place 7 days, 4 days, and 1 day before the 5MEODMT session. Preparatory sessions are designed to take place via telemedicine, but can be in-person if possible.

Preparatory Session 1

The following topics may be covered in the first preparatory session.

Getting to Know the Participant

The therapist will spend some of the preparation session time getting to know the participant. The therapist may ask open-ended questions about:
How they found out about the treatment and what their expectations are;
Current life situation with regards to living situation, work, school, and important relationships;
Understanding of their own depression;
Key life events that the participant feels might be of relevance The therapist should be listening for how the participant talks about themselves and their relationship to their depression, how they relate to the therapist and study environment, and stay attuned to establishing a sense of trust and rapport with the participant. Clinical impressions of difficulty forming a trusting relationship with the therapist or any other clinical factors that could interfere with the participants' ability to engage in the treatment should be noted and discussed with the study team. Although in the preparatory session stage, the therapist may learn more of the participant that could be reasons for study exclusion.

Establishing the Role of the Therapist

Therapists in the 5MEODMT-assisted therapy treatment model form a relationship with study participants which becomes part of the container in which the 5MDE (subjective experience of 5MeODMT) takes place. This formation of this relationship is deliberate on the therapists part and characterized by the therapist establishing transparency and trust, taking clinical responsibility for the patient's wellbeing, and relational and emotional safety for the patient. The therapeutic relationship is understood as a critical component of the set and setting for the therapeutic use of the 5MDE. The communication and establishment of this relationship is both explicit (overt) and implicit (covert) in the therapists behaviors and mannerisms throughout the treatment.

Explaining the therapeutic model with participant as active participant in their process The therapist should explain the therapeutic model used in this research study to the participant in the first preparation session. The explanation should include:
Practical aspects:
How many meetings with the therapist will occur, and for how long.
That the therapy is thought to work by:
Creating a safe container for the experience so that the participant knows what to expect and can fully let go into their experience,
Helping the participant focus on and explore their own responses to the experience,
Facilitating a process of the participant determining for themselves how they will put their insights into practice in their life.
That the therapists role is:
Supporting the participant through the session, engaging in a series of activities to elicit the participant's unique experience and insights, fostering the participant's process of implementing the resulting changes in their life.

That the therapy is:

Not a full deep dive into participant's personal history, not a place to do specific problem solving or engage in CBT, Psychodynamic interpretations, get general advice, or receive other interventions the participant may be familiar with.

Establishing Physical, Emotional, and Psychological/Relational Safety

Beginning in the first preparatory session the therapist establishes the environment of physical, emotional, and psychological safety. The therapist explains the safety of 5MEODMT and the safety procedures relevant to the participants physical health for the session. With regards to emotional safety the therapist states that all emotional experiences are welcomed, that there is no area of experience that the participant is not welcome to share. Safety can also be established through the calm reassuring presence of the therapist, which does not always require the use of language.

The use of self-disclosure is not prohibited, but should be used very sparingly. A participant may be seeking safety by asking personal questions of the therapist. If the therapist chooses to disclose, it should be brief and under the condition the participant share why this personal information is important to them.

Psychological/relational safety is established by assuring the participant that their wishes will be respected with regards to the use of touch. Also, the participant is to be reassured that if they choose not to participate in the 5MDE experience they may do so at any point up until drug administration and that this will be respected, and that the therapy sessions will still be available to them if they make that choice.

The therapist can use the following techniques to establish safety with the participant:

Ask open-ended questions that invite the expression of doubts, hesitancies, or concerns:
What questions do you have for me?
What more would you like to know about 5MeODMT?
What would you find helpful in the event . . . ?
How could I be of assistance to you if you feel . . . ?

Encourage and engage with the full range of participant's emotions and experiences without trying to fix or resolve them:
Participant expresses skepticism about the 5MEODMT Experience: I appreciate you sharing that doubt with me. What do you make of that in light of your presence here at this time?
Participant expresses fear about the 5MDE Experience: What more can you tell me about your fear and how it manifests for you? How could I be helpful to you as you experience this?

Use affirmations to establish an environment of valuing the participant's time and effort:
I really appreciate the time you are putting into this treatment and your willingness to participate in research.
Your experience is unique to you and I appreciate the opportunity to see you through this process.

Expected Potential Subjective Drug Effects (Unity, "Feeling Like Dying", "the Void")

It may be helpful to discuss the concept of "non-ordinary state of consciousness" with participants. In the past, "altered state of consciousness" was often associated with experienced engendered by psychedelic compounds. However, alterations of consciousness are experienced on a daily basis, as moods or feelings shift, or when people shift from awake alertness to feeling tired and drowsy. "Non-ordinary state of consciousness" emphasizes the quality of an experience that is not ordinarily had on a daily occurrence, but can still be within human experience.

The therapist may begin this conversation by asking the participant about their existing knowledge of 5MEODMT effects, and listen for specific expectation or ideas about it. The therapist is to encourage an attitude of openness toward the experience, encouraging participants to explore what kinds/ideas they may have and be open to the possibility that it will not be possible to imagine what this will be like. Participants may have specific expectations based on the media, prior experience with 5MEODMT or other psychedelics, or other kinds of non-ordinary states of consciousness. It is important for therapists to provide a balanced description of what the participant may experience.

Different people have different levels of comfort with "not knowing" what something will be like, or what to expect. The therapist may explore the participant's level of comfort with the unknown, their relationship to the idea the future not being fully knowable in any situation, and how they generally relate to this. Among participants with depression there may be deep fear of the unknown, anticipation of what is expected in the future (more negative experiences), resulting in a feedback loop of feeling fearful and depressed. Therapists should elicit and explore this area during preparation.

Common 5MeODMT Experiences: The therapist should also introduce a few key terms and commonly reported experiences known to occur under 5MEODMT. These include a feeling of unity, a feeling of dying, and a feeling of entering or experiencing a "void" (absence of material reality). Some participants may have an existing spiritual, philosophical, or religious belief system through which they will interpret or make meaning of these experiences. Therapists should enquire about this and work with the participant's own explanation and terms, without taking a stance as to whether these are correct or erroneous.

Social Support and Social Media

Participant's social support may be assessed during preparation sessions and be determined by the therapist to be adequate to support the patient through the process of change, especially in the event of either disappointment or dramatic symptom reduction. In the event the participant has a psychotherapist outside of the study the study therapist may, with the participant's permission, have a phone call with the participants therapist to describe the nature of the study and therapeutic approach and answer any questions the therapist may have. The study therapist may also educate any friends or family members who are close to the participant and have questions regarding the nature of the study, the 5MEODMT experience, and what to expect. The therapist should discuss social support with the participant including preparing the participant for the variety of reactions their friends and family may have.

Therapists may advise participants to take caution around posting about their experience on social media so as not to elicit excessive public commentary. Inadequate social support or use of social media in a way that may be disruptive to the therapeutic process may be discussed and resolved prior to 5MEODMT administration.

Preparatory Session 2

The following topics may be covered in the second preparatory session.

Drug experience preparation: trust, surrender (let go), embrace, transcendence.

There are several key attitudes towards psychedelic experiences that are considered to be conducive to a positive and clinically helpful experience. The more participants can embody a relaxed stance toward their experience the less likely they are to struggle, inadvertently creating a loop of stress and distress that heightens attention to negative aspects and interpretations. The therapist may educate the participant on the purpose of deliberately generating an attitude of trust, surrendering to the experience, and letting go of attempts to control the experience. Therapists may encourage participants to develop an attitude of welcoming and embracing all experiences they may have as part of their 5MEODMT experience. The therapist may suggest to a participant that all aspects of the experience (feelings, sensations, and thoughts) can be welcomed. Previous research with psychedelics has demonstrated that a capacity to be absorbed by the experience can contribute to the potency of a mystical experience.

The Drug Administration

The therapist should explain that on the day of the session that a member of the research team will enter the room briefly to administer the study drug. The therapist should explain the participant positioning, e.g. they will be in a seated position on the bed or couch, that the research team member will insert the nasal spray device in one nostril, and that they will be asked to allow the therapist to assist them in lying down on the bed or couch immediately afterward.

Session Procedures Including Boundaries, Use of Touch, Safety, Etc.

The therapist will explain the process of the session. The session is contained by the timing of the dosing and the physical environment of the dosing room. It begins when the participant enters the room and engages with the therapist in the Session Opening. Session Opening is a formal moment in which the participant and therapist sit together in the room, all preparations having been made, and playlist started. The therapist may lead a breathing exercise of the participant's choice, if the participant is open to engaging in one, and ask the participant to reflect on the values they choose in the preparation session, or any other value or intention that is important to them. Once the participant signals that they are ready, a member of the research team will administer the nasal spray to the participant. Trust and safety are not only communicated verbally, but also this may be nonverbally through how a therapist holds themselves in the presence of the participant. If a therapist is overly anxious, or fearful, this may be felt by the participant. It is important that the therapist is centered throughout the dosing session, particularly at times when a participant is expressing intense affect, unusual somatic expressions, or is asking for support.

Somatic Changes and Shifts in One's Sense of their Body

Some participants may experience an intensified awareness of their body such as feeling their heart rate more strongly or physical sensations in their temple. Other participants may be aware of a tingling in their body, changes or perceived difficulty breathing, or other unusual physiological experiences. It is important for the therapist to communicate that these changes in perception are normal and should not be a focus of preoccupation or fear. If these sensations arise, the participant should be encouraged to communicate these to the therapist, if they so desire. The therapist should reassure the participant that these sensations are expected and are normal to have. The therapist can inform and remind the participant that naturally occurring 5MEODMT has been consumed in other settings for hundreds of years with no indication that it is physically harmful, and that these changes are expected and will resolve shortly.

Discussing Expectations and Intentions

Expectations can be defined as mental representations and beliefs of how something in the future will be. Sometimes expectations can be explicitly identified, and sometimes they are subperceptual, taken for granted. Both kinds of expectations may be important to treatment. The therapist should ask about explicit expectations and encourage the participant to acknowledge and set these aside such that they do not engage in comparing their experience to expectations. The therapist is also listening for subperceptual expectations that may come into awareness through the therapy. Intentions are ways of relating to a behavior or experience. In the 5MEODMT treatment, it can be important for the therapist to elicit and understand the participant's intentions as these can vary greatly and may be taken for granted. Therapists are to engage participants in a process of identifying and setting their intentions such that these are explicit and can be referenced later in integration. The purpose of the intention is for it to be identified and then let go of, with the knowledge that it can be part of the 5M ED.

Recurrence of Acute Effects

Some individuals who used 5MEODMT in non-clinical contexts have reported re-experiencing 5MEODMT's subjective effects in the days after. The dose used, purity, and other factors were not monitored in these cases. The likelihood of these reactivations occurring in a controlled clinical study context is not known, but estimated to be less likely. Nonetheless, it is important for participants to be made aware of this phenomenon. The experience of reactivations are often reported as pleasant, brief (lasting a few moments to minutes), and do not occur with enough frequency to interfere with a person's life. These reactivations are thought by some as part of the integration process. If a participant notices certain activities trigger reactivations, such as certain meditative states, stimulants, or other drugs, and the participant finds these reactivations unpleasant, it should be suggested to the participant that they avoid such triggers. Processing the 5MEODMT experience in therapy, as part of integration, may also be helpful.

Discussing the Use of Touch

Therapists in this modality may engage in two types of touch: therapeutic touch, and touch for safety reasons. During preparation the therapist should explain and define each. Therapeutic touch is touch that is intended to connect with, sooth, or otherwise communicate with the participant for therapeutic aims. It is always fully consensual, non-sexual, and the participant is encouraged to decline or cease therapeutic touch at any time. Touch for safety reasons can include supporting a participant who is having trouble walking by offering an arm to hold, or blocking a patient back from leaving the room while under acute drug effects. This touch is agreed to in advance, is always non-sexual, and limited to specific safety concerns. Therapists should discuss both of these and establish boundaries with participants ahead of session.

Preparing for after the Session (What to Expect, What to do, Setting Aside Time for Integration)

Participants should be encouraged to take some time to rest and integrate their experience after their session day. Study therapists should ask participants to plan for time off after their session, at least the full day of the session and the day after the session. Therapists should explain that after the acute effects of the 5MeODMT have worn off they will stay together in the room for a while. This period of time will be for the participant to readjust to their experience after the acute effects. They will be asked to share what they can recall about their experience and any reactions they have. They will not be asked to share anything they don't want to share, and are welcome to keep their experience private. They may choose to write or draw about their experience, art supplies and writing supplies will be available. They may be encouraged to spend some time continue to stay with their experience, with the therapist's support, for around an hour. They will then meet with the study team for a safety assessment before going home. Once at home they are encouraged to rest and continue to stay with the experience and the insights, ideas, or new understanding they may have from it. Participants should be reminded that they do not need to share their experience with others unless they want to, and are encouraged to continue to focus on it in whatever way they find most helpful. Participants should refrain from returning to work, from driving, drinking alcohol, drug use, or being a sole caregiver for a child or dependent for the rest of the day.

Therapist Teaches Breathing Exercise for Dosing Session

When stressed, breaths become shorter and shallower, and when relaxed, the breath becomes longer and slower. Working with the breath is a way of modulating and regulating one's mental state. The therapist may teach and practice two breathing techniques with the participant. These are designed to help the participant relax their body and mind, tolerate stressful or uncomfortable experiences, and develop autonomy through practice on their own. These are not for use during the acute effects of 5MeODMT, but can be used prior to dosing and afterward.

When teaching the practices, the therapist elicits the participant's individual response to each practice to assess suitability of using it. Breathing practices include: Balancing Breath, Diaphragmatic Breath and Counted Breath.

Preparatory Session 3

Values Card Sort with Prompts

The therapeutic protocol may use a customized Personal Values Card Sort to assist with the therapeutic focus on shift in sense of self. This is done by asking about how people relate to their chosen values before the session, and how they relate to them afterward, drawing attention to shifts, changes, and using these as a guide for the kind of changes the participant may desire to make. It is used as a way to elicit conversation about the participant's sense of self, beliefs about self, and changes in those senses/beliefs throughout the therapy. Therapists may engage participants in the card sort exercise in the third preparation session such that it occurs 1-2 days before the dosing session.

The Values Card Sort Instructions are:
1. Place five anchor cards in order from 1-5 in front of the participant from left to right in order of least to most important.
2. Shuffle the 100 value cards; keep the 2 blank cards separate.
3. Instruct the participant to sort the cards using the following script: "1 placed five title cards in front of you—not important to me, somewhat important to me, important to me, very important to me, most important to me. I'm going to give you a stack of 100 personal value cards. I would like you to look at each card and place it under one of the five title cards. There are also two blank cards. If there is a value you would like to include, write it on the card and put it in whichever pile you would like. I would like you to sort all 100 cards, but whether you use the two additional cards is optional. Do you have any questions?"
4. When the participant is finished sorting, thank them and invite them to look at the "most important" category, removing the other cards from the table.
5. Read the following: "For the second task, I'd like you to focus on the top values you put in the "most important" category and choose the top five."
6. When the participant has chosen their top five cards, thank them read the following: "For the third task, I'd like you to focus on the top five values you chose and rank them in order from most to least important."
7. When the participant indicates they are finished ordering, check to make sure you understand how the cards were sorted (ascending or descending). Point to the #1 spot and say, "I want to make sure I have this right—is this your number one value?"
8. Record values on a scoring sheet, journal or by taking a picture of the cards. Participants should keep a record of their card selections as well.

Debriefing and Discussion:

Next, invite the participant to engage in a structured discussion of each value using a few of the following open-ended prompts, or similar prompts depending on the context of your work:

You selected _ as your #_ value?;
Please tell me more about what _ means to you?
What are some ways has _ been represented in your life?
What are some ways you'd like to see more of _ in your life?
How does your decision to _ or not relate to this value?
How much _ would you like to have in your life?
How would you know if _ was increasing or decreasing in your life?
How does _ relate to the change you are trying to make (or considering making)?

Invite the participant to journal about their answers to the same questions with the remaining cards afterwards. In later sessions it can be helpful to check in on the values and revisit these questions, see how answers have changed, and how participants are currently relating to their values.

Assistant Therapist

The session may be conducted by the therapist with an assistant therapist such that a second person is available to assist in case of any adverse event or physical complication in the participants safety. The assistant who will be present for the session should be introduced in Prep Session 3 and included in a conversation such that they get to know the participant.

Session-Specific Therapeutic Tasks

Therapists should aim to complete the therapeutic tasks outlined above according to the chart below, while acknowledging that some variation will occur based on individual participant needs.

| Prep Session 1 | Getting to know the participant Establishing the role of the therapist Explaining the therapeutic approach/model with participant as active participant in their process Establishing physical, emotional, and psychological/relational safety. Expected potential subjective drug effects (unity, "feeling like dying", "the void",) Social Support and Social Media |
|---|---|

| | |
|---|---|
| Prep Session 2 | Drug specific preparation: trust, surrender (let go), embrace, transcendence, Drug Administration<br>Session procedures including boundaries, use of touch, safety, etc.<br>Discussing expectations and intentions<br>Discussing the use of touch<br>Preparing for after the session (what to expect, what to do, setting aside time for integration)<br>Teach and practice Breathing Exercises |
| Prep Session 3 | Values card sort with prompts<br>Instruction to continue values card sort inquiry for homework after session if needed.<br>Confirm plans for session and review any questions participant has.<br>Assistant Therapist joins the session for an introduction if needed |

5MeODMT Experience Session

The therapist is present with the participant during the session—including pre-experience and post-experience times. This is the only session that must be conducted in-person. The site and therapist should schedule about 3 hours for the session, including pre-experience and post-experience time. This does not include the time allotted to engage in baseline measures and enrolment confirmation prior to the session. Local regulatory approvals will determine the minimum length of time a participant must be under observation following 5MEODMT administration.

Pre-Experience (Around 30 Minutes)

After the participant has completed all enrolment confirmation and randomization procedures and is cleared to participate, the Therapist, Assistant Therapist, and participant together in the room review all aspects of the room and safety procedures. The therapist should introduce the participant to the team member administering the 5MEODMT, to create a sense of familiarity. Therapist introduces any Assistant Therapist and reviews safety features of the room and the equipment present. Participant has time to ask any questions. The therapist will ask about any responses to the situation and how the participant is feeling about their session. The participant should not be rushed into the dosing by the therapists. The therapist will ask the participant to engage in a period of relaxation prior to dosing. Participant will be asked to lie down, close their eyes, listen to the music, and, if willing, engage in at least one of the breathing exercises with the therapist's guidance. When the participant is settled and comfortable, the therapist will initiate the Session Opening. This practice helps contain and emphasize the specialness of the experience. Therapists will contact the member of the research team to come to the room and administer the 5MEODMT. The team member should be aware not to disrupt the peaceful atmosphere of the room. The participant should be in a seated position when insufflating the 5MEODMT, as the effects may be felt quickly, the participant should be transitioned to a prone position and remain prone for the duration of the effect of the 5MEODMT.

Experience (Around 60 Minutes)

It is expected that the onset of acute effects will occur very rapidly after administration. Therapists should be aware of the time of administration so they can be aware of the participant's response in relation to the expected course of duration. Some participants may want to know how long they experienced the effects of the 5MEODMT and it is appropriate to share this information if asked. A significant portion of the time the participant may be nonverbal, focused inward, and engaging in their experience. It is important for the therapist to be mindfully aware of the participant, but not interfering with the participant's experience, unless it is clear that participant is seeking the therapist's support. Therapists are encouraged to engage in self-regulation techniques while the participant is undergoing their experience. This may be in the form of slow intentional inhaling and exhaling, or any other activity that helps the therapist ground and self-regulate. This is both for the therapist's benefit, as well as the participants', because a participant in a heightened non-ordinary state may be particularly attune to or pick up on their therapist's anxiety. It is optimal for the therapist to follow the participant's lead when choosing to verbally engage as the 5MEODMT experience appears to be subsiding. Therapists may be eager to ask the participant about their experience, but it is preferable to wait until the participant is ready to share on their own. A participant may wish to remain in a period of silence, even after the apparent acute 5MEODMT effect is gone. It is appropriate for therapists to greet participants with a friendly smile and welcoming nonverbal behavior, and allow participants to take the lead on sharing when they feel ready.

Post-Experience (Around 90 Minutes)

Therapist will encourage the participant to stay with their experience for a period of time of at least one hour after the acute effects of the 5MEODMT have worn off and the participant is once again aware of their surroundings and situation in the treatment room. To stay with the experience means to continue directing attention toward it in whatever way feels most appropriate to the participant, without turning to engagement in distractions, entertainment, or the concerns of daily life. During this time the therapist will invite the participant to describe their experience, if they choose to, and respect the choice not to if the participant is unready. If the participant does describe their experience the therapist is to listen and encourage the participant to express whatever they would like to share without interpretation or attempts to make meaning. The therapist practices simply listening, encouraging the participant to describe what they can about the experience. The therapist also offers the participant the option of resting and listening to the music, or to write about or draw any aspects of the experience they desire. At the end of this time period, the therapist will verify with the participant that they feel ready to close the session, will engage in the Session Closing, and contact the study team for exit assessment.

Integration Sessions

The key principle of integration sessions is to help the participant focus on shifts in their perception of themselves and the implications of these as they relate to their depression. Self, for the purpose of this study, is broadly defined as the narrative or historical self, the sense of a coherent "I" that moves through experiences, and the self-identities one may use. It is key to remember that the sense of self, or the "I," is reflected in both the experiencer's self-experience and experience of the object of experience, therefore descriptions may, on the surface, be of changes in the perception of the external world, but reflect shifts in the internal processes. To this end, the following therapeutic tasks will guide the integration sessions.

These sessions are less structured than preparatory sessions to accommodate variations in participant responses. There are three tasks: The first should occur at all sessions, the second and third may be introduced and engaged in if and when the participant is ready and willing. The tasks are:

Listening and Hearing about the Participant's Experience

Therapists ask open-ended questions about the participant's experience and listen with non-judgmental curiosity to the participant's descriptions. Therapists ask only that participants focus on the 5MDE and related material, such that their time together is focused on the treatment. Therapists should focus inquiry on the participant's experience, asking them to tune into any aspect of the three types of sense of self they can identify.

Reintroducing the Values and Discussing Relationship to Each

The therapist will reintroduce the values identified in the Values Card Sort from preparation and bring discussion back to them if and when appropriate in the integration sessions. There is by no means a requirement to engage in the structured discussion of the values, but it serves as a framework where needed to direct the focus of sessions toward participants' shift in sense of self.

The Therapist May Ask for Example, to Reintroduce the Values:

Therapist: Before your 5MDE we discussed a list of Values you hold and how you were relating to each of those. I'd like to draw our attention back to that and ask for a little detail about how those ways of relating might have shifted. For instance you named "Family" as one thing that was important to you, but you were concerned that you weren't feeling well enough to be present for family relationships. You said you were isolating from your family a lot by working on your computer from your makeshift office in the garage every evening. How do you relate to the value of "Family" now?

In the dialogue, the therapist can for example continue to focus on shifts in how the participant is relating to his value of "Family" by enquiring about what he is noticing in this area.

Create ways the participant can act to enhance their relationship to their chosen values; identify value-oriented action in their life as an integration practice. Integration can be understood as a process of embodying or living out the insights one has. In at least one of the integration sessions, the earliest the therapist feels the participant can engage in this stage, the therapist should introduce the idea of identifying value-oriented actions they can take in their lives as integration practices. Explaining the concept as above, the therapist can invite the participant to recall the values they identified (or any other that is important to them), recall the insights or experiences of their 5MEODMT session, and think creatively about things they might try intentionally doing differently in order to implement positive change in their relationship to the values based on those insights and experiences Items:
1. A method of administering 5MeODMT or a pharmaceutically acceptable salt thereof to a patient who is diagnosed with depression, the method comprising:
   the discontinuation of the use by the patient of any mood-altering substance or any other substance, medications or preparation which may affect serotonergic function;
   the relaxation of the patient, such as the patient is instructed to lay down, close their eyes, and listen to music and/or engage in one or more breathing exercises guided by a therapist;
   optionally, the clearing of their nasal passages, by blowing their nose, by the patient e.g. whilst sat down;
   the administration of 5MeODMT, optionally by via insufflation, and optionally wherein the patient is in a prone position for the duration of the effects of 5MeODMT.
2. The method of item 1, wherein the patient has discontinued the use of monoamine oxidase (MAO) inhibitors, CYP2D6 inhibitors, selective serotonin reuptake inhibitors (SSRIs), serotonin-norepinephrine reuptake inhibitors (SNRIs), tricyclic antidepressants (TCAs), lithium, antipsychotics, triptans, tramadol, 5-hydroxytryptophan, herbal preparations which may contain 5-HTP, St John's Wort and any benzodiazepines prior to administration of 5MeODMT.
3. The method of item 1 or item 2, wherein the 5MeODMT is administered via the Aptar Unidose (UDS) liquid delivery system.
4. The method of item 1, item 2 or item 3, wherein the 5MeODMT is the benzoate salt, optionally a polymorph of the benzoate salt.
5. The method of any one of items 1 to 4, wherein the patient participates in at least one psychological support session before administration of the 5MeODMT.
6. The method of item 5, wherein the patient participates in at least three psychological support sessions before administration of the 5MeODMT.
7. The method of item 6, wherein the patient participates in three psychological support sessions, wherein these sessions take place 7 days, 4 days and 1 day before the administration of the 5MeODMT.
8. The method of any one of items 5 to 7, wherein the psychological support sessions are 60-90 minutes in length.
9. The method of any one of items 5 to 8, wherein at least one therapeutic intention is discussed during the psychological support session.
10. The method of any one of items 5 to 9, wherein self-directed inquiry and experiential processing are practiced during the psychological support session.
11. The method of any one of items 1 to 10, wherein the patient participates in at least one psychological support session after administration of the 5MeODMT.
12. The method of item 11, wherein the patient participates in at least three psychological support sessions after administration of the 5MeODMT.
13. The method of item 11 or item 12, wherein the patient participates in three psychological support sessions, wherein these sessions take place 1 day, 4 days and 7 days after the administration of the 5MeODMT.
14. The method of any one of items 11 to 13, wherein the psychological support sessions are 60-90 minutes in length.
15. The method of any one of items 1 to 14, wherein the 5MeODMT is administered to the patient in a room with a substantially non-clinical appearance.
16. The method of item 15, wherein the room comprises soft furniture.
17. The method of item 15 or 16, wherein the room is decorated using muted colours.
18. The method of any one of items 15 to 17, wherein the room comprises a high-resolution sound system.
19. The method of any one of items 15 to 18 wherein the room comprises food and drink for the patient and therapist.
20. The method of any one of items 15 to 19 wherein the room comprises an approved safe for storing 5MeODMT.

21. The method of any one of items 15 to 20 wherein the room is insulated such that the patient is shielded from sights and sounds of the world beyond the room.
22. The method of any one of items 15 to 21 wherein the room does not contain any artwork or decoration with any specific religious iconography, ideological connotation, or other such artwork or decoration which may evoke negative emotions in a patient.
23. The method of any one of items 15 to 22, wherein the room comprises a bed or a couch.
24. The method of item 23, wherein the patient lies in the bed or on the couch for approximately 0.5-8 hours, or a substantial fraction thereof, after administration of the 5MeODMT.
25. The method of any one of items 1 to 24, wherein the patient listens to music for approximately 0.5-8 hours, or a substantial fraction thereof, after administration of the 5MeODMT.
26. The method of any one of items 1 to 25, wherein the patient wears an eye mask for approximately 0.5-8 hours, or a substantial fraction thereof, after administration of the 5MeODMT.
27. The method of any one of items 1 to 26, wherein a therapist provides psychological support to the patient for approximately 0.5-8 hours after administration of the 5MeODMT
28. The method of any one of items 1 to 27, wherein the therapist uses guided imagery and/or breathing exercises to calm the patient and/or focus the patient's attention.
29. The method of any one of items 1 to 28, wherein the therapist provides reassuring physical contact with the patient.
30. The method of item 29, wherein the therapist holds the hand, arm, or shoulder of the patient.
31. The method of any one of items 1 to 30, wherein the therapist encourages the patient to perform self-directed inquiry and experiential processing.
32. The method of item 31, wherein the therapist reminds the patient of at least one therapeutic intention.
33. The method of any one of items 1 to 32, wherein the therapist counsels the patient to do one or more of the following:
    (1) to accept feelings of anxiety,
    (2) to allow the experience to unfold naturally,
    (3) to avoid psychologically resisting the experience,
    (4) to relax, and/or
    (5) to explore the patient's own mental space.
34. The method of any one of items 1 to 33, wherein the therapist does not initiate conversation with the patient.
35. The method of item 34, wherein the therapist responds to the patient if the patient initiates conversation.
36. The method of any one of items 5 to 35, wherein psychological support is provided remotely to the patient.
37. The method of item 36, wherein the psychological support is provided via a digital or electronic system.
38. The method of item 37, wherein the digital or electronic system is a mobile phone app.
39. The method of item 38, wherein the digital or electronic system is a website.

Example 36: Mouse Forced Swim Test

This study aimed to assess the effect of 5MeODMT Benzoate at three doses in the mouse Forced Swim Test (FST). The forced swim test is a model of behavioural despair and is sensitive to detection of various classes of antidepressant drugs.

Husbandry

Housing and Acclimation

Animals received a 72-hour period of acclimation to the test facility prior to the commencement of testing. Animals were housed four per cage in polycarbonate cages bedded with ¼" bed-o'cob. Cages were changed, and enrichment provided according to standard operating procedures. Animals were maintained on a 12-hour light/12-hour dark cycle with all experimental activity occurring during the animals' light cycle. All animal use procedures were performed in accordance with the principles of the Canadian Council on Animal Care (CCAC).

Food and Water

Certified Rodent Diet (LabDiet® 5001) was offered ad libitum. Animals were not fasted prior to, or after the experiment was initiated. Water was provided ad libitum in glass bottles with stainless steel sippers.

Study Design

Test Subjects

Male CD-1 mice from Charles River Laboratories (St. Constant, Quebec, Canada) served as test subjects in this study. Animals generally weighed 25-30 g at the time of testing.

| Schedule of Events | | |
|---|---|---|
| Study Day | Key Event | Procedure |
| −8 | Animal arrival | Acclimation to the animal facility |
| −7, to −1 | Daily obs. | Daily health observations |
| 0 | Forced Swim Test | Body weights and observations Dosing with 5-MeO DMT Benzoate, Imipramine, and vehicle Pre-FST behavioural test Forced swim test |

Treatment Groups

Animals were randomly allocated into the following treatment groups:

| Group | Treatment | Route | Pre-treatment time | Group Size |
|---|---|---|---|---|
| A | Vehicle | SC | 3 hr | N = 8 |
| B | 5-MeO DMT Benzoate (0.5 mg/kg) | SC | 3 hr | N = 8 |
| C | 5-MeO DMT Benzoate (1.5 mg/kg) | SC | 3 hr | N = 8 |
| D | 5-MeO DMT Benzoate (5 mg/kg) | SC | 3 hr | N = 8 |
| E | Imipramine (30 mg/kg) | IP | 3 hr | N = 8 |

Pre-FST Behavioural Test

On day 0, in addition to the forced swim test animals were evaluated for signs of 5-HT (serotonin) syndrome. Animals were exposed to activity chambers for 10 minutes at two timepoints post dose: (1) 5-15 minutes post dose, and (2) 2.5 hours post dose.

Forced Swim Test

Male CD-1 mice received the appropriate dose of vehicle, test article, or positive control (treatments summarized above). Following the appropriate pre-treatment time, animals were gently placed into tall glass cylinders filled with water (20-25*C). After a period of vigorous activity, each mouse adopted a characteristic immobile posture which is readily identifiable. The swim test involves scoring the duration of immobility. Over a 6-minute test session, the latency to first immobility is recorded (in seconds). The duration of immobility (in seconds) during the last 4 minutes of the test is also measured. Activity or inactivity from 0-2 minutes is not recorded.

Test Articles

5-MeODMT Benzoate

BEW: 1.59 (Benzoate salt form)

MW: 340.40 g/mol

Doses: 0.5, 1.5, 5 mg/kg (doses corrected to base)

Route of administration, dose volume: SC., 10 mL/kg

Pre-treatment time: 3 hr

Vehicle: 0.9% Saline

Imipramine

BEW: 1.13

MW: 280.415 g/mol

Doses: 30 mg/kg (doses corrected to base)

Route of administration, dose volume: IP., 10 mL/kg

Pre-treatment time: 3 hr

Vehicle: 0.9% Saline

Results

Figure 94:
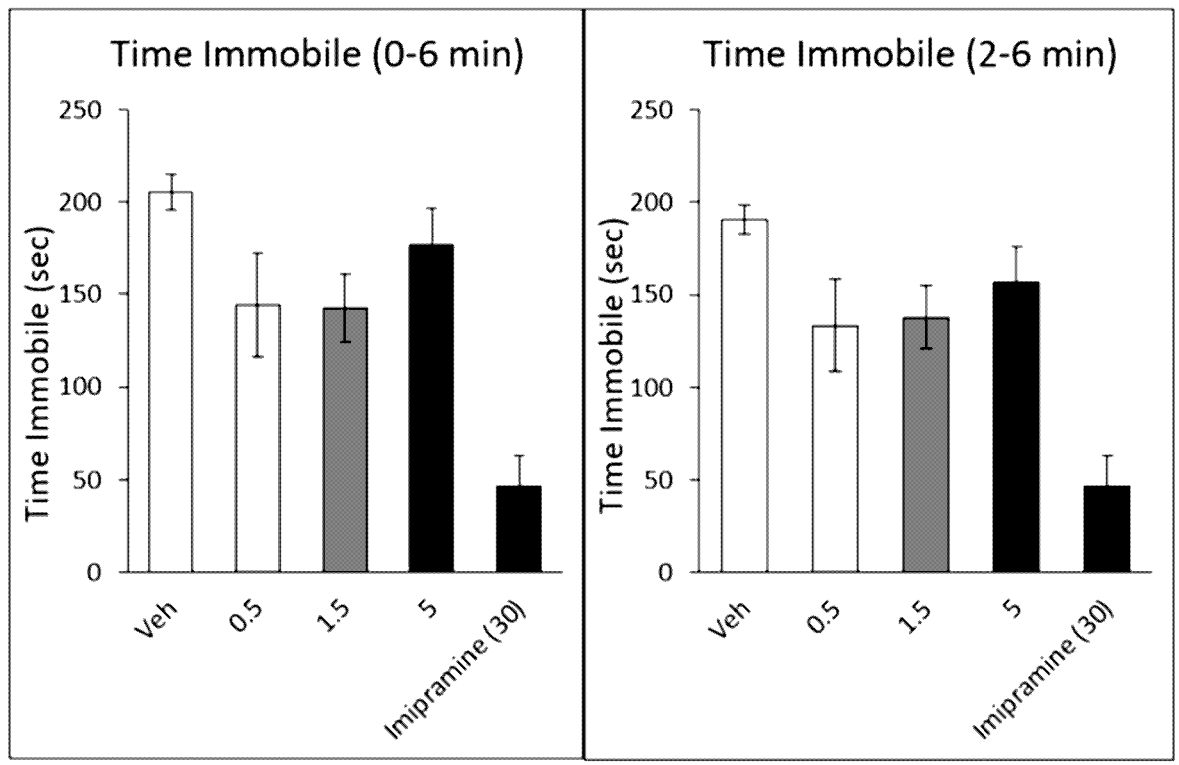
FIG. 94 shows Forced Swim Test results, Time Immobile, for 5MeODMT benzoate, vehicle and imipramine.
Figure 95:
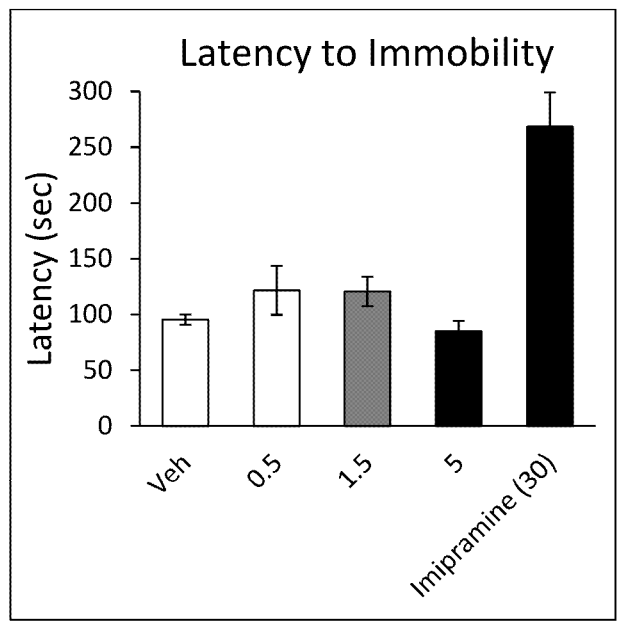
FIG. 95 shows Forced Swim Test results, Latency to Immobility, for 5MeODMT benzoate, vehicle and imipramine.

At 3-hour post-dose, over the 6-minute test session, there is a positive trend in reducing the duration of immobility and increasing latency to immobility by the low doses of 5MeODMT benzoate (0.5 and 1.5 mg/kg), compared to vehicle-treated mice (time immobile 2-6 minutes, vehicle: 190.4±7.7 seconds—5MeODMT benzoate: 133.2±24.9 seconds (0.5 mg/kg), 137.6±17.0 seconds (1.5 mg/kg), 156.8±18.7 seconds (5 mg/kg)—Imipramine 46.8±16.6 seconds, FIG. 94. Latency to immobility, vehicle: 95.5±4.6 seconds—5MeODMT benzoate 121.8±22.0 seconds (0.5 mg/kg), 120.9±13.3 seconds (1.5 mg/kg), 85.0±9.5 seconds (5 mg/kg), imipramine 268.6±30.3 second, FIG. 95).

Example 37: Study 5MEO-TOX-PK-DOG

The objective of this toxicokinetic study was to assess and compare the toxicokinetic profile of the test items, 5MeODMT-HCl (in a vehicle of 0.1% metolose, Group 2) and 5MeODMT-benzoate (in a vehicle of 0.2% metolose+ 0.01% BZK, Group 4).

On day 1, the vehicle or active test item formulations were administered to male Beagle dogs intranasally, at a dose level of 0.4 mg/kg in the active groups (corresponding to freebase). Following administration, a series of blood samples was collected from each dog at the following time points: pre-dose (0), 2, 5, 8, 10, 15, 30 and 60 minutes, and 2- and 8-hours post-dose. Plasma samples were analysed for quantification of concentration of 5MeODMT in each sample using a validated method.

Figure 96:
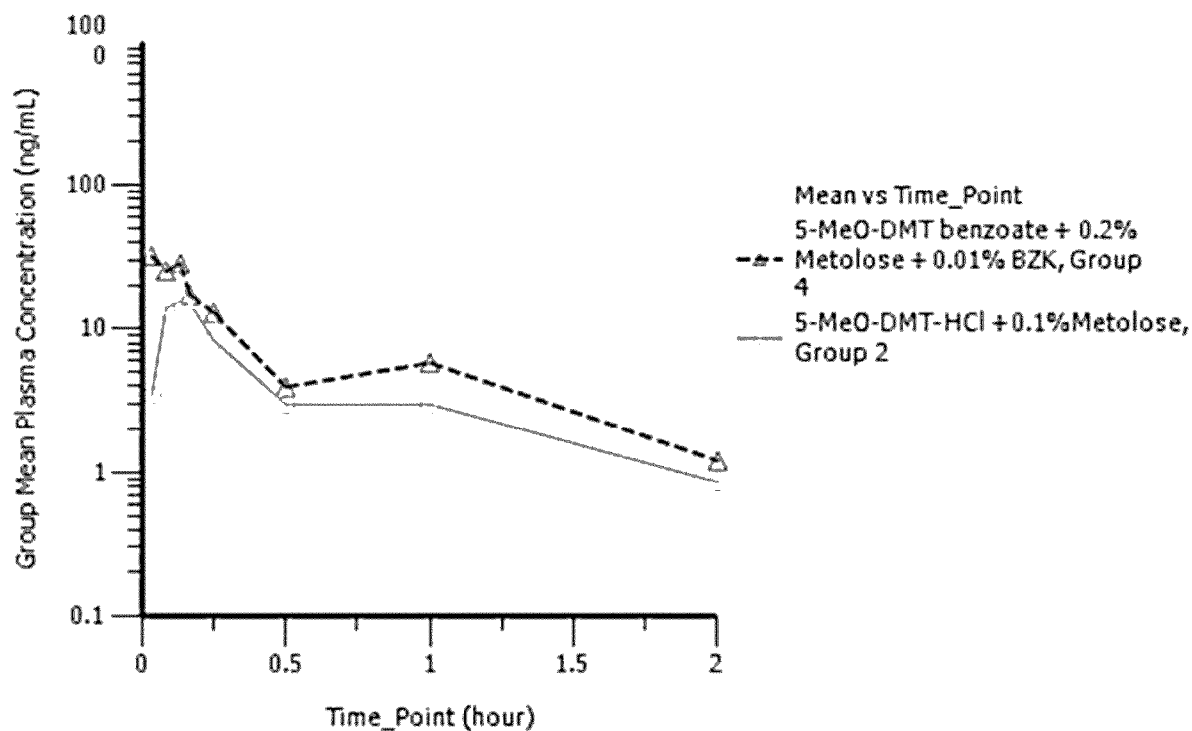
FIG. 96 shows 5MeODMT Group Mean Plasma Concentration (ng/mL) in Male Beagle Dogs—Group 2 (HCl salt) and Group 4 (benzoate salt)—Dose Level (0.4 mg/kg); wherein the Mean Plasma Concentration of Groups 2 and 4 are substantially the same with dose time.

5MeODMT was not detected in any of the samples collected from the control animals on Day 1 (not shown). Peak plasma exposure levels ($C_{max}$) were reported at 16.4 ng/mL and 35.4 ng/mL, for Groups 2 and 4, respectively (see table below). FIG. 96 presents the time-course plot of mean plasma concentrations, which shows a broadly comparable TK profile between the HCl and benzoate salt formulations.

| Mean $C_{max}$ values for 5MeODMT in groups 2 and 4 on day 1 | | | | | |
|---|---|---|---|---|---|
| Group Designation | Day | Dose Level (mg/kg) | $C_{max}$ (ng/mL) Mean | SE | N |
| Group 2 | | | | | |
| 5MeODMT- HCl + 0.1% Metolose | 1 | 0.4 | 16.4 | 1.37 | 3 |
| Group 4 | | | | | |
| 5MeODMT benzoate + 0.2% Metolose + 0.01% BZK | 1 | 0.4 | 35.4 | 16.6 | 3 |

See also FIG. 96 which shows 5MeODMT Group Mean Plasma Concentration (ng/mL) in Male Beagle Dogs— Group 2 (the 5MEODMT HCl salt formulation) and Group 4 (the 5MEODMT benzoate salt formulation)—Dose Level (0.4 mg/kg); wherein the Mean Plasma Concentration of Groups 2 and 4 are substantially the same with dose time.

Example 38: Further Embodiments

In one embodiment, there is provided a polymorph of 5MeODMT benzoate as characterised by an XRPD pattern as substantially illustrated in any one of the Figures or as previously or subsequently described.

In one embodiment, there is provided a polymorph of 5MeODMT benzoate as characterised by one or more peaks in an XRPD diffractogram as substantially illustrated in any one of the Figures or as previously or subsequently described.

In one embodiment, there is provided a polymorph of 5MeODMT benzoate as characterised by one or more endothermic events in a DSC thermograph as substantially illustrated in any one of the Figures or as previously or subsequently described.

In one embodiment, there is provided a polymorph of 5MeODMT benzoate as characterised by TGA thermograph as substantially illustrated in any one of the Figures or as previously or subsequently described.

In one embodiment, there is provided a polymorph of 5MeODMT benzoate as characterised by a DVS isotherm profile as substantially illustrated in any one of the Figures or as previously or subsequently described.

In one embodiment, there is provided a polymorph of 5MeODMT benzoate as characterised by a crystalline appearance as substantially illustrated in any one of the Figures or as previously or subsequently described.

In one embodiment, there is provided a polymorph of 5MeODMT benzoate as characterised by a particle size distribution as substantially illustrated in any one of the Figures or as previously or subsequently described.

In one embodiment, there is provided a polymorph of 5MeODMT benzoate as characterised by a FITR spectra as substantially illustrated in any one of the Figures or as previously or subsequently described.

In one embodiment, there is provided a polymorph of 5MeODMT benzoate produced as previously or subsequently described. In one embodiment, there is provided a method of producing a polymorph of 5MeODMT benzoate as previously or subsequently described.

In one embodiment, there is provided a composition comprising a polymorph of 5MeODMT benzoate as previously or subsequently described.

In one embodiment, there is provided a 5MeODMT benzoate solvate as characterised as substantially illustrated in any one of the Figures or as previously or subsequently described.

In one embodiment, there is provided a 5MeODMT benzoate hemi-solvate as characterised as substantially illustrated in any one of the Figures or as previously or subsequently described.

In one embodiment, there is provided the use of any previously or subsequently described form of 5MeODMT benzoate in any previously or subsequently described method of treatment.

Herein disclosed is the use of a composition as herein described for the manufacture of a medicament for the treatment of any one of: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic disorders.

Herein disclosed is a method of treating any one of: conditions caused by dysfunctions of the central nervous system, conditions caused by dysfunctions of the peripheral nervous system, conditions benefiting from sleep regulation (such as insomnia), conditions benefiting from analgesics (such as chronic pain), migraines, trigeminal autonomic cephalgias (such as short-lasting unilateral neuralgiform headache with conjunctival injection and tearing (SUNCT), and short-lasting neuralgiform headaches with cranial autonomic symptoms (SUNA)), conditions benefiting from neurogenesis (such as stroke, traumatic brain injury, Parkinson's dementia), conditions benefiting from anti-inflammatory treatment, depression, treatment resistant depression, anxiety, substance use disorder, addictive disorder, gambling disorder, eating disorders, obsessive-compulsive disorders, or body dysmorphic in a patient by the administration of a composition as described herein.

The invention claimed is:

1. Crystalline 5-methoxy-N,N-dimethyltryptamine (5-MeO-DMT) benzoate as characterized by peaks in an X-ray powder diffraction (XRPD) diffractogram at 2θ values of 17.5°±0.1°, 17.7°±0.1°, and 21.0°±0.1° using an X-ray wavelength of 1.5406 A.

2. The crystalline 5-MeO-DMT benzoate of claim 1, characterized by peaks in the XRPD diffractogram at 17.5°±0.1°, 17.7°±0.1°, 21.0°±0.1°, and 25.3°±0.1°.

3. The crystalline 5-MeO-DMT benzoate of claim 1, characterized by peaks in the XRPD diffractogram at 9.0°±0.1°, 11.5°±0.1°, 14.5°±0.1°, 16.5°±0.1°, 17.5°±0.1°, 17.7°±0.1°, 18.5°±0.1°, 21.0°±0.1°, 22.7°±0.1°, 24.7°±0.1°, and 25.3°±0.1°.

4. The crystalline 5-MeO-DMT benzoate of claim 1, characterized by peaks in the XRPD diffractogram at 9.0°±0.1°, 11.5°±0.1°, 14.5°±0.1°, 16.3°±0.1°, 16.5°±0.1°, 17.5°±0.1°, 17.7°±0.1°, 18.5°±0.1°, 21.0°±0.1°, 22.7°±0.1°, 24.7°±0.1°, 25.3°±0.1°, and 30.5°±0.1°.

5. The crystalline 5-MeO-DMT benzoate of claim 1, characterized by an endothermic event in a differential scanning calorimetry (DSC) thermograph, using a 10° C./min heating rate and having an onset temperature of 123° C.

6. The crystalline 5-MeO-DMT benzoate of claim 1, characterized by an endothermic event in a differential scanning calorimetry (DSC) thermograph, using a 10° C./min heating rate and having an onset temperature of 124° C.

7. The crystalline 5-MeO-DMT benzoate of claim 1, characterized by an endothermic event in a differential scanning calorimetry (DSC) thermograph, using a 10° C./min heating rate, and having an onset temperature of between 120° C. and 130° C. with a peak of between 124° C. and 126° C.

8. The crystalline 5-MeO-DMT benzoate of claim 7, characterized by an enthalpy between −130 J/g and −140 J/g in the DSC thermograph.

9. The crystalline 5-MeO-DMT benzoate of claim 1, characterized by an onset of decomposition of between 128° C. and 135° C. in a thermogravimetric analysis (TGA) thermograph, using a 10° C./min heating rate.

10. The crystalline 5-MeO-DMT benzoate of claim 1, characterized by water uptake less than or equal to approximately 0.2% as measured by a dynamic vapor sorption (DVS) isotherm from 0% to 90% relative humidity.

11. The crystalline 5-MeO-DMT benzoate of claim 1, characterized by bands at about 3130 cm$^{-1}$, 1540 cm$^{-1}$, 1460 cm$^{-1}$, 1160 cm$^{-1}$, and 690 cm$^{-1}$ in a Fourier-transform infrared spectroscopy (FTIR) spectrum.

12. A composition comprising the crystalline 5-MeO-DMT benzoate of claim 1.

13. The composition of claim 12, wherein the composition further comprises one or more pharmaceutically acceptable carriers or excipients.

14. The composition of claim 12, wherein the composition is formulated for intranasal administration.

* * * * *

UNITED STATES PATENT AND TRADEMARK OFFICE
CERTIFICATE OF CORRECTION

| | |
|---|---|
| PATENT NO. | : 11,518,742 B2 |
| APPLICATION NO. | : 17/660873 |
| DATED | : December 6, 2022 |
| INVENTOR(S) | : Cosmo Feilding-Mellen et al. |

It is certified that error appears in the above-identified patent and that said Letters Patent is hereby corrected as shown below:

In the Claims

In Claim 1, Column 99, Line 52, delete "1.5406 A" and insert -- 1.5406 Å --.

Signed and Sealed this
Fourteenth Day of March, 2023

*Katherine Kelly Vidal*

Katherine Kelly Vidal
*Director of the United States Patent and Trademark Office*